(12) United States Patent
Zhou et al.

(10) Patent No.: US 8,410,265 B2
(45) Date of Patent: Apr. 2, 2013

(54) PROCESSES FOR PREPARING JAK INHIBITORS AND RELATED INTERMEDIATE COMPOUNDS

(75) Inventors: Jiacheng Zhou, Newark, DE (US); Pingli Liu, Newark, DE (US); Qiyan Lin, Newark, DE (US); Brian W. Metcalf, Moraga, CA (US); David Meloni, Bear, DE (US); Yongchun Pan, Newark, DE (US); Michael Xia, Wilmington, DE (US); Mei Li, Newark, DE (US); Tai-Yuen Yue, Hockessin, DE (US); James D. Rodgers, Landenberg, PA (US); Haisheng Wang, Hockessin, DE (US)

(73) Assignee: Incyte Corporation, Wilmington, DE (US)

( * ) Notice: Subject to any disclaimer, the term of this patent is extended or adjusted under 35 U.S.C. 154(b) by 205 days.

(21) Appl. No.: 12/687,623

(22) Filed: Jan. 14, 2010

(65) Prior Publication Data

US 2010/0190981 A1    Jul. 29, 2010

Related U.S. Application Data

(60) Provisional application No. 61/144,991, filed on Jan. 15, 2009.

(51) Int. Cl.
*C07D 487/00* (2006.01)
(52) U.S. Cl. ..................................... 544/280
(58) Field of Classification Search .................. None
See application file for complete search history.

(56) References Cited

U.S. PATENT DOCUMENTS

| 7,598,257 B2 * | 10/2009 | Rodgers et al. ............ 514/265.1 |
| 7,834,022 B2 | 11/2010 | Rodgers |
| 8,158,616 B2 | 4/2012 | Rodgers et al. |
| 2007/0135461 A1 | 6/2007 | Rodgers et al. |
| 2008/0312258 A1 | 12/2008 | Rodgers et al. |
| 2008/0312259 A1 | 12/2008 | Rodgers et al. |
| 2009/0181959 A1 | 7/2009 | Rodgers et al. |
| 2009/0233903 A1 * | 9/2009 | Rodgers et al. .......... 514/210.21 |
| 2010/0190981 A1 | 7/2010 | Zhou et al. |
| 2010/0298334 A1 | 11/2010 | Rodgers et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0207754 A1 | 8/2011 | Li et al. |

FOREIGN PATENT DOCUMENTS

| WO | 01/42246 A | 6/2001 |
| WO | 2006/096270 A | 9/2006 |
| WO | WO2007070514 | * 6/2007 |
| WO | WO 2007070514 | 6/2007 |
| WO | WO2007117494 | * 9/2007 |
| WO | 2007/117494 A | 10/2007 |
| WO | WO 2008157207 | 12/2008 |

OTHER PUBLICATIONS http://www.organic-chemistry.org/protectivegroups/, last accessed on Mar. 20, 2012.*
http://www.vanderbilt.edu/AnS/Chemistry/Rizzo/chem223/protect.pdf, see p. 12, last accessed on Mar. 20, 2012.*
U.S. Appl. No. 12/137,892, filed Jun. 12, 2008, James D. Rodgers.
U.S. Appl. No. 12/900,180, filed Oct. 7, 2010, James D. Rodgers.
U.S. Appl. No. 12/901,001, filed Oct. 8, 2010, James D. Rodgers.
U.S. Appl. No. 13/030,682, filed Feb. 18, 2011, Yun-Long Li.
Choi Ha-Soon et al; "Design and synthesis of 7H-pyrrolo[2,3-d]pyrimidines as focal adhesion kinase inhibitors. Part 1"; Bioorganic & Medicinal Chemistry Letters 2006, vol. 16, No. 8, 2173-2176.
Deng, Jun et al; "Rh-Catalyzed Asymmetric Hydrogenation of y-Phthalimido-substituted a,b-Unsaturated Carboxylic Acid Esters: An Efficient Enantioselective Synthesis of b-Aryl-y-amino Acids"; Organic Letters 2007, vol. 9, No. 23, 4825-4828.
Gomtsyan, Arthur et al; "Design, Synthesis, and Struction-Activity Relationship of 6-Alkynylpyrimidines as Potent Adenosine Kinase Inhibitors"; Journal of Medicinal Chemistry 2002, vol. 45, No. 17, 3639-3648.
Larock, Richard C; "Comprehensive Organic Transformations" 1999, Wiley-VCH.
Lin, Qiyan, et al; "Enantioselective Synthesis of Janus Kinase Inhibitor INCB018424 via an Organocatalytic Aza-Michael Reaction"; Organic Letters 2009, vol. 11, No. 9, 1999-2002.
Miyata, Okiko. et al; "Stereospecific Nucleophilic Additional Reactions to Olefins. Addition of Thiols to a,b-Unsaturated Carboxylic Acid Derivatives"; Journal of Organic Chemistry 1991, vol. 56, 6556-6564.
Tan, Kimny, et al; Tetrahedron Letters 2001, vol. 42, No. 30, 5021-5023.
International Search Report for PCT/US2010/021003, filed Jan. 14, 2010.
Written Opinion for PCT/US2010/021003 filed Jan. 14, 2010.

* cited by examiner

*Primary Examiner* — Jeffrey Murray
(74) *Attorney, Agent, or Firm* — Lathrop & Gage LLP; Brian C. Trinque

(57) ABSTRACT

The present invention is related to processes for preparing chiral substituted pyrazolyl pyrrolo[2,3-d]pyrimidines of Formula III, and related synthetic intermediate compounds. The chiral substituted pyrazolyl pyrrolo[2,3-d]pyrimidines are useful as inhibitors of the Janus Kinase family of protein tyrosine kinases (JAKs) for treatment of inflammatory diseases, myeloproliferative disorders, and other diseases.

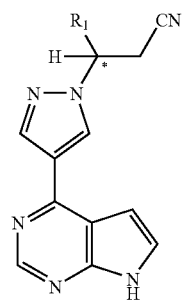

III

4 Claims, No Drawings

PROCESSES FOR PREPARING JAK INHIBITORS AND RELATED INTERMEDIATE COMPOUNDS

CROSS REFERENCE TO RELATED APPLICATIONS

This application claims the benefit of U.S. Ser. No. 61/144,991, filed Jan. 15, 2009, the disclosure of which is incorporated herein by reference in its entirety.

FIELD OF THE INVENTION

The present invention is related to processes for preparing chiral substituted pyrazolyl pyrrolo[2,3-d]pyrimidines and related synthetic intermediate compounds. The chiral substituted pyrazolyl pyrrolo[2,3-d]pyrimidines are useful as inhibitors of the Janus Kinase family of protein tyrosine kinases (JAKs) for treatment of inflammatory diseases, myeloproliferative disorders, and other diseases.

BACKGROUND

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. The Janus kinase family of protein tyrosine kinases (JAKs) belong to the non-receptor type of tyrosine kinases and include family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2).

The pathway involving JAKs and Signal Transducers and Activators of Transcription (STATs) is engaged in the signaling of a wide range of cytokines Cytokines are low-molecular weight polypeptides or glycoproteins that stimulate biological responses in virtually all cell types. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "Jaks, STATs, Cytokines, and Sepsis." Clin Diagn Lab Immunol 9(6): 1153-9).

The JAK family plays a role in the cytokine-dependent regulation of proliferation and function of cells involved in immune response. The JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. Moreover, multiple cytokines that signal through JAK kinases have been linked to inflammatory diseases or conditions of the upper respiratory tract such as those affecting the nose and sinuses (e.g. rhinitis, sinusitis) whether classically allergic reactions or not. The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of these diseases.

Blocking signal transduction at the level of the JAK kinases holds promise for developing treatments for human cancers. Inhibition of the JAK kinases is also envisioned to have therapeutic benefits in patients suffering from skin immune disorders such as psoriasis, and skin sensitization. Accordingly, inhibitors of Janus kinases or related kinases are widely sought and several publications report effective classes of compounds. For example, certain JAK inhibitors, including (R)-3-(4-(7H-pyrrolo[2,3-d]pyrimidin-4-yl)-1H-pyrazol-1-yl)-3-cyclopentylpropanenitrile, are reported in U.S. Pat. App. Pub. No. 2007/0135461, the disclosure of which is incorporated herein by reference.

In view of the growing demand for compounds for the treatment of disorders related to the inhibition of kinases such as Janus kinases, new and more efficient routes to inhibitors such as chiral substituted pyrazolyl pyrrolo[2,3-d]pyrimidines and intermediates related thereto, are needed. The processes and compounds described herein help meet these and other needs.

SUMMARY

The present invention provides, inter alia, processes of preparing a composition comprising a compound of Formula I:

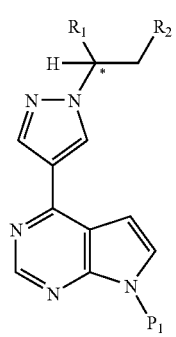

comprising reacting a compound of Formula II:

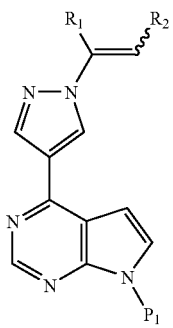

with hydrogen gas in the presence of a hydrogenation catalyst; wherein:
* indicates a chiral carbon;
R$_1$ is selected from C$_{3-7}$ cycloalkyl, C$_{1-6}$ alkyl, and C$_{1-6}$ fluoroalkyl;
R$_2$ is selected from —C(=O)—NH$_2$, —C(=O)O—R$_3$, and cyano;
R$_3$ is selected from C$_{1-4}$ alkyl or C$_{1-4}$ fluoroalkyl; and
P$_1$ is a protecting group.

The present invention further provides processes of preparing a composition comprising an enantiomeric excess of a (R)- or (S)-enantiomer of a compound of Formula I:

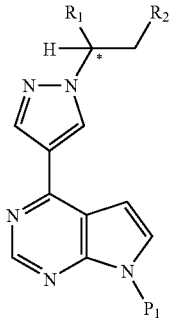

comprising reacting a compound of Formula II:

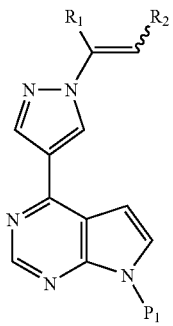

with hydrogen gas in the presence of a ruthenium or rhodium catalyst having L1, wherein L$_1$ is a chiral phosphine ligand; wherein:
* indicates a chiral carbon;
R$_1$ is selected from C$_{3-7}$ cycloalkyl, C$_{1-6}$ alkyl, and C$_{1-6}$ fluoroalkyl;
R$_2$ is selected from —C(=O)—NH$_2$, —C(=O)O—R$_3$, and cyano;
R$_3$ is selected from C$_{1-4}$ alkyl or C$_{1-4}$ fluoroalkyl; and
P$_1$ is a protecting group.

The present invention further provides processes for converting a compound of Formula I to a compound of Formula Ic, comprising reacting a compound of Formula I:

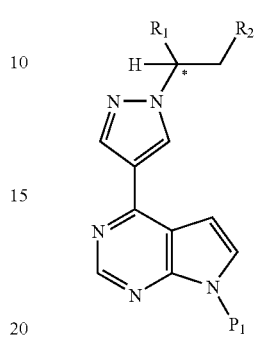

with a metal hydroxide to form a compound of Formula Ic:

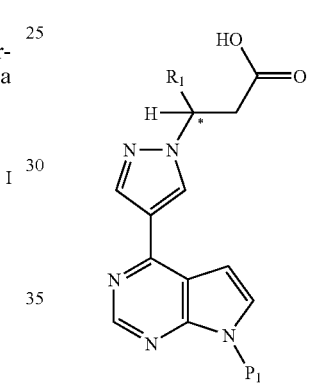

wherein:
* indicates a chiral carbon;
R$_1$ is selected from C$_{3-7}$ cycloalkyl, C$_{1-6}$ alkyl, and C$_{1-6}$ fluoroalkyl;
R$_2$ is —C(=O)O—R$_3$; and
P$_1$ is a protecting group.

The present invention also provides process for converting a compound of Formula Ic to a compound of Formula Ib, comprising reacting a compound of Formula Ic:

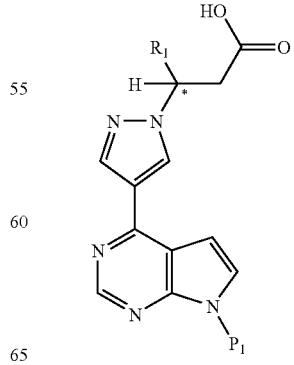

with ammonia or ammonium hydroxide in the presence of a coupling reagent to form a compound of Formula Ib:

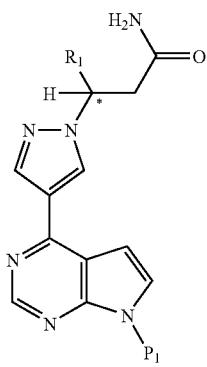

wherein:
 * indicates a chiral carbon;
 $R_1$ is selected from $C_{3-7}$ cycloalkyl, $C_{1-6}$ alkyl, and $C_{1-6}$ fluoroalkyl; and
 $P_1$ is a protecting group.

The present invention also provides processes for converting a compound of Formula Ib to a compound of Formula Ia, comprising reacting the compound of Formula Ib:

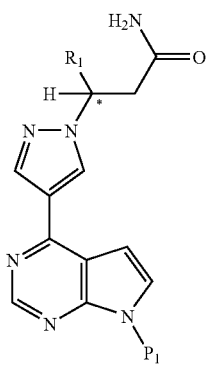

under dehydrating conditions to form a compound of Formula Ia:

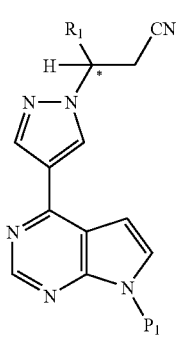

wherein:
 * indicates a chiral carbon;
 $R_1$ is selected from $C_{3-7}$ cycloalkyl, $C_{1-6}$ alkyl, and $C_{1-6}$ fluoroalkyl; and
 $P_1$ is a protecting group.

The present invention provide processes of preparing a composition comprising an enantiomeric excess of a (R)- or (S)-enantiomer of a compound of Formula Id:

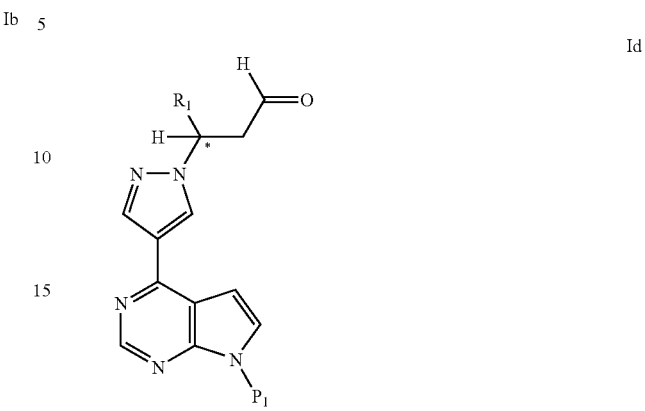

comprising reacting a compound of Formula IV:

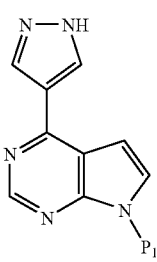

with a compound of Formula V:

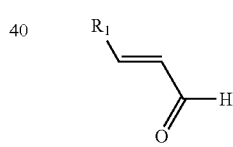

in the presence of a chiral amine and an organic acid;
wherein:
 * indicates a chiral carbon;
 $R_1$ is selected from $C_{3-7}$ cycloalkyl, $C_{1-6}$ alkyl, and $C_{1-6}$ fluoroalkyl; and
 $P_1$ is a protecting group.

The present invention further provides processes of preparing a composition comprising an enantiomeric excess of a (R)- or (S)-enantiomer of a compound of Formula VI:

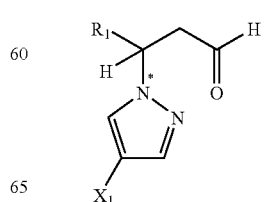

comprising reacting a compound of Formula V:

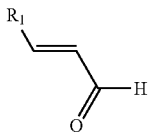

V with a compound of Formula VII:

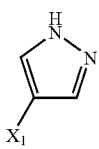

VII in the presence of a chiral amine and an organic acid;
wherein:
* indicates a chiral carbon;
$R_1$ is selected from $C_{3-7}$ cycloalkyl, $C_{1-6}$ alkyl, and $C_{1-6}$ fluoroalkyl; and
$X_1$ is halogen.

The present invention further provides a process of converting a compound of Formula VI to a compound of Formula III, comprising treating the compound of Formula VI:

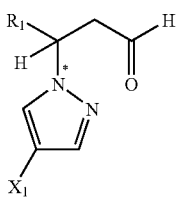

VI with ammonia or ammonium hydroxide and iodine to form the compound of Formula VIII:

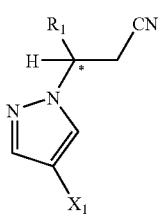

VIII wherein:
* indicates a chiral carbon;
$R_1$ is selected from $C_{3-7}$ cycloalkyl, $C_{1-6}$ alkyl, and $C_{1-6}$ fluoroalkyl;
$P_1$ is a protecting group; and
$X_1$ is halogen.

The present invention also provides a process of converting a compound of Formula VIII to a compound of Formula IX, comprising reacting the compound of Formula VIII:

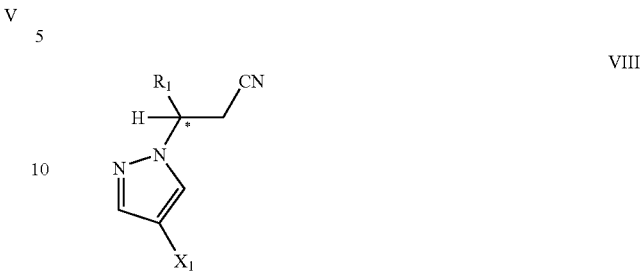

VIII with a compound of Formula B-1:

B-1 to form a compound of Formula IX:

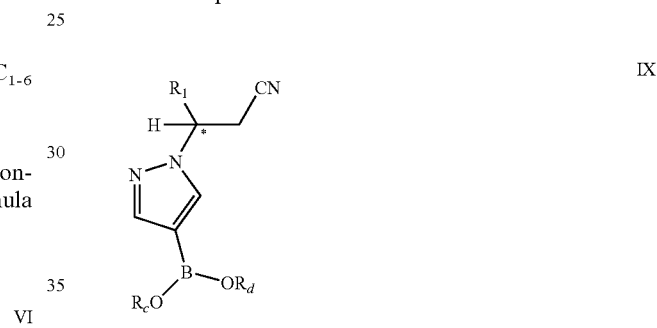

IX wherein:
* indicates a chiral carbon;
$R_1$ is selected from $C_{3-7}$ cycloalkyl, $C_{1-6}$ alkyl, and $C_{1-6}$ fluoroalkyl;
$X_1$ is halo; and
$R_c$ and $R_d$ are each independently selected from H and $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups.

The present invention also provides processes of converting a compound of Formula IX to a compound of Formula Ia, comprising reacting the compound of Formula IX:

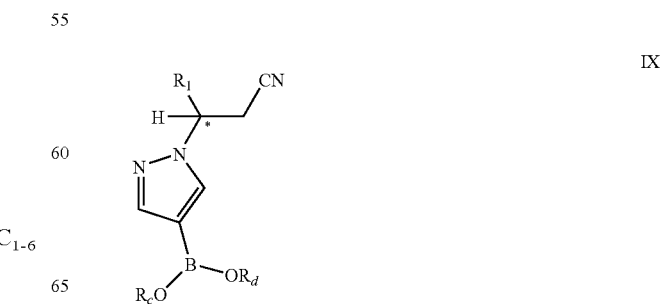

IX with a compound of Formula X:

X in the presence of a palladium catalyst and a base to form a compound of Formula Ia:

Ia wherein:
* indicates a chiral carbon;
$R_1$ is selected from $C_{3-7}$ cycloalkyl, $C_{1-6}$ alkyl, and $C_{1-6}$ fluoroalkyl;
$X_2$ is a tosylate group, a triflate group, iodo, chloro, or bromo;
$P_1$ is a protecting group; and
$R_c$ and $R_d$ are each independently selected from H and $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups.

In some embodiments, the present invention provides compositions comprising an enantiomeric excess of a (R)- or (S)-enantiomer of a compound of Formula IX:

IX wherein:
* indicates a chiral carbon;
$R_1$ is selected from $C_{3-7}$ cycloalkyl, $C_{1-6}$ alkyl, and $C_{1-6}$ fluoroalkyl; and
$R_c$ and $R_d$ are each independently $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups.

The present invention further provides processes of preparing a composition comprising an enantiomeric excess of a (R)- or (S)-enantiomer of a compound of Formula IX:

IX comprising passing a composition comprising a racemate of a compound of Formula IX through a chiral chromatography unit using a mobile phase and collecting a composition comprising an enantiomeric excess of the (R)- or (S)-enantiomer of a compound of Formula IX;
wherein:
* indicates a chiral carbon;
$R_1$ is selected from $C_{3-7}$ cycloalkyl, $C_{1-6}$ alkyl, and $C_{1-6}$ fluoroalkyl; and
$R_c$ and $R_d$ are each independently $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups.

The present invention provides processes of preparing a composition comprising a racemate of a compound of Formula Ia:

Ia comprising:
a) treating a composition comprising an enantiomeric excess of the (R)- or (S)-enantiomer of a compound of Formula Ia with a compound of Formula D-1:

D-1 in the presence of a first base under conditions sufficient to form a compound of Formula IV:

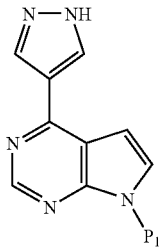

IV and (b) reacting a compound of Formula IV with a compound of Formula D-1 in the presence of a second base;

wherein:

* is a chiral carbon;

$P_1$ is a protecting group; and $R_1$ is selected from $C_{3-7}$ cycloalkyl, $C_{1-6}$ alkyl, and $C_{1-6}$ fluoroalkyl.

The present invention further provides processes of preparing a composition comprising a racemate of a compound of Formula Ia:

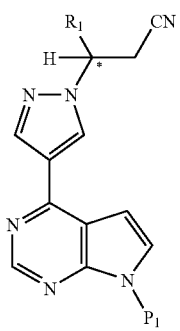

Ia comprising treating a composition comprising an enantiomeric excess of the (R)- or (S)-enantiomer of a compound of Formula Ia with a compound of Formula D-1:

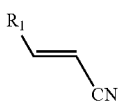

D-1 in the presence of a base under conditions sufficient to form the racemate of the compound of Formula Ia;

wherein:

* is a chiral carbon;

$P_1$ is a protecting group; and $R_1$ is selected from $C_{3-7}$ cycloalkyl, $C_{1-6}$ alkyl, and $C_{1-6}$ fluoroalkyl.

The present invention further provides processes of preparing a composition comprising an enantiomeric excess of the (R)- or (S)-enantiomer of a compound of Formula Ia:

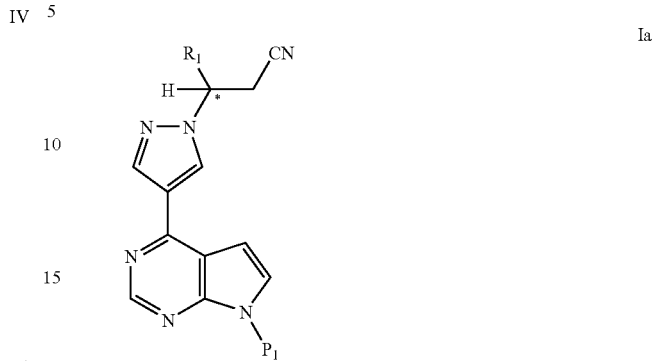

Ia comprising passing a composition comprising a racemate of a compound of Formula Ia through a chiral chromatography unit using a mobile phase and collecting a composition comprising an enantiomeric excess of the (R)- or (S)-enantiomer of a compound of Formula Ia;

wherein:

* is a chiral carbon;

$R_1$ is selected from $C_{3-7}$ cycloalkyl, $C_{1-6}$ alkyl, and $C_{1-6}$ fluoroalkyl; and $P_1$ is a protecting group.

The present invention provides processes of preparing a composition comprising an enantiomeric excess of a (R)-or (S)-enantiomer of a compound of Formula Ia:

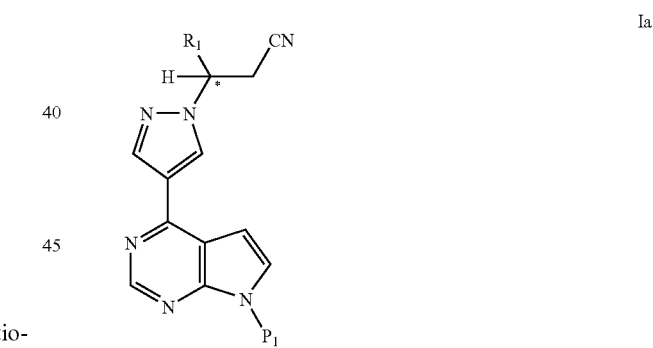

Ia comprising:

(a) reacting a composition comprising a racemate of a compound of Formula Ia with a chiral acid in the presence of a solvent to form a salt of a compound of Formula Ia;

(b) separating a composition comprising an enantiomer excess of a chiral salt of the (R)- or (S)-enantiomer of the compound of Formula Ia; and (c) treating the chiral salt with a base to form a composition comprising an enantiomeric excess of the (R)- or (S)-enantiomer of the compound of Formula Ia;

wherein:

* is a chiral carbon;

$R_1$ is selected from $C_{3-7}$ cycloalkyl, $C_{1-6}$ alkyl, and $C_{1-6}$ fluoroalkyl; and $P_1$ is a protecting group.

The present invention further provides processes for converting a compound of Formula Ia to a compound of Formula III, comprising reacting the compound of Formula Ia:

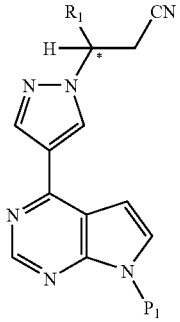

Ia under deprotection conditions to form a compound of Formula III:

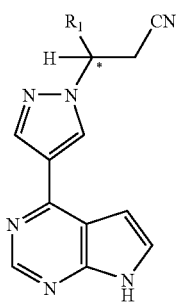

III

* is a chiral carbon;
$R_1$ is selected from $C_{3-7}$ cycloalkyl, $C_{1-6}$ alkyl, and $C_{1-6}$ fluoroalkyl; and
$P_1$ is a protecting group.

The present invention further provides a process of preparing a compound of Formula XII:

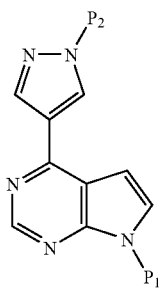

XII comprising reacting a compound of Formula X:

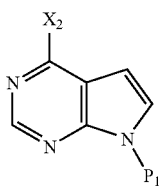

X with a compound of Formula XIII:

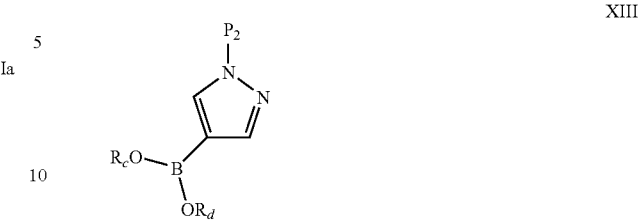

XIII in the presence of a palladium catalyst, base, and a solvent, to form a compound of Formula XII.

wherein:
* is a chiral carbon;
$X_2$ is a tosylate group, a triflate group, iodo, chloro, or bromo;
$R_1$ is selected from $C_{3-7}$ cycloalkyl, $C_{1-6}$ alkyl, and $C_{1-6}$ fluoroalkyl; and
$R_c$ and $R_d$ are each independently H or $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups; and
$P_1$ and $P_2$ are each independently a protecting group.

The present invention further provides processes for preparing a compound of Formula XVI:

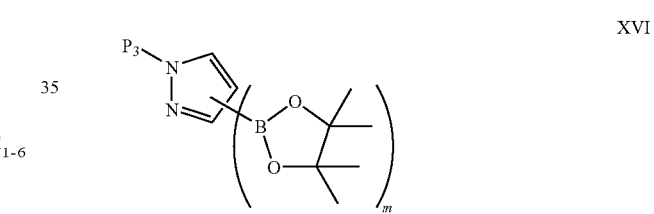

XVI comprising:
(a) reacting a compound of Formula XVIII

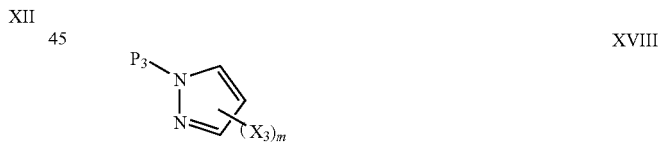

XVIII with about 1 or more equivalents of an $C_{1-6}$ alkyl Grignard reagent or $C_{1-6}$ alkyl lithium reagent followed by treating with about or more equivalents of compound of Formula XVII:

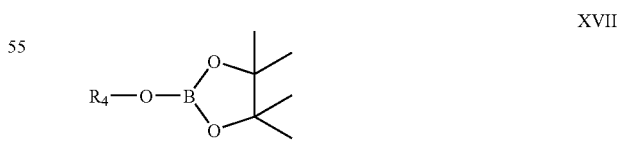

XVII and
(b) optionally, reprotecting the product of step (a) to give a compound of Formula XVI;
wherein:
$P_3$ is a protecting group;
$X_3$ is halogen;
$R_4$ is $C_{1-6}$ alkyl; and
m is an integer selected from 1 and 2.

The present invention also provides a process for preparing a compound of Formula XIa:

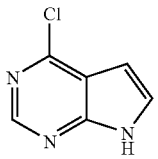

XIa comprising treating a compound of Formula F-1:

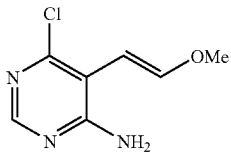

F-1 with acid under conditions sufficient to form a compound of Formula XIa.

The present invention further provides compositions comprising an enantiomeric excess of a (R)- or (S)-enantiomer of a compound of Formula I:

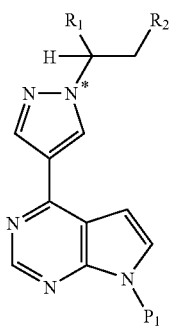

I wherein:
* indicates a chiral carbon;
$R_1$ is selected from $C_{3-7}$ cycloalkyl, $C_{1-6}$ alkyl, and $C_{1-6}$ fluoroalkyl;
$R_2$ is selected from —C(=O)—NH$_2$, —C(=O)O—R$_3$, —C(=O)OH, and —C(=O)H;
$R_3$ is selected from $C_{1-4}$ alkyl or $C_{1-4}$ fluoroalkyl; and
$P_1$ is a protecting group.

The present invention also provides compounds of Formula II:

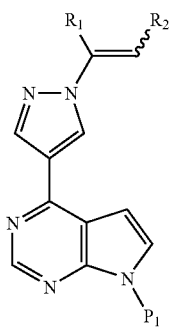

II wherein:
$R_1$ is selected from $C_{3-7}$ cycloalkyl, $C_{1-6}$ alkyl, and $C_{1-6}$ fluoroalkyl;
$R_2$ is selected from —C(=O)—NH$_2$ and —C(=O)O—R$_3$;

$R_3$ is selected from $C_{1-4}$ alkyl or $C_{1-4}$ fluoroalkyl; and
$P_1$ is a protecting group.

The details of one or more embodiments of the invention are set forth in the accompanying drawings and the description below. Other features, objects, and advantages of the invention will be apparent from the description and drawings, and from the claims.

DETAILED DESCRIPTION

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

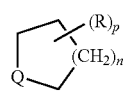

then it is understood that substituent R can occur p number of times on the ring, and R can be a different moiety at each occurrence. It is understood that each R group may replace any hydrogen atom attached to a ring atom, including one or both of the (CH$_2$)$_n$ hydrogen atoms. Further, in the above example, should the variable Q be defined to include hydrogens, such as when Q is the to be CH$_2$, NH, etc., any floating substituent such as R in the above example, can replace a hydrogen of the Q variable as well as a hydrogen in any other non-variable component of the ring.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted. As used herein, the term "substituted" means that a hydrogen atom is removed and replaced by a substitutent. As used herein, the phrase "substituted with oxo" means that two hydrogen atoms are removed from a carbon atom and replaced by an oxygen bound by a double bond to the carbon atom. It is understood that substitution at a given atom is limited by valency.

As used herein, the term "alkyl", employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl. In some embodiments, the alkyl moiety is methyl.

As used herein, the term "alkylcarboxamide" or "alkylaminocarbonyl" refers to a group of formula —C(O)—NH(alkyl). In some embodiments, each alkyl group has 1 to 6 carbons.

As used herein, "alkenyl", employed alone or in combination with other terms, refers to an alkyl group having one or more double carbon-carbon bonds. In some embodiments, the alkenyl moiety contains 2 to 10 or 2 to 6 carbon atoms. Example alkenyl groups include, but are not limited to, ethenyl, n-propenyl, isopropenyl, n-butenyl, sec-butenyl, and the like.

As used herein, "alkynyl", employed alone or in combination with other terms, refers to an alkyl group having one or more triple carbon-carbon bonds. Example alkynyl groups include, but are not limited to, ethynyl, propyn-l-yl, propyn-2-yl, and the like. In some embodiments, the alkynyl moiety contains 2 to 10 or 2 to 6 carbon atoms.

As used herein, the term "alkoxy", employed alone or in combination with other terms, refers to an group of formula —O-alkyl. Example alkoxy groups include methoxy, ethoxy, propoxy (e.g., n-propoxy and isopropoxy), t-butoxy, and the like. In some embodiments, each alkyl group has 1 to 6 carbons.

As used herein, the term "alkoxycarbonyl" refers to a group of formula —C(O)O-alkyl. In some embodiments, each alkyl group has 1 to 6 carbons.

As used herein, the term "tri-$C_{n-m}$ alkylsilyl" refers to a group of formula —Si(alkyl)$_3$, wherein each alkyl group has n to m carbon atoms. In some embodiments, each alkyl group has 1 to 6 carbons.

As used herein, the term "tri-$C_{n-m}$ alkylsilyloxy" refers to a group of formula —OSi(alkyl)$_3$, wherein each alkyl group has n to m carbon atoms. In some embodiments, each alkyl group has 1 to 6 carbons.

As used herein, the term "aryl", employed alone or in combination with other terms, refers to a monocyclic or polycyclic (e.g., having 2, 3 or 4 fused rings) aromatic hydrocarbon moiety, such as, but not limited to, phenyl, 1-naphthyl, 2-naphthyl, anthracenyl, phenanthrenyl, and the like. In some embodiments, the aryl moiety may be further fused to a cycloalkyl ring. In some embodiments, aryl groups have from 6 to 20 carbon atoms, about 6 to 10 carbon atoms, or about 6 to 8 carbons atoms.

As used herein, the term "arylamino" refers to a group of formula —NH(aryl).

As used herein, the term "carboxy" refers to a group of formula —C(O)OH.

As used herein, the term "cycloalkyl", employed alone or in combination with other terms, refers to a non-aromatic cyclic hydrocarbon moiety, which may optionally contain one or more alkenylene or alkynylene groups as part of the ring structure. Cycloalkyl groups can include mono- or polycyclic (e.g., having 2, 3 or 4 fused or covalently linked rings) ring systems. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopentyl.

As used herein, the term "haloalkyl", employed alone or in combination with other terms, refers to an alkyl group having from one halogen atom to 2n+1 halogen atoms which may be the same or different, where "n" is the number of carbon atoms in the alkyl group.

As used herein, the term "fluorinated alkyl", employed alone or in combination with other terms, refers to an alkyl group having from one fluoro atom to 2n+1 fluoro atoms which may be the same or different, where "n" is the number of carbon atoms in the alkyl group. In some embodiments, the fluorinated alkyl group is trifluoromethyl.

As used herein, the terms "halo" and "halogen", employed alone or in combination with other terms, refer to fluoro, chloro, bromo, and iodo.

As used herein, the term "heteroaryl", "heteroaryl ring", or "heteroaryl group", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, the heteroaryl ring or group has 1, 2, 3, or 4 heteratoms selected from N, O, or S. In some embodiments, the heteroaryl ring or group has 1 or 2 rings. When the heteroaryl group contains more than one heteroatom ring member, the heteroatoms may be the same or different. In some embodiments, the heteroaryl moiety may be further fused to a cycloalkyl or heterocycloalkyl ring. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms. A linking heteroaryl group is referred to herein as "heteroarylene."

As used herein, the term "heteroarylamino" refers to a group of formula —NH(heteroaryl).

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Heterocycloalkyl groups include monocyclic and polycyclic (e.g., having 2, 3 or 4 fused rings) systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. The heterocycloalkyl group can be attached through a ring-forming carbon atom or a ring-forming heteroatom. The heterocycloalkyl group containing a fused aromatic ring can be attached through any ring-forming atom including a ring-forming atom of the fused aromatic ring. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds. A linking heterocycloalkyl group is referred to herein as "heterocycloalkylene."

As used herein, the term "oxo" refers to a group of formula =O.

As used herein, the term "triflate group" refers to a trifluoromethylsulfonyloxy group.

As used herein, the term "tosylate group" refers to a p-tolylsulfonyloxy group.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, or spectrophotometry (e.g., UV-visible); or by chromatography such as high performance liquid chromatograpy (HPLC) or thin layer chromatography (TLC) or other related techniques.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

As used herein, the term "chiral chromatography" or "chiral chromatography column" or "chiral column" relates to a chromatographic device or method for separating mixtures of enantiomers or diastereomers which are dissolved in mobile phase. When the term "preparative" is used in conjunction with any of the aforementioned terms, this means the device or method is of sufficient scale to isolate relevant quantities of the desired enantiomer or diastereomer. Example separation methods suitable for chiral chromatography include HPLC (High Performance Liquid Chromatography), SFC (Supercritical Fluid Chromatography), both in batch mode and in continuous mode, e.g SMB (Simulated Moving Bed), and related techniques. The process of the present invention can utilize any chromatographic method for separating racemic compounds to produce the optically pure desired enantiomer. Such methods include, but are not limited to, traditional single column batch chromatography, continuous chromatography, or a steady state, sequential injection process (as described in, for example, U.S. Pat. No. 5,630,943 and PCT Publ. No. WO 98/51391). Continuous chromatographic methods include, but are not limited to multicolumn continuous chromatographic processes, including such countercurrent chromatographic processes as SMB (as described in, for example U.S. Pat. Nos 2,985,589, 4,402,832 and 4,498,991), or a non-steady state continuous chromatographic method known as the "Varicol™" Process (as described in, for example, U.S. Pat. Nos. 6,136,198; 6,375, 839; 6,413,419; and 6,712,973).

In the separation of enantiomers these methods involve the use of a chiral stationary phase. An achiral stationary phase may be used for the separation of diastereomers. The term "stationary phase" relates to a suitable inert carrier material on which an interacting agent is coated or immobilized.

As used herein, the term "chiral stationary phase" relates to stationary phases in which the interacting agent is an enantiomerically enriched resolving agent, for instance immobilized by coating, by chemically binding or by insolubilizing via cross-linking on an inert carrier material. A suitable inert carrier material is preferably macroporous, e.g crosslinked polystyrene, polyacrylamide, polyacrylate, alumina, kieselgur (diatomaceous), quartz, kaolin, magnesium oxide or titanium dioxide. In some embodiments, the inert carrier material comprises silica gel. The average particle diameter of the packing material varies depending on the volume flow rate of the solvent flowing in the chromatographic system In some embodiments, it is 1 to 300 μm, 2 to 100 μm, 5 to 75 μm or 10 to 30 μm. Appropriate selection of the average particle diameter of the packing material will help to adjust the pressure drop in the chromatographic process and the efficiency of the packing material. Examples of stationary phases containing an enantiomerically enriched resolving agent are, for instance, phases based on either synthetic or naturally occurring chiral polymers, macrocyclic phases, ligand-exchange phases and pirkle-type phases. Such chiral stationary phases are known and commercially available. In some embodiments, the chiral stationary phase is derivatized with at least one sugar derivative, and in particular is a derivatized polysaccharide that is selected from the amylosic, cellulosic, chitosan, xylan, curdlan, dextran, and inulan class of polysaccharides. In certain embodiments, the chiral stationary phase is a member of the amylosic or cellulosic class of polysaccharides. Esters and carbamates of these materials in particular are suitable. In additional embodiments, the chiral stationary phase is selected from cellulose phenyl carbamate derivatives, such as cellulose tris(3,5-dimethylphenyl)carbamate (available from Daicel Chemical Industries, Ltd. (Daicel) as "Chiralcel® OD" or "Chiralpak® IB", wherein the carbamate derivative is bonded to the cellulosic backbone); cellulose tribenzoate derivatives, such as cellulose tri 4-methylbenzoate (available from Daicel as "Chiralcel® OJ"); cellulose tricinnamate (available from Daicel as "Chiralcel® OK"); amylase phenyl and benzyl carbamate derivatives, such as amylose tris[(S)-α-methyl benzylcarbamate] (available from Daicel as "Chiralpak® AS"); amylose tris(3,5-dimethylphenyl)carbamate (available from Daicel as "Chiralpak® AD" or "Chiralpak® IA", wherein the carbamate derivative is bonded to the amylosic backbone); amylose 3,4-substituted phenyl carbamate or amylose 4-substituted phenyl-carbamate; and amylose tricinnamate. In some embodiments, the chiral phase is a member of the Pirkle-phases family; (S,S) Whelk-O® 1 and (R,R) Whelk-O® 1 are preferred (available from Regis technologies Inc.).

As used herein, the term "mobile phase" relates to a solvent or mixture of solvents in which the mixture of enantiomers to be separated is dissolved. Suitable solvents to be used in the preparative chromatographic process according to the invention are the solvents that are known to be used in analytical chromatography. In liquid chromatography usually, non-polar, polar protic or aprotic solvents or mixture thereof are used. In supercritical chromatography preferably mixtures of carbon dioxide and polar protic solvents are used. Suitable non polar solvents are for example hydrocarbons, for instance, n-pentane, n-hexane, hexanes, n-heptane, heptanes, cyclohexane, and methylcyclohexane. Suitable protic or aprotic solvents are for example alcohols, in particular methanol, ethanol, 1-propanol, 2-propanol, 1-butanol, 2-butanol, isobutanol, tert butanol, ethers, for instance methyl tert butyl ether, esters, for instance ethylacetate, halogenated hydrocarbons and acetonitrile. The addition of water, acid (for instance formic acid, acetic acid, trifluoroacetic acid) or base (for instance organic bases, e.g. trietylamine) for example less than 1% (v/v) in the solvent may have advantageous effects.

In liquid chromatography, $C_1$-$C_3$ alcohols or mixtures of these alcohols with hydrocarbons, for instance n-hexane or n-heptane can be used. In supercritical chromatography mixtures of carbon dioxide and polar protic solvents e.g. methanol, can be used. The optimal solvent (combination) can be screened using methods known in the art. A different optimal solvent (combination) may be found when another stationary phase is used.

The compounds of the present invention also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3- pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide and ionic liquids can also be used as solvents.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to affect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The present invention also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in Remington's Pharmaceutical Sciences, 17th ed., Mack Publishing Company, Easton, Pa., 1985, p. 1418, the disclosure of which is hereby incorporated by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Processes and Imtermediates

The present invention provides, inter alia, processes of synthesizing nitrile compounds of Formula III, and intermediates thereof, which are useful as JAK inhibitors. In one aspect, the process is a hydrogenation method. In some embodiments, the process is an asymmetric hydrogenation method, which produces an enantiomeric excess of the (R)- or (S)-enantiomer of the JAK inhibitor or intermediate thereof. In another aspect, the process is an asymmetric aza-Michael addition method, which produces an enantiomeric excess of the (R)- or (S)-enantiomer of the JAK inhibitor or intermediate thereof.

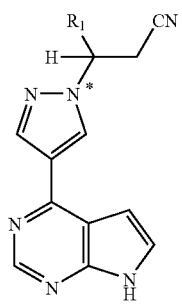

III

In a further aspect, the present invention provides a process for enriching the enantiomeric excess of compounds of Formula III by chiral separation techniques or chiral salt resolution. In some embodiments, these processes involve chiral separation (such as chiral preparative chromatography) or chiral salt resolution of intermediate compounds, followed by subsequent reaction to form the compounds of Formula III. In some embodiments, the present invention further provides a process for racemization of undesired enantiomers of intermediate compounds for producing compounds of Formula III, which can then be resolved to give an enantiomeric excess of the desired enantiomer by the techniques described previously.

In a still further aspect, the present invention provides processes for preparing intermediate compounds useful for producing compounds of Formula III. In another aspect, the present invention provides intermediate compounds of any of the intermediates described herein. In still another aspect, the present invention provides enantiomerically enriched compositions of any of the intermediates described herein, provided the intermediates have at least one chiral center.

The processes described herein include processes for preparing compounds and intermediates and compositions thereof, wherein $R_1$ is selected from cyclopentyl, methyl and trifluoromethyl. In some embodiments, $R_1$ is cyclopentyl or cyclopropyl. In some embodiments, $R_1$ is cyclopentyl. In some embodiments, $R_1$ is methyl. In some embodiments, $R_1$ is trifluoromethyl. These embodiments can apply to any of the intermediates or compounds described herein in any of the processes, as appropriate.

In some embodiments, the process can be used to form a compound of Formula III, which is 3-cyclopentyl-3-[4-(7H-pyrrolo[2,3-d]pyrimidin-4-yl)-1H-pyrazol-1-yl]propanenitrile, or pharmaceutically acceptable salt thereof. In some embodiments, the process can be used to form a compound of Formula III, which is (3R)-3-cyclopentyl-3-[4-(7H-pyrrolo[2,3-d]pyrimidin-4-yl)-1H-pyrazol-1-yl]propanenitrile, or pharmaceutically acceptable salt thereof. The processes described herein are understood to include processes of preparing these compounds, especially (3R)-3-cyclopentyl-3-[4-(7H-pyrrolo[2,3-d]pyrimidin-4-yl)-1H-pyrazol-1-yl]propanenitrile.

Processes for preparing some of the intermediates can be found in U.S. Patent Publ. No. US 20070135461, published Jun. 14, 2007 (application Ser. No. 11/637,545, filed Dec. 12, 2006); and U.S. patent applcation Ser. No. 12/138,082, filed Jun. 12, 2008, each of which is incorporated herein by reference in its entirety.

I. Catalytic Hydrogenation Methods (Including Asymmetric Hydrogenation Methods)

Compounds of Formula III can be formed by catalytic hydrogenation of a compound of Formula II to form a compound of Formula I, which can then be converted to a compound of Formula III through functional group transformation and/or deprotection steps. In some embodiments, the processes form a compound of Formula I as the racemate, while in more preferred embodiments, the processes produce an enantiomeric excess of the (S)- or (R)-enantiomer of the compound of Formula I. One step of the process involves the hydrogenation of α,β-unsatuated compounds of Formula II as shown below.

Accordingly, in one aspect, the present invention provides a process of preparing a composition comprising a compound of Formula I:

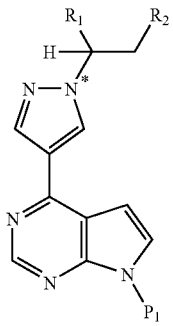

I comprising reacting a compound of Formula II:

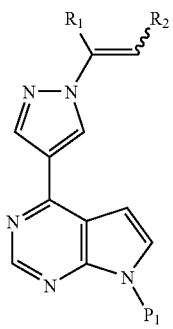

II with hydrogen gas in the presence of a hydrogenation catalyst;
wherein:
* indicates a chiral carbon;
$R_1$ is selected from $C_{3-7}$ cycloalkyl, $C_{1-6}$ alkyl, and $C_{1-6}$ fluoroalkyl;
$R_2$ is selected from —C(=O)—NH$_2$, —C(=O)O—R$_3$, and cyano;
$R_3$ is selected from $C_{1-4}$ alkyl or $C_{1-4}$ fluoroalkyl; and
$P_1$ is a protecting group.

In some embodiments, $R_1$ is selected from cyclopentyl, methyl and trifluoromethyl. In some embodiments, $R_1$ is cyclopentyl or cyclopropyl. In some embodiments, $R_1$ is cyclopentyl. In some embodiments, $R_1$ is methyl. In some embodiments, $R_1$ is trifluoromethyl.

In some embodiments, $R_2$ is —C(=O)O—R$_3$. In some embodiments, $R_2$ is —C(=O)OCH$_3$. In some embodiments, $R_2$ is cyano.

In some embodiments, $R_3$ is selected from $C_{1-4}$ alkyl. In some embodiments, $R_3$ is selected from methyl.

The squiggly symbol for the bond connected to $R_2$ indicates that the compound can be in the (E)- or (Z)-conformation. In some embodiments, when $R_2$ is cyano or —C(=O)—NH$_2$, the compound of Formula II is the (Z)-isomer, and when $R_2$ is —C(=O)O—R$_3$, the compound of Formula II is the (E)-isomer. In some embodiments, the compound of Formula II is the (Z)-isomer. In some embodiments, the compound of Formula II is the (E)-isomer.

In some embodiments, $P_1$ is —CH$_2$OC(=O)C(CH$_3$)$_3$. In some embodiments, $P_1$ is selected from —CH$_2$OCH$_2$CH$_2$Si(CH$_3$)$_3$. Appropriate $P_1$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, the protecting group for the $P_1$ group is one which is stable to conditions for removing the $P_2$ protecting group in other process steps described infra. In some embodiments, $P_1$ is a group which is resistant to room temperature acidic conditions. In some embodiments, $P_1$ is a group which is not removed in from about 1 to about 5 N hydrochloric acid at room temperature, at a temperature from about 10° C. to about 40° C., at a temperature from about 15° C. to about 40° C., or at a temperature from about 15° C. to about 30° C. In some embodiments, $P_1$ is benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP). In some embodiments, $P_1$ is tri($C_{1-4}$ alkyl)silyl (e.g., tri(isopropyl)silyl). In some embodiments, $P_1$ is 1,1-diethoxymethyl. In some embodiments, $P_1$ is 2-(trimethylsilyl)ethoxymethyl (SEM). In some embodiments, $P_1$ is N-pivaloyloxymethyl (POM).

In some embodiments, the process produces a composition comprising a racemate of the compound of Formula II. Where a racemate is desired, any hydrogenation catalyst known in the art can be utilized. In some embodiments, the hydrogenation catalyst is palladium-on-carbon.

In further embodiments, the process produces a composition comprising an enantiomeric excess of a (R)- or (S)-enantiomer of the compound of Formula I. In general, when an enantiomeric excess of the compound of Formula I is desired, an asymmetric hydrogenation catalyst is utilized. In some embodiments, the hydrogenation catalyst is a ruthenium or rhodium catalyst having $L_1$; wherein $L_1$ is a chiral ligand. Many suitable catalysts are known in the art. In some embodiments, a chiral phosphine ligands are used. The active catalyst systems (metal, ligand, and additives) can be generated in situ during the reaction or generated prior to the reaction.

In some embodiments, the catalyst can be first screened by carrying out the catalytic asymmetric hydrogenation experiments using a relatively high catalyst loading. Once the catalyst systems are selected, the experimental conditions including the catalyst loading, hydrogen pressure, reaction solvent or solvent system, reaction temperature, and reaction time can be further optimized to improve the chemical conversion and enentioselectivity. In some embodiments, the catalyst loading is from about 0.005 to about 0.1 mole % based on the compound of Formula II.

In some embodiments, it will be known which enantiomer of the compound of Formula I will be produced by a particular chiral ligand. In some embodiments, the chiral ligand in the asymmetric hydrogenation catalyst can be screened to determine which enantiomer of the compound of Formula I is produced by the process. The desired chiral ligand can then be selected so as to provide the desired enantiomer of the com pound of Formula I. For example, in some embodiments, the process further comprises, prior the reacting, the steps of:

(i) reacting the compound of Formula II with hydrogen gas in the presence of a ruthenium or rhodium catalyst having $L_2$; and analyzing the resultant composition to determine whether the (R)- or (S)-enantiomer is in excess; wherein $L_2$ is a chiral ligand;

(ii) reacting the compound of Formula II with hydrogen gas in the presence of a ruthenium or rhodium catalyst having $L_3$; and analyzing the resultant composition to determine whether the (R)- or (S)-enantiomer is in excess; wherein $L_3$ is the same chiral ligand as $L_2$ having the opposite stereochemistry; and (iii) choosing $L_2$ or $L_3$ for use as $L_1$ based on the desired stereochemistry for the enantiomeric excess of the composition.

In some embodiments, the hydrogenation catalyst is selected from [Ru(p-cymene)($L_1$)Cl]Cl, Rh(COD)($L_1$)(BF$_4$), Rh(COD)$_2$($L_1$)(CF$_3$SO$_3$), and Ru($L_1$)(CF$_3$CO$_2$)$_2$. In some embodiments, the hydrogenation catalyst is selected from [Ru($L_4$)($L_1$)Cl]Cl, Rh($L_4$)($L_1$)(BF$_4$), Rh($L_4$)$_2$($L_1$)(CF$_3$SO$_3$), and Ru($L_1$)(CF$_3$CO$_2$)$_2$. In some embodiments, $L_4$ is cumene or COD. In some embodiments, X' is halogen. In some embodiments, X' is chloro. In some embodiments, the hydrogenation catalyst is a mixture of [Rh(COD)$_2$]CF$_3$SO$_3$ and a chiral phosphine ligand. In some embodiments, the solvent is 2,2,2-trifluoroethanol (TFE). In some embodiments, the hydrogenation catalyst loading is about 0.005 to about 0.01 mol %; and the ratio of the compound of Formula II to the hydrogenation catalyst is from about 20000/1 to about 10000/1. In some embodiments, the reaction concentration is from about 5 to about 6 mL TFE/g, the hydrogen pressure is from about 7 to about 60 bar, the reacting is run at a temperature from about room temperature to about 75° C. In some embodiments, the reacting is run until the conversion of the compound of Formula II to the compound of Formula is about equal to or greater than 99.5%. In some embodiments, the reacting is from about 10 to about 25 hours. In some embodiments, the enantiomeric excess is equal to or greater than about 94%.

In some embodiments:
the hydrogenation catalyst is a mixture of [Rh(COD)$_2$]CF$_3$SO$_3$ and a chiral phosphine ligand selected from:

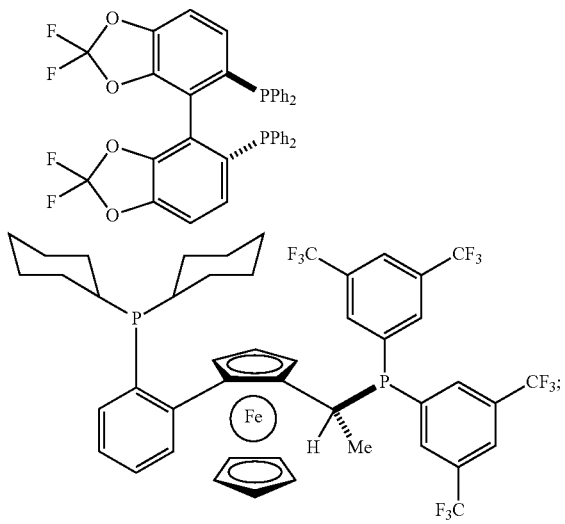

the solvent is 2,2,2-trifluoroethanol (TFE);
the hydrogenation catalyst loading is about 0.005 to about 0.01 mol %;

the ratio of the compound of Formula II to the hydrogenation catalyst is from about 20000/1 to about 10000/1;

the hydrogen pressure is from about 7 to about 60 bar;

the reacting is run at a temperature from about room temperature to about 75° C.;

the reacting is run until the conversion of the compound of Formula II to the compound of Formula is about equal to or greater than 99.5%;

the reacting is from about 10 to about 25 hours; and the enantiomeric excess is equal to or greater than about 94%.

In some embodiments, the chiral ligand is a chiral phosphine ligand. In some embodiments, the chiral ligand is selected from one of the following:

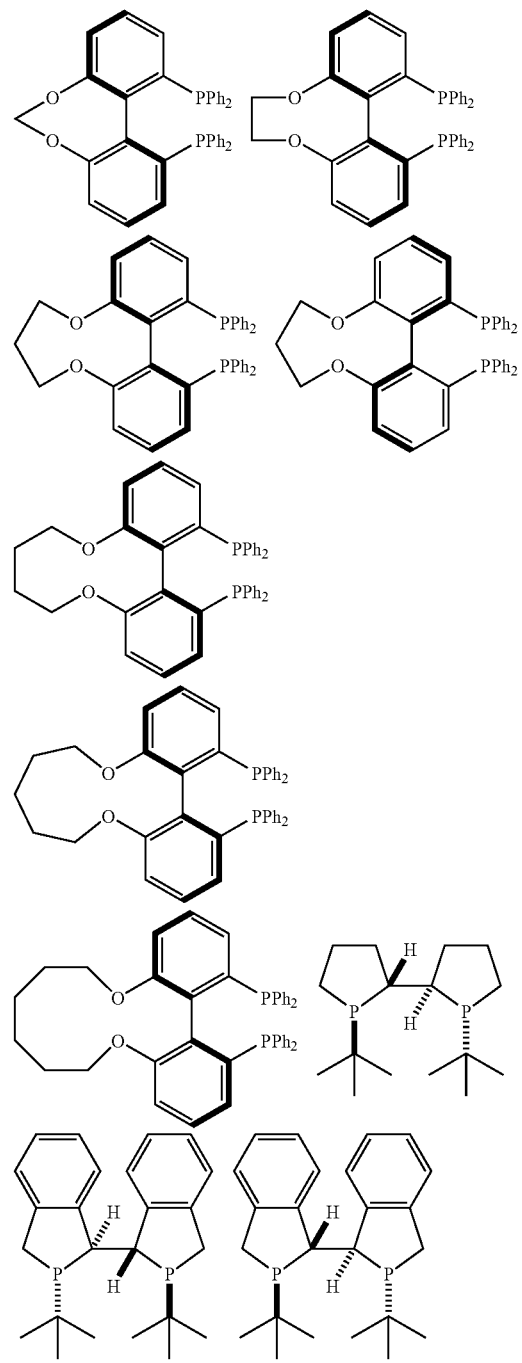

-continued

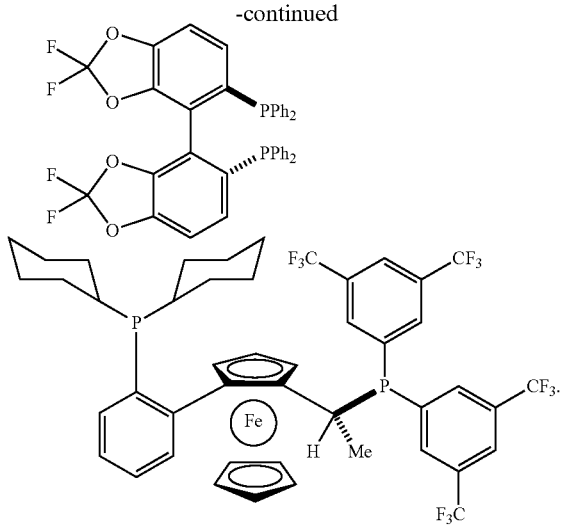

In further embodiments, the composition comprises an enantiomeric excess of the (S)-enantiomer of the compound of Formula I. In some embodiments, $L_1$ is selected from one of the following ligands:

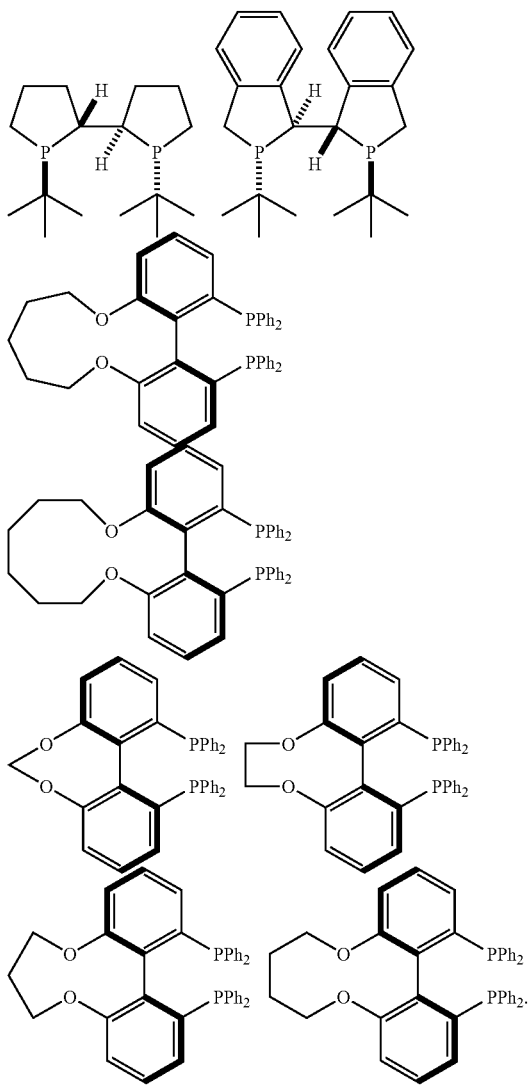

In other embodiments, composition comprises an enantiomeric excess of the (R)-enantiomer of the compound of Formula I. In some embodiments, $L_1$ is selected from one of the following ligands:

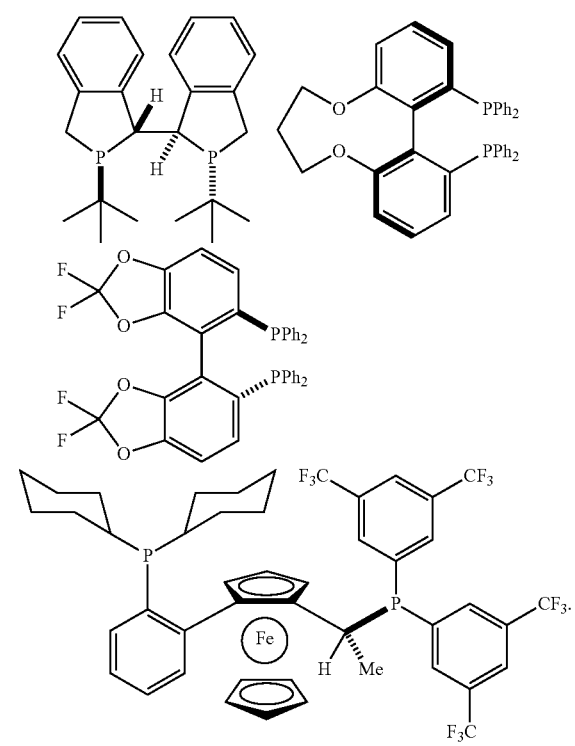

In some embodiments, the chiral catalyst is selected from the hydrogenation catalysts in Sigma Aldrich, "Asymmetric Catalysis: Privileged Ligands and Complexes", ChemFiles, vol. 8, no. 2, pages 1-88, which is incorporated herein by reference in its entirety. In some embodiments, the enantiomeric excess is equal to or greater than about 10%, about 20%, about 30%, about 40%, about 50%, about 60%, about 70%, about 80%, about 90%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 99.99%.

In further embodiments, the process further comprises reacting the compound of Formula Ic under deprotection conditions to form a compound of Formula III:

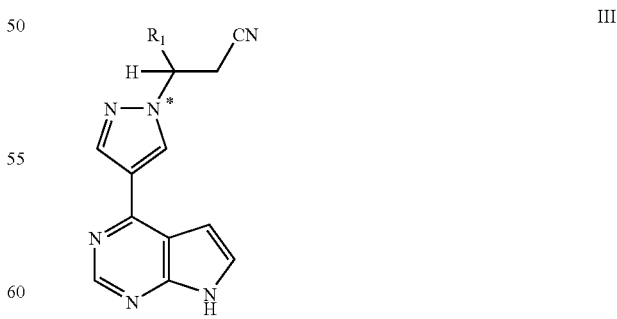

wherein:
* indicates a chiral carbon;
$R_1$ is selected from $C_{3-7}$ cycloalkyl, $C_{1-6}$ alkyl, and $C_{1-6}$ fluoroalkyl; and
$P_1$ is a protecting group.

In some embodiments, the process further comprises a compound of Formula III with phosphoric acid to form a phosphate salt of the compound of Formula III.

Treatment of the compound of Formula Ic to remove the P₁ group can be accomplished by methods known in the art for the removal of particular protecting groups for amines, such as those in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. For example, in some embodiments, the P₁ group is removed by treating with fluoride ion (e.g., treating with tetrabutylammonium fluoride), hydrochloric acid, pyridinium p-toluenesulfonic acid (PPTS), or a Lewis acid (e.g., lithium tetrafluoroborate)). In some embodiments, the treating comprises treating with lithium tetrafluoroborate, followed by treating with ammonium hydroxide (e.g., when P₁ is 2-(trimethylsilyl)ethoxymethyl). In some embodiments, the treating comprises treating with base (e.g., P₁ is N-pivaloyloxymethyl). In some embodiments, the base is an alkali metal hydroxide. In some embodiments, the base is sodium hydroxide. In some embodiments, the treating comprises treating with sodium hydroxide or ammonia in a solvent such as methanol or water.

In some embodiments, to deprotect the SEM-protection group, a mild, two stage protocol is employed. The SEM-protected substrate of Formula Ic is treated with lithium tetrafluoroborate (LiBF₄) in aqueous acetonitrile at elevated temperature, such as 80° C. for ten to twenty hours. The resulting corresponding hydroxymethyl intermediate is then subsequently treated with aqueous ammonium hydroxide (NH₄OH) at room temperature to provide the compound of Formula III.

In some embodiments, for the POM-deprotection, an aqueous sodium hydroxide solution (NaOH) is used. Thus, a suspension of the POM-protected compound of Formula Ic is treated with a 1 N aqueous sodium hydroxide solution at room temperature for two to three hours. The desired product of Formula III can be obtained after the typical acid-base work-up. In some embodiments, the deprotecting conditions comprise treating with lithium tetrafluoroborate, followed by treating with aqueous ammonium hydroxide.

In some embodiments, the process further comprises reacting a compound of Formula III with phosphoric acid to form a phosphate salt of the compound of Formula III.

Processes of Converting the Amide of Formula I to a Nitrile of Formula III

The present invention further provides a process of converting an amide of Formula I to a nitrile compound of Formula I. The methods of converting the amide of Formula I involve dehydrating the amide to form a nitrile. The protecting group can then be removed and the resultant amine can be protonated to form a pharmaceutically acceptable salt. Accordingly, in some embodiments, the present invention provides a process comprising reacting a compound of Formula I:

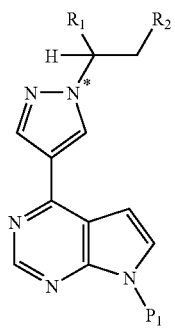

I under dehydrating conditions to form a compound of Formula Ia:

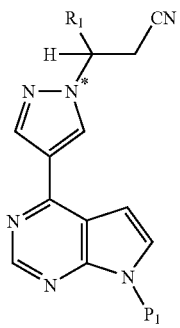

Ia wherein:
* indicates a chiral carbon;
R₁ is selected from C₃₋₇ cycloalkyl, C₁₋₆ alkyl, and C₁₋₆ fluoroalkyl;
R₂ is selected from —C(=O)—NH₂;
P₁ is a protecting group.

In some embodiments, the dehydrating conditions comprise trichloroacetyl chloride in the presence of triethylamine. In some embodiments, the dehydrating conditions comprise any dehydrating agent for dehydration of amides, including but not limited to, an acid chloride (e.g., trichloroacetyl chloride), P₂O₅; ZnCl₂ (under microwave conditions); triphenylphosphine and N-chlorosuccinimide; ethyl dichlorophosphate/DBU; and PdCl₂. In some embodiments, the dehydrating conditions are those described in Kuo, C-W.; Zhu, J.-L.; Wu, J.; et al. *Chem. Commun.* 2007, 301; Manjula, K.; Pasha, M. A. *Syn. Commun.* 2007, 37, 1545; Takahashi, T.; Sugimoto, O.; Koshio, J.; Tanji, K. *Heterocycles* 2006, 68, 1973; Maffioli, S. I.; Marzorati, E.; Marazzi, A. *Organic Letters* 2005, 7, 5237; or Iranpoor, N.; Firouzabadi, H.; Aghapour, G. *Syn. Commun.* 2002, 32, 2535, each of which is incorporated by reference in its entirety.

In further embodiments, the process further comprises reacting the compound of Formula Ic under deprotection conditions to form a compound of Formula III:

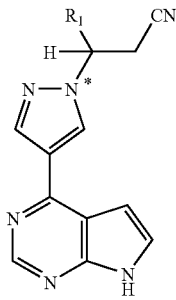

III wherein:
* indicates a chiral carbon;
R₁ is selected from C₃₋₇ cycloalkyl, C₁₋₆ alkyl, and C₁₋₆ fluoroalkyl; and
P₁ is a protecting group.

Appropriate P₁ groups and deprotection methods include, but are not limited to those described supra.

In some embodiments, the process further comprises reacting a compound of Formula III with phosphoric acid to form a phosphate salt of the compound of Formula III.

Processes of Converting the Ester of Formula I to a Nitrile of Formula III

The present invention further provides a process of converting an ester of Formula I to a nitrile compound of Formula I. The processes of converting the ester of Formula I involves saponification of the ester to form an acid, selective ammonlysis, and dehydration of the amide. The protecting group can then be removed and the resultant amine can be protonated to form a pharmaceutically acceptable salt.

Accordingly, the present invention provides a process comprising reacting the compound of Formula I:

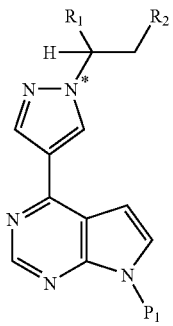

with a metal hydroxide to form a compound of Formula Ic:

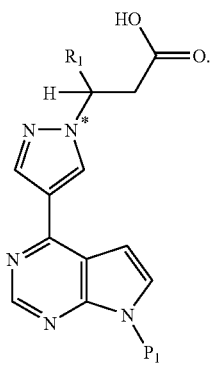

wherein:
* indicates a chiral carbon;
$R_1$ is selected from $C_{3-7}$ cycloalkyl, $C_{1-6}$ alkyl, and $C_{1-6}$ fluoroalkyl;
$R_2$ is —C(=O)OR$_3$;
$R_3$ is selected from $C_{1-4}$ alkyl; and
$P_1$ is a protecting group.

In some embodiments, the metal hydroxide is an alkali metal hydroxide or an alkaline earth hydroxide. In some embodiments, the metal hydroxide is lithium hydroxide.

In further embodiments, the process further comprises reacting the compound of Formula Ic with ammonia or ammonium hydroxide in the presence of a coupling reagent to form a compound of Formula Ib:

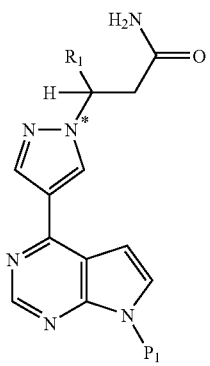

wherein:
* indicates a chiral carbon;
$R_1$ is selected from $C_{3-7}$ cycloalkyl, $C_{1-6}$ alkyl, and $C_{1-6}$ fluoroalkyl; and
$P_1$ is a protecting group.

In some embodiments, the coupling agent is N,N-carbonyldiimidazole. In some embodiments, the coupling agent is selected from 1,2-benzisoxazol-3-yl diphenyl phosphate; ClCO$_2$-i-Bu and Et$_3$N; carbodiimide; SOCl$_2$ and Cl—C(O)—C(O)—Cl; tosyl chloride and DMAP; and ClCO$_2$-i-Bu and triethylamine. In some embodiments, the coupling agent is selected from those in: Ueda, M.; Oikawa, H. *J. Org. Chem.* 1985, 50, 760. (1,2-benzisoxazol-3-yl diphenyl phosphate); Lai, M.; Liu, H. *J. Am. Chem. Soc.* 1991, 113, 7388.(ClCO$_2$-i-Bu, Et$_3$N); Williams, A.; Ibrahim, I. Chem. Rev. 1991, 81, 589. (Carbodiimide); Weiss, M. M.; Harmange, J; Polverino, A. J. *J. Med. Chem.*, 2008, 51, 1668.(SOCl2, Cl—CO—CO—Cl); Hong, C. Y.; and Kishi.Y. *J. Am. Chem. Soc.*, 1991, 113, 9693. (TsCl, DMAP); and Nitta, H.; Yu, D.; Kudo, M.; Mori, A.; Inoue, S. *J. Am. Chem. Soc.*, 1992, 114, 7969. (ClCO$_2$-i-Bu, Et$_3$N).

In other embodiments, the process further comprises reacting the compound of Formula Ib under dehydrating conditions to form a compound of Formula Ia:

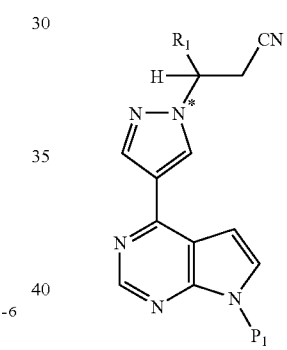

wherein:
* indicates a chiral carbon;
$R_1$ is selected from $C_{3-7}$ cycloalkyl, $C_{1-6}$ alkyl, and $C_{1-6}$ fluoroalkyl; and
$P_1$ is a protecting group.

In some embodiments, the dehydrating conditions comprise trichloroacetyl chloride in the presence of triethylamine. In some embodiments, the dehydrating conditions comprise any dehydrating agent for dehydration of amides, including but not limited to, an acid chloride (e.g., trichloroacetyl chloride), P$_2$O$_5$; ZnCl$_2$ (under microwave conditions); triphenylphosphine and N-chlorosuccinimide; ethyl dichlorophosphate/DBU; and PdCl$_2$. In some embodiments, the dehydrating conditions are those described in Kuo, C-W.; Zhu, J.-L.; Wu, J.; et al. *Chem. Commun.* 2007, 301; Manjula, K.; Pasha, M. A. *Syn. Commun.* 2007, 37, 1545; Takahashi, T.; Sugimoto, O.; Koshio, J.; Tanji, K. *Heterocycles* 2006, 68, 1973; Maffioli, S. I.; Marzorati, E.; Marazzi, A. *Organic Letters* 2005, 7, 5237; or Iranpoor, N.; Firouzabadi, H.; Aghapour, G. *Syn. Commun.* 2002, 32, 2535, each of which is incorporated by reference in its entirety.

In further embodiments, the process further comprises reacting the compound of Formula Ic under deprotection conditions to form a compound of Formula III:

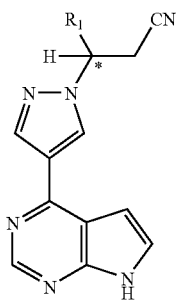

III wherein:
* indicates a chiral carbon;
$R_1$ is selected from $C_{3-7}$ cycloalkyl, $C_{1-6}$ alkyl, and $C_{1-6}$ fluoroalkyl; and
$P_1$ is a protecting group.

Appropriate $P_1$ groups and deprotection methods include, but are not limited to those described supra.

In some embodiments, the process further comprises reacting a compound of Formula III with phosphoric acid to form a phosphate salt of the compound of Formula III.

Starting Materials for the Hydrogenation Processes (Compounds of Formula II)

The compounds of Formula II, used in the asymmetric hydrogenation processes (supra), can be made as shown in the Scheme 1, wherein $P_1$ and $P_2$ are each, independently, a protecting group, $R_1$ is selected from $C_{3-7}$ cycloalkyl, $C_{1-6}$ alkyl, and $C_{1-6}$ fluoroalkyl, and $R_2$ is cyano or an alkyl ester. The routes for preparing compounds of Formula IV are described infra.

The process involves an aza-Michael addition reaction between an appropriately substituted acetylene of Formula XIV with a protected 4-(1H-pyrazol-4-yl)-7H-pyrrolo[2,3-d]pyrimidine compound of Formula IV (preparation of compounds of Formula IV and XIV are described infra). This reaction can be conducted under the influence of catalytic amount of solid potassium carbonate in DMF at room temperature to afford the corresponding compound of Formula I.

Compounds of Formula II, wherein $R_1$ is $-C(=O)NH_2$, can be formed as shown in Scheme 2, by treating a compound of Formula IIa with an acid to form a compound of Formula IIb.

Scheme 2

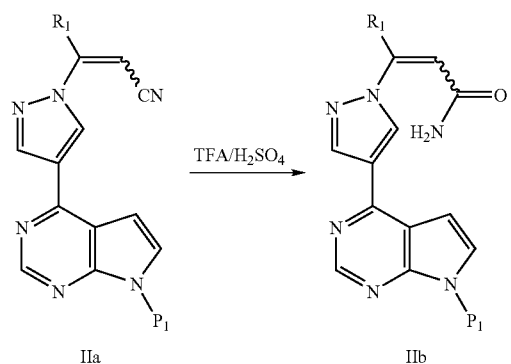

Accordingly, the present invention provides a method of preparing a compound of Formula II:

Scheme 1

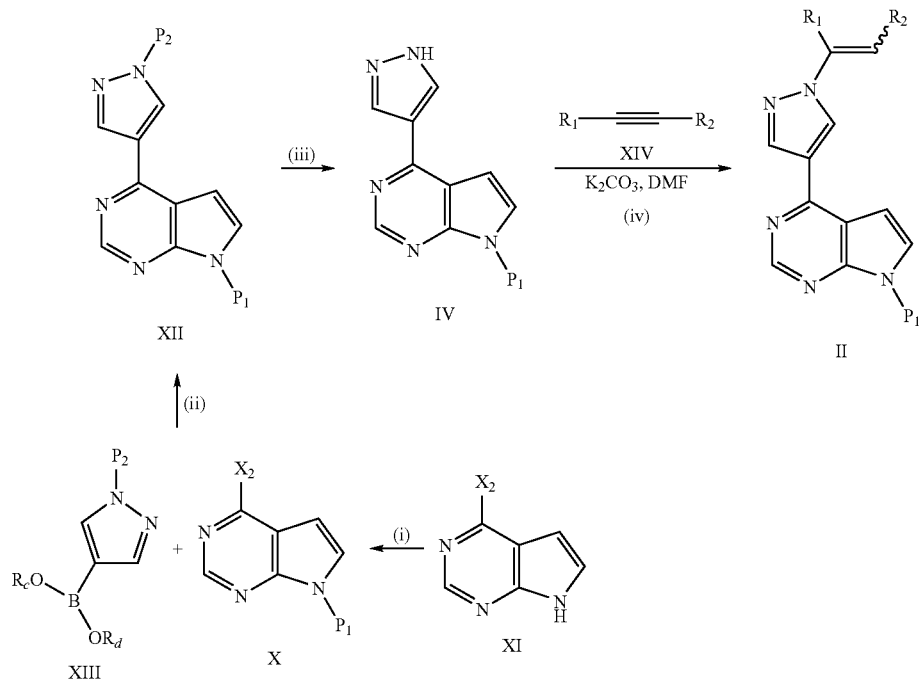

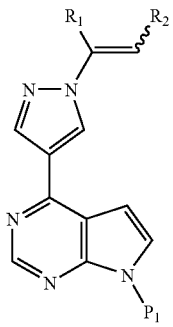

comprising reacting a compound of Formula IV:

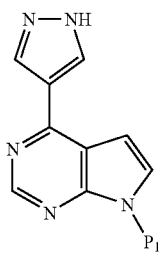

with a compound of Formula XIV:

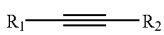

in the presence of a base;
wherein:
* indicates a chiral carbon;
$R_1$ is selected from $C_{3-7}$ cycloalkyl, $C_{1-6}$ alkyl, and $C_{1-6}$ fluoroalkyl;
$R_2$ is selected from —C(=O)O—$R_3$ and cyano;
$R_3$ is selected from $C_{1-4}$ alkyl or $C_{1-4}$ fluoroalkyl; and
$P_1$ is a protecting group.

Appropriate $P_1$ protecting groups include, but are not limited to, those listed supra.

In some embodiments, the aza-Michael addition is conducted in an organic solvent at room temperature in the presence of a catalytic amound of base. The base can be suitable solvent or base for aza-Michael reactions. In some embodiments, the solvent is acetonitrile or dimethylformide (DMF). In some embodiments, the base is a tetraalkylammonium halide, tetraalkylammonium hydroxide, guanidine, amidine, hydroxide, alkoxide, silicate, alkali metal phosphate, oxide, tertiary amine, alkali metal carbonate, alkali metal bicarbonate, alkali metal hydrogen phosphate, phosphine, or alkali metal salt of a carboxylic acid. In some embodiments, the base is tetramethyl guanidine, 1,8-diazabicyclo(5.4.0)undec-7-ene, 1,5-diazabicyclo(4.3.0)non-5-ene, 1,4-diazabicyclo(2.2.2)octane, tert-butyl ammonium hydroxide, sodium hydroxide, potassium hydroxide, sodium methoxide, sodium ethoxide, tripotassium phosphate, sodium silicate, calcium oxide, triethylamine, sodium carbonate, potassium carbonate, sodium bicarbonate, potassium bicarbonate, potassium hydrogen phosphate, triphenyl phosphine, triethyl phosphine, potassium acetate, or potassium acrylate. In some embodiments, the base is 1,8-diazabicyclo[5.4.0]undec-7-ene (DBU) or potassium carbonate. In some embodiments, the base is DBU. In some embodiments, the base is present in a catalytic amount. In some embodiments, the amount of base is about 0.1 to about 5 equivalents, or about 0.5 to about 3 equivalents, or about 0.1 to about 0.5 equivalents. In some embodiments, the reaction is complete in about 1 to about 3 hours.

In some embodiments, $R_1$ is selected from cyclopentyl, methyl and trifluoromethyl. In some embodiments, $R_1$ is cyclopentyl or cyclopropyl. In some embodiments, $R_1$ is cyclopentyl. In some embodiments, $R_1$ is methyl. In some embodiments, $R_1$ is trifluoromethyl.

In some embodiments, the base is an alkali metal or alkaline earth metal carbonate. In some embodiments, the base is potassium carbonate.

In some embodiments, the present invention provides a compound of Formula II:

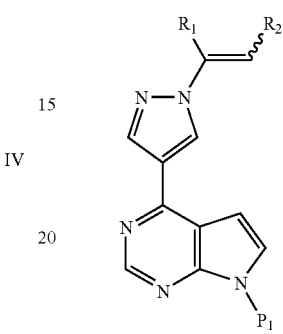

wherein:
$R_1$ is selected from $C_{3-7}$ cycloalkyl, $C_{1-6}$ alkyl, and $C_{1-6}$ fluoroalkyl;
$R_2$ is selected from —C(=O)—NH$_2$ and —C(=O)O—$R_3$;
$R_3$ is selected from $C_{1-4}$ alkyl or $C_{1-4}$ fluoroalkyl; and
$P_1$ is a protecting group.

In some embodiments, $P_1$ is —CH$_2$OC(=O)C(CH$_3$)$_3$ or —CH$_2$OCH$_2$CH$_2$Si(CH$_3$)$_3$. In some embodiments, $R_1$ is cyclopentyl.

Compounds of Formula IIb, wherein $R_1$ is —C(=O)NH$_2$, can be formed by treating a compound of Formula IIa:

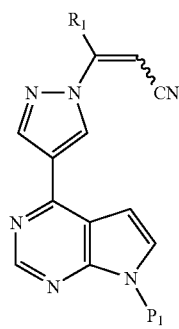

with an acid to form a racemic form of a compound of IIb:

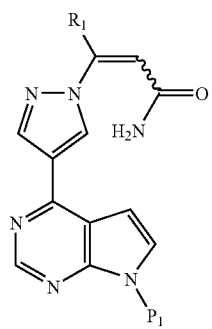

wherein:

$R_1$ is selected from $C_{3-7}$ cycloalkyl, $C_{1-6}$ alkyl, and $C_{1-6}$ fluoroalkyl; and $P_1$ is a protecting group.

In some embodiments, the acid is trifluoroacetic acid, sulfuric acid, or a combination thereof. In some embodiments, the treating comprises treating with trifluoroacetic acid (TFA) and sulfuric acid ($H_2SO_4$) at room temperature. In some embodiments, the ratio of TFA to $H_2SO_4$ is about 10:1 by volume. In some embodiments, the reaction is complete within about one hour.

Compounds of Formula XIV, used in the process described in Scheme 1, can be formed by methods such as those shown in Scheme 3 below. Accordingly, a compound of Formula XIVa (wherein $R_2$ of Formula XIV is cyano) is prepared by treating the lithium salt of a compound of Formula C-1 with cyanatobenzene (C-2), which is in situ generated from phenol and cyanic bromide, in an organic solvent, such as anhydrous THF, at about −78° C. to about room temperature to afford the corresponding 3-substituted propiolonitrile of Formula XIVa. Similarly, the lithium salt of a compound of Formula C-1 treated with an chloroformate of Formula C-3 provides a 3-substituted propiolate compound of Formula XIVb (wherein $R_2$ of Formula XIV is —C(=O)$OR_3$).

Scheme 3

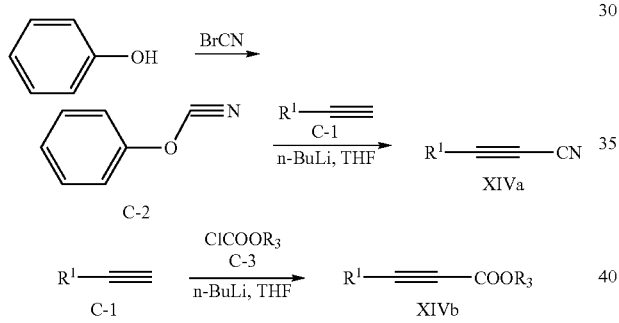

II. Asymmetric Aza-Michael Addition Processes for Preparing an Aldehyde Intermediate of Formula Id or VI In another aspect, the present invention provides, inter alia, an enantiomeric excess of a (R)- or (S)-enantiomer of a compound of Formula Id:

Id

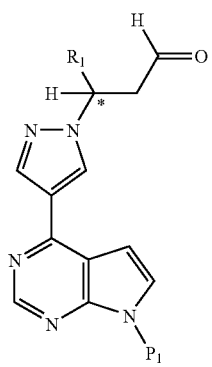

comprising reacting a compound of Formula IV:

IV

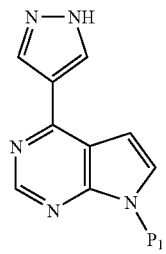

with a compound of Formula V:

V

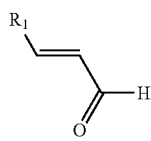

in the presence of a chiral amine and an organic acid;
wherein:
* indicates a chiral carbon;
$R_1$ is selected from $C_{3-7}$ cycloalkyl, $C_{1-6}$ alkyl, and $C_{1-6}$ fluoroalkyl;
$P_1$ is a protecting group.

In a further aspect, the present invention provides a method of preparing an enantiomeric excess of a (R)- or (S)-enantiomer of a compound of Formula VI:

VI

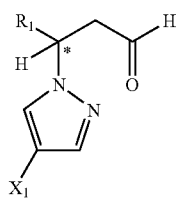

comprising reacting a compound of Formula V:

V

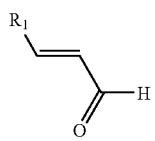

with a compound of Formula VII:

VII

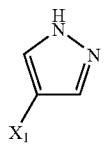

in the presence of a chiral amine and an organic acid;
wherein:
* indicates a chiral carbon;
$R_1$ is selected from $C_{3-7}$ cycloalkyl, $C_{1-6}$ alkyl, and $C_{1-6}$ fluoroalkyl; and
$X_1$ is halogen.

While not wishing to be bound by any particular theory, the mechanism of these chiral amine catalyzed aza-Michael conjugate addition of N-heterocyclic compounds to α,β-unsaturated aldehydes is understood to involve the following pathways. First, the α,β-unsaturated aldehyde of Formula V reacts with the protonated catalyst formed from the combination of the chiral amine and the organic acid and forms an iminium ion with loss of water. Owing to the chirality of the catalyst, two different iminium ions that have E and Z configurations can be formed. The corresponding E configuration is expected to be the major intermediate present in which the Si face is shielded by the chiral group in the catalyst, leaving Re face available for the approach of the N-heterocyclic compounds. Second, the addition of substituted pyrazole to the iminium ion gives the enamine intermediate, which bears a positive charge on the protonated pyrazole ring. This proton is then transferred from the nitrogen atom in the pyrazole ring to the enamine carbon atom to form iminium intermediate. Third, the hydrolysis of the iminium ion leads to regeneration of the catalyst and product. Based on the understanding of reaction mechanism, the reaction conditions for this organocatalyzed aza-Michael reaction were defined.

In some embodiments, the compound of Formula V is present in excess amounts (e.g., from about 1.5 to about 5 equivalents). In some embodiments, the chiral amine is present in about 0.02 to about 0.15 equivalents, or about 0.05 to about 0.10 equivalents.

In some embodiments of either asymmetric aza-Michael addition process, the organic acid is p-toluenesulfonic acid, benzoic acid or 4-nitrobenzoic acid. In some embodiments, the organic acid is benzoic acid. In some embodiments, organic acid is present in about 0.05 to about 0.10 equivalents.

In some embodiments, the reacting is conducted in an organic solvent selected from chloroform ($CHCl_3$) or toluene. In some embodiments, the reacting is at a temperature of about room temperature, or from about 0 to about 5° C. In some embodiments, the reaction is complete in about 10 to about 24 hours. In some embodiments, the reaction conversion reaches over 95% with the isolated yield to about 80 to about 90%. Chiral HPLC methods have been developed to determine the chiral purity of each aza-Michael adduct or its derivative.

In some embodiments of either asymmetric aza-Michael addition process, the chiral amine is a (R)- or (S)-enantiomer of a compound of Formula A-1:

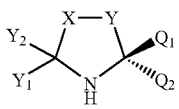

A-1 wherein:
X is $CY_3Y_4$ and Y is $CY_5Y_6$; or
X is S or $NY_7$ and Y is $CY_5Y_6$; or
X is $CY_3Y_4$ and Y is S;
$Q_1$ and $Q_2$ are each independently selected from H, $C_{1-6}$ alkyl, $C_{1-6}$ haloalkyl, carboxy, $C_{1-6}$ alkylcarboxamide, $C_{1-6}$ alkoxycarbonyl, and phenyl; wherein the $C_{1-6}$ alkyl, $C_{1-6}$ haloalkyl, $C_{1-6}$ alkylcarboxamide, $C_{1-6}$ alkoxycarbonyl, and phenyl are each optionally substituted by 1, 2, or 3 groups independently selected from hydroxyl, carboxy, tri-$C_{1-6}$ alkylsilyl, tri-$C_{1-6}$ alkylsilyloxy, $C_{6-10}$ aryl, $C_{6-10}$ arylamino, $C_{1-9}$ heteroaryl, and $C_{1-6}$ heteroarylamino; wherein the $C_{6-10}$ aryl, $C_{6-10}$ arylamino, $C_{1-9}$ heteroaryl, and $C_{1-9}$ heteroarylamino are each optionally substituted by 1, 2, 3, or 4 groups independently selected from halogen, $C_{1-6}$ alkyl, and $C_{1-6}$ haloalkyl; and $Y_1, Y_2, Y_3, Y_4, Y_5, Y_6$ are each independently selected from H, hydroxyl, carboxy, $C_{1-6}$ alkyl, $C_{1-6}$ haloalkyl, $C_{1-6}$ alkoxycarbonyl, and phenyl; or
$Y_1$ and $Y_2$ together form oxo; or
$Y_3$ and $Y_4$ together form oxo; or
$Y_5$ and $Y_6$ together form oxo; or
$Y_1$ and $Y_2$, together with the carbon to which they are attached, form a 5- or 6-membered cycloalkyl ring; or
$Q_1$ and $Y_5$, together with the carbon atoms to which they are attached, form a 5- or 6-membered cycloalkyl ring.

In some embodiments of the compounds of Formula A-1:
X is $CY_3Y_4$ and Y is $CY_5Y_6$; or
X is S or $NY_7$ and Y is $CY_5Y_6$; or
X is $CY_3Y_4$ and Y is S;
$Q_1$ is H or methyl;
$Q_2$ is selected from H, methyl, isopropyl, butyl, carboxy, $C_{1-5}$ alkylaminocarbonyl, methoxycarbonyl, and phenyl; wherein the methyl and $C_{1-5}$ alkylaminocarbonyl are each optionally substituted by 1, 2, or 3 groups independently selected from hydroxyl, carboxy, tri-$C_{1-6}$ alkylsilyl, tri-$C_{1-4}$ alkylsilyloxy, phenyl, phenylamino, and indol-3-yl; wherein the phenyl and the indol-3-yl are each optionally substituted by 1 or 2 groups independently selected from methyl and trifluormethyl;
$Y_1$ is H, hydroxyl, carboxy, methyl, and methoxycarbonyl;
$Y_2$ is H or methyl;
$Y_3, Y_4, Y_5,$ and $Y_6$ are each independently selected from H, hydroxyl, methyl, and phenyl;
$Y_7$ is H or methyl; or
$Y_1$ and $Y_2$ together form oxo; or
$Y_3$ and $Y_4$ together form oxo; or
$Y_5$ and $Y_6$ together form oxo; or
$Y_1$ and $Y_2$, together with the carbon to which they are attached, form a 6-membered cycloalkyl ring; or
$Q_1$ and $Y_5$, together with the carbon atoms to which they are attached, form a 6-membered cycloalkyl ring.

In some embodiments of either asymmetric aza-Michael addition process, the chiral amine is a (R)- or (S)-enantiomer of a compound of Formula A-2:

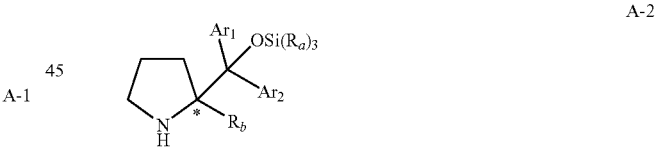

A-2 wherein
* is a chiral carbon having a (R)- or (S)-configuration;
$Ar_1$ and $Ar_2$ are each independently $C_{6-10}$ aryl, which is optionally substituted by 1, 2, 3, or 4 groups independently selected from $C_{1-6}$ alkyl and $C_{1-6}$ haloalkyl;
each $R_a$ are independently selected from $C_{1-6}$ alkyl; and
$R_b$ is selected from H, $C_{1-6}$ alkyl, and $C_{1-6}$ haloalkyl.

In some embodiments, $Ar_1$ and $Ar_2$ are each independently phenyl, which is optionally substituted by 1, 2, 3, or 4 groups independently selected from methyl and trifluoromethyl; each $R_a$ is independently selected from methyl, ethyl, or t-butyl; and $R_b$ is H.

In some embodiments of either asymmetric aza-Michael addition process, the chiral amine is a (R)- or (S)-enantiomer of a compound selected from proline, prolinamide, prolyl-L-leucine, prolyl-L-alanine, prolylglycine, prolyl-L-phenylalanine, diphenylpyrrolidine, dibenzylpyrrolidine, N-(1-methylethyl)-pyrrolidinecarboxamide, 2-(anilinomethyl)

pyrrolidine, 2-[bis(3,5-dimethylphenyl)methyl]pyrrolidine, diphenyl(pyrrolidin-2-yl)methanol, prolinol, 4-thiazolidinecarboxylic acid, trans-3-hydroxyproline, trans-4-hydroxyproline, 4-benzyl-1-methyl-imidazolidine-2-carboxylic acid, 1-methyl-4-phenyl-imidazolidine-2-carboxylic acid, 4,5-octahydro-benzoimidazole-2-carboxylic acid, 4,5-diphenyl-imidazolidine-2-carboxylic acid, N1-methyl-3-phenyl-propane-1,2-diamine, 1,2-diphenylethanediamine, 1-methyl-4-(1-methyl-1H-indol-3-ylmethyl)-imidazolidine-2-carboxylic acid, 4-benzyl-1-methyl-imidazolidine-2-carboxylic acid, 1,2-cyclohexanediamine, 2-phenyl-thiazolidine-4-carboxylic acid, tert-leucine methyl ester, 5-benzyl-2,2,3-trimethyl-imidazoline-4-one, methyl prolinate, 4,5-diphenylimidazolidine, 2-cyclohexyl-4,5-diphenylimidazolidine, 2-{bis-[3,5-bis(trifluoromethyl)phenyl]-trimethylsilanyloxy-methyl}-pyrrolidine, 2-{bis-[3,5-dimethylphenyl]-trimethylsilanyloxy-methyl}-pyrrolidine, 2-{diphenyl-trimethylsilanyloxy-methyl}-pyrrolidine, 2-{bis[naphth-2-yl]-trimethylsilanyloxy-methyl}-pyrrolidine, 2-{tert-butyldimethylsilyloxy-diphenyl-methyl}-pyrrolidine, 2-{bis-[3,5-bis(trifluoromethyl)phenyl]-triethylsilanyloxy-methyl}-pyrrolidine, and 2-{bis-[3,5-bis(trifluoromethyl)phenyl]-ethyl-dimethylsilyloxy-methyl}-pyrrolidine; wherein the (R)- or (S)-configuration is at the carbon adjacent to a NH group in the compound.

In some of the preceding embodiments, the chiral amine is the (R)-enantiomer.

In some embodiments of either asymmetric aza-Michael addition process, the chiral amine is selected from one of the following compounds:

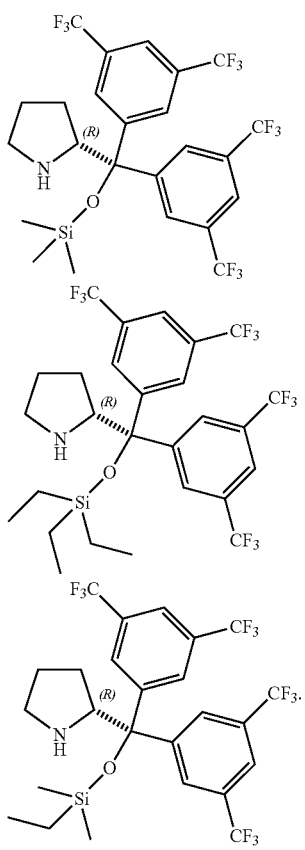

In some embodiments, the enantiomeric excess is from about 85% to about 95%. In some embodiments, the enantiomeric excess is equal to or greater than about 10%, about 20%, about 30%, about 40%, about 50%, about 60%, about 70%, about 80%, about 90%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 99.99%.

In some embodiments, the present invention provides a composition comprising an enantiomeric excess of a (R)- or (S)-enantiomer of a compound of Formula I:

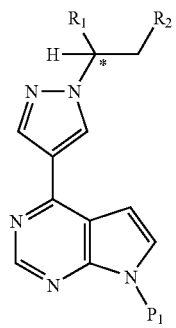

wherein:
* indicates a chiral carbon;
$R_1$ is selected from $C_{3-7}$ cycloalkyl, $C_{1-6}$ alkyl, and $C_{1-6}$ fluoroalkyl;
$R_2$ is selected from —C(=O)—NH$_2$, —C(=O)O—R$_3$, —C(=O)OH, and —C(=O)H;
$R_3$ is selected from $C_{1-4}$ alkyl or $C_{1-4}$ fluoroalkyl; and
$P_1$ is a protecting group.

In some embodiments, $P_1$ is —CH$_2$OC(=O)C(CH$_3$)$_3$ or —CH$_2$OCH$_2$CH$_2$Si(CH$_3$)$_3$. In some embodiments, $R_1$ is cyclopentyl.

In other embodiments, the present invention provides a composition comprising an enantiomeric excess of a (R)- or (S)-enantiomer of a compound of Formula IX:

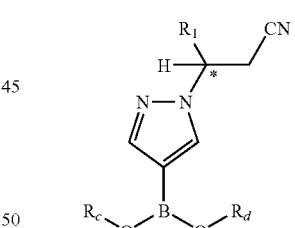

wherein:
* indicates a chiral carbon;
$R_1$ is selected from $C_{3-7}$ cycloalkyl, $C_{1-6}$ alkyl, and $C_{1-6}$ fluoroalkyl; and
$R_c$ and $R_d$ are each independently $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups.

In some embodiments, $R_1$ is cyclopentyl.

Processes for Converting the Aldehyde Intermediates of Formula I or VI to a Nitrile Compound In another aspect, the present invention provides a process for preparing a nitrile compound from a compound of Formula Id. Accordingly, in some embodiments, the present invention provides a process comprising treating the compound of Formula Id:

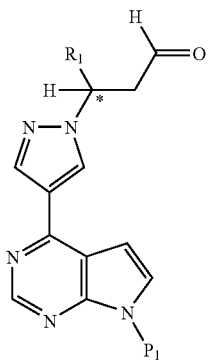

Id with ammonia or ammonium hydroxide and iodine to form the compound of Formula Ia:

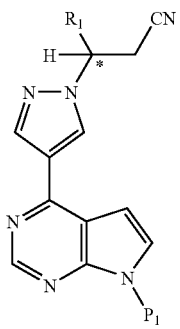

Ia wherein:
* indicates a chiral carbon;
$R_1$ is selected from $C_{3-7}$ cycloalkyl, $C_{1-6}$ alkyl, and $C_{1-6}$ fluoroalkyl; and
$P_1$ is a protecting group.

In some embodiments, the treating is accomplished by treatment of the chiral aldehyde of Formula I with excess amount of aqueous ammonium ($NH_4OH$) and stoichiometric amount of iodine ($I_2$) in an organic solvent, such tetrahydrofuran (THF), at room temperature. In some embodiments, the reaction is complete within about 1 to about 2 hours at room temperature. The chirality of the chiral aldehydes is kept intact under such reaction conditions. The chirality of the chiral nitriles can be checked by chiral HPLC analysis.

In some embodiments, the process further comprises reacting the compound of Formula Ic under deprotection conditions to form a compound of Formula III:

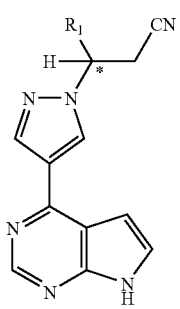

III wherein:
* indicates a chiral carbon;
$R_1$ is selected from $C_{3-7}$ cycloalkyl, $C_{1-6}$ alkyl, and $C_{1-6}$ fluoroalkyl; and
$P_1$ is a protecting group.

Appropriate $P_1$ groups include, but are not limited to those described supra.

In some embodiments, the process further comprises reacting the compound of Formula III with phosphoric acid to form a phosphate salt of the compound of Formula III.

In a further aspect, the present invention provides a process for preparing a nitrile compound from a compound of Formula VI. Accordingly, in some embodiments, the present invention provides a process comprising treating the compound of Formula VI:

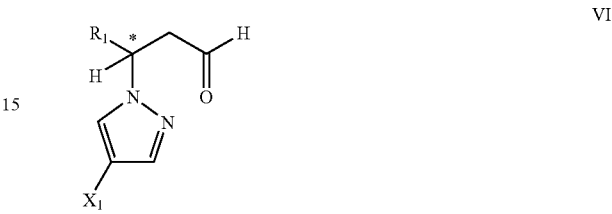

VI with ammonia or ammonium hydroxide and iodine to form the compound of Formula VIII:

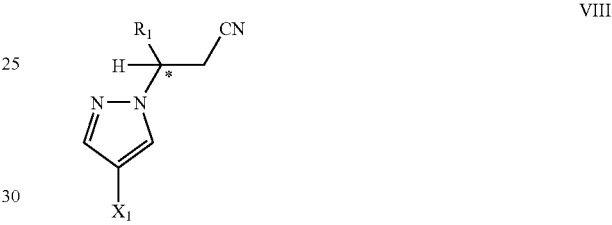

VIII wherein:
* indicates a chiral carbon;
$R_1$ is selected from $C_{3-7}$ cycloalkyl, $C_{1-6}$ alkyl, and $C_{1-6}$ fluoroalkyl; and
$X_1$ is halogen.

In some embodiments, the process further comprises reacting the compound of Formula VIII with a compound of Formula B-1:

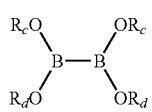

B-1 to form a compound of Formula IX:

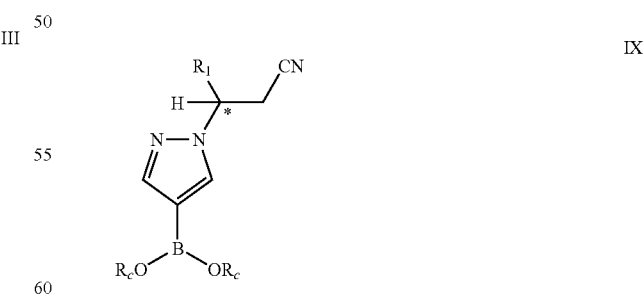

IX wherein:
* indicates a chiral carbon;
$R_1$ is selected from $C_{3-7}$ cycloalkyl, $C_{1-6}$ alkyl, and $C_{1-6}$ fluoroalkyl; and
$R_c$ and $R_d$ are each independently selected from H and $C_{1-6}$ alkyl; or $R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups.

In some embodiments, the compound of Formula B-1 is 4,4,5,5,4',4',5',5'-octamethyl-[2,2']bis[1,3,2-dioxaborolanyl].

In further embodiments, the process further comprises reacting the compound of Formula IX with a compound of Formula X:

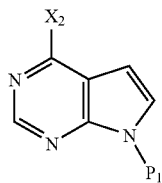

X in the presence of a palladium catalyst and a base to form a compound of Formula Ic:

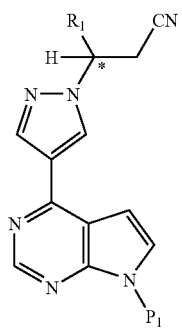

Ia wherein
* indicates a chiral carbon;
$R_1$ is selected from $C_{3-7}$ cycloalkyl, $C_{1-6}$ alkyl, and $C_{1-6}$ fluoroalkyl;
$R_c$ and $R_d$ are each independently selected from H and $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups;
$X_2$ is a tosylate group, a triflate group, iodo, chloro, or bromo; and
$P_1$ is a protecting group.

In further embodiments, the process further comprises reacting a compound of Formula IX with a compound of Formula XI:

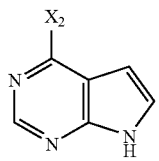

XI in the presence of a palladium catalyst, base, and a solvent, to form a compound of Formula III:

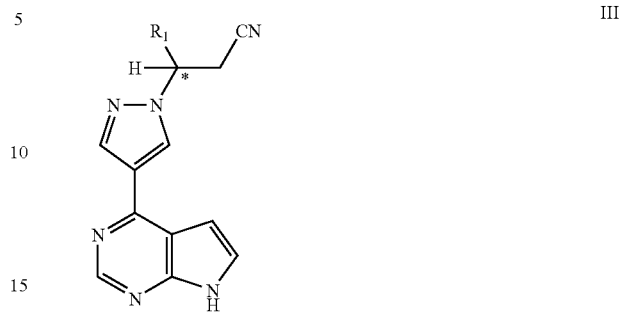

III wherein:
* indicates a chiral carbon;
$R_1$ is selected from $C_{3-7}$ cycloalkyl, $C_{1-6}$ alkyl, and $C_{1-6}$ fluoroalkyl;
$R_c$ and $R_d$ are each independently selected from H and $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups; and
$X_2$ is a tosylate group, a triflate group, iodo, chloro, or bromo.

In some embodiments, $X_2$ is bromo, iodo, or chloro. In some embodiments, $X_2$ is chloro.

The Suzuki coupling reaction can be initiated using a number of palladium(0) and palladium(II) catalysts and performed under conditions known in the art (see, e.g., Miyaura and Suzuki, *Chem. Rev.* 1995, 95, 2457-2483, which is hereby incorporated in its entirety). In some embodiments, the palladium catalyst is $Pd(PPh_3)_4$ and $Pd(dppf)_2Cl_2$.

In some embodiments, the palladium catalyst is tetrakis(triphenylphosphine)palladium(0) or tetrakis(tri(o-tolyl)phosphine)palladium(0).

In some embodiments, the palladium catalyst is tetrakis(triphenylphosphine)palladium(0).

In some embodiments, the palladium catalyst loading is from about $1 \times 10^{-4}$ to about 0.1 equivalents. In some embodiments, the palladium catalyst loading is from about 0.0010 to about 0.0015 equivalents. In some embodiments, the stoichiometric ratio of the compound of Formula X or XI to the compound of Formula IX is from about 1:1.05 to about 1:1.35.

In some embodiments, the solvent comprises water and an organic solvent. In some embodiments, the organic solvent is 1,4-dioxane, 1-butanol, 1,2-dimethoxyethane (DME), 2-propanol, toluene or ethanol, or a combination thereof. In some embodiments, the organic solvent comprises DME. In some embodiments, the organic solvent comprises DMF.

In some embodiments, the base is an inorganic base. In some embodiments, the base is an organic base. In some embodiments, the base is an alkali metal carbonate. In some embodiments, the base is potassium carbonate ($K_2CO_3$). In some embodiments, two to five equivalents of base (e.g., $K_2CO_3$) are used.

In some embodiments, the Suzuki coupling reaction is conducted at a temperature of about 80 to about 100° C. In some embodiments, the reaction is carried out for two to twelve hours. In some embodiments, the compound of Formula XII can be optionally isolated from aqueous work-up of the Suzuki coupling reaction mixture or directly used. Appropriate P₂ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety.

In other embodiments, the process further comprises reacting the compound of Formula Ia under deprotection conditions to form a compound of Formula III:

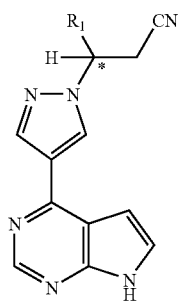

III

* indicates a chiral carbon;

$R_1$ is selected from $C_{3-7}$ cycloalkyl, $C_{1-6}$ alkyl, and $C_{1-6}$ fluoroalkyl; and $P_1$ is a protecting group.

Appropriate $P_1$ groups and deprotection methods include, but are not limited to those described supra.

In some embodiments, the process further comprises reacting a compound of Formula III with phosphoric acid to form a phosphate salt of the compound of Formula III.

Starting Materials for the Aza-Michael Addition Processes

A compound of Formula IV can be formed by methods analogous to those described infra. 3-Substituted acrylaldehydes of Formula V can, in turn, be prepared as shown in Scheme 4. Accordingly, treatment of an aldehyde of Formula C-4 under typical Wittig conditions (e.g., reaction with (triphenylphosphoranylidene)acetaldehyde) provides the corresponding compound of Formula V.

Scheme 4

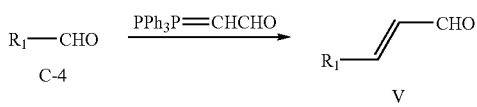

III. Synthesis and Racemic Resolution of Pyrazole Intermediates

Chiral compounds of Formula III can be produced by chiral column separation (such as by chiral preparative chromatography) of a racemate of a protected pyrazole borate derivative of Formula IX, followed by a Suzuki coupling reaction of the chiral intermediate of IX with a unprotected pyrrolo[2,3-d]pyrimidine of Formula XI (Scheme 5). Alternatively, the chiral intermediate of Formula (S)-IX or (R)-IX can be reacted under Suzuki coupling conditions with a protected pyrrolo[2,3-d]pyrimidine of Formula X, followed by deprotection to remove the $P_1$ protecting group to give a chiral compound of Formula III (Scheme 5). The racemic substituted pyrazole borate derivatives of Formula IX can be produced via the Michael addition reaction between pyrazole boronic derivative of Formula XV and a Michael acceptor of Formula D-1 (Scheme 5).

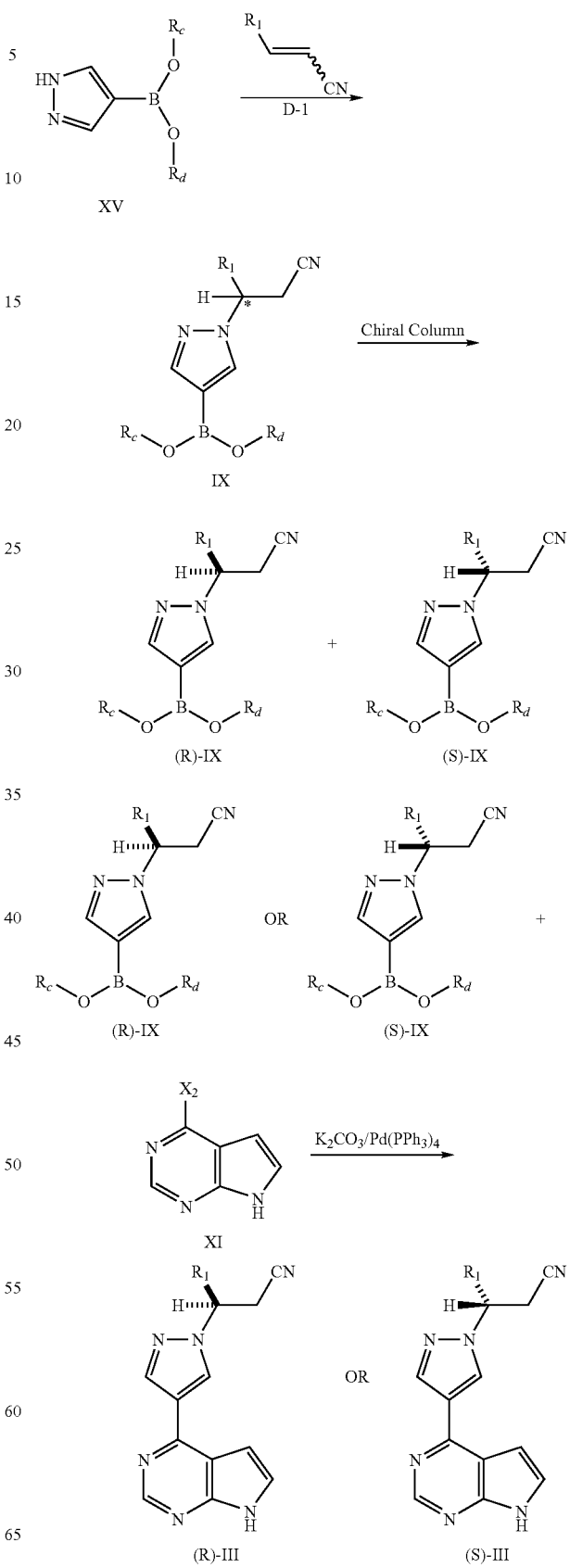

-continued

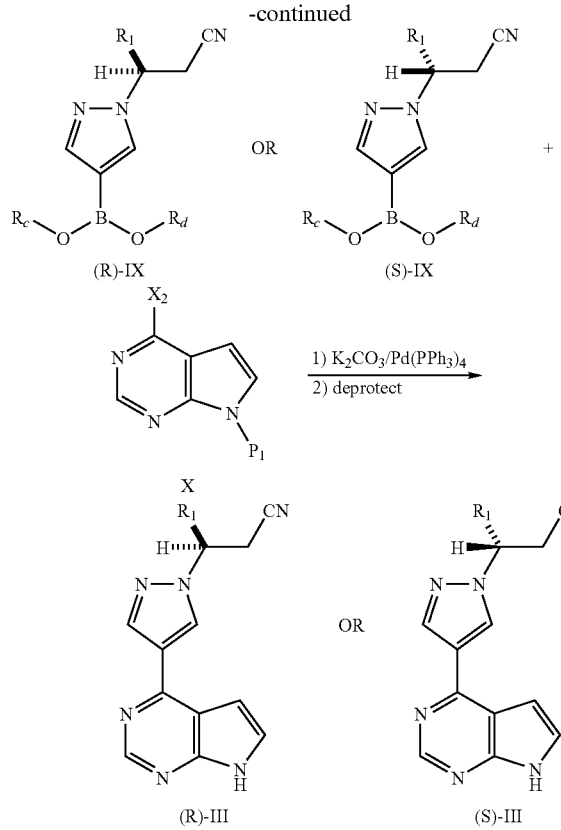

Accordingly, in some embodiments, the present invention provides a process of preparing a composition comprising an enantiomeric excess of the (R)- or (S)-enantiomer of a compound of Formula IX:

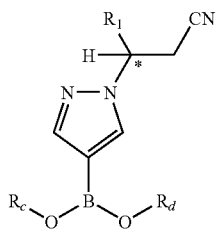

comprising passing a composition comprising a racemate of a compound of Formula IX through a chiral chromatography unit using a mobile phase and collecting a composition comprising an enantiomeric excess of the (R)- or (S)-enantiomer of a compound of Formula IX;
wherein:
* indicates a chiral carbon;
$R_1$ is selected from $C_{3-7}$ cycloalkyl, $C_{1-6}$ alkyl, and $C_{1-6}$ fluoroalkyl;
$R_c$ and $R_d$ are each independently $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups. In some embodiments, the chromatography is carried out in either batch or continuous mode using a chiral stationary phase and a mobile phase in isocratic or gradient mode.

In some embodiments, the chiral chromatography unit is a preparative high performance liquid chromatography (HPLC) system equipped with a chiral column, which is packed with a chiral stationary phase. In some embodiments, the chiral column is packed with a chiral stationary phase comprising amylose tris(3,5-dimethylphenyl carbamate immobilized on silica gel (available from Daicel as "Chiralpak® IA"). In some embodiments, the chiral column is packed with a chiral stationary phase comprising cellulose tris(3,5-dimethylphenyl carbamate) coated on silica gel (available from Daicel as "Chiralcel® ChiralcelOD"). In some embodiments, the chromatography unit is a continuous chromatography process such as simulated moving bed (SMB) chromatography or Varicol process using a unit equipped with a set of eight columns each packed with a chiral stationary phase. In some embodiments the unit is equipped with 3 to 12 columns, or 5 to 10 columns, or 5 to 8 columns, each packed with a chiral stationary phase, in some instances, the same chiral stationary phase. In some embodiments, the column is packed with chiral stationary phase made of amylose tris(3,5-dimethylphenyl carbamate) immobilized on silica gel (available from Daicel as "Chiralpak® IA). In some embodiments, the column is packed with a chiral stationary phase made of cellulose tris(3,5-dimethylphenyl carbamate) coated on silica gel (available from Daicel as "Chiralcel® OD"). In some embodiments, the chiral stationary phase is cellulose modified chiral stationary phase (CSP, Chiral Technologies. In some embodiments, the chiral stationary phase is a silica gel based stationary phase coated with 4-(3,5-dinitro benzamido)tetrahydrophenanthrene (available from Regis Technologies as "(S,S) Whelk-O® 1"). In some embodiments, the mobile phase comprises ethanol and hexanes. In some embodiments, the mobile phase comprises about 1:9 ratio of ethanol to hexanes. In some embodiment the hexanes are replaced by heptanes, n-heptane, cyclohexane or methylcyclohexane. In some embodiments, the ethanol is present in an amount of about 10% to about 100% by volume, or about 10% to about 25% by volume, or about 15% ethanol. In some embodiments, the mobile phase comprises about 15% ethanol and about 85% hexanes by volume. In some embodiments, the mobile phase comprise ethanol and hexanes, wherein the ethanol is present in an amount of about 25% to about 10% by volume. In some embodiments, the mobile phase comprises isopropanol and hexanes, wherein the isopropanol is present in an amount of about 25% to about 10% by volume. In some embodiments, the hexanes are replaced by heptanes, n-heptane, cyclohexane or methylcyclohexane. In some embodiments, the isopropanol is present in an amount of about 10% to about 25% by volume. In some embodiments, the mobile phase comprises methyl-tent-butyl ether and hexanes. In some embodiments the hexanes are replaced by heptanes, n-heptane, cyclohexane or methylcyclohexane. In some embodiement the methyl-tent-butyl ether is present in an amount of about 10% to about 100% by volume, preferably about 50% to about 100% by volume, and most preferably about 90% to about 100% by volume. In some embodiments, the mobile phase comprises ethyl acetate and hexanes. In some embodiments, the hexanes are replaced by heptanes, n-heptane, cyclohexane or methylcyclohexane. In some embodiments, the ethyl acetate is present in an amount of about 10% to about 100% by volume, about 50% to about 100% by volume, or about 75% by volume. In some embodiments, the mobile phase comprises tetrahydrofuran and hexanes. In some embodiments, the hexanes are replaced by heptanes, n-heptane, cyclohexane or methylcyclohexane. In some embodiments, the tetrahydrofuran is present in an amount of about 10% to about 100% by volume, about 10% to about 50% by volume, or about 25% by volume. In some embodiments, the chromatography unit is kept at room temperature. In some embodiments, the mobile phase is passed at a flow rate of about 1 mL per minute to about 20 mL per minute. In some embodiments, the mobile phase is passed at a flow rate of about 1 mL per minute. In some embodiments, the mobile phase is passed at a flow rate of about 18 mL per minute. In some embodiments, the eluent is monitored by ultraviolet (UV) spectroscopy. In some embodiments, the eluent is monitored by ultraviolet spectroscopy at about 220 nm. Collection of the portion of the eluent containing the enantiomerically enriched composition can be determined by detection of the elution of the desired enantiomer by UV spectroscopy. Determination of the % ee (enantiomeric excess) of the composition can then be determined by analytical chiral HPLC.

In some embodiments, the chromatographic method employed is batch preparative chromatography, supercritical fluide chromatography (SFC), a cyclojet process, a continuous multicolumn chromatography process, a simulated moving bed process, a Varicol™ process, or a PowerFeed process.

In some embodiments, the chiral stationary phase comprises an interacting agent which is an enantiomerically enriched resolving agent, immobilized to an inert carrier material by, for example, chemically binding or by insolubilizing via cross-linking. The suitable inert carrier material can be macroporous, e.g crosslinked polystyrene, polyacrylamide, polyacrylate, alumina, kieselgur (diatomaceous), quartz, kaolin, magnesium oxide, titanium dioxide or silica gel. In some embodiments, the inert carrier material is Silicagel.

In some embodiments, the chiral stationary phase is a member of the amylosic or cellulosic class of polysaccharides that is selected from cellulose phenyl carbamate derivatives, such as cellulose tris(3,5-dimethylphenyl)carbamate (available from Daicel Chemical Industries, Ltd. (Daicel) as "Chiralcel® OD" or "Chiralpak® IB", wherein the carbamate derivative is bonded to the cellulosic backbone); cellulose tribenzoate derivatives, such as cellulose tri 4-methylbenzoate (available from Daicel as "Chiralcel® OJ"); cellulose tricinnamate (available from Daicel as "Chiralcel® OK"); amylase phenyl and benzyl carbamate derivatives, such as amylose tris[(S)-α-methyl benzylcarbamate] (available from Daicel as "Chiralpak® AS"); amylose tris(3,5-dimethylphenyl)carbamate (available from Daicel as "Chiralpak® AD" or "Chiralpak® IA", wherein the carbamate derivative is bonded to the amylosic backbone); amylose 3,4-substituted phenyl carbamate or amylose 4-substituted phenyl-carbamate; and amylose tricinnamate. In some embodiments, the chiral stationary phase comprises Chiralpak® IA or Chiralpak AD. In some embodiments, the chiral stationary phase comprises Chiralcel® OD. In some embodiments, the chiral stationary phase is a member of the Pirkle-phases family such as 3,5-dinitrobenzoyl derivatives of phenylglycine (available from Regis Technologies Inc as "phenylglycine"; 5-dinitrobenzoyl derivative of leucine (available from Regis Technologies Inc as "Leucine"); N-3,5-dinitrobenzoyl-3-amino-3-phenyl-2-(1,1-dimethylethyl)-propanoate (available from Regis Technologies Inc as "β-GEM 1"); dimethyl N-3,5-dinitrobenzoyl-amino-2,2-dimethyl-4-pentenyl phosphonate (available from Regis Technologies Inc as "α-BURKE 2"); 3-(3,5-dinitrobenzamido)-4-phenyl-β-lactam (available from Regis Technologies Inc as "PIRKLE 1-J"); 3,5-Dinitrobenzoyl derivative of diphenylethylenediamine (available from Regis Technologies Inc as "ULMO"); 4-(3,5-dinitro benzamido)tetrahydrophenanthrene (available from Regis technologies Inc. as "(S,S) Whelk-O® 1" and "(R,R) Whelk-O® 1" or "(S,S) Whelk-O®2" and "(R,R) Whelk-O®2"); 3,5-dinitro-benzoyl derivative of 1,2-diaminocyclohexane, (available from Regis technologies Inc. as "DACH-DNB). In some embodiments, the chiral stationary phase comprises "(S,S) Whelk-O® 1" or "(R,R) Whelk-O® 1.

In some embodiments, the particle diameter of the chiral stationary phase is usually 1 to 300 μm, 2 to 100 μm, 5 to 75 μm, or 10 to 30 μm.

In some embodiments, the mobile phase is non-polar, polar protic or aprotic solvents or mixture thereof. In some embodiments, the mobile phase is a mixture of carbon dioxide and polar protic solvents. Suitable non polar solvents include, for example, hydrocarbons, for instance, n-pentane, n-hexane, hexanes, n-heptane, heptanes, cyclohexane, and methylcyclohexane. Suitable protic or aprotic solvents include, for example, alcohols, in particular methanol, ethanol, 1-propanol, 2-propanol, 1-butanol, 2-butanol, isobutanol, tert butanol, ethers, for instance methyl tert butyl ether, esters, for instance ethylacetate, halogenated hydrocarbons and acetonitrile. In some embodiments, the non-polar solvent is n-heptane. In some embodiments, the protic or aprotic solvent is ethanol, 2-propanol or methyl-tert-butyl ether. In some embodiments, the mobile phase is a mixture of heptane and ethanol. In some embodiments, the ethanol is present in the mobile phase in an amount of about 10% to about 100%, about 10% to about 25%., or about 15%. In some embodiments, the mobile phase is a mixture of heptane and 2-propanol. In some embodiments, the 2-propanol is present in the mobile phase in an amount of about 10% to about 100%, about 10% to about 25%, or about 20%. In some embodiments, the mobile phase is a mixture of heptane and methyl-tert-butyl ether. In some embodiments, the methyl-tert-butyl ether is present in the mobile phase in an amount of about 10% to about 100%, about 75% to about 100%, or about 90% to about 100%.

In some embodiments, the chromatography is carried out at a temperature range of about 0° C. to 50° C., about 10° C. to 30° C., or about 25° C.

In some embodiments, the desired enantiomer is recovered at an enantiomeric purity greater than about 90%, greater than about 98%, or greater than about 99.0%. In some embodiments, the desired enantiomer is recovered with a yield greater than about 70%, greater than about 90%, or greater than about 95%.

In some embodiments, the desired enantiomer is produced at a rate throughput greater than about 0.1 kg, 0.4 kg, or 0.8 kg pure enantiomer per day per kilogram of stationary phase.

In some embodiments, the separated enantiomers are recovered after evaporation under reduced pressure as concentrated oils.

In some embodiments, the mobile phase used in the chiral chromatography process is recycled.

In some embodiments, the undesired enantiomer is racemized and reused as racemic feed for the chiral separation.

In some embodiments, the compound of Formula IX has the formula:

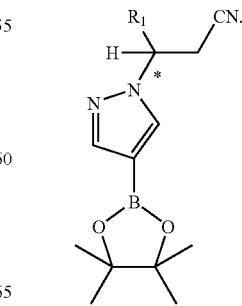

In some embodiments, the enantiomeric excess is equal to or greater than about 10%, about 20%, about 30%, about 40%, about 50%, about 60%, about 70%, about 80%, about 90%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 99.99%.

In some embodiments, the desired enantiomer is recovered in at least a 91%, 92%, 93%, 94%, 95%, 96%, 97%, 98%, or 99% yield, and preferably greater than 90% or 95% yield.

In some embodiments, the process further comprises reacting the compound of Formula IX:

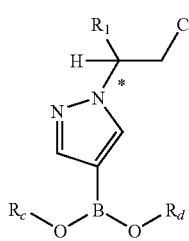

IX with a compound of Formula XI:

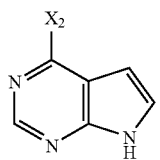

XI in the presence of a palladium catalyst, base, and a solvent under conditions and for a time sufficient to form a composition comprising an enantiomeric excess of the (R)- or (S)-enantiomer of a compound of Formula III:

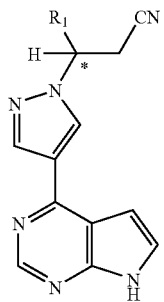

III wherein:
* indicates a chiral carbon;
$R_1$ is selected from $C_{3-7}$ cycloalkyl, $C_{1-6}$ alkyl, and $C_{1-6}$ fluoroalkyl;
$R_c$ and $R_d$ are each independently $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups; and
$X_2$ is a tosylate group, a triflate group, iodo, chloro, or bromo.

In some embodiments, the process further comprises reacting the compound of Formula IX:

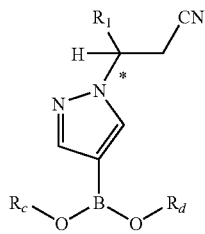

IX with a compound of Formula X:

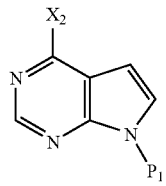

X in the presence of a palladium catalyst, base, and a solvent under conditions and for a time sufficient to form a composition comprising an enantiomeric excess of the (R)- or (S)-enantiomer of a compound of Formula Ia:

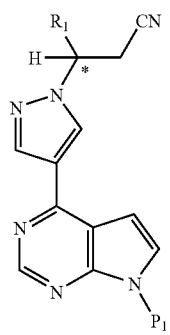

Ia wherein:
* indicates a chiral carbon;
$R_1$ is selected from $C_{3-7}$ cycloalkyl, $C_{1-6}$ alkyl, and $C_{1-6}$ fluoroalkyl;
$R_c$ and $R_d$ are each independently $C_{1-6}$ alkyl; or
$R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups;
$X_2$ is a tosylate group, a triflate group, iodo, chloro, or bromo; and
$P_1$ is a protecting group.

In some embodiments, $X_2$ is bromo, iodo, or chloro. In some embodiments, $X_2$ is chloro.

The Suzuki coupling reactions can be initiated using a number of palladium(0) and palladium(II) catalysts and performed under conditions known in the art (see, e.g., Miyaura and Suzuki, Chem. Rev. 1995, 95, 2457-2483, which is hereby incorporated in its entirety). In some embodiments, the palladium catalyst is Pd(PPh$_3$)$_4$ and Pd(dppf)$_2$Cl$_2$.

In some embodiments, the palladium catalyst is tetrakis(triphenylphosphine)palladium(0) or tetrakis(tri(o-tolyl)phosphine)palladium(0). In some embodiments, the palladium catalyst is tetrakis(triphenylphosphine)palladium(0).

In some embodiments, the palladium catalyst loading is from about 1×10$^{-4}$ to about 0.1 equivalents. In some embodiments, the palladium catalyst loading is from about 0.0010 to about 0.0015 equivalents. In some embodiments, the stoichiometric ratio of the compound of Formula X or XI to the compound of Formula IX is from about 1:1.05 to about 1:1.35.

In some embodiments, the solvent comprises water and an organic solvent. In some embodiments, the organic solvent is 1,4-dioxane, 1-butanol, 1,2-dimethoxyethane (DME), 2-propanol, toluene or ethanol, or a combination thereof. In some embodiments, the organic solvent comprises DME. In some embodiments, the organic solvent comprises DMF.

In some embodiments, the base is an inorganic base. In some embodiments, the base is an organic base. In some embodiments, the base is an alkali metal carbonate. In some embodiments, the base is potassium carbonate (K$_2$CO$_3$). In some embodiments, two to five equivalents of base (e.g., K$_2$CO$_3$) are used.

In some embodiments, the Suzuki coupling reaction is conducted at a temperature of about 80 to about 100° C. In some embodiments, the reaction is carried out for two to twelve hours. In some embodiments, the compound of Formula Ia or III can be optionally isolated from aqueous workup of the Suzuki coupling reaction mixture or directly used.

Appropriate P$_1$ groups and deprotection conditions are provided supra.

In some embodiments, the present invention provides a process of preparing a racemate of a compounds of Formula IX

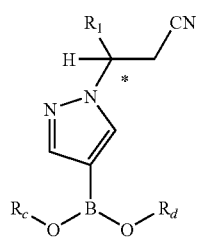

IX comprising reacting a compound of Formula XV:

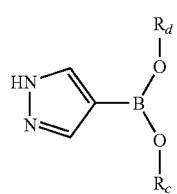

XV with a compound of Formula D-1:

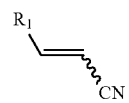

D-1 in the presence of a base to produce compound of Formula IX; wherein:
* indicates a chiral carbon;
R$_1$ is selected from C$_{3-7}$ cycloalkyl, C$_{1-6}$ alkyl, and C$_{1-6}$ fluoroalkyl; and
R$_c$ and R$_d$ are each independently C$_{1-6}$ alkyl; or
R$_c$ and R$_d$, together with the oxygen atoms to which they are attached and the boron atom to which the oxygen atoms are attached, form a 5- to 6-membered heterocyclic ring, which is optionally substituted with 1, 2, 3, or 4 C$_{1-4}$ alkyl groups.

In some embodiments, the aza-Michael addition is conducted in an organic solvent at room temperature in the presence of a catalytic amound of base. The base can be suitable solvent or base for aza-Michael reactions. In some embodiments, the solvent is acetonitrile or dimethylformide (DMF). In some embodiments, the base is a tetraalkylammonium halide, tetraalkylammonium hydroxide, guanidine, amidine, hydroxide, alkoxide, silicate, alkali metal phosphate, oxide, tertiary amine, alkali metal carbonate, alkali metal bicarbonate, alkali metal hydrogen phosphate, phosphine, or alkali metal salt of a carboxylic acid. In some embodiments, the Michael addition catalyst is tetramethyl guanidine, 1,8-diazabicyclo(5.4.0)undec-7-ene, 1,5-diazabicyclo(4.3.0)non-5-ene, 1,4-diazabicyclo(2.2.2)octane, tert-butyl ammonium hydroxide, sodium hydroxide, potassium hydroxide, sodium methoxide, sodium ethoxide, tripotassium phosphate, sodium silicate, calcium oxide, triethylamine, sodium carbonate, potassium carbonate, sodium bicarbonate, potassium bicarbonate, potassium hydrogen phosphate, triphenyl phosphine, triethyl phosphine, potassium acetate, or potassium acrylate. In some embodiments, the base is 1,8-diazabicyclo[5.4.0]unde-7-ene (DBU) or potassium carbonate. In some embodiments, the base is DBU. In some embodiments, the base is present in a catalytic amount. In some embodiments, the amount of base is about about 0.1 to about 5 equivalents, or about 0.5 to about 3 equivalents. In some embodiments, the reaction is complete in about 10 to about 24 hours.

In some embodiments, the process further comprises treating the compound of Formula Ia under deprotection conditions sufficient to provide a composition comprising an enantiomeric excess of a (R)- or (S)-enantiomer of a compound of Formula III:

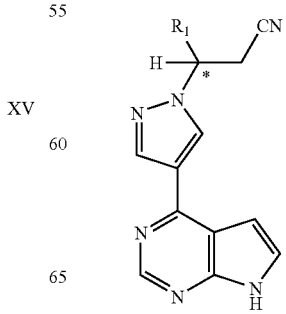

III wherein:
* indicates a chiral carbon;
R$_1$ is selected from C$_{3-7}$ cycloalkyl, C$_{1-6}$ alkyl, and C$_{1-6}$ fluoroalkyl; and
P$_1$ is a protecting group.

Appropriate P$_1$ groups and deprotection methods include, but are not limited to those described supra.

In some embodiments, the process further comprises reacting a compound of Formula III with phosphoric acid to form a phosphate salt of the compound of Formula III.

IV. Chiral Enrichment of Racemates of Formula Ia and Racemization of Undesired Enantiomers of Formula Ia Racemates of Formula Ia can be formed by a Michael addition process in Scheme 6 below. Accordingly, a compound of Formula IV can be reacted with an acrylonitrile of Formula D-1 to form a racemate of Formula Ia. The racemate of Formula Ia can then be separated by chiral column chromatography to give a composition comprising an enantiomeric excess of the (R)- or (S)-enantiomer of the compound of Formula Ia. The protecting group can then be removed to produce an enantiomeric excess of the (R)- or (S)-enantiomer of the compound of Formula III.

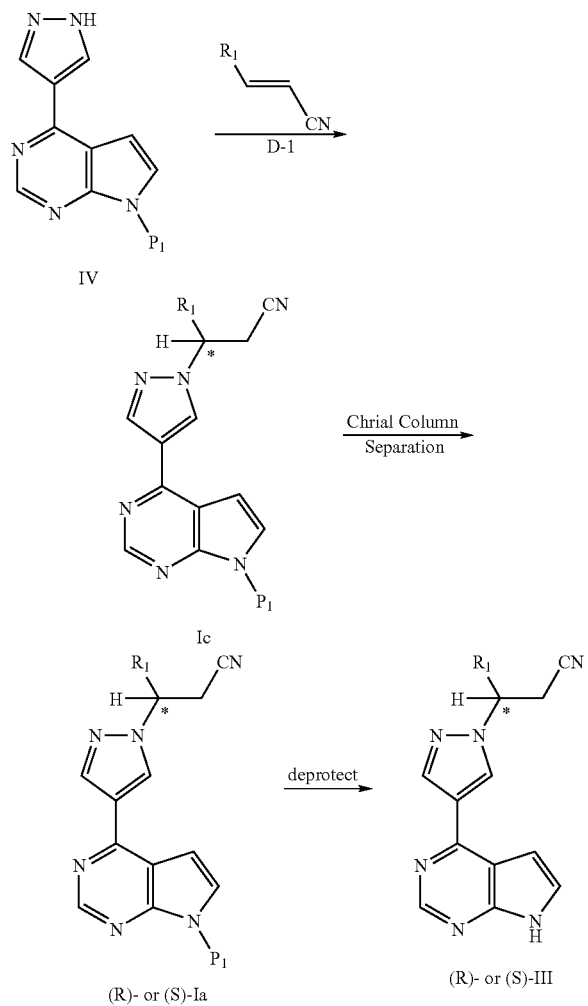

Scheme 6

Accordingly, in some embodiments, the present invention provides a process of preparing a composition comprising an enantiomeric excess of the (R)- or (S)-enantiomer of a compound of Formula Ia:

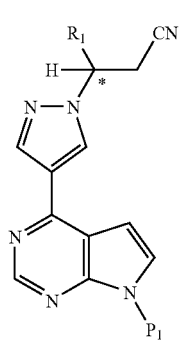

Ia comprising passing a composition comprising a racemate of a compound of Formula Ia through a chiral chromatography unit using a mobile phase and collecting a composition comprising an enantiomeric excess of the (R)- or (S)-enantiomer of a compound of Formula Ia;
wherein:
* indicates a chiral carbon;
R$_1$ is selected from C$_{3-7}$ cycloalkyl, C$_{1-6}$ alkyl, and C$_{1-6}$ fluoroalkyl; and
P$_1$ is a protecting group.

In some embodiments, the chiral chromatography unit is a preparative high performance liquid chromatography (HPLC) system equipped with a chiral column, which is packed with a chiral stationary phase. In some embodiments, the chiral column is Chiralpak® IA. In some embodiments, the chiral column is ChiralCel® OD-H. In some embodiments, the chromatography unit is stimulated moving bed (SMB) chromatography unit equipped with a set of eight columns, each packed with a chiral stationary phase. In some embodiments, the chiral stationary phase is cellulose modified chiral stationary phase (CSP, Chiral Technologies In some embodiments, the mobile phase comprises ethanol and hexanes. In some embodiments, the mobile phase comprises about 1:9 ratio of ethanol to hexanes by volume. In some embodiments, the mobile phase comprises about 15% ethanol and about 85% hexanes by volume. In some embodiments, the mobile phase comprise ethanol and hexanes, wherein the ethanol is present in an amount of about 25% to about 10% by volume. In some embodiments, the mobile phase comprises isopropanol and hexanes, wherein the isopropanol is present in an amount of about 25% to about 10% by volume. In some embodiments, the chromatography unit is kept at room temperature. In some embodiments, the mobile phase is passed at a flow rate of about 1 mL per minute to about 20 mL per minute. In some embodiments, the mobile phase is passed at a flow rate of about 1 mL per minute. In some embodiments, the mobile phase is passed at a flow rate of about 18 mL per minute. In some embodiments, the eluent is monitored by ultraviolet (UV) spectroscopy. In some embodiments, the eluent is monitored by ultraviolet spectroscopy at about 220 nm. Collection of the portion of the eluent containing the enantiomerically enriched composition can be determined by detection of the elution of the desired enantiomer by UV spectroscopy. Determination of the % ee (enantiomeric excess) of the composition can then be determined by analytical chiral HPLC.

In some embodiments, the enantiomeric excess is equal to or greater than about 10%, about 20%, about 30%, about 40%, about 50%, about 60%, about 70%, about 80%, about 90%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 99.99%.

In some embodiments, the chiral chromatography is performed using a preparative high performance liquid chromatography (HPLC) system equipped with a chromatographic column, which is packed with a chiral stationary phase. In some embodiments, the column is packed with chiral stationary phase made of amylose tris(3,5-dimethylphenyl carbamate) immobilized on silica gel (available from Daicel as "Chiralpak® IA"). In some embodiments, the column is packed with a chiral stationary phase made of cellulose tris (3,5-dimethylphenyl carbamate) coated on silica gel (available from Daicel as 'Chiralce® OD"). In some embodiments, the chromatography process is a continuous chromatography process such as simulated moving bed (SMB) chromatography or Varicol process using a unit equipped with a set of 3 to 12 columns, preferably 5 to 10, most preferably 5 to 8, each column packed with the same chiral stationary phase. In some embodiments, the column is packed with chiral stationary phase made of amylose tris(3,5-dimethylphenyl carbamate) immobilized on silica gel (available from Daicel as "Chiralpak® IA"). In some embodiments, the column is packed with a chiral stationary phase made of cellulose tris(3,5-dimethylphenyl carbamate) coated on silica gel (available from Daicel as "Chiralcel® OD"). In some embodiments, the chiral stationary phase is a silica gel-based stationary phase coated with 4-(3,5-dinitro benzamido)tetrahydrophenanthrene (available from Regis Technologies as "(S,S) Whelk-O® 1"). In some embodiments, the mobile phase comprises ethanol and hexanes. In some embodiments, the hexanes are replaced by heptanes, n-heptane, cyclohexane or methylcyclohexane. In some embodiments, the ethanol is present in an amount of about 10% to about 100% by volume, about 10% to about 25% by volume, or about 15% by volume. In some embodiments, the mobile phase comprises isopropanol and hexanes. In some embodiments the hexanes are replaced by heptanes, n-heptane, cyclohexane or methylcyclohexane. In some embodiments, the isopropanol is present in an amout of about 10% to about 25% by volume. In some embodiments, the mobile phase comprises methyl-tent-butyl ether and hexanes. In some embodiments, the hexanes are replaced by heptanes, n-heptane, cyclohexane or methylcyclohexane. In some embodiments, the methyl-tent-butyl ether is present in an amount of about 10% to about 100% by volume, about 50% to about 100% by volume, or about 90% to about 100% by volume. In some embodiments, the mobile phase comprises ethyl acetate and hexanes. In some embodiements, the hexanes are replaced by heptanes, n-heptane, cyclohexane or methylcyclohexane. In some embodiments, the ethyl acetate is present in amount of about 10% to about 100% by volume, about 50% to about 100% by volume, or about 75% by volume. In some embodiments, the mobile phase comprises tetrahydrofuran and hexanes. In some embodiments, the hexanes are replaced by heptanes, n-heptane, cyclohexane or methylcyclohexane. In some embodiments, the tetrahydrofuran is present in an amount of about 10% to about 100% by volume, about 10% to about 50% by volume, or about 25% by volume. In some embodiments, the chromatography unit is operated at a temperature of about 5° C. to about 50° C., at about 10° C. to about 30° C., or at about 25° C., or at ambient temperature.

In some embodiments, the chromatographic method employed is batch preparative chromatography, supercritical fluide chromatography (SFC), a cyclojet process, a continuous multicolumn chromatography process, a simulated moving bed process, a Varicol™ process, or a PowerFeed process.

In some embodiments, the chiral stationary phase comprises an interacting agent which is an enantiomerically enriched resolving agent, immobilized to an inert carrier material by, for example, chemically binding or by insolubilizing via cross-linking. The suitable inert carrier material can be macroporous, e.g crosslinked polystyrene, polyacrylamide, polyacrylate, alumina, kieselgur (diatomaceous), quartz, kaolin, magnesium oxide, titanium dioxide or silica gel. In some embodiments, the inert carrier material is Silicagel.

In some embodiments, the chiral stationary phase is a member of the amylosic or cellulosic class of polysaccharides that is selected from cellulose phenyl carbamate derivatives, such as cellulose tris(3,5-dimethylphenyl)carbamate (available from Daicel Chemical Industries, Ltd. (Daicel) as "Chiralcel® OD" or "Chiralpak® IB", wherein the carbamate derivative is bonded to the cellulosic backbone); cellulose tribenzoate derivatives, such as cellulose tri 4-methylbenzoate (available from Daicel as "Chiralcel® OJ"); cellulose tricinnamate (available from Daicel as "Chiralcel® OK"); amylase phenyl and benzyl carbamate derivatives, such as amylose tris[(S)-α-methyl benzylcarbamate] (available from Daicel as "Chiralpak® AS"); amylose tris(3,5-dimethylphenyl)carbamate (available from Daicel as "Chiralpak® AD" or "Chiralpak® IA", wherein the carbamate derivative is bonded to the amylosic backbone); amylose 3,4-substituted phenyl carbamate or amylose 4-substituted phenyl-carbamate; and amylose tricinnamate. In some embodiments, the chiral stationary phase comprises Chiralpak® IA or Chiralpak AD. In some embodiments, the chiral stationary phase comprises Chiralcel® OD. In some embodiments, the chiral stationary phase is a member of the Pirkle-phases family such as 3,5-dinitrobenzoyl derivatives of phenylglycine (available from Regis Technologies Inc as "phenylglycine"; 5-dinitrobenzoyl derivative of leucine (available from Regis Technologies Inc as "Leucine"); N-3,5-dinitrobenzoyl-3-amino-3-phenyl-2-(1,1-dimethylethyl)-propanoate (available from Regis Technologies Inc as "β-GEM 1"); dimethyl N-3,5-dinitrobenzoyl-amino-2,2-dimethyl-4-pentenyl phosphonate (available from Regis Technologies Inc as "α-BURKE 2"); 3-(3,5-dinitrobenzamido)-4-phenyl-β-lactam (available from Regis Technologies Inc as "PIRKLE 1-J"); 3,5-Dintrobenzoyl derivative of diphenylethylenediamine (available from Regis Technologies Inc as "ULMO"); 4-(3,5-dinitro benzamido)tetrahydrophenanthrene (available from Regis technologies Inc. as "(S,S) Whelk-O® 1" and "(R,R) Whelk-O® 1" or "(S,S) Whelk-O®2" and "(R,R) Whelk-O®2"); 3,5-dinitro-benzoyl derivative of 1,2-diaminocyclohexane, (available from Regis technologies Inc. as "DACH-DNB). In some embodiments, the chiral stationary phase comprises "(S,S) Whelk-O® 1" or "(R,R) Whelk-O® 1.

In some embodiments, the particle diameter of the chiral stationary phase is usually 1 to 300 μm, 2 to 100 μm, 5 to 75 μm, or 10 to 30 μm.

In some embodiments, the mobile phase is non-polar, polar protic or aprotic solvents or mixture thereof. In some embodiments, the mobile phase is a mixture of carbon dioxide and polar protic solvents. Suitable non polar solvents include, for example, hydrocarbons, for instance, n-pentane, n-hexane, hexanes, n-heptane, heptanes, cyclohexane, and methylcyclohexane. Suitable protic or aprotic solvents include, for example, alcohols, in particular methanol, ethanol, 1-propanol, 2-propanol, 1-butanol, 2-butanol, isobutanol, tert butanol, ethers, for instance methyl tert butyl ether, esters, for instance ethylacetate, halogenated hydrocarbons and acetonitrile. In some embodiments, the non-polar solvent is n-heptane. In some embodiments, the protic or aprotic solvent is ethanol, 2-propanol or methyl-tert-butyl ether. In some embodiments, the mobile phase is a mixture of heptane and ethanol. In some embodiments, the ethanol is present in the mobile phase in an amount of about 10% to about 100%, about 10% to about 25%, or about 15%. In some embodiments, the mobile phase is a mixture of heptane and 2-propanol. In some embodiments, the 2-propanol is present in the mobile phase in an amount of about 10% to about 100%, about 10% to about 25%, or about 20%. In some embodiments, the mobile phase is a mixture of heptane and methyl-tert-butyl ether. In some embodiments, the methyl-tent-butyl ether is present in the mobile phase in an amount of about 10% to about 100%, about 75% to about 100%, or about 90% to about 100%.

In some embodiments, the chromatography is carried out at a temperature range of about 0° C. to 50° C., about 10° C. to 30° C., or about 25° C.

In some embodiments, the desired enantiomer is recovered at an enantiomeric purity greater than about 90%, greater than about 98%, or greater than about 99.0%. In some embodiments, the desired enantiomer is recovered with a yield greater than about 70%, greater than about 90%, or greater than about 95%.

In some embodiments, the desired enantiomer is produced at a rate throughput greater than about 0.1 kg, 0.4 kg, or 0.8 kg pure enantiomer per day per kilogram of stationary phase.

In some embodiments, the separated enantiomers are recovered after evaporation under reduced pressure as concentrated oils.

In some embodiments, the mobile phase used in the chiral chromatography process is recycled.

In some embodiments, the undesired enantiomer is racemized and reused as racemic feed for the chiral separation.

In some embodiments, the desired enantiomer is recovered in at least a 91%, 92%, 93%, 94%, 95%, 96%, 97%, 98%, or 99% yield, or preferably greater than 90% or 95% yield.

Alternatively, the racemate of Formula Ia can be reacted with a chiral acid (E-1), such as (+)-dibenzoyl-D-tartaric acid, to form a chiral salt (E-2) (Scheme 7). After crystallization, filtration, and treatment with base, a composition comprising an enantiomeric excess of the (R)- or (S)-enantiomer of the compound of Formula Ia is produced. The protecting group can then be removed to produce an enantiomeric excess of the (R)- or (S)-enantiomer of the compound of Formula III.

Scheme 7

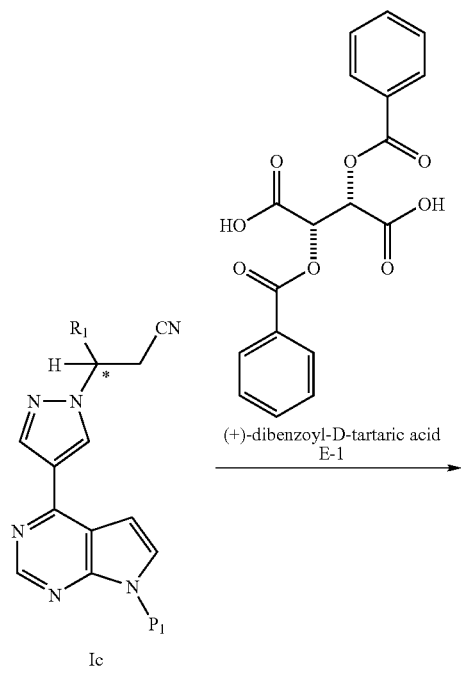

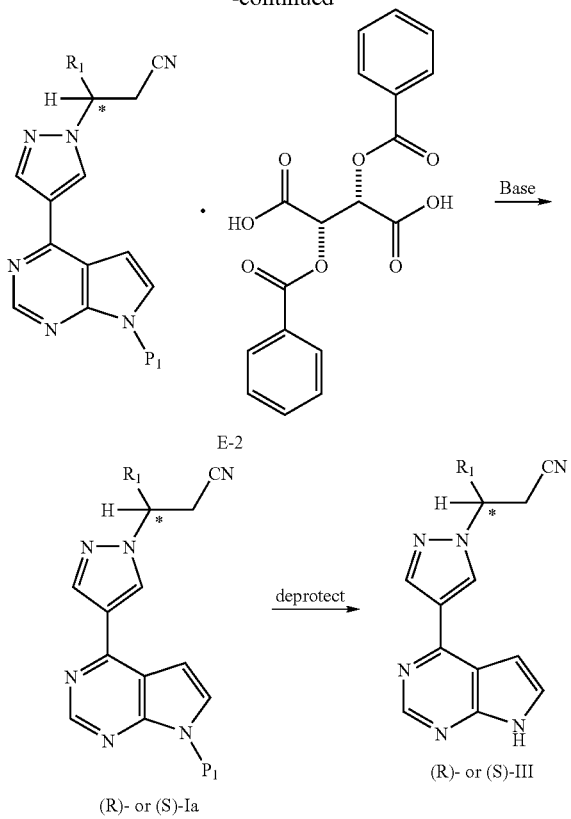

Accordingly, in some embodiments, the present invention provides a process of preparing a composition comprising an enantiomeric excess of a (R)- or (S)-enantiomer of a compound of Formula Ia:

Ia

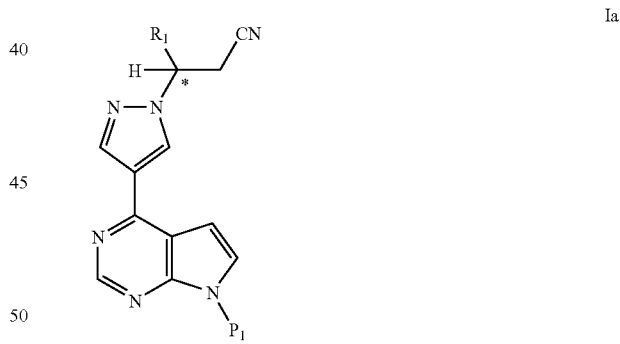

comprising:
(a) reacting a composition comprising a racemate of a compound of Formula Ia with a chiral acid in the presence of a solvent to form a salt of a compound of Formula Ia;
(b) separating a composition comprising an enantiomer excess of a chiral salt of the (R)- or (S)-enantiomer of the compound of Formula Ia; and
(c) treating the chiral salt with a base to form a composition comprising an enantiomeric excess of the (R)- or (S)-enantiomer of the compound of Formula Ia;
wherein:
* indicates a chiral carbon;
$R_1$ is selected from $C_{3-7}$ cycloalkyl, $C_{1-6}$ alkyl, and $C_{1-6}$fluoroalkyl; and
$P_1$ is a protecting group.

Any chiral acid useful for chiral resolution can be used. In some embodiments, the chiral acid is selected from optically active forms of mandelic acid, 2-chloromandelic acid, camphorsulfonic acid, tartaric acid, lactic acid, malic acid, 3-bromocamphor-8-sulfonic acid, 3-bromocamphor-10-sulfonic acid, 10-camphorsulfonic acid, dibenzoyl tartaric acid, di-p-toluoyltartaric acid, 2-amino-7,7-dimethylbicyclop[2,2,1] heptan-1-methylene sulfonic acid, and 2-acrylamide-7,7-dimethylbicyclo[2,2,1] heptan-1-methylene sulfonic acid. In some embodiments, the chiral acid is (+)-dibenzoyl-D-tartaric acid.

In some embodiments, the solvent comprises acetonitrile, tetrahydrofuran, acetone, or combination thereof. In some embodiments, the solvent is about a 90:15:15 ratio by volume of acetonitrile, tetrahydrofuran, and acetone (15.0 mL, 0.204 mol).

In some embodiments, the enantiomeric excess is equal to or greater than about 10%, about 20%, about 30%, about 40%, about 50%, about 60%, about 70%, about 80%, about 90%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 99.99%.

In some embodiments, the separating involves cooling the solvent to precipitate the chiral salt. In some embodiments, the separating involves adding a second solvent to precipitate the chiral salt. In some embodiments, the separating comprises filtering the solvent to recover the chiral salt. In some embodiments, the solvent comprises acetonitrile, tetrahydrofuran, acetone, or combination thereof. In some embodiments, the reacting is conducted at a temperature of about room temperature to about 60° C.

Any base suitable for preparing the free base of the chiral salt can be utilized in the process. In some embodiments, the base is an alkali metal or alkaline earth metal hydroxide or carbonate. In some embodiments, the base is an alkali metal hydroxide. In some embodiments, the base is sodium hydroxide. In some embodiments, the treating comprises adding an aqueous solution of base to a solution of the chiral salt, followed by separation of the solution from the aqueous solution. In some embodiments, the process further comprises removal of the solvent.

In addition to the processes for chiral enrichment described supra, undesired enantiomers of compounds of Formula Ia can be converted to racemic material by base-catalyzed retro-Michael addition to form the compound of Formula IV, followed by reaction with the acrylonitrile of Formula D-1 to produce the racemic Michael adduct of Formula Ia as shown in Scheme 8. Alternatively, the undesired enantiomer of Formula Ia can be epimerized in the presence of a Michael acceptor of Formula D-1 to give the racemate of Formula Ia as shown in Scheme 8. The racemate can then be resolved to give the desired enantiomer by the chiral column separation and chiral salt methods described supra.

Scheme 8

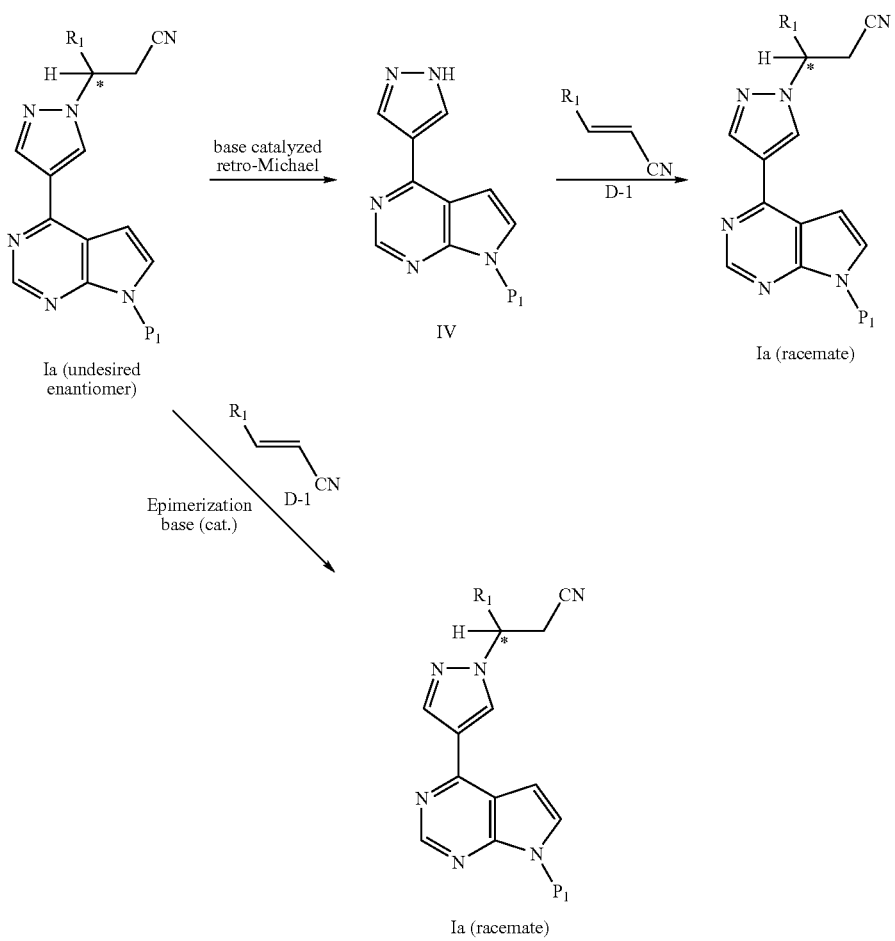

Accordingly, the present invention provides a process of preparing a composition comprising a racemate of a compound of Formula Ia:

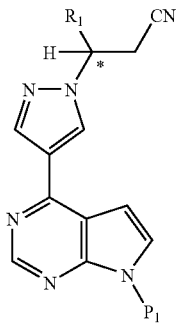

comprising:

a) treating a composition comprising an enantiomeric excess of the (R)- or (S)-enantiomer of a compound of Formula Ia with a compound of Formula D-1

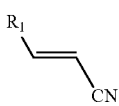

in the presence of a first base under conditions sufficient to form a compound of Formula IV:

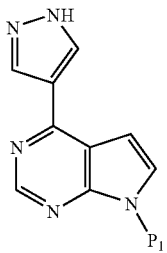

and (b) reacting a compound of Formula IV with a compound of Formula D-1 in the presence of a second base; wherein:

* indicates a chiral carbon;
$P_1$ is a protecting group; and
$R_1$ is selected from $C_{3-7}$ cycloalkyl, $C_{1-6}$ alkyl, and $C_{1-6}$ fluoroalkyl.

In some embodiments, the first base is an alkali metal or alkaline earth metal base. In some embodiments, the first base is an alkali metal or alkaline earth metal base alkoxide, hydroxide or carbonate. In some embodiments, the first base is an alkali metal or alkaline earth carbonate. In some embodiments, the first base is an alkaline earth carbonate. In some embodiments, the first base is cesium carbonate. In some embodiments, the first base is an alkali metal t-butoxide. In some embodiments, the first base is potassium t-butoxide.

In some embodiments, the second step is conducted in an organic solvent at room temperature in the presence of a catalytic amound of the second base. The second base can be suitable solvent or second base for aza-Michael reactions. In some embodiments, the solvent is acetonitrile or dimethylformide (DMF). In some embodiments, the second base is a tetraalkylammonium halide, tetraalkylammonium hydroxide, guanidine, amidine, hydroxide, alkoxide, silicate, alkali metal phosphate, oxide, tertiary amine, alkali metal carbonate, alkali metal bicarbonate, alkali metal hydrogen phosphate, phosphine, or alkali metal salt of a carboxylic acid. In some embodiments, the base is tetramethyl guanidine, 1,8-diazabicyclo(5.4.0)undec-7-ene, 1,5-diazabicyclo(4.3.0)non-5-ene, 1,4-diazabicyclo(2.2.2)octane, tert-butyl ammonium hydroxide, sodium hydroxide, potassium hydroxide, sodium methoxide, sodium ethoxide, tripotassium phosphate, sodium silicate, calcium oxide, triethylamine, sodium carbonate, potassium carbonate, sodium bicarbonate, potassium bicarbonate, potassium hydrogen phosphate, triphenyl phosphine, triethyl phosphine, potassium acetate, or potassium acrylate. In some embodiments, the second base is 1,8-diazabicyclo[5.4.0]undec-7-ene (DBU) or potassium carbonate. In some embodiments, the second base is DBU. In some embodiments, the base is present in a catalytic amount. In some embodiments, the amount of second base is about about 0.1 to about 5 equivalents, or about 0.5 to about 3 equivalents, or about 0.1 to about 0.5 equivalents. In some embodiments, the reaction is complete in about 1 to about 3 hours.

Alternatively, the present invention further provides a process of preparing a composition comprising a racemate of a compound of Formula Ia:

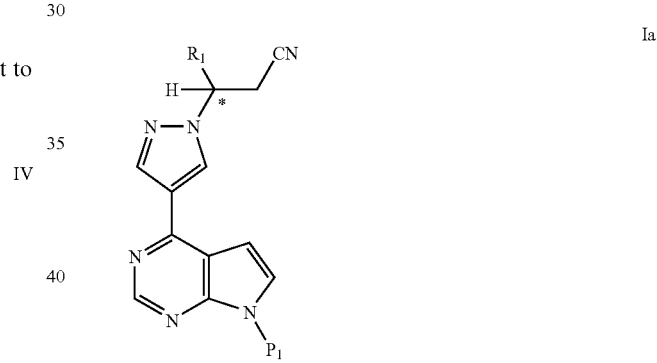

comprising treating a composition comprising an enantiomeric excess of the (R)- or (S)-enantiomer of a compound of Formula Ia with a compound of Formula D-1:

in the presence of a base under conditions sufficient to form the racemate of the compound of Formula Ia; wherein:

* indicates a chiral carbon;
$P_1$ is a protecting group; and
$R_1$ is selected from $C_{3-7}$ cycloalkyl, $C_{1-6}$ alkyl, and $C_{1-6}$ fluoroalkyl.

In some embodiments, the base is an alkali metal or alkaline earth metal base. In some embodiments, the base is an alkali metal or alkaline earth metal base alkoxide, hydroxide or carbonate. In some embodiments, the base is an alkali metal or alkaline earth carbonate. In some embodiments, the base is an alkaline earth carbonate. In some embodiments, the base is cesium carbonate. In some embodiments, the base is an alkali metal t-butoxide. In some embodiments, the base is potassium t-butoxide.

The racemate of compounds of Formula Ia:

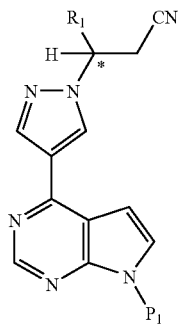

Ia can be prepared by a process comprising treating a compound of Formula IV:

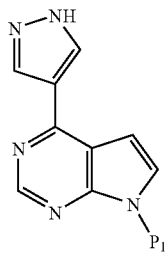

IV with a compound of Formula D-1:

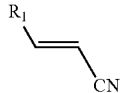

D-1 under conditions sufficient to form the racemate of the compound of Formula Ia;

wherein:

* indicates a chiral carbon;

$P_1$ is a protecting group; and $R_1$ is selected from $C_{3-7}$ cycloalkyl, $C_{1-6}$ alkyl, and $C_{1-6}$ fluoroalkyl.

3-Substituted acrylnitriles of Formula D-1 are prepared as shown in Scheme 9. Olefination of an aldehyde of Formula D-2, such as cyclopentanecarbaldehyde or cyclopropanecarbaldehyde, with a Wittig-type reagent having a ylide of formula —CH$_2$CN, such as diethyl cyanomethylphosphonate, is conducted in an organic solvent, such as THF, under the influence a base, such as potassium tert-butoxide, at about 0 to about 5° C. In some embodiments, the resulting 3-substituted acrylnitriles of Formula D-1 can be purified by vacuum distillation.

Scheme 9

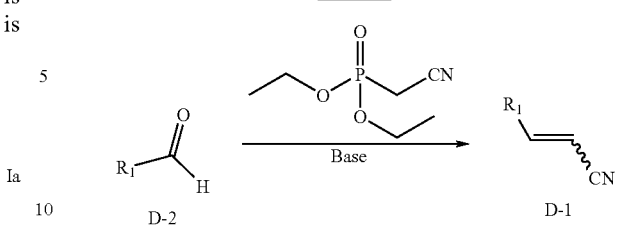

Accordingly, in some embodiments, the compound of Formula D-1:

D-1 is prepared by a process comprising reacting a compound of Formula D-2:

D-2 with a Wittig-type reagent having a ylide of formula —CH$_2$CN in the presence of a base; wherein $R_1$ is selected from $C_{3-7}$ cycloalkyl, $C_{1-6}$ alkyl, and $C_{1-6}$ fluoroalkyl.

As used herein, the term "Wittig-type reagent" refers to reagents used in the Wittig reaction, the Wadsworth-Emmons reaction, and the Horner-Wittig reaction as described in the art (see e.g., Carey and Sundberg, Advanced Organic Chemistry, Part B: Reactions and Synthesis, 4th ed., Kluwer Academic/Plenum Publishers: New York, pages 111-119 (2001); and March, Advanced Organic Chemistry: Reactions, Mechanisms, and Structure, 3rd ed., John Wiley & Sons: New York, pages 845-855 (1985), each of which is incorporated herein by references in its entirety). Exemplative Wittig-type reagents containing a cyanomethyl or cyanomethyl glide group include, but are not limited to, compounds of general formula (R'O)$_2$P(=O)-L-R$^1$, R"$_3$P(+)-L(-)-R$^1$, R"$_3$P(+)-L-R$^1$X; R"$_2$P(=O)-L-R$^1$, and (R'N)$_2$P(=O)-L-R$^1$, wherein R' is $C_{1-6}$ alkoxy or optionally substituted phenyl; R" is optionally substituted phenyl; L is —CH$_2$— or —CH—; and R$^1$ is cynao; and X is an anion (e.g., halo anion, such as chloride). In some embodiments, the Wittig-type reagent is diethyl cyanomethyl phosphate. In some embodiments, the reacting of the compound of Formula D-2 with the Wittig-type reagent in the presence of a base. In some embodiments, the base is a strong base. In some embodiments, the base is potassium t-butoxide, sodium t-butoxide, sodium hydride, sodium ethoxide, sodium hydroxide, potassium carbonate, or sodium carbonate. In some embodiments, the base is an alkali metal alkoxide. In some embodiments, the base is an alkali metal t-butoxide. In some embodiments, the base is potassium t-butoxide. In some embodiments, the olefination of the aldehyde of Formula D-2 with a Wittig-type reagent is conducted in an organic solvent, such as THF, under the influence a base, such as potassium tert-butoxide, at a temperature from about 0 to about 5° C. In some embodiments, the base is present in about 1 to about 1.2 equivalents, or about 1.05 to about 1.1 equivalents, with respect to the compound of Formula D-2. In some embodiments, the Wittig-type reagent is present in about 1 to about 1.2 equivalents, or about 1.05 to about 1.1 equivalents with respect to the compound of Formula D-2. In some embodiments, the Wittig-type reagent is (methoxymethyl) triphenylphosphinium chloride.

In other embodiments, the processes further comprise reacting the compound of Formula Ia under deprotection conditions to form a compound of Formula III:

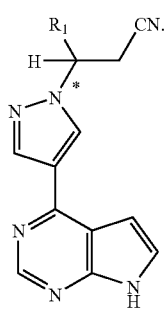

III

Appropriate $P_1$ groups and deprotection methods include, but are not limited to those described supra.

In some embodiments, the process further comprises reacting a compound of Formula III with phosphoric acid to form a phosphate salt of the compound of Formula III.

V. Routes to Intermediate Compounds i) Higher Yield Routes to Intermediate Compounds of Formula IV Compounds of Formula IV are important intermediates in the various synthetic routes for the compounds of Formula III described supra. These compounds are generally formed by Suzuki coupling processes. Suzuki coupling of protected protected 7H-pyrrolo[2,3-d]pyrimidine derivative of Formula X with a unprotected pyrazole borate derivative of Formula XV using a palladium catalyst result in a lower yield (Scheme 10). Without wishing to be bound by any particular theory, it is believed that the lower yields result from interference of unprotected amine functionality in the Suzuki coupling reaction.

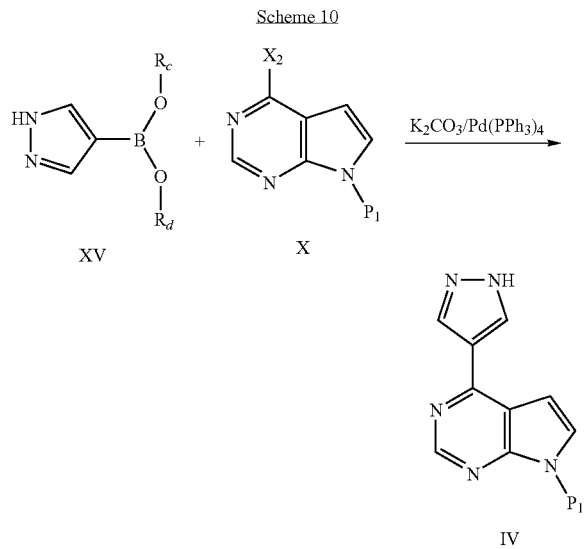

Accordingly, a new process for preparing the compound of Formula IV was developed involving the use of protected pyrazole borate derivative of Formula XIII (Scheme 11). Accordingly, the compound of Formula XIII can be generated and then reacted with the the protected 7H-pyrrolo[2,3-d] pyrimidine derivative of Formula X to form a compound of Formula XII, followed by deprotection to give the compound of Formula IV. In some embodiments, the compound of Formula XIII can be formed by in-situ protection of pyrazole pinacol borate. For example, when $P_2$ is 1-(ethoxy)ethyl, a pyrazol-4-yl pinacol borate can be reacted with vinyl ether in-situ to generate the protected compound of Formula XIII. The Suzuki coupling reaction between the protected pyrazole pinacol borate of Formula XIII and the compound of Formula X then proceeds smoothly under the typical Suzuki reaction conditions to generate the compound of Formula IV in higher yield after the acidic work-up of the corresponding coupling intermediate of Formula XII.

In other embodiments, the compound of Formula XIII is the isolated and fully characterized compound. For example, the use of isolated, fully characterized compound of Formula XIII, wherein $P_2$ is 1-(ethoxy)ethyl and the borate moiety is a pinacol group, afforded the product of Formula XII, and subsequently the compound of Formula IV in better yield and purity.

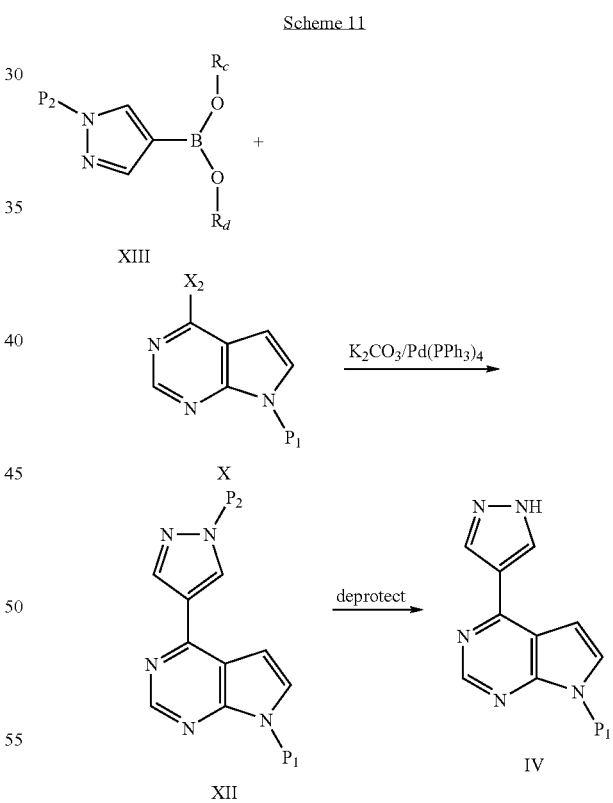

In other embodiments, the compound of Formula X can be in-situ generated from a compound of Formula XI and then subsequently reacted with the compound of Formula XIII. This eliminates the necessity of having to isolate and purify the compound of Formula X during large-scale production. For example, when $P_1$ is SEM, the compound of Formula XI can be reacted with sodium hydride and SEM chloride to generate the compound of Formula X in situ (Scheme 12).

Scheme 12

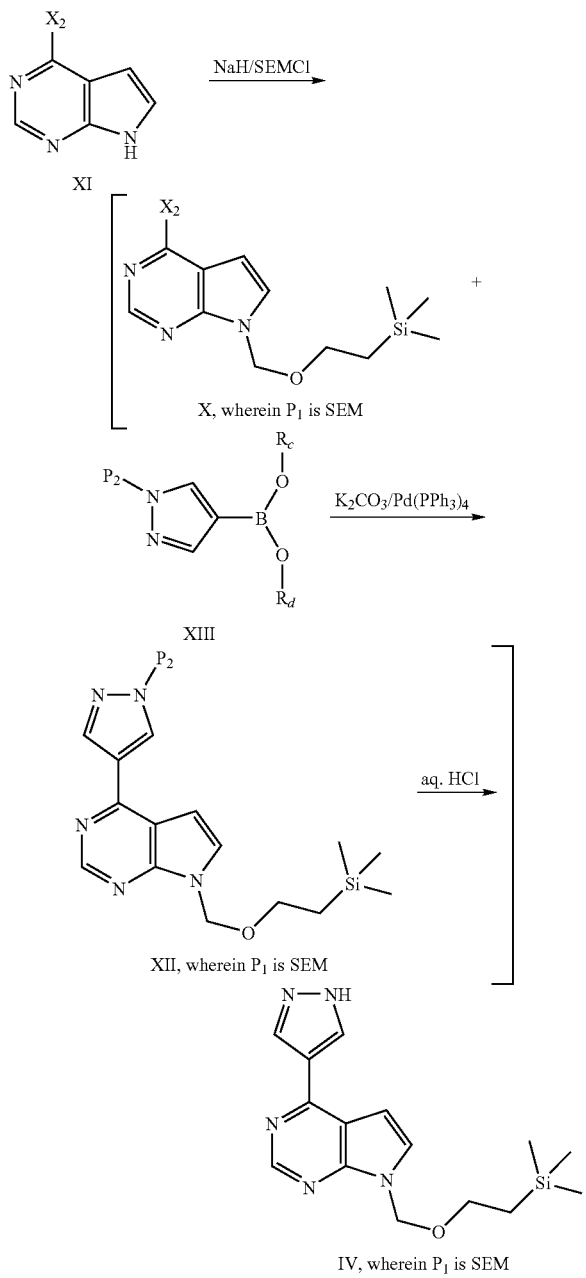

Accordingly, the present invention provides a process of preparing a compound of Formula XII:

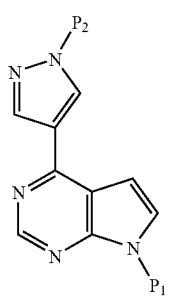

comprising reacting a compound of Formula X:

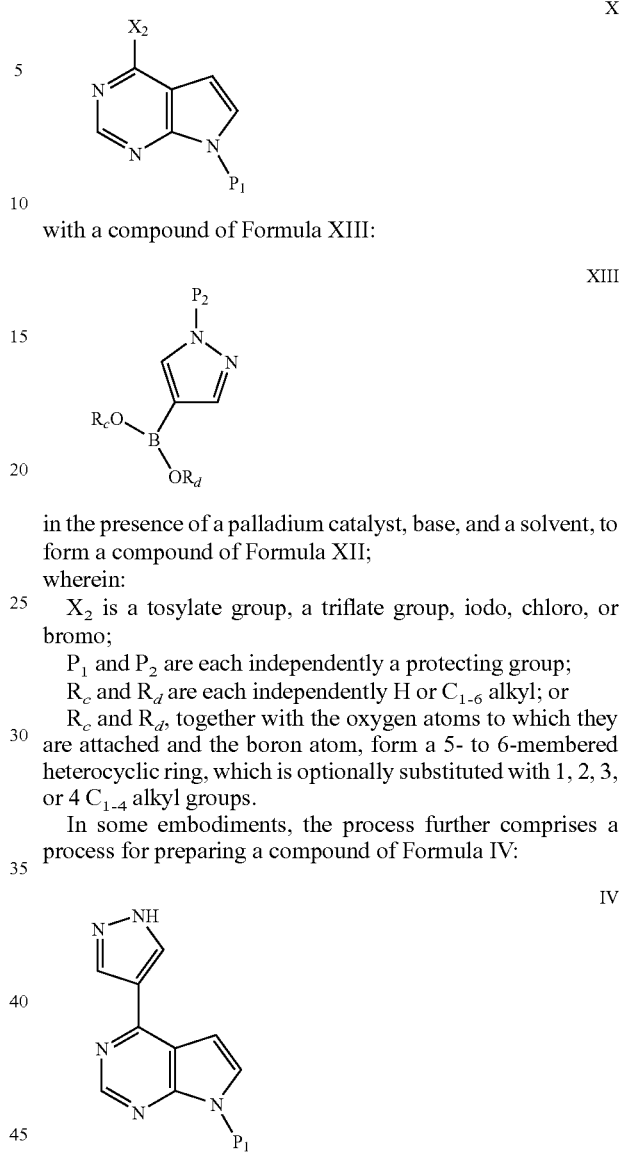

with a compound of Formula XIII:

in the presence of a palladium catalyst, base, and a solvent, to form a compound of Formula XII; wherein:

$X_2$ is a tosylate group, a triflate group, iodo, chloro, or bromo;

$P_1$ and $P_2$ are each independently a protecting group;

$R_c$ and $R_d$ are each independently H or $C_{1-6}$ alkyl; or $R_c$ and $R_d$, together with the oxygen atoms to which they are attached and the boron atom, form a 5- to 6-membered heterocyclic ring, which is optionally substituted with 1, 2, 3, or 4 $C_{1-4}$ alkyl groups.

In some embodiments, the process further comprises a process for preparing a compound of Formula IV:

comprising reacting the compound of Formula XII under deprotection conditions to produce a compound of Formula IV;

wherein:

$P_1$ and $P_2$ are each independently a protecting group; and $R_c$ and $R_d$ are each independently H or $C_{1-6}$ alkyl; or $R_c$ and $R_d$, together with the oxygen atoms to which they are attached and the boron atom, form a 5- to 6-membered heterocyclic ring, which is optionally substituted with 1, 2, 3, or 4 $C_{1-4}$ alkyl groups.

In some embodiments, the compound of Formula XIII is:

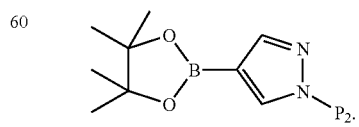

In some embodiments, $X_2$ is chloro, bromo, or iodo. In some embodiments, $X_2$ is chloro.

The Suzuki coupling reaction can be initiated using a number of palladium(0) and palladium(II) catalysts and performed under conditions known in the art (see, e.g., Miyaura and Suzuki, *Chem. Rev.* 1995, 95, 2457-2483, which is hereby incorporated in its entirety). In some embodiments, the palladium catalyst is $Pd(PPh_3)_4$ and $Pd(dppf)_2Cl_2$.

In some embodiments, the palladium catalyst is tetrakis(triphenylphosphine)palladium(0) or tetrakis(tri(o-tolyl)phosphine)palladium(0). In some embodiments, the palladium catalyst is tetrakis(triphenylphosphine)palladium(0).

In some embodiments, the palladium catalyst loading is from about $1\times10^{-4}$ to about 0.1 equivalents. In some embodiments, the palladium catalyst loading is from about 0.0010 to about 0.0015 equivalents. In some embodiments, the stoichiometric ratio of the compound of Formula X to the compound of Formula XIII is from about 1:1.05 to about 1:1.35.

In some embodiments, the solvent comprises water and an organic solvent. In some embodiments, the organic solvent is 1,4-dioxane, 1-butanol, 1,2-dimethoxyethane (DME), 2-propanol, toluene or ethanol, or a combination thereof. In some embodiments, the organic solvent comprises DME. In some embodiments, the organic solvent comprises DMF.

In some embodiments, the base is an inorganic base. In some embodiments, the base is an organic base. In some embodiments, the base is an alkali metal carbonate. In some embodiments, the base is potassium carbonate ($K_2CO_3$). In some embodiments, two to five equivalents of base (e.g., $K_2CO_3$) are used.

In some embodiments, the Suzuki coupling reaction is conducted at a temperature of about 80 to about 100° C. In some embodiments, the reaction is carried out for two to twelve hours. In some embodiments, the compound of Formula XII can be optionally isolated from aqueous work-up of the Suzuki coupling reaction mixture or directly used.

In some embodiments, the compound of X is selected from those in Scheme 13 and can be formed starting from a compound of Formula XI as shown. In some embodiments, $X_2$ is chloro. In some embodiments, the compounds of Formula X are isolated or in-situ generated as the starting materials for subsequent Suzuki reaction with or without further purification. In some embodiments, the $P_1$ protecting group is one of those listed supra.

Scheme 13

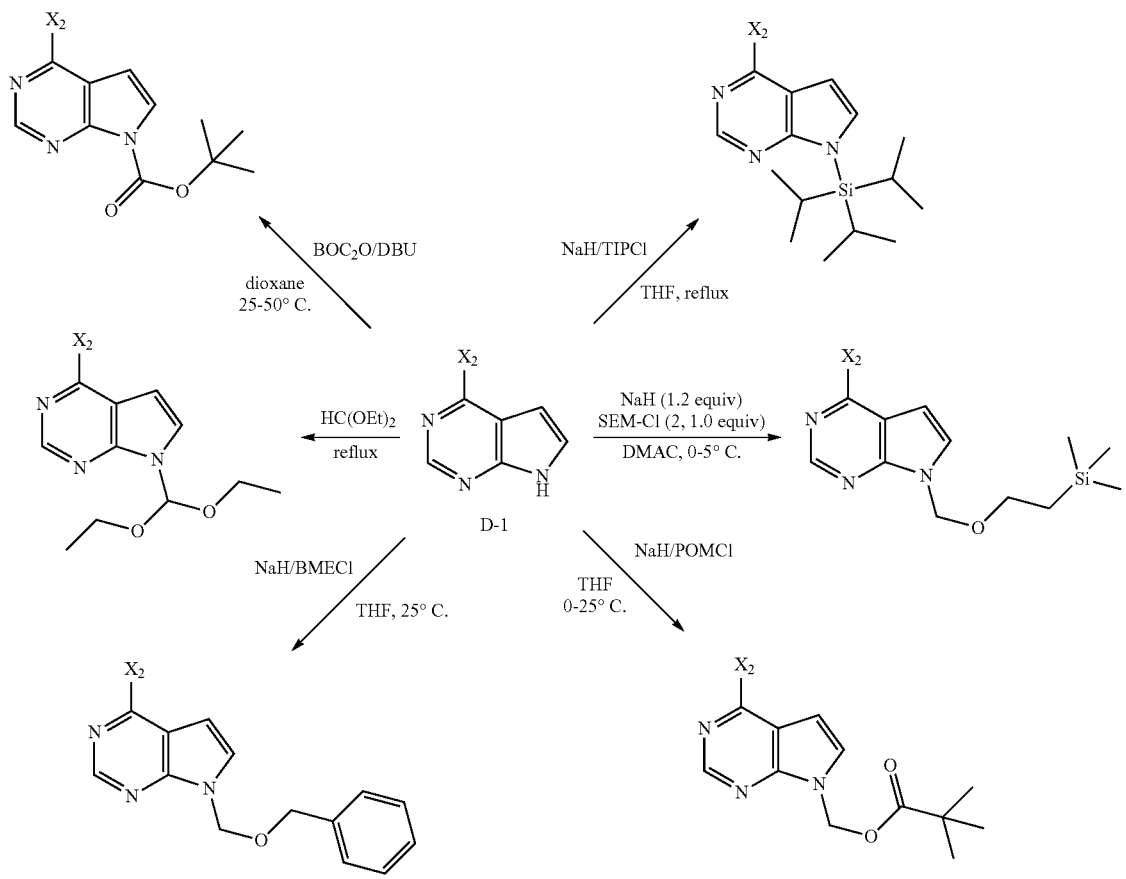

Appropriate $P_2$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, $P_2$ is a protecting group which can be selectively removed under conditions which do not displace the $P_1$ protecting group. In some embodiments, $P_2$ is protecting group which can be removed under acidic conditions at room temperature, at a temperature from about 15° C. to about 40° C., or at a temperature from about 15° C. to about 30° C. In some embodiments, $P_2$ is a group which is deprotected under room temperature acidic conditions. In some embodiments, $P_2$ is 1-(ethoxy)ethyl, tri($C_{1-6}$ alkyl)silyl (e.g., t-butyldimethylsilyl or triisopropylsilyl), p-methoxybenzyl (PMB), triphenylmethyl (Tr), diphenylmethyl, hydroxymethyl, methoxymethyl (MOM), diethoxymethyl, or t-butyldimethylsilylmethyl. In some embodiments, $P_2$ is 1-(ethoxy)ethyl.

Treatment of the compound of Formula XII to remove the $P_2$ group can be accomplished by methods known in the art for the removal of particular protecting groups for amines, such as those in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, the treating comprises treating the compound of Formula XII under acidic conditions (e.g., hydrochloric acid or trifluoroacetic acid) at room temperature, at a temperature from about 15° C. to about 40° C., or at a temperature from about 15° C. to about 30° C. In some embodiments, the treating comprises treating the compound of Formula XII with an aqueous solution of from about 1 N to about 5 N hydrochloric acid at a temperature of from about 10° C. to about 30° C.

Appropriate $P_1$ groups include, but are not limited to, those described supra.

Compounds of Formula X can be formed by protecting a compound of Formula XI. Accordingly, in some embodiments, the process for preparing a compound of Formula X, comprises treating a compound of Formula XI:

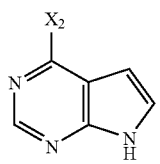

XI to add a protecting group in order to form a compound of Formula X

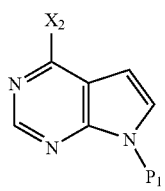

X wherein:

$X_2$ is a tosylate group, a triflate group, iodo, chloro, or bromo; and $P_1$ is a protecting group.

In some embodiments, the compound of Formula XI can be deprotonated with a base, preferably with sodium hydride (NaH), in an organic solvent, such as THF, 1,4-dioxane, 1,2-dimethoxyethane (DME), or N,N-dimethylacetamide (DMAC), at low temperature, preferably at a temperature of about 0 to about 5° C. before being treated with an electrophile, such as chloromethyl pivalate (POM-Cl) or trimethylsilylethoxymethyl chloride (SEM-Cl) to add the protecting group, $P_1$. The protected compound X is isolated or in-situ generated as the starting material for subsequent Suzuki reaction with or without further purification.

The intermediates formed from the processes described herein can be used as appropriate in the other processes described herein.

ii. Preparation of Pinacol Borates of Formula C-9

The present invention further provides methods of preparing pyrazol pinacol borates of Formula XVI, which are useful in the processes described herein. A specific subset of the compounds of Formula XVI are the 4-substituted pyrazole borate derivatives of Formula XIIIa, which can be substituted for the compounds of Formula XIII above.

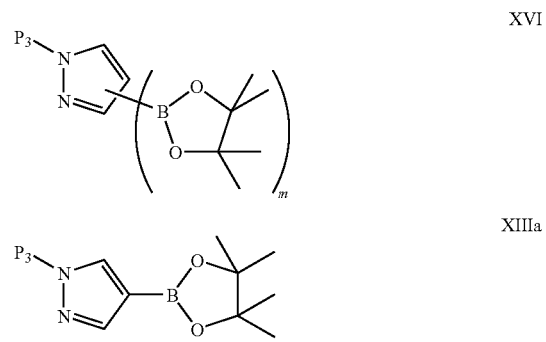

The compounds of XVI can be produced by the methods shown in Scheme 14. First, pyrazole is reacted with a halogenating agent to give the monohalo or dihalo pyrazole of Formula XIX (wherein $X_3$ is iodo or bromo and m is 1 or 2). The compound of Formula XIX is then protected to give the protected monohalo or dihalo pyrazole of Formula XVIII. The compound of Formula XVIII can then be treated with an alkyl Grignard or alkyllithium reagent, followed by treatment with a 2-alkoxy-4,4,5,5-tetramethyl-1,3,2-dioxaborolane reagent of Formula XVII, to form the desired pinacol borate of Formula XVI. In some embodiments, the $P_3$ protecting group is one which is stable to an aqueous workup of the Grignard or lithium reaction (e.g., wherein $P_3$ is 1-(ethoxy)ethyl). In other cases, $P_3$ is a protecting group is not stable to the aqueous workup of the Grignard or alkyllithium reaction. In this case, an additional protecting step will be needed to add the protecting group, $P_3$. In some embodiments, $P_3$ will be selected from the groups listed supra for $P_2$, for ease of processing.

Scheme 14

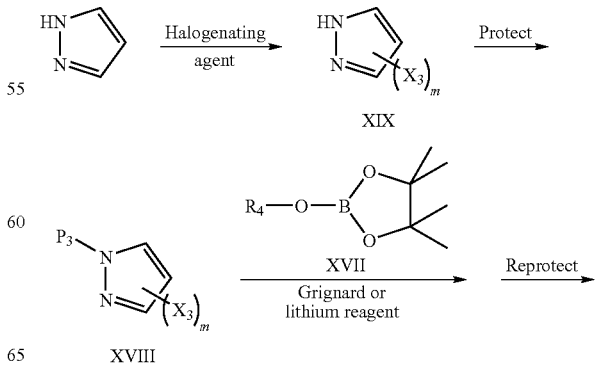

-continued

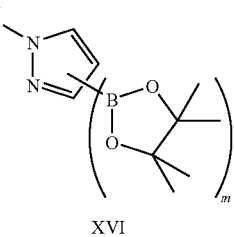

XVI

Accordingly, in some embodiments, the present invention provides a process for preparing a compound of Formula XVI:

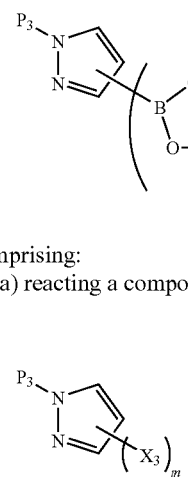

XVI comprising:
(a) reacting a compound of Formula XVIII

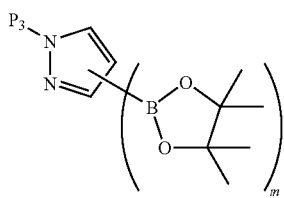

XVIII with about 1 or more equivalents of an $C_{1-6}$ alkyl Grignard reagent or $C_{1-6}$ alkyl lithium reagent followed by treating with about 1 or more equivalents of a compound of Formula XVII:

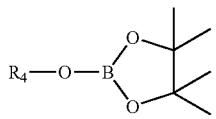

XVII and
(b) optionally, reprotecting the product of step (a) to give a compound of Formula XVI;
wherein:
$P_3$ is a protecting group;
$X_3$ is halogen;
$R_4$ is $C_{1-6}$ alkyl; and
m is an integer selected from 1 and 2.

In some embodiments, the ratio of the compound of Formula XVIII and the Grignard or lithium reagent is from about 1:1 to about 1:2.0, about 1:1 to about 1:1.8, or about 1:1 to about 1.2. Typically, the reaction is conducted in a non-protic organic solvent. In some embodiments, the solvent is tetrahydrofuran. In some embodiments, the ratio of the compound of Formula XVIII to the compound of Formula XVII is from about 1:1 to about 1:5, about 1:1 to about 1:3, or about 1:1.5 to about 1:2.5.

In some embodiments, a Grignard reagent is used in step (a) and the temperature is from –30° C. to about room temperature, about –30 to about 0° C., or about –25 to about –5° C. In some embodiments, a lithium reagent is used in step (a) and the temperature is from about –80° C. to about –60° C., or about –78° C.

In some embodiments, the Grignard reagent is isopropyl magnesium bromide, or adduct thereof.

In some embodiments, $R_4$ is $C_{1-4}$ alkyl. In some embodiments, $R_4$ is $C_{1-3}$ alkyl. In some embodiments, $R_4$ is methyl or isopropyl. In some embodiments, $X_3$ is iodo or bromo. In some embodiments, m is 2. In some embodiments, m is 1.

Compounds of Formula XVIII may be known in some cases (see, e.g., Abe, et al., *Heterocycles*, 2005, 66, 229-240; Korolev, et al., *Tet. Lett.* 2005, 46, 5751-5754; Vasilevsky, *Heterocycles*, 2003, 60(4), 879-886; and WO 2008/082198, each of which is incorporated herein by reference in its entirety). In other embodiments, the process further comprises a method for preparing a compound of Formula XVIII, comprising protecting a compound of Formula XIX:

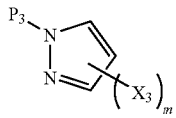

XIX wherein:
$P_3$ is a protecting group;
$X_3$ is halogen; and
m is an integer selected from 1 and 2.

Di-substituted and mono-substituted compounds of Formula XIX may be known in some case (see, e.g., WO 2007/043677; Vasilevsky, *Heterocycles*, 2003, 60(4), 879-886; WO 2008/013925; and Huttel, et al., *Ann.* 1959, 625, 55, each of which is incorporated herein by reference in its entirety). In some embodiments, the process further comprises a method for preparing a compound of Formula XIX, comprising reacting a 1H-pyrazole with a halogenating agent;
wherein:
$X_3$ is halogen; and
m is an integer selected from 1 and 2.

In some embodiments, $X_3$ is iodo or bromo. In some embodiments, the halogenating agent is selected from N-bromosuccinimide (NBS) or N-iodosuccinimide, wherein $X_3$ is bromo or iodo.

The intermediates formed from the processes described herein can be used as appropriate in the other processes described herein.

iii. Preparation of 4-Chloro-7H-pyrrolo[2,3-d]pyrimidine

Compounds of Formula XI are useful intermediates in some of the synthetic processes described herein. In some embodiments, the present invention provides a process for preparing 4-chloro-7H-pyrrolo[2,3-d]pyrimidine (XIa), which is a compound of Formula XI, wherein $X_2$ is chloro (Scheme 15).

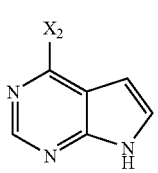

XI

-continued

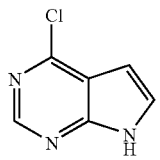

4-Chloro-7H-pyrrolo[2,3-d]pyrimidine (XIa) is synthesized by treating a compound of Formula F-1 with acid. The compound of Formula F-1 can be synthesized by treating a compound of Formula F-2 with a Wittig reagent having a glide of formula $CH_2OCH_3$. The compound of Formula F-2 can be formed starting from commercially available 4,6-dihydroxypyrimidine (compound F-4) by a Vilsmeier Formylation-chlorination to form a compound of Formula F-3, followed by selective ammonolysis to form a compound of Formula F-2.

Scheme 15

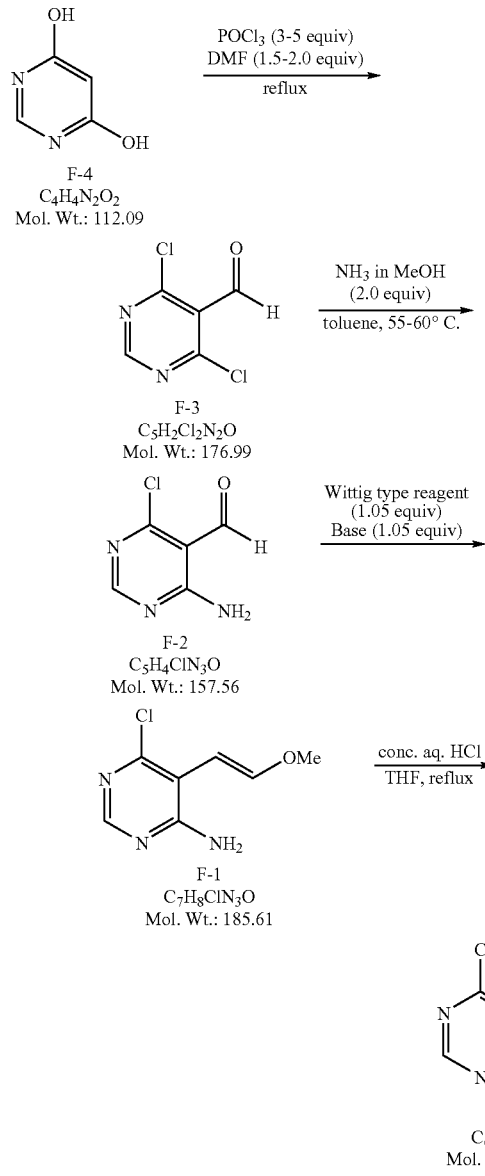

Accordingly, in some embodiments, the present invention provides a process for preparing a compound of Formula XIa:

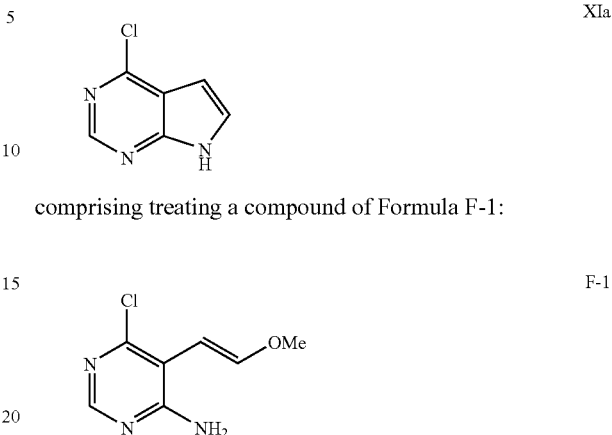

comprising treating a compound of Formula F-1:

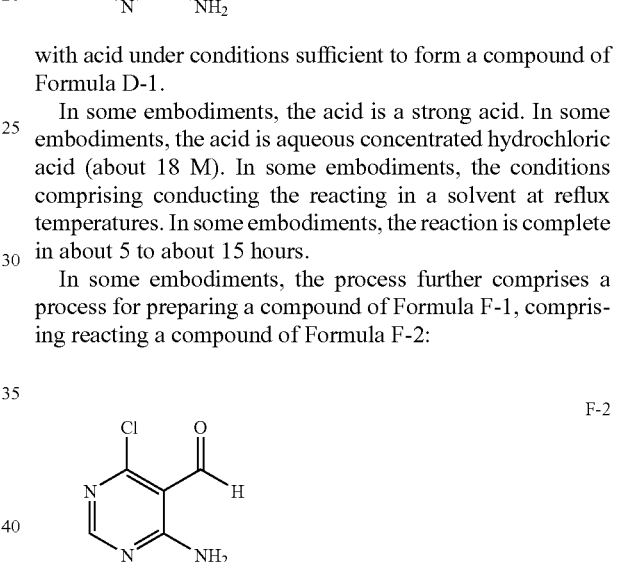

with acid under conditions sufficient to form a compound of Formula D-1.

In some embodiments, the acid is a strong acid. In some embodiments, the acid is aqueous concentrated hydrochloric acid (about 18 M). In some embodiments, the conditions comprising conducting the reacting in a solvent at reflux temperatures. In some embodiments, the reaction is complete in about 5 to about 15 hours.

In some embodiments, the process further comprises a process for preparing a compound of Formula F-1, comprising reacting a compound of Formula F-2:

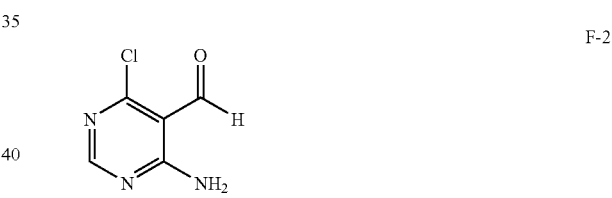

with about 1 or more equivalents of a Wittig-type reagent having a ylide of formula $—CH_2OCH_3$ in the presence of a base.

As used herein, the term "Wittig-type reagent" refers to reagents used in the Wittig reaction, the Wadsworth-Emmons reaction, and the Horner-Wittig reaction as described in the art (see e.g., Carey and Sundberg, Advanced Organic Chemistry, Part B: Reactions and Synthesis, 4th ed., Kluwer Academic/Plenum Publishers: New York, pages 111-119 (2001); and March, Advanced Organic Chemistry: Reactions, Mechanisms, and Structure, 3rd ed., John Wiley & Sons: New York, pages 845-855 (1985), each of which is incorporated herein by references in its entirety). Exemplative Wittig-type reagents containing a cyanomethyl or cyanomethyl ylide group include, but are not limited to, compounds of general formula $(R'O)_2P(=O)-L-R^1$, $R''_3P(+)-L(-)-R^1$, $R''_3P(+)-L-R^1X$; $R''_2P(=O)-L-R^1$, and $(R'N)_2P(=O)-L-R^1$, wherein R' is $C_{1-6}$ alkoxy or optionally substituted phenyl; R'' is optionally substituted phenyl; L is $—CH_2—$ or $—CH—$; and $R^1$ is methoxy; and X is an anion (e.g., halo anion, such as chloride). In some embodiments, the Wittig-type reagent is diethyl methoxymethyl phosphate. In some embodiments, the reacting of the compound of Formula F-1 with the Wittig-type reagent in the presence of a base. In some embodiments, the base is a strong base. In some embodiments, the base is potassium t-butoxide, sodium t-butoxide, sodium hydride, sodium ethoxide, sodium hydroxide, potassium carbonate, or sodium carbonate. In some embodiments, the base is an alkali metal alkoxide. In some embodiments, the base is an alkali metal t-butoxide. In some embodiments, the base is potassium t-butoxide. In some embodiments, the olefination of the aldehyde of Formula F-1 with a Wittig-type reagent is conducted in an organic solvent, such as THF, under the influence a base, such as potassium tert-butoxide, at a temperature from about 0 to about 5° C. In some embodiments, the base is present in about 1 to about 1.2 equivalents, or about 1.05 to about 1.1 equivalents, with respect to the compound of Formula F-1. In some embodiments, the Wittig-type reagent is present in about 1 to about 1.2 equivalents, or about 1.05 to about 1.1 equivalents with respect to the compound of Formula F-1. In some embodiments, the Wittig-type reagent is (methoxymethyl)triphenylphosphinium chloride.

In some embodiments, the process further comprises a process for preparing a compound of Formula F-2, comprising reacting a compound of Formula F-3:

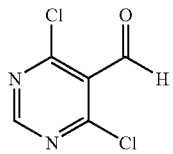

F-3 with about 2 or more equivalents of ammonia in a solvent.

In some embodiments, the solvent is methanol. In some embodiments, the ammonia is present in about two equivalents with respect to the compound of Formula F-2.

In some embodiments, the process further comprises a process for preparing a compound of Formula F-3, comprising reacting a compound of Formula F-4:

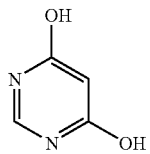

F-4 with a chlorinating agent.

In some embodiments, the chlorinating agent is phosphorous oxychloride. In some embodiments, the chlorinating agent is present in about or greater than about 2 equivalents, about or greater than about 3 equivalents, or about or greater than about 4 equivalents, or from about 3 to about 5 equivalents with respect to the compound of Formula F-3.

The intermediates formed from the processes described herein can be used as appropriate in the other processes described herein.

Specific Embodiments

In some embodiments, the present invention provides a process of preparing a composition comprising an enantiomeric excess of equal to or greater than 90% of the (R)-enantiomer of a compound of Formula III':

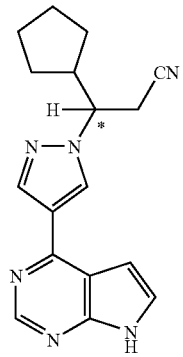

III' comprising:

(a) treating a compound of Formula XI':

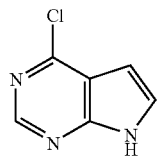

XI' with sodium hydride and N-pivaloyloxymethyl chloride to form a compound of Formula X':

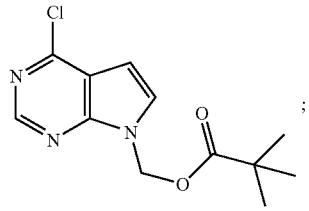

X'

(b) treating the compound of Formula X' with a compound of Formula XIII':

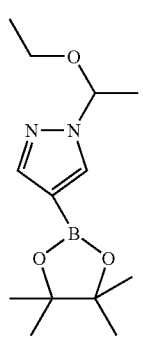

XIII' in the presence of Pd(triphenylphosphine)$_4$, potassium carbonate, and a solvent, to form a compound of Formula XII':

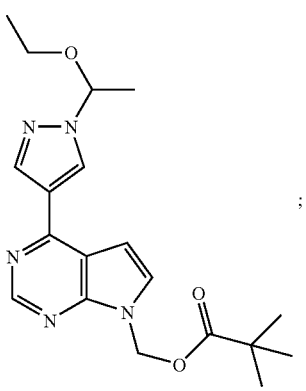

(c) reacting the compound of Formula XII' under deprotection conditions to give a compound of Formula IV':

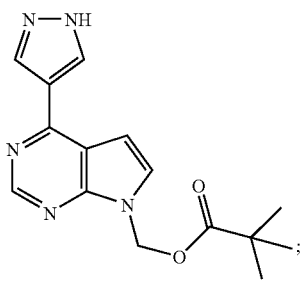

(d) reacting the compound of Formula IV'' with a compound of Formula XIV':

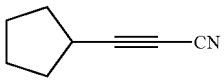

in the presence of 1,8-diazabicyclo[5.4.0]undec-7-ene to give a compound of Formula II':

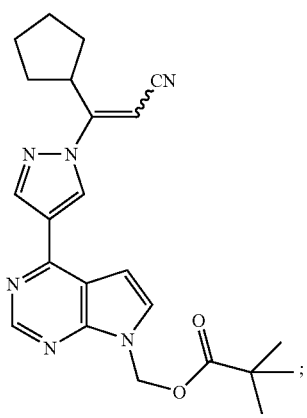

(e) reacting the compound of Formula II' with hydrogen gas in the presence of $[Rh(COD)_2]CF_3SO_3$ and a chiral phosphine ligand selected from:

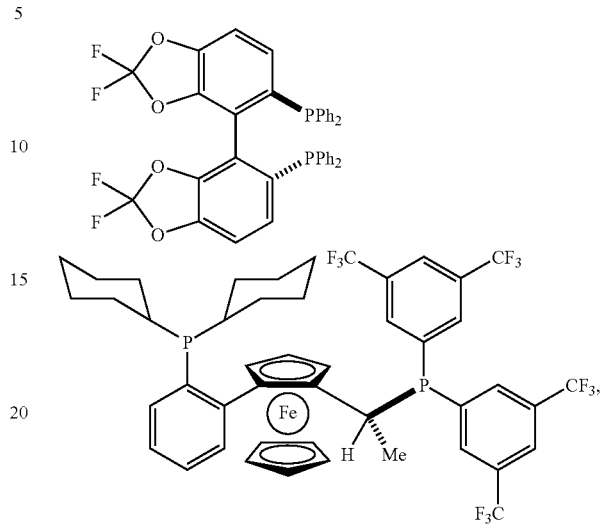

to form a compound of Formula I':

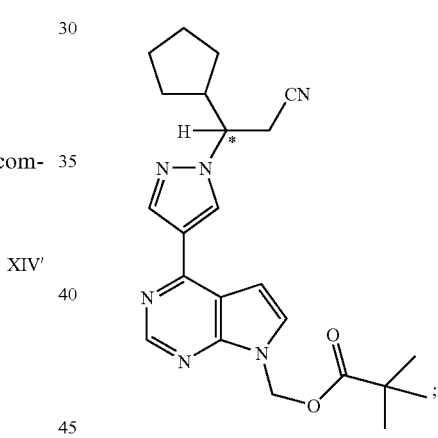

and (f) reacting the compound of Formula I' under deprotection conditions to form the compound of Formula III';

wherein * indicates a chiral carbon.

In some embodiments of step (e):

the solvent is 2,2,2-trifluoroethanol (TFE);

the hydrogenation catalyst loading is about 0.005 to about 0.01 mol %;

the ratio of the compound of Formula II to the hydrogenation catalyst is from about 20000/1 to about 10000/1;

the hydrogen pressure is from about 7 to about 60 bar;

the reacting is run at a temperature from about room temperature to about 75° C.;

the reacting is run until the conversion of the compound of Formula II to the compound of Formula is about equal to or greater than 99.5%; and the reacting is from about 10 to about 25 hours.

In some embodiments, the process further comprises preparing the compound of Formula XI':

XI' comprising:

(i) reacting a compound of F-4:

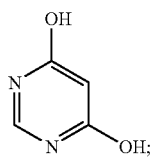

F-4 with from about three to about five equivalents of POCl$_3$ in the presence of about one to about two equivalents of dimethylformamide to form a compound of Formula F-3:

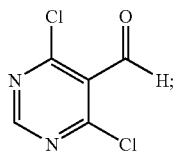

F-3

(ii) reacting the compound of F-3 with about two equivalents of ammonia in methanol to form a compound of Formula F-2:

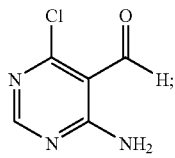

F-2

(iii) reacting the compound of Formula F-2 with from about 1 to about 1.5 equivalents of a Wittig-type reagent of formula [Ph$_3$P$^+$(CH$_2$OCH$_3$)]Cl—, wherein Ph is phenyl, in the presence of from about 1 to about 1.5 equivalents of potassium tert-butoxide to form a compound of Formula F-1:

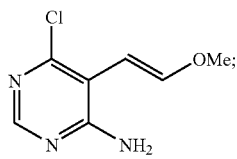

F-1 and (iv) treating the compound of Formula F-1 with aqueous concentrated hydrochloric acid in tetrahydrofuran at reflux to form compound of Formula XI'.

In some embodiments, the process further comprises preparing the compound of Formula XIII':

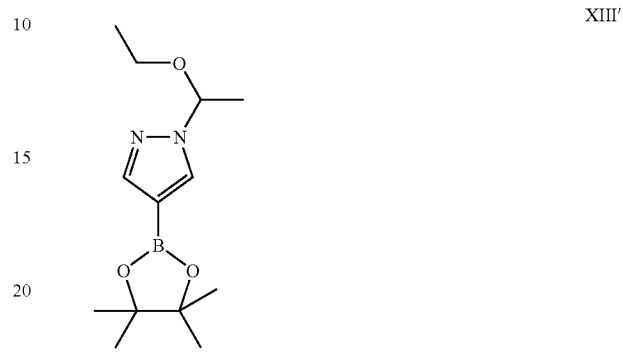

XIII' comprising:

(i) reacting 1H-pyrazole with N-bromosuccinimide to form a compound of Formula XIX';

XIX'

(ii) protecting the compound of Formula XIX to form a compound of Formula XVIII':

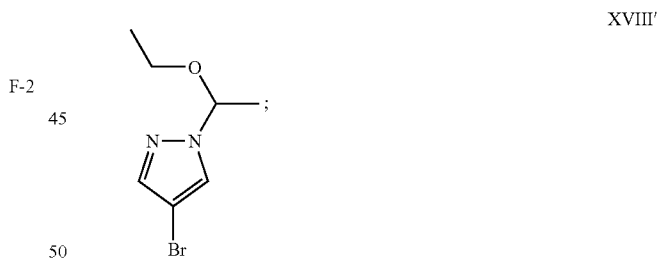

XVIII' and (iii) reacting the compound of Formula XVIII' with about one or more equivalents of a isopropylmagnesium chloride followed by treating with about one or more equivalents of compound of Formula XVII':

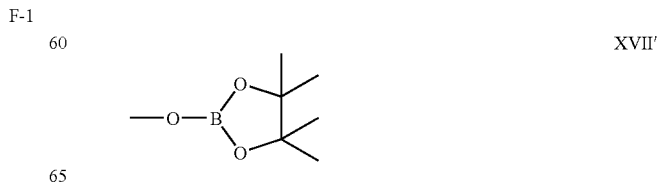

XVII' to form a compound of Formula XIII'.

In some embodiments, the process further comprises preparing the compound of Formula XIII':

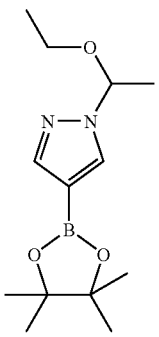

XIII' comprising:

(i) protecting 4-iodo-1H-pyrazole to form a compound of Formula XVIII":

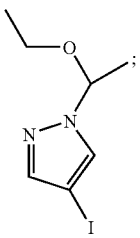

XVIII"

and (ii) reacting a compound of Formula XVIII" with about one or more equivalents of a isopropylmagnesium chloride in tetrahydrofuran followed by treating with about one or more equivalents of compound of Formula XVII':

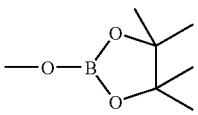

XVII' to form a compound of Formula XIII'.

In further embodiments, the present invention provides a process of preparing a composition comprising an enantiomeric excess of the (R)-enantiomer of a compound of Formula III':

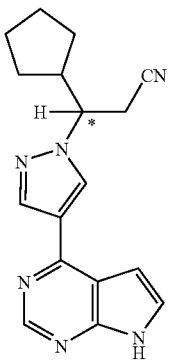

III' comprising:

(a) treating a compound of Formula XI':

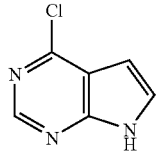

XI' with sodium hydride and 2-(trimethylsilyl)ethoxymethyl to form a compound of Formula X":

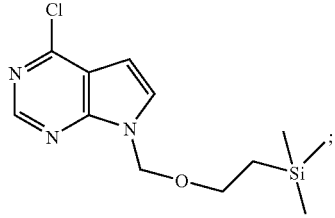

X"

(b) treating the compound of Formula X" with a compound of Formula XIII':

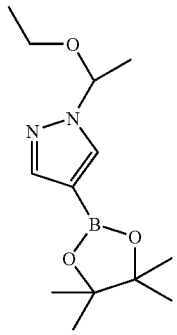

XIII' in the presence of Pd(triphenylphosphine)$_4$, potassium carbonate, and a solvent, to form a compound of Formula XII":

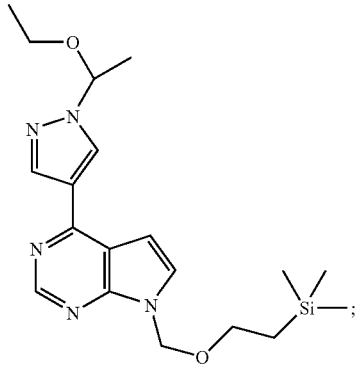

XII"

(c) reacting the compound of Formula XII" under deprotection conditions to form a compound of Formula IV":

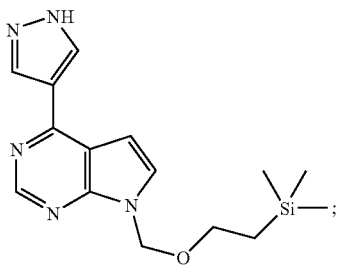

IV"

(d) reacting the compound of Formula IV" with a compound of Formula D-1':

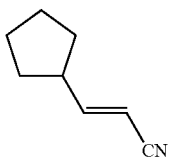

D-1' under conditions sufficient to form a composition comprising a racemate of a compound of Formula I":

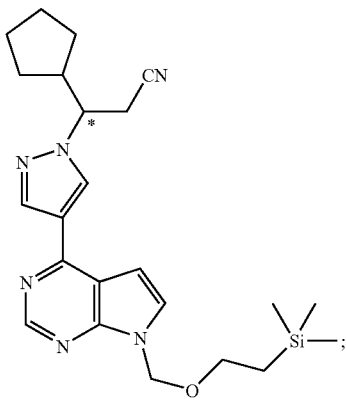

I"

(e) passing the composition comprising the racemate of the compound of Formula I" through a chiral chromatography unit using a mobile phase and collecting a composition comprising an enantiomeric excess of the (R)-enantiomer of the compound of Formula I"; and (f) reacting the compound of Formula I" with lithium tetrafluoroborate, followed by aqueous ammonium hydroxide to form a composition comprising an enantiomeric excess of the (R)-enantiomer of the compound of Formula III';

wherein * is a chiral carbon.

In other embodiments, the present invention provides a process of preparing a composition comprising an enantiomeric excess of the (R)-enantiomer of a compound of Formula III':

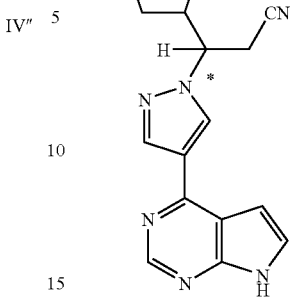

III' comprising:

(a) treating a composition comprising an enantiomeric excess of the (S)-enantiomer of a compound of Formula I":

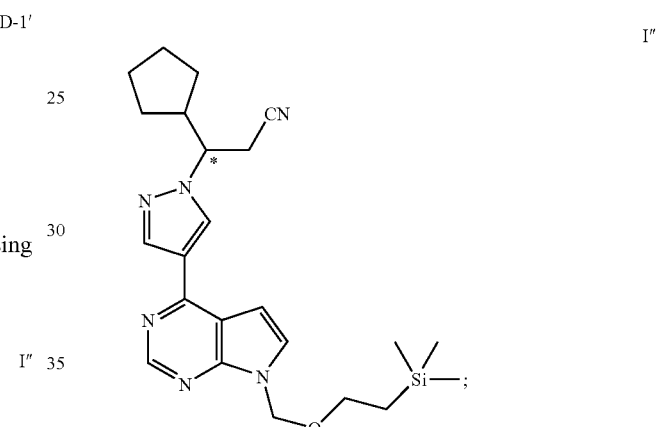

I"

with a compound of Formula D-1':

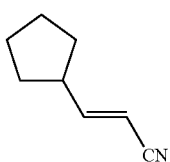

D-1' in the presence of cesium carbonate in acetonitrile under conditions sufficient to form the racemate of the compound of Formula I";

(b) passing the composition comprising the racemate of the compound of Formula I" through a chiral chromatography unit using a mobile phase and collecting a composition comprising an enantiomeric excess of the (R)-enantiomer of the compound of Formula I"; and (c) reacting the compound of Formula I" with lithium tetrafluoroborate, followed by aqueous ammonium hydroxide to form a composition comprising an enantiomeric excess of the (R)-enantiomer of the compound of Formula III';

wherein * is a chiral carbon.

In other embodiments, the present invention provides a process of preparing a composition comprising an enantiomeric excess of the (R)-enantiomer of a compound of Formula III':

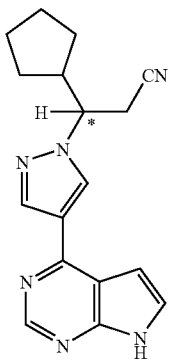

comprising:

(a) treating a compound of Formula XI':

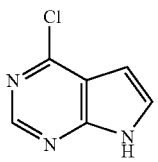

with sodium hydride and 2-(trimethylsilyl)ethoxymethyl to form a compound of Formula X":

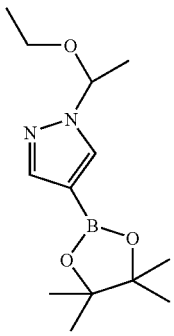

(b) treating said compound of Formula X" with a compound of Formula XIII':

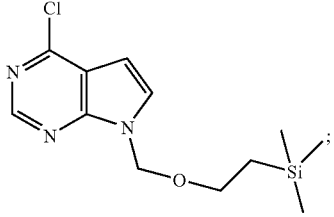

in the presence of Pd(triphenylphosphine)$_4$, potassium carbonate, and a solvent, to form a compound of Formula XII":

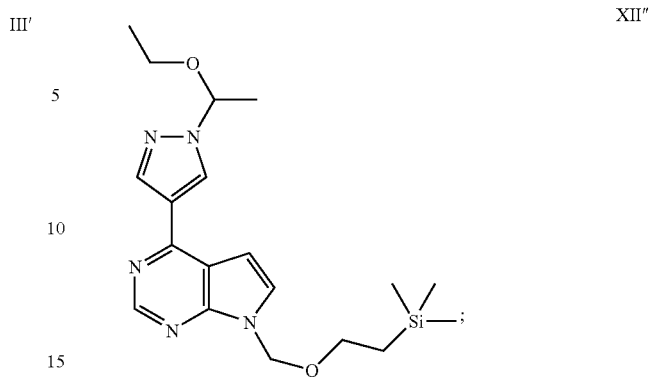

(c) reacting said compound of Formula XII" under deprotection conditions to form a compound of Formula IV":

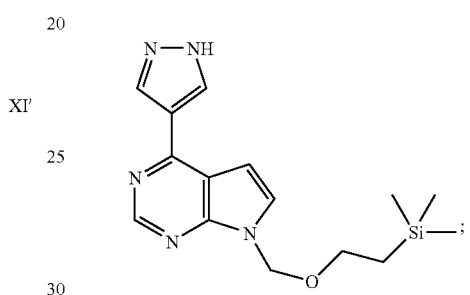

(d) reacting said compound of Formula IV" with a compound of Formula D-1':

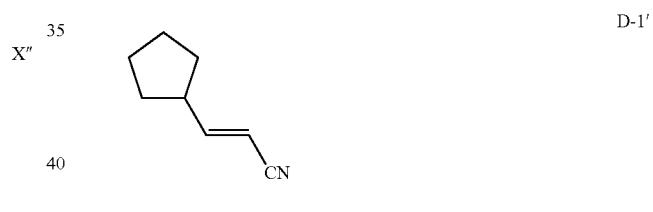

under conditions sufficient to form a composition comprising a racemate of a compound of Formula I":

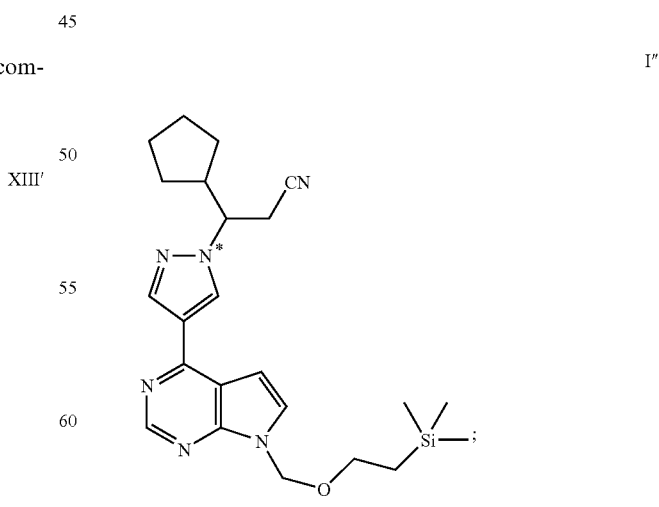

(e) passing said composition comprising said racemate of said compound of Formula I" through a chiral chromatography unit using a mobile phase and collecting a composition comprising an enantiomeric excess of the (R)-enantiomer of said compound of Formula I"; and (f) reacting said compound of Formula I" with boron trifluoride diethyl etherate, followed by aqueous ammonium hydroxide to form a composition comprising an enantiomeric excess of the (R)-enantiomer of said compound of Formula III';

wherein * is a chiral carbon.

In other embodiments, the present invention provides a process of preparing a composition comprising an enantiomeric excess of the (R)-enantiomer of a compound of Formula III':

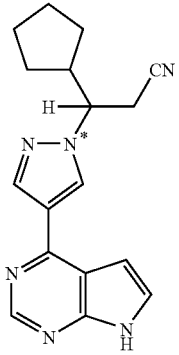

III' comprising:
(a) treating a composition comprising an enantiomeric excess of the (S)-enantiomer of a compound of Formula I":

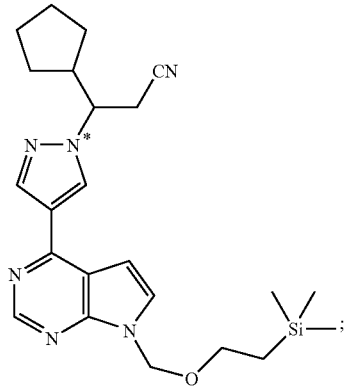

I"

with a compound of Formula D-1':

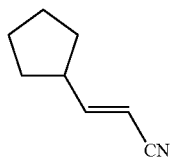

D-1' in the presence of cesium carbonate in acetonitrile under conditions sufficient to form the racemate of the compound of Formula I";

(b) passing said composition comprising said racemate of said compound of Formula I" through a chiral chromatography unit using a mobile phase and collecting a composition comprising an enantiomeric excess of the (R)-enantiomer of said compound of Formula I"; and (c) reacting said compound of Formula I" with boron trifluoride diethyl etherate, followed by aqueous ammonium hydroxide to form a composition comprising an enantiomeric excess of the (R)-enantiomer of said compound of Formula III';

wherein * is a chiral carbon.

In other embodiments, the present invention provides a process of preparing a composition comprising an enantiomeric excess of the (R)-enantiomer of a compound of Formula III':

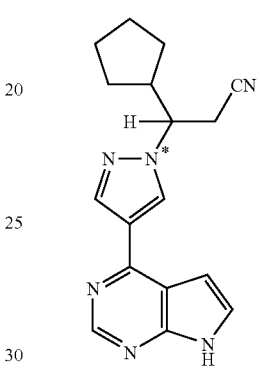

III' comprising: reacting said compound of Formula I":

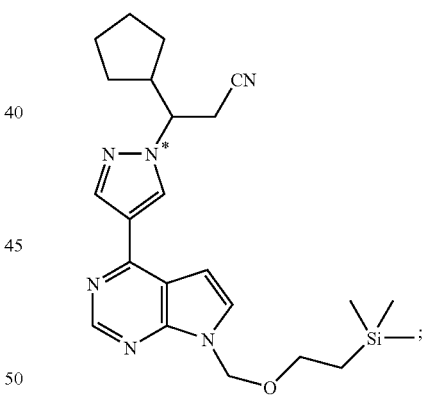

I"

with boron trifluoride diethyl etherate, followed by aqueous ammonium hydroxide to form a composition comprising an enantiomeric excess of the (R)-enantiomer of said compound of Formula III'; wherein * is a chiral carbon.

In other embodiments, the present invention provides a process for preparing (3R)-cyclopentyl-3-[4-(7H-pyrrolo[2,3-d]pyrimidin-4-yl)pyrazol-1-yl]propionitrile phosphate salt comprising reacting (3R)-cyclopentyl-3-[4-(7H-pyrrolo[2,3-d]pyrimidin-4-yl)pyrazol-1-yl]propionitrile with phosphoric acid in the presence of 2-propanol and dichloromethane.

In other embodiments, the present invention provides a method of purifying (3R)-cyclopentyl-3-[4-(7H-pyrrolo[2,3-d]pyrimidin-4-yl)pyrazol-1-yl]propionitrile phosphate salt comprising recrystallizing (3R)-cyclopentyl-3-[4-(7H-pyrrolo[2,3-d]pyrimidin-4-yl)pyrazol-1-yl]propionitrile phosphate salt from a solvent mixture comprising methanol, 2-propanol, and n-heptane. In some embodiments, the 2-propanol and n-heptane are added to a mixture of (3R)-cyclopentyl-3-[4-(7H-pyrrolo[2,3-d]pyrimidin-4-yl)pyrazol-1-yl]propionitrile phosphate salt in methanol.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

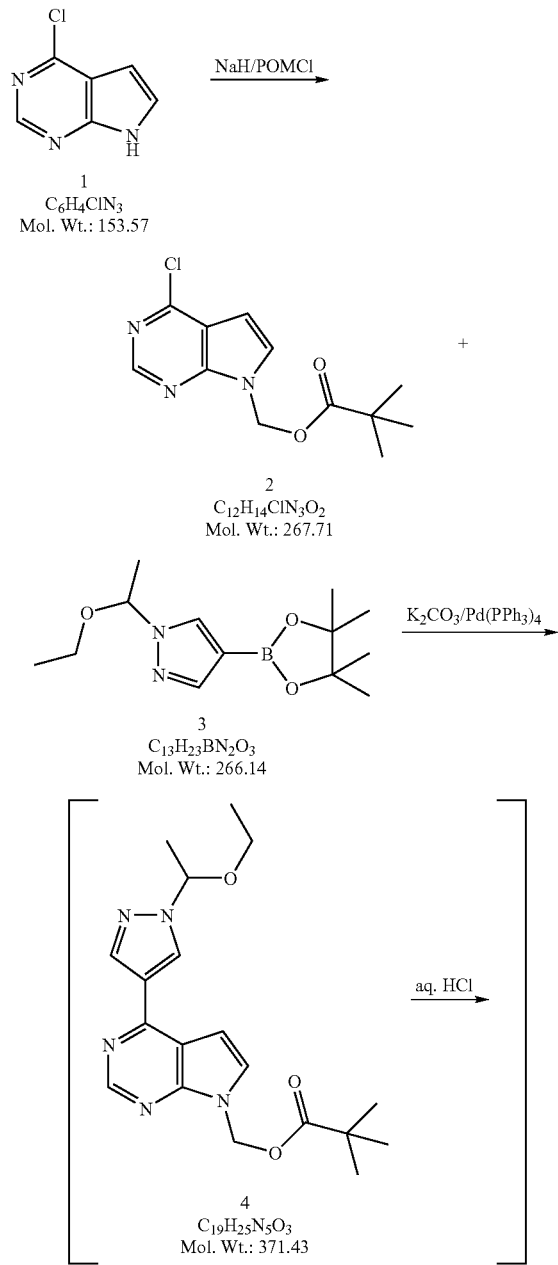

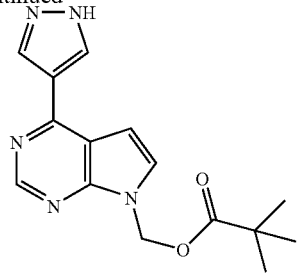

[4-(1H-Pyrazol-4-yl)-7H-pyrrolo[2,3-d]pyrimidin-7-yl]methyl pivalate (5). To a oven dried 3 L 4-neck round bottom flask equipped with a stirring bar, a septa, a thermocouple, a 500 mL addition funnel and the nitrogen inlet was charged sodium hydride (NaH, 60 wt % in mineral oil, 32.82 g, 0.82 mol, 1.20 equiv) and anhydrous 1,2-dimethoxyethane (DME, 500 mL, 4.8 mol) and the resulting mixture was cooled to 0-3° C. To a oven dried 1 L round bottom flask was charged 4-chloro-7H-pyrrolo[2,3-d]pyrimidine (1, 105.0 g, 0.684 mol) and 1,2-dimethoxyethane (DME, 750 mL, 7.2 mol) and the resulting slurry was then portion wise added to the suspension of sodium hydride in DME via large bore canula over 30 min at 5-12° C. The resulting reaction mixture was heterogeneous. Following the addition, the cold bath was removed and the mixture was gradually warmed to room temperature and allowed to stir at room temperature for 1 hour before being cooled to 0-5° C. Chloromethyl pivalate (pivaloyloxymethyl chloride, POM-Cl, 112 ml, 0.752 mol, 1.1 equiv) was added dropwise into the reaction mixture over 30 minutes with stirring at 0-5° C. The addition of chloromethyl pivalate was mildly exothermic and the reaction temperature went up to as high as 14° C. After addition of chloromethyl pivalate, the cooling bath was removed and the reaction mixture was allowed to return to room temperature and stirred at room temperature for 90 min. When the reaction was deemed complete as confirmed by TLC and LCMS, the reaction was carefully quenched with water (100 mL). And this quenched reaction mixture, which contains crude POM-protected chlorodeazapurine (2), was directly used in the subsequent Suzuki coupling reaction without further work-up and purification.

To the quenched reaction mixture, which contains crude POM-protected chlorodeazapurine (2) made as described above, 4-(4,4,5,5-tetramethyl-1,3,2-dioxaborolan-2-yl)-1H-pyrazole (3, 200 g, 0.75 mol, 1.10 equiv) and potassium carbonate ($K_2CO_3$, 189 g, 1.37 mol, 2.0 equiv) were added at room temperature. The resulting mixture was degassed by passing a stream of nitrogen through the solution for 15 minutes before being treated with tetrakis(triphenylphosphine)palladium(0) ($Pd(PPh_3)_4$, 7.9 g, 0.68 mmol, 0.01 equiv) and the resulting reaction mixture was heated at reflux (about 82° C.) for 10 h. When the reaction was deemed complete as confirmed by TLC (1:1 hexanes/ethyl acetate) and LCMS, the reaction mixture was cooled down to room temperature and diluted with ethyl acetate (2 L) and water (1 L). The two layers were separated, and the aqueous layer was extracted with ethyl acetate (EtOAc, 500 mL). The combined organic layers were washed with water (2×1 L) and brine (1 L) before being concentrated under reduced pressure to afford crude {4-[1-(1-ethoxyethyl)-1H-pyrazol-4-yl]-7H-pyrrolo[2,3-d]pyrimidin-7-yl}methyl pivalate (4) as a pale-yellow oil, which was directly used in the subsequent de-protection reaction without further purification.

To a solution of crude {4-[1-(1-ethoxyethyl)-1H-pyrazol-4-yl]-7H-pyrrolo[2,3-d]pyrimidin-7-yl]methyl pivalate (4) in THF (1 L, 12.3 mol), a 4 N aqueous HCl solution (500 mL) was added at room temperature. The resulting reaction mixture was subsequently stirred at room temperature for 5 h. When the reaction was deemed complete as confirmed by TLC and LCMS, the reaction mixture was cooled to 0-5° C. before pH was adjusted to 9-10 with a 1 M aqueous sodium hydroxide (NaOH) solution (2 L). The mixture was concentrated under reduced pressure to remove most of THF and the resulting suspension was stirred at room temperature for 2 h. The solids were collected by filtration, washed with water (3×500 mL), and dried in vacuum to afford crude [4-(1H-pyrazol-4-yl)-7H-pyrrolo[2,3-d]pyrimidin-7-yl]methyl pivalate (5, 157.5 g, 204.43 g theoretical, 77% yield for three steps) as white to off-white solids, which was found to be sufficiently pure (>98area % by HPLC) to do the subsequent reaction without further purification. For 5: $^1$H NMR (DMSO-d$_6$, 400 MHz) δ ppm 13.42 (br s, 1H), 8.76 (s, 1H), 8.67 (s, 1H), 8.33 (s, 1H), 7.68 (d, 1H, J=3.8 Hz), 7.11 (d, 1H, J=3.8 Hz), 6.21 (s, 2H), 1.06 (s, 9H); $^{13}$C NMR (DMSO-d$_6$, 100 MHz) δ ppm 177.74, 152.31, 152.09, 151.91, 139.52, 130.39, 120.51, 113.93, 101.91, 67.26, 38.98, 27.26; C$_{15}$H$_{17}$N$_5$O$_2$ (MW, 299.33), LCMS (EI) m/e 300 (M$^+$+H).

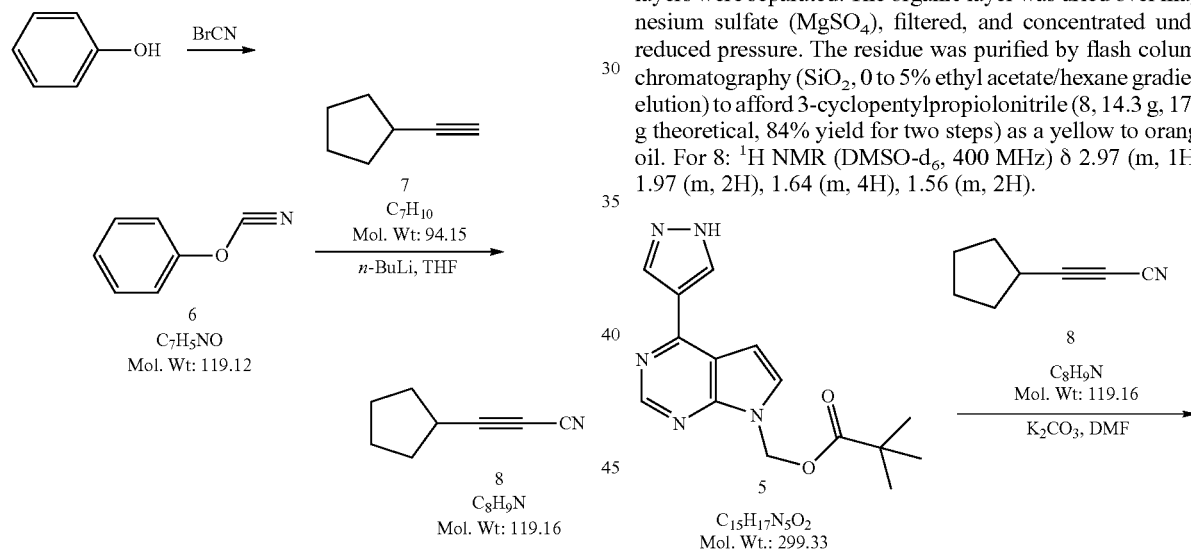

Cyanatobenzene (6). To a oven dried 500 mL 3-neck round bottom flask equipped with a overhead stirring, a septa, a thermocouple and the nitrogen inlet, phenol (20.0 g, 0.210 mol), diethyl ether (Et$_2$O, 290 mL) and cyanic bromide (BrCN, 23.0 g, 0.210 mol, 1.0 equiv) were added at room temperature. The resulting solution was cooled down to 0-3° C. before triethylamine (TEA, 61.9 mL, 0.442 mol, 2.1 equiv) was added dropwise via syringe over 25 min. The addition of triethylamine to reaction mixture was mildly exothermic and the reaction temperature went up to as high as 15° C. After addition of triethylamine, the reaction mixture became a white slurry which was stirred vigorously at 0° C. for 2 h at 5-15° C. When the reaction was deemed complete as confirmed by TLC and LCMS, the reaction mixture was diluted with pentane (150 mL, 1.30 mol). The precipitated triethylamine hydrochloride was filtered off and the salt was washed with diethyl ether and pentane (1 to 1 by volume, 200 mL). The filtrate was then concentrated under reduced pressure to remove the majority of the solvent, and the residue, which contains the crude cyanatobenzene (6), was directly used in the subsequent reaction without further purification assuming the theoretical yield.

3-Cyclopentylpropiolonitrile (8). To a oven dried 500 mL 3-neck round bottom flask equipped with a stir bar, a nitrogen inlet, a 125 mL addition funnel and a thermocouple, cyclopentylacetylene (7, 15.0 g, 0.143 mol) and anhydrous tetrahydrofuran (THF, 170 mL, 2.10 mol) were added at room temperature. The resulting solution was then cooled to −78° C. before a solution of 2.5 M n-butyllithium in hexane (63.1 mL, 0.158 mol, 1.1 equiv) was added dropwise over 25 min. The resulting lithium cyclopentylacetylene solution was stirred at −78° C. for 15 minutes before a solution of crude cyanatobenzene (6, 25.0 g, 0.210 mol, 1.5 equiv) in anhydrous tetrahydrofuran (THF, 30.0 mL, 0.400 mol) was added dropwise via a canula at −78° C. The resulting reaction mixture was stirred at −78° C. for an additional 10 min before the cooling batch was removed and the reaction mixture was allowed to gradually warm to room temperature and stirred at room temperature for 1-2 h. When the reaction was deemed complete, the reaction mixture was quenched with a 6 N aqueous sodium hydroxide solution (NaOH, 200 mL) and a 20% aqueous brine solution (200 mL). The aqueous solution was treated with ethyl acetate (EtOAc, 200 mL) before the two layers were separated. The organic layer was dried over magnesium sulfate (MgSO$_4$), filtered, and concentrated under reduced pressure. The residue was purified by flash column chromatography (SiO$_2$, 0 to 5% ethyl acetate/hexane gradient elution) to afford 3-cyclopentylpropiolonitrile (8, 14.3 g, 17.0 g theoretical, 84% yield for two steps) as a yellow to orange oil. For 8: $^1$H NMR (DMSO-d$_6$, 400 MHz) δ 2.97 (m, 1H), 1.97 (m, 2H), 1.64 (m, 4H), 1.56 (m, 2H).

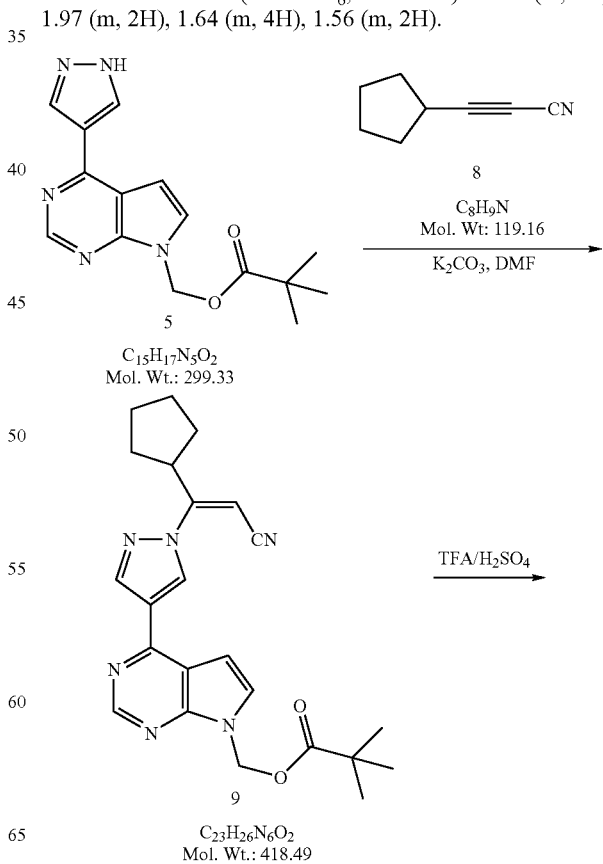

-continued

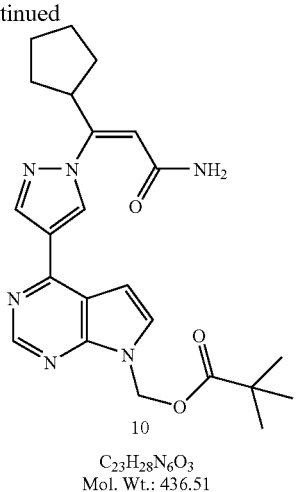

10
C₂₃H₂₈N₆O₃
Mol. Wt.: 436.51

4-(1-(2-Cyano-1-cyclopentylvinyl)-1H-pyrazol-4-yl)-7H-pyrrolo[2,3-d]pyrimidin-7-yl)methyl pivalate (9). To a 500 mL round bottom flask equipped with a stir bar and the nitrogen inlet was charged 3-cyclopentylpropiolonitrile (8, 8.50 g, 0.0713 mol, 1.52 equiv), N,N-dimethylformamide (DMF, 84 mL, 1.08 mol) and [4-(1H-pyrazol-4-yl)-7H-pyrrolo[2,3-d]pyrimidin-7-yl]methyl pivalate (5, 14.0 g, 0.0468 mol) and solid potassium carbonate (K₂CO₃, 0.329 g, 0.00238 mol, 0.05 equiv) at room temperature. The resulting reaction mixture was then stirred at room temperature for 60 min. When TLC and HPLC showed that the reaction was deemed complete, the reaction mixture was quenched with 20% aqueous brine (75 mL) and the resulting solution was extracted with ethyl acetate (EtOAc, 3×75 mL). The combined organic extracts were washed with 20% aqueous brine (75 mL), dried over magnesium sulfate (MgSO₄), filtered, and concentrated under reduced pressure. The residue was purified by flash chromatography (SiO₂, 0 to 20% ethyl acetate/hexane gradient elution) to afford 4-(1-(2-cyano-1-cyclopentylvinyl)-1H-pyrazol-4-yl)-7H-pyrrolo[2,3-d]pyrimidin-7-yl)methyl pivalate (9, 16.4 g, 19.6 g theoretical, 83.7% yield) as white solids. For 9: ¹H NMR (DMSO-d₆, 300 MHz) δ 9.09 (s, 1H), 8.84 (s, 1H), 8.63 (s, 1H), 7.78 (d, 1H, J=3.8 Hz), 7.17 (d, 1H, J=3.8 Hz), 6.24 (s, 2H), 5.82 (s, 1H), 3.55 (m, 1H), 1.92 (m, 2H), 1.59 (br m, 6H), 1.06 (s, 9H); C₂₃H₂₆N₆O₂ (MW, 418.49), LCMS (EI) m/e 419 (M⁺+H).

(Z)-(4-(1-(3-Amino-1-cyclopentyl-3-oxoprop-1-enyl)-1H-pyrazol-4-yl)-7H-pyrrolo[2,3-d]pyrimidin-7-yl)methyl pivalate (10). To a 200 ml round bottom flask equipped with a stir bar and the nitrogen inlet was charged 4-(1-(2-cyano-1-cyclopentylvinyl)-1H-pyrazol-4-yl)-7H-pyrrolo[2,3-d]pyrimidin-7-yl)methyl pivalate (9, 8.00 g, 0.0191 mol), trifluoroacetic acid (TFA, 40.6 mL, 0.528 mol) and concentrated sulfuric acid (H₂SO₄, 3.77 mL, 0.0707 mol) at room temperature. The resulting reaction mixture was stirred at room temperature for 60 min. When TLC and HPLC showed that the reaction was deemed complete, the reaction mixture was quenched with water (30.1 mL, 1.67 mol). The quenched reaction mixture was stirred at room temperature for 30 min before being cooled to 0-5° C. The cold solution was then treated with a 3 N sodium hydroxide aqueous solution (NaOH, 223 mL) to adjust pH to 8 before being treated with ethyl acetate (EtOAc, 200 mL). The two layers were separated, and the aqueous was then extracted with ethyl acetate (EtOAc, 2×50 mL). The combine organic extracts were washed with a saturated aqueous NaCl (100 mL), dried over magnesium sulfate (MgSO₄), filtered, and concentrate under reduced pressure. The residue was purified by flash chromatography (SiO₂, 0 to 100% ethyl acetate/hexane gradient elution) to provide (Z)-(4-(1-(3-amino-1-cyclopentyl-3-oxoprop-1-enyl)-1H-pyrazol-4-yl)-7H-pyrrolo[2,3-d]pyrimidin-7-yl)methyl pivalate (10, 6.79 g, 8.34 g theoretical, 81.4% yield) as light yellow solids. For 10: ¹H NMR (DMSO-d₆, 300 MHz) δ 8.77 (s, 1H), 8.68 (s, 1H), 8.41 (s, 1H), 7.71 (d, 1H, J=3.8 Hz), 7.51 (br. s, 1H), 7.09 (br. s, 1H), 7.05 (d, 1H, J=3.8 Hz), 6.22 (s, 2H), 5.97 (s, 1H), 3.27 (m, 1H), 1.77 (m, 2H), 1.54 (m, 6H), 1.06 (s, 9H); C₂₃H₂₈N₆O₃ (MW, 436.51), LCMS (EI) m/e 437 (M⁺+H).

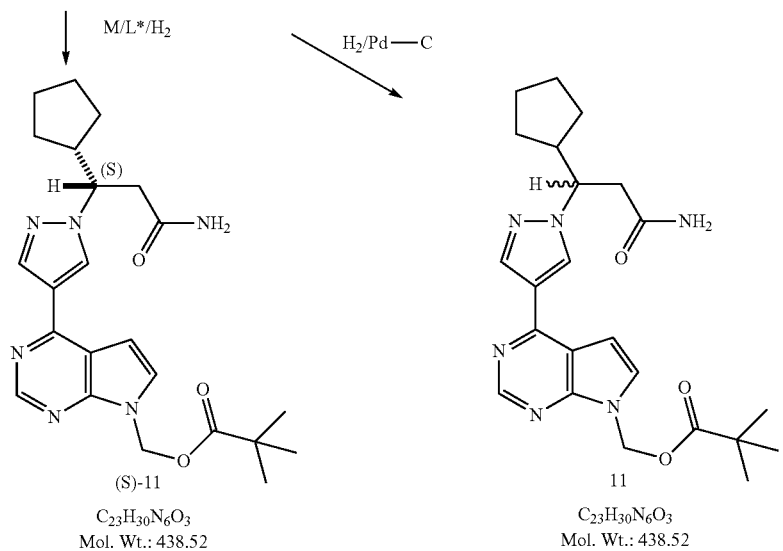

(4-(1-(3-Amino-1-cyclopentyl-3-oxopropyl)-1H-pyrazol-4-yl)-7H-pyrrolo[2,3-d]pyrimidin-7-yl)methyl pivalate (11). To a 25 ml round bottom flask equipped with a stir bar was charged (Z)-(4-(1-(3-amino-1-cyclopentyl-3-oxoprop-1-enyl)-1H-pyrazol-4-yl)-7H-pyrrolo[2,3-d]pyrimidin-7-yl)methyl pivalate (10, 1.15 g, 2.63 mmol), tetrahydrofuran (THF, 20.0 ml, 246 mmol) and 10% palladium on carbon (50% wet, 130 mg) at room temperature. The resulting reaction mixture was degassed three times back filling with hydrogen gas each time before the hydrogenation reaction was conducted under a steady stream of hydrogen gas released by a hydrogen balloon. The reaction was checked after 17 h and was found to be complete. The reaction mixture was then filtered through a Celite bed to remove the catalyst and the Celite bed was rinsed with a small volume of tetrahydrofuran (THF). The combined filtrates were concentrated under reduced pressure to afford the crude (4-(1-(3-amino-1-cyclopentyl-3-oxopropyl)-1H-pyrazol-4-yl)-7H-pyrrolo[2,3-d]pyrimidin-7-yl)methyl pivalate (11, 1.15 g, 1.153 g theoretical, 99% yield) as a yellow to brown oil, which solidified upon standing in vacuum at room temperature. This crude product (11) was found to be pure enough (>98% by HPLC) to do the following reaction without further purification. For 11: $^1$H NMR (DMSO-$d_6$, 300 MHz) δ ppm 8.73 (s, 1H), 8.60 (s, 1H), 8.27 (s, 1H), 7.70 (d, 1H, J=3.8 Hz), 7.32 (bs, 1H), 7.09 (d, 1H, J=3.8 Hz), 6.75 (bs, 1H), 6.21 (s, 2), 4.56 (td, 1H, J=4.0, 9.8 Hz), 2.86 (dd, 1H, J=10.5, 5.6 Hz), 2.63 (dd, 1H, J=4.0, 15.3 Hz), 2.32 (m, 1H), 1.77 (m, 1H), 1.56-1.19 (m, 7H), 1.06 (s, 9H); LCMS (EI) m/e 439 (M$^+$+H); $C_{23}H_{30}N_6O_3$ (MW, 438.52), LCMS (EI) m/e 439 (M$^+$+H).

(R)-(4-(1-(3-Amino-1-cyclopentyl-3-oxopropyl)-1H-pyrazol-4-yl)-7H-pyrrolo[2,3-d]pyrimidin-7-yl)methyl pivalate ((R)-11) and (S)-(4-(1-(3-Amino-1-cyclopentyl-3-oxopropyl)-1H-pyrazol-4-yl)-7H-pyrrolo[2,3-d]pyrimidin-7-yl)methyl pivalate ((S)-11)

General screening procedure for asymmetric hydrogenation using the substrate, (Z)-(4-(1-(3-amino-1-cyclopentyl-3-oxoprop-1-enyl)-1H-pyrazol-4-yl)-7H-pyrrolo[2,3-d]pyrimidin-7-yl)methyl pivalate (10) to afford optically enriched product, (4-(1-(3-amino-1-cyclopentyl-3-oxopropyl]-1H-pyrazol-4-yl}-7H-pyrrolo[2,3-d]pyrimidin-7-yl)methyl pivalate ((R)-11 or (S)-11): A 300 mL-volume autoclave with glass vial (20 mL) was charged with the substrate (10), the catalyst (metal, ligand, and catalyst precursor), and oxygen-free solvent (4-6 mL) under nitrogen. This autoclave was charged with hydrogen gas to the desired pressure and stirred at room temperature or heated with oil bath. After hydrogen gas was released, the reaction mixture was concentrated under reduced pressure. The residue was purified by eluting through a silica gel pad using a mixture of ethyl acetate and methanol (v/v=9/1) to afford product, (4-(1-(3-amino-1-cyclopentyl-3-oxopropyl]-1H-pyrazol-4-yl}-7H-pyrrolo[2,3-d]pyrimidin-7-yl)methyl pivalate ((R)-11 or (S)-11), for chemical conversion (HPLC and chiral HPLC), LC/MS and NMR spectroscopy and enantiomeric excess (% ee by chiral HPLC) determination.

The determination of enantiomeric excess (% ee) of the product was carried out by chiral HPLC analysis. A Chiralpak® IA column was used. The mobile phase was a mixture of hexane and ethanol (v/v=90/10). The flow rate was 1 mL/min and UV detection wavelength was set at 254 nm. The substrate (10), undesired enantiomer ((S)-11, $1^{st}$ peak) and desired enantiomer ((R)-11, $2^{nd}$ peak) were well-resolved at retention times 46 min, 36 min, and 38 min respectively.

For (R)-11 or (S)-11: $^1$H NMR (DMSO-$d_6$, 300 MHz) δ ppm 8.73 (s, 1H), 8.60 (s, 1H), 8.27 (s, 1H), 7.70 (d, 1H, J=3.8 Hz), 7.32 (bs, 1H), 7.09 (d, 1H, J=3.8 Hz), 6.75 (bs, 1H), 6.21 (s, 2H), 4.56 (td, 1H, J=4.0, 9.8 Hz), 2.86 (dd, 1H, J=10.5, 5.6 Hz), 2.63 (dd, 1H, J=4.0, 15.3 Hz), 2.32 (m, 1H), 1.77 (m, 1H), 1.56-1.19 (m, 7H), 1.06 (s, 9H); LCMS (EI) m/e 439 (M$^+$+H); $C_{23}H_{30}N_6O_3$ (MW, 438.52), LCMS (EI) m/e 439 (M$^+$+H).

The following table summarizes analyses and reaction conditions for this asymmetric hydrogenation.

| Metal/Ligand/ Catalyst Precursor | Solvent | Temp. (° C.) | H₂ Pressure (Bar) | Time (h) | Conversion (HPLC Area %) | % ee | Major Enantiomer (R)- or (S)-11 |
|---|---|---|---|---|---|---|---|
| Rh(COD)(SSRR-TangPhos)(BF₄) | CF₃CH₂OH | 23 | 40 | 20 | 99 | 66 | (S)-11 (1st peak) |
| Rh(COD)(SSRR-TangPhos)(BF₄) | CH₂Cl₂ | 23 | 40 | 20 | 91 | 92 | (S)-11 (1st peak) |
| Rh(COD)(SSRR-TangPhos)(BF₄) | CF₃CH₂OH & CH₂Cl₂ | 23 | 10 | 20 | 99 | 91 | (S)-11 (1st peak) |
| Rh(COD)(+)- DuanPhos)(BF₄) | MeOH | 23 | 40 | 20 | 94 | 66 | (S)-11 (1st peak) |
| Rh(COD)(+)- DuanPhos)(BF₄) | CF₃CH₂OH | 23 | 40 | 20 | 99 | 61 | (S)-11 (1st peak) |
| Ru(R-C3- TunePhos)(CF₃CO₂)₂ | MeOH | 50 | 50 | 2 | 84 | 87 | (R)-11 (2nd peak) |
| Ru(R-C3- TunePhos)(CF₃CO₂)₂ | CF₃CH₂OH & MeOH | 50 | 50 | 2 | 99 | 88 | (R)-11 (2nd peak) |
| Ru(COD)(SL-A153-1)(CF₃CO₂)₂ | MeOH | 30 | 50 | 21 | 100 | 98 | (R)-11 (2nd peak) |
| Rh(COD)₂ (SL-W008-1)(CF₃SO₃) | MeOH | 30 | 50 | 21 | 100 | 94 | (R)-11 (2nd peak) |

Structures of chiral phosphine ligands used in this study are listed below.

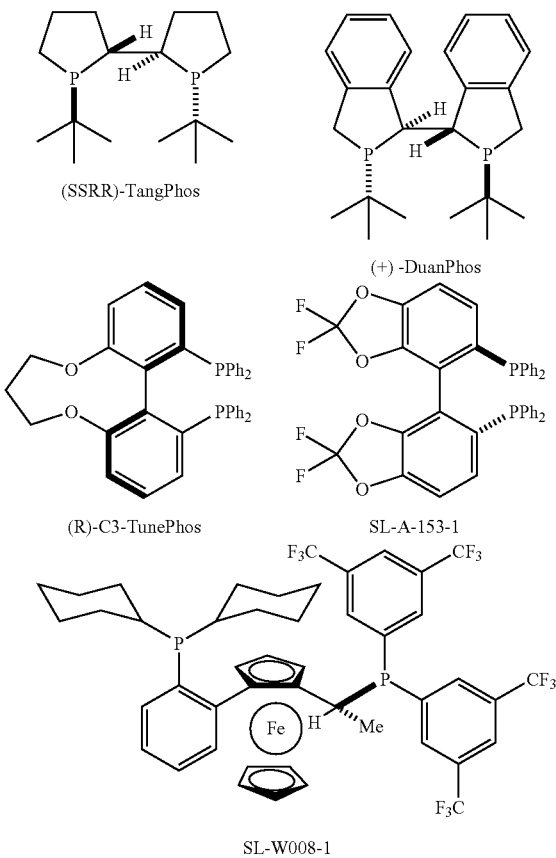

Representative preparative asymmetric hydrogenation procedure and product chiral purity upgrade by crystallization are described below.

(S)-(4-(1-(3-Amino-1-cyclopentyl-3-oxopropyl)-1H-pyrazol-4-yl)-7H-pyrrolo[2,3-d]pyrimidin-7-yl)methyl pivalate ((S)-11). A solution of (4-{1-[(1Z)-3-amino-1-cyclopentyl-3-oxoprop-1-en-1-yl]-1H-pyrazol-4-yl}-7H-pyrrolo[2,3-d]pyrimidin-7-yl)methyl pivalate (10, 215 mg) in a mixture of methylene chloride (CH₂Cl₂, 12.5 mL) and trifluoroethanol (CF₃CH₂OH, 0.25 mL) in a pressure glass tube was treated with the catalyst Rh(COD)(SSRR-TangPhos)BF₄ (8.8 mg) under nitrogen before the reaction mixture was pressurized with hydrogen gas to 40 bar pressure. The reaction mixture was stirred at 50° C. under this hydrogen pressure for 20 h. When HPLC analysis showed that the substrate was completely consumed, the reaction mixture was cooled down to room temperature. The enantiomeric excess of the reaction mixture was determined to be 88% ee (94% of the first peak, (S)-11; 6% of the second peak, (R)-11) by chiral HPLC analysis. The reaction mixture was filtered through a thin silica gel pad and the pad was washed with methylene chloride (5 mL). The filtrate was then concentrated under reduced pressure to dryness. The resultant foamy solid (180 mg) was charged with a mixture of heptane (5 mL) and ethyl acetate (EtOAc, 5 mL). White solids precipitated out upon stirring at 20° C. The slurry was stirred at 20° C. for 16 h. The solid was collected by filtration and the chiral HPLC analysis for the collected solids (52 mg) showed a 66.0% of enantiomeric excess favoring the first peak (83.0% of the first peak, (S)-11; 17.0% of the second peak, (R)-11). The filtrate obtained was then evaporated to dryness. The resultant oil (108 mg) was analyzed by chiral HPLC and showed a 99.6% of enantiomeric excess favoring the first peak (99.83% of the first peak, (S)-11; 0.17% of the second peak, (R)-11). This result showed in principle that the optical purity of the asymmetric hydrogenation product can be significantly enhanced by selective removal of the minor enantiomer by precipitation of the solid using a suitable solvent system such as ethyl acetate/heptane as described.

(R)-(4-(1-(3-Amino-1-cyclopentyl-3-oxopropyl)-1H-pyrazol-4-yl)-7H-pyrrolo[2,3-d]pyrimidin-7-yl)methyl pivalate ((R)-11). A solution of (4-{1-[(1Z)-3-amino-1-cyclopentyl-3-oxoprop-1-en-1-yl]-1H-pyrazol-4-yl}-7H-pyrrolo[2,3-d]pyrimidin-7-yl)methyl pivalate, (10, 500 mg) in methanol (MeOH, 8.0 mL) in a pressure glass tube was treated with the catalyst Ru(COD)(SL-A153-1)(CF₃CO₂)₂ (6.6 mg) under nitrogen before the reaction mixture was pressurized with hydrogen gas to 50 bar pressure. The reaction mixture was stirred at 30° C. under this hydrogen pressure for 21 h. When HPLC analysis showed that the substrate was completely consumed, the reaction mixture was cooled down to room temperature. The enantiomeric excess of the reaction mixture was determined to be 98% ee (99% of the second peak, (R)-11; 1% of the first peak, (S)-11) by chiral HPLC analysis. The reaction mixture was then filtered through a thin silica gel pad and the pad was washed with methanol (5 mL). The filtrate was then concentrated under reduced pressure to dryness. The resultant foamy solid (470 mg) was analyzed by chiral HPLC analysis and result showed a 98.0% of enantiomeric excess favoring the second peak (99.0% of the second peak, (R)-11; 1.0% of the first peak, (S)-11).

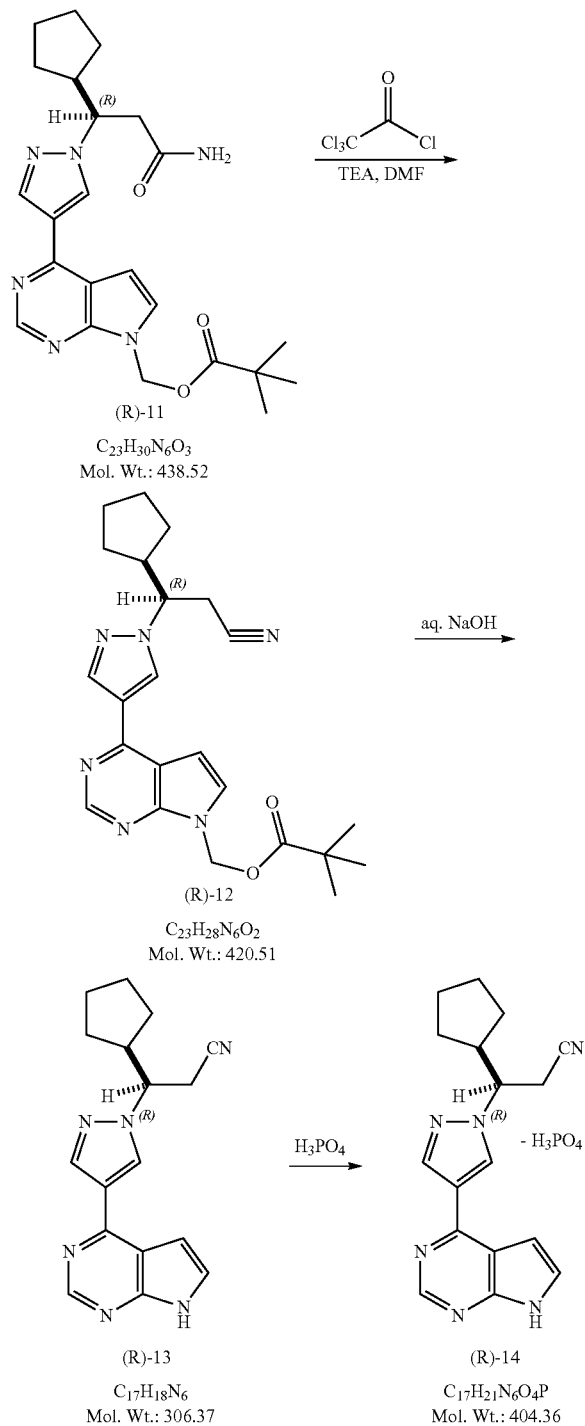

(R)-(4-(1-(2-Cyano-1-cyclopentylethyl)-1H-pyrazol-4-yl)-7H-pyrrolo[2,3-d]pyrimidin-7-yl)methyl pivalate ((R)-12). Method A. To a 50 mL round bottom flask equipped with a stir bar and the nitrogen inlet was charged (R)-(4-(1-(3-amino-1-cyclopentyl-3-oxopropyl)-1H-pyrazol-4-yl)-7H-pyrrolo[2,3-d]pyrimidin-7-yl)methyl pivalate ((R)-11, 413 mg, 0.942 mmol), N,N-dimethylformamide (DMF, 10 mL, 129 mmol) and triethylamine (TEA, 0.525 mL, 3.77 mmol, 4.0 equiv) at room temperature. The resulting mixture was then cooled to 0-5° C. in an ice bath before trichloroacetyl chloride (0.315 mL, 2.82 mmol, 3.0 equiv) was added drop wise via a syringe at room temperature. The resulting reaction mixture was stirred at 0-5° C. for 90 min. When TLC and HPLC showed that the reaction was deemed complete, the reaction mixture was treated with ethyl acetate (EtOAc, 25 mL) and 20% aqueous brine (20 mL). The two layers were separated, and the aqueous layer was extracted with ethyl acetate (EtOAc, 2×25 mL). The combined organic extracts were washed with 20% aqueous brine (35 mL), dried over magnesium sulfate ($MgSO_4$), filtered, and concentrated under reduced pressure. The residual brown oily crude product was purified by flash chromatography ($SiO_2$, 0 to 50% ethyl acetate/hexane gradient elution) to afford (R)-(4-(1-(2-cyano-1-cyclopentylethyl)-1H-pyrazol-4-yl)-7H-pyrrolo[2,3-d]pyrimidin-7-yl)methyl pivalate ((R)-12, 278 mg, 396.1 mg theoretical, 70.2% yield) as the light oil, which was solidified upon standing at room temperature in vacuum. For (R)-12: achiral purity (99.1 area % by HPLC detected at 220 nm); chiral purity (99.6 area % by chiral HPLC; 99.2% ee); $^1$H NMR (DMSO-$d_6$, 400 MHz) δ ppm 8.84 (s, 1H), 8.78 (s, 1H), 8.39 (s, 1H), 7.74 (d, 1H, J=3.7 Hz,), 7.11 (d, 1H, J=3.8 Hz), 6.23 (s, 2H), 4.53 (ddd, 1H, J=9.9, 9.6, 4.2 Hz), 3.26 (dd, 1H, J=17.4, 9.9 Hz), 3.19 (dd, 1H, J=17.2, 4.3 Hz), 2.41 (m, 1H), 1.87-1.13 (m, 8H), 1.07 (s, 9H); $C_{23}H_{28}N_6O_2$ (MW, 420.51), LCMS (EI) m/e 421.4 ($M^+$+H).

(3R)-Cyclopentyl-3-[4-(7H-pyrrolo[2,3-d]pyrimidin-4-yl)pyrazol-1-yl]propionitrile ((R)-13, free base). Method A. To a 25 ml round bottom flask equipped with a stir bar and the nitrogen inlet was charged (R)-(4-(1-(2-cyano-1-cyclopentylethyl)-1H-pyrazol-4-yl)-7H-pyrrolo[2,3-d]pyrimidin-7-yl)methyl pivalate ((R)-12, 278 mg, 0.661 mmol) and methanol (MeOH, 2.50 mL, 37.0 mmol) at room temperature. The resulting homogeneous reaction solution was then treated with a 0.10 M aqueous sodium hydroxide solution (NaOH, 1.5 mL, 0.15 mmol, 2.3 equiv) at room temperature. The resulting reaction mixture was stirred at room temperature for 22 hours. When the reaction was deemed complete, the reaction mixture was diluted with 20% aqueous brine (10 mL) and ethyl acetate (EtOAc, 25 mL). The two layers were separated, and the aqueous layer was extracted with ethyl acetate (EtOAc, 25 mL). The combined organic fractions were dried over magnesium sulfate ($MgSO_4$), filtered, and concentrated under reduced pressure. The residue was purified by flash chromatography ($SiO_2$, 0 to 100% ethyl acetate/hexane gradient elution) to afford (3R)-cyclopentyl-3-[4-(7H-pyrrolo[2,3-d]pyrimidin-4-yl)pyrazol-1-yl]propionitrile ((R)-13, free base, 188 mg, 202.5 mg theoretical, 92.8% yield) as a colorless oil, which solidified upon standing at room temperature in vacuum. For (R)-13 (free base): $^1$H NMR (DMSO-$d_6$, 400 MHz) δ ppm 12.1 (bs, 1H), 8.80 (d, 1H, J=0.42 Hz), 8.67 (s, 1H), 8.37 (s, 1H), 7.59 (dd, 1H, J=2.34, 3.51 Hz), 6.98 (dd, 1H, J=1.40, 3.44 Hz), 4.53 (td, 1H, J=19.5, 4.63 Hz), 3.26 (dd, 1H, J=9.77, 17.2 Hz), 3.18 (dd, 1H, J=4.32, 17.3 Hz), 2.40 (m, 1H), 1.79 (m, 1H), 1.65 to 1.13 (m, 7H); $C_{17}H_{18}N_6$ (MW, 306.37) LCMS (EI) m/e 307 ($M^+$+H).

(3R)-Cyclopentyl-3-[4-(7H-pyrrolo[2,3-d]pyrimidin-4-yl)pyrazol-1-yl]propionitrile phosphate salt ((R)-14, phosphate). To a solution of (3R)-cyclopentyl-3-[4-(7H-pyrrolo[2,3-d]pyrimidin-4-yl)pyrazol-1-yl]propionitrile ((R)-13, free base, 572 g, 1.87 mol) in isopropanol (IPA, 8 L) at 60-65° C. was added a solution of phosphoric acid (186.2 g, 1.9 mol, 1.10 equiv) in isopropanol (1.6 L). No exotherm was observed while adding a solution of phosphoric acid, and a precipitate was formed almost immediately. The resulting mixture was then heated at 76° C. for 1.5 hours, then cooled gradually to ambient temperature and stirred at room temperature for overnight. The mixture was filtered and the solids were washed with a mixture of heptane and isopropanol (1/1, v/v, 3 L) before being transferred back to the original flask and stirred in heptane (8 L) for one hour. The solids were collected by filtration, washed with heptane (1 L), and dried in a convection oven in vacuum at 40° C. to a constant weight to afford (3R)-cyclopentyl-3-[4-(7H-pyrrolo[2,3-d]pyrimidin-4-yl)pyrazol-1-yl]propionitrile phosphate salt ((R)-14, phosphate, 634.2 g , 755 g theoretical, 84% yield) as white to off-white crystalline solids. For (R)-14 (phosphate): mp. 197.6° C.; $^1$H NMR (DMSO-d$_6$, 500 MHz) δ ppm 12.10 (s, 1H), 8.78 (s, 1H), 8.68 (s, 1H), 8.36 (s 1H), 7.58 (dd, 1H, J=1.9, 3.5 Hz), 6.97 (d, 1H, J=3.6 Hz), 4.52 (td, 1H, J=3.9, 9.7 Hz), 3.25 (dd, 1H, J=9.8, 17.2 Hz), 3.16 (dd, 1H, J=4.0, 17.0 Hz), 2.41, (m, 1H), 1.79 (m, 1H), 1.59 (m, 1H), 1.51 (m, 2H), 1.42 (m, 1H), 1.29 (m, 2H), 1.18 (m, 1H); $^{13}$C NMR (DMSO-d$_6$, 125 MHz) δ ppm 152.1, 150.8, 149.8, 139.2, 131.0, 126.8, 120.4, 118.1, 112.8, 99.8, 62.5, 44.3, 29.1, 29.0, 24.9, 24.3, 22.5; C$_{17}$H$_{18}$N$_6$ (MW, 306.37 for free base) LCMS (EI) m/e 307 (M$^+$+H, base peak), 329.1 (M$^+$+Na).

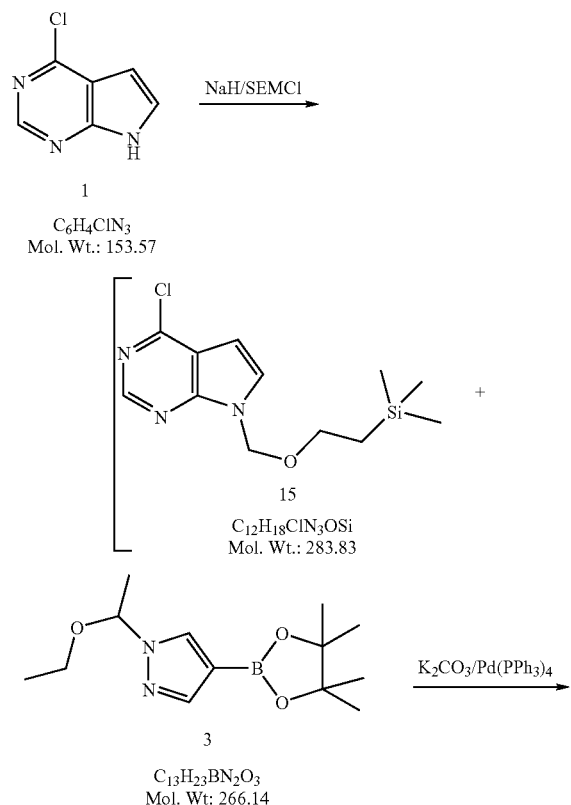

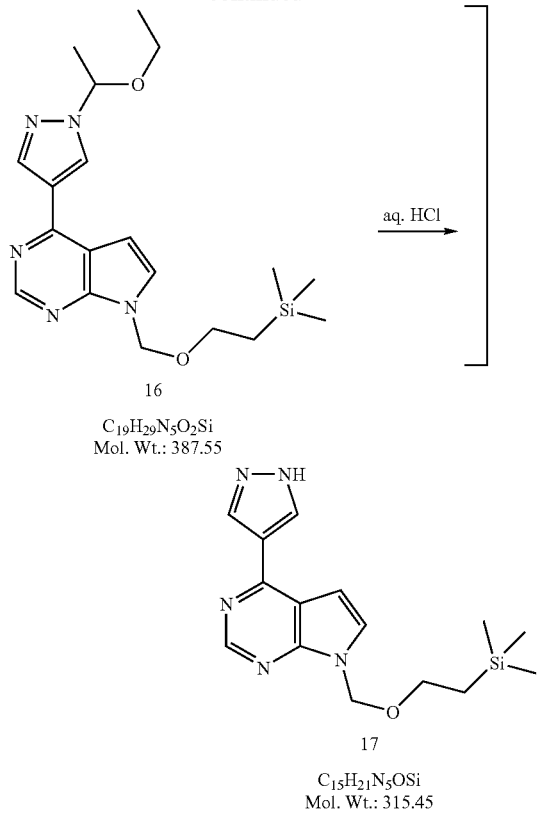

4-(1H-Pyrazol-4-yl)-7-(2-trimethylsilanylethoxymethyl)-7H-pyrrolo[2,3-d]pyrimidine (17). To a suspension of sodium hydride (NaH, 60 wt % oil disposition, 4.05 g, 101.3 mmol, 1.54 equiv) in 1,2-dimethoxyethane (DME, 20.0 mL, 192.4 mmol) at 0-5° C. (ice bath) was added 4-chloropyrrolo[2,3-d]pyrimidine (1, 10.08 g, 65.6 mmol) in 1,2-dimethoxyethane (DME, 80.0 mL, 769.6 mmol) slowly so that the temperature was kept at below 5° C. (−7° C. to 5° C.). A large amount of gas was evolved immediately after the solution of substrate (1) was introduced. The resulting reaction mixture was stirred at 0-5° C. for 30 min before trimethylsilylethoxymethyl chloride (SEM-C1, 12.56 g, 75.3 mmol, 1.15 equiv) was added slowly while the reaction temperature was maintained at below 5° C. After the addition, the reaction was stirred at 0° C. for 1 h before being warmed to room temperature for 23 h. When the HPLC and TLC showed that the reaction was deemed complete, the reaction mixture was quenched with water (46 mL) at room temperature, and the quenched reaction mixture, which contains the desired product (15), was carried into the next Suzuki coupling reaction directly without further work-up and purification.

To the quenched reaction mixture, which contains crude 4-chloro-7-[2-(trimethylsilyl)ethoxy]methyl}-7H-pyrrolo[2,3-d]pyrimidine (15, 18.63 g, 65.64 mmol) from previous reaction as described above, was added 1,2-dimethoxyethane (DME, 38 mL), powder potassium carbonate (K$_2$CO$_3$, 23.56 g, 170.5 mmol, 2.6 equiv), 1-(1-ethoxyethyl)-4-(4,4,5,5-tetramethyl-1,3,2-dioxaborolan-2-yl)-1H-pyrazole (3, 18.60 g, 69.89 mmol, 1.06 equiv) at room temperature. The resulting mixture was degassed four times backfilling with nitrogen gas each time before being treated with tetrakis(triphenylphosphine)palladium(0) (Pd(PPh$_3$)$_4$, 244.2 mg, 0.21 mmol, 0.003 equiv) at room temperature. The resulting reaction mixture was degassed four times backfilling with nitrogen gas each time before being warmed to 80° C. for 4-8 h. When TLC and HPLC showed that the reaction was deemed complete, the reaction mixture was gradually cooled to room temperature and filtered through a short bed of Celite (10 g). The Celite bed was washed with ethyl acetate (EtOAc, 20 mL). The two layers of the filtrate were separated, and the aqueous layer was extracted with ethyl acetate (EtOAc, 2×30 mL). The combined organic extracts were washed with saturated aqueous NaCl solution (20 mL), dried over magnesium sulfate ($MgSO_4$), and concentrated under reduced pressure. The residue, which contains the crude desired Suzuki coupling product (16), was then transferred to a 500 mL round bottom flask with THF (22 mL) for subsequent de-protection reaction without further purification.

A solution of crude Suzuki coupling product (16) in THF (22 mL) was treated with water (108 mL) and a solution of 10% aqueous HCl prepared by mixing 19.6 mL of concentrated HCl with 64 mL of $H_2O$ at room temperature. The resulting reaction mixture was stirred at room temperature for 4-6 h. When TLC and HPLC showed the de-protection reaction was deemed complete, a 30% aqueous sodium hydroxide (NaOH) solution prepared by dissolving 10.4 g of NaOH in 21.0 mL of $H_2O$ was added slowly to the reaction mixture while maintaining the temperature below 25° C. The solid gradually dissolved and re-precipitated after 10 min. The mixture was stirred at room temperature for 1-2 h before the solids were collected by filtration and washed with $H_2O$ (50 mL). The wet cake was transferred to a 250 mL three-necked flask and treated with acetonitrile (MeCN, 112 mL) at room temperature. The mixture was heated to reflux for 2 h before being cooled gradually to room temperature and stirred at room temperature for 1 h. The solids were collected by filtration, washed with MeCN (36 mL) and dried at 40-45° C. in a vacuum oven to afford 4-(1H-pyrazol-4-yl)-7-(2-trimethylsilanyl-ethoxymethyl)-7H-pyrrolo[2,3-d]pyrimidine (17, 15.3 g, 20.7 g theoretical, 73.9% yield for three steps) as white crystalline solids (99.4 area % by HPLC). For 17: $^1$H NMR (DMSO-$d_6$, 400 MHz) δ ppm 13.41 (bs, 1H), 8.74 (s, 1H), 8.67 (bs, 1H), 8.35 (bs, 1H), 7.72 (d, 1H, J=3.7 Hz), 7.10 (d, 1H, J=3.7 Hz), 5.61 (s, 2H), 3.51 (t, 2H, J=8.2 Hz), 0.81 (t, 2H, J=8.2 Hz), 0.13 (s, 9H); $C_{15}H_{21}N_5OSi$ (MW, 315.45), LCMS (EI) m/e 316 ($M^+$+H).

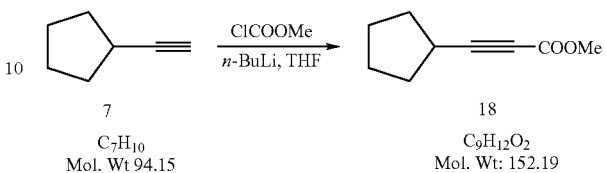

7
$C_7H_{10}$
Mol. Wt 94.15

18
$C_9H_{12}O_2$
Mol. Wt: 152.19

Methyl 3-cyclopentylpropiolate (18). To a stirred solution of cyclopentylacetylene (7, 17.49 mL, 150.0 mmol) in anhydrous tetrahydrofuran (THF, 200 mL, 2466 mmol) at −78° C. was added 2.50 M of n-butyllithium in hexane (66.0 mL, 165 mmol, 1.1 equiv). The resulting milky suspension was stirred at −78° C. for 30 min. Methyl chloroformate (17.6 mL, 225 mmol, 1.5 equiv) was then added. The reaction mixture became a clear solution. The cooling bath was then removed, and the reaction mixture was allowed to warm to room temperature and stirred at room temperature for 1 h. The reaction mixture became a suspension again. When TLC (5% EtOAc/hexane, KMnO4 stain) showed the reaction was deemed complete, the reaction mixture was quenched with saturated aqueous $NH_4Cl$ solution (150 mL) and extracted with diethyl ether ($Et_2O$, 2×200 mL). The combined organic layers were washed with saturated aqueous NaCl solution, dried over magnesium sulfate ($MgSO_4$), filtered and concentrated under the reduced pressure. The residue was distilled under vacuum (99-101° C./16 mbar) to afford methyl 3-cyclopentylpropiolate (18, 21.856 g, 22.83 g theoretical, 96% yield) as a colorless oil. For 18: $^1$H NMR ($CDCl_3$, 400 MHz) δ ppm 3.74 (s, 3H), 2.73 (m, 1H), 1.95 (m, 2H), 1.72 (m, 4H), 1.57 (m, 2H).

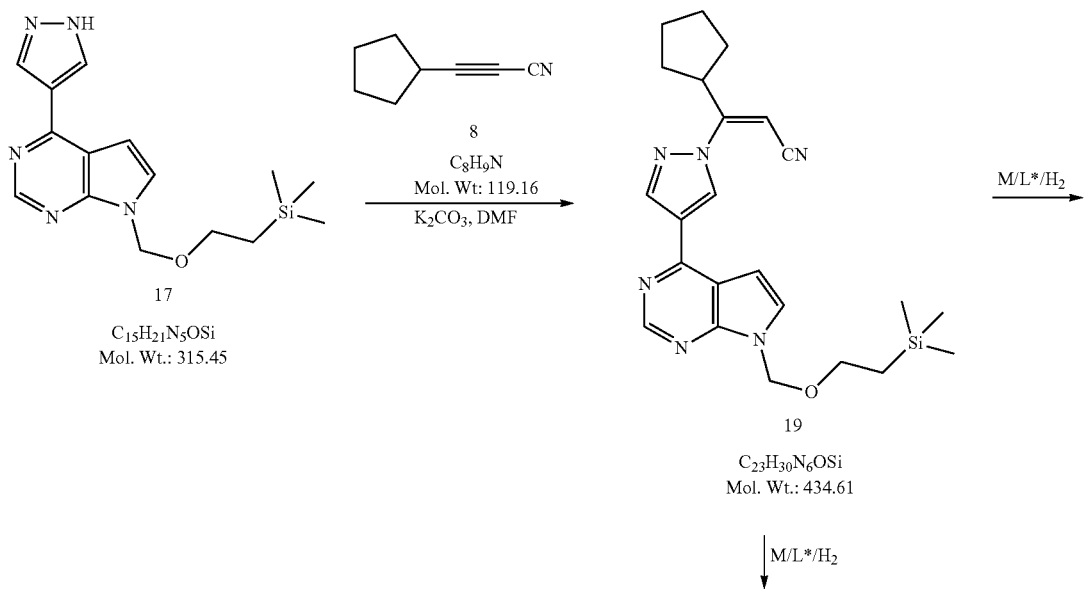

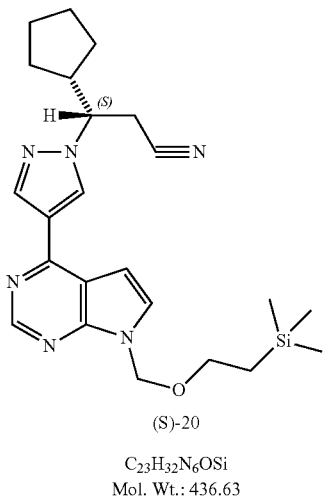

(S)-20

C₂₃H₃₂N₆OSi
Mol. Wt.: 436.63

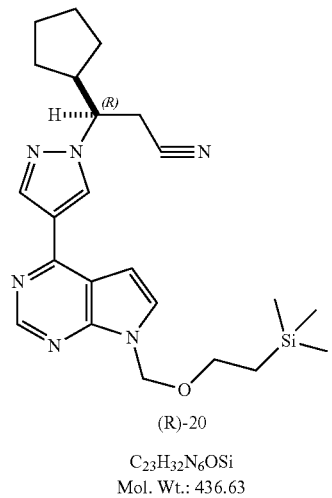

(R)-20

C₂₃H₃₂N₆OSi
Mol. Wt.: 436.63

(Z)-3-Cyclopentyl-3-(4-(7-((2-(trimethylsily)ethoxy)methyl)-7H-pyrrolo[2,3-d]pyrimidin-4-yl)-1H-pyrazol-1-yl)acrylonitrile (19). To a stirred solution of 4-(1H-pyrazol-4-yl)-7-{[2-(trimethylsilyl)ethoxy]methyl}-7H-pyrrolo[2,3-d]pyrimidine (17, 7.260 g, 23.01 mmol) and 3-cyclopentylprop-2-ynenitrile (8, 6.140 g, 34.52 mmol, 1.5 equiv) in N,N-Dimethylformamide (DMF, 40.0 mL, 516 mmol) at room temperature was added solid potassium carbonate (K₂CO₃, 318 mg, 2.30 mmol, 0.1 equiv). The resulting reaction mixture was stirred at room temperature for 30 min. When LCMS showed the reaction was deemed complete, the reaction mixture was quenched with water (80 mL), extracted with EtOAc (2×150 mL). The combined organic layers were washed with water (80 mL) and brine (50 mL), dried over magnesium sulfate (MgSO₄), filtered and concentrated under reduced pressure. The residue was purified by flash chromatography (SiO₂, 0-30% EtOAc/hexane gradient elution) to give (Z)-3-cyclopentyl-3-(4-(7((2-(trimethylsilyl)ethoxy)methyl)-7H-pyrrolo[2,3-d]pyrimidin-4-yl)-1H-pyrazol-1-yl)acrylonitrile (19, 8.256 g, 10.0 g theoretical, 82.6% yield) as a colorless syrup. For 19: ¹H NMR (CDCl₃, 300 MHz) δ ppm 9.15 (bs, 1H), 8.96 (s, 1H), 8.56 (s, 1H), 7.51 (d, 1H, J=3.5 Hz), 6.93 (d, 1H, J=3.5 Hz), 5.75 (s, 2H), 5.29 (s, 1H), 3.62 (m, 1H), 3.60 (t, 2H, J=8.2 Hz), 2.16 (m, 2H), 1.81 (m, 4H), 1.59 (m, 2H), 0.98 (t, 2H, J=8.2 Hz), 0.00 (s, 9H); C₂₃H₃₀N₆OSi (MW, 434.61), LCMS (EI) m/e 435.2 (M⁺+H).

(R)-3-Cyclopentyl-3-(4-(7-((2-(trimethylsilyl)ethoxy)methyl)-7H-pyrrolo[2,3-d]pyrimidin-4-yl)-1H-pyrazol-1-yl)propanenitrile ((R)-20) and (S)-3-Cyclopentyl-3-(4-(7-((2-(trimethylsilyl)ethoxy)methyl)-7H-pyrrolo[2,3-d]pyrimidin-4-yl)-1H-pyrazol-1-yl)propanenitrile ((S)-20).

General screening procedure for asymmetric hydrogenation using the substrate, (Z)-3-cyclopentyl-3-(4-(7-((2-(trimethylsilyl)ethoxy)methyl)-7H-pyrrolo[2,3-d]pyrimidin-4-yl)-1H-pyrazol-1-yl)acrylonitrile (19), to afford optically enriched product, 3-cyclopentyl-3-(4-(7-((2-(trimethylsilyl)ethoxy)methyl)-7H-pyrrolo[2,3-d]pyrimidin-4-yl)-1H-pyrazol-1-yl)propanenitrile ((R)-20 or (S)-20): A 300 mL-volume autoclave with glass vial (20 mL) was charged with the substrate (19), the catalyst (metal, ligand, and catalyst precursor), and oxygen-free solvent (4-6 mL) under nitrogen. This autoclave was charged with hydrogen gas to the desired pressure and stirred at room temperature or heated with oil bath. After hydrogen gas was released, the reaction mixture was concentrated under reduced pressure. The residue was purified by eluting through a silica gel pad using a mixture of ethyl acetate and methanol (v/v=9/1) to afford product, 3-cyclopentyl-3-(4-(7-((2-(trimethylsilyl)ethoxy)methyl)-7H-pyrrolo[2,3-d]pyrimidin-4-yl)-1H-pyrazol-1-yl)propanenitrile ((R)-20 or (S)-20), for chemical conversion (HPLC and chiral HPLC), LC/MS and NMR spectroscopy and enantiomeric excess (% ee by chiral HPLC) determination.

The determination of enantiomeric excess (% ee) of the product was carried by chiral HPLC analysis. A chiral HPLC method was developed using a ChiralcelChiralcel® OD-H column (4.6×250 mm, 5 μm), purchased from Chiral Technologies, Inc., packed with a silicagel coated with cellulose tris(3,5-dimethylphenyl carbamate) (Chiralcel® OD). The two enantiomers, (R)-20 or (S)-20, are separated with a resolution greater than 3.0 by using a mobile phase made of 10% ethanol and 90% hexanes at room temperature with a flow rate of 1 mL/min. The UV detection wavelength is 220 nm. The retention times for (S)-enantiomer ((S)-20) and (R)-enantiomer ((R)-20) are 10.3 minutes (the first peak) and 13.1 minutes (the second peak), respectively.

For (R)-20 or (S)-20: ¹H NMR (DMSO-d₆, 400 MHz) δ ppm 8.83 (s, 1H), 8.75 (s, 1H), 8.39 (s, 1H), 7.77 (d, 1H, J=3.7 Hz), 7.09 (d, 1H, J=3.7 Hz), 5.63 (s, 2H), 4.53 (td, 1H, J=19.4, 4.0 Hz), 3.51 (t, 2H, J=8.1 Hz), 3.23 (dq, 2H, J=9.3, 4.3 Hz), 2.41 (m, 1H), 1.79 (m, 1H), 1.66-1.13 (m, 7H), 0.81 (t, 2H, J=8.2 Hz), 0.124 (s, 9H); C₂₃H₃₂N₆OSi (MW, 436.63), LCMS (EI) m/e 437 (M⁺+H) and 459 (M⁺+Na).

The following table summarizes analyses and reaction conditions for this asymmetric hydrogenation.

| Metal/Ligand/ Catalyst Precursor | Solvent | Temp. (° C.) | H₂ Pressure (Bar) | Time (h) | Conversion (HPLC area %) | % ee | Major Enantiomer (R)- or (S)-20 |
|---|---|---|---|---|---|---|---|
| [Ru(p-cymene) (S-C3-TunePhos)Cl]Cl | MeOH | 50 | 60 | 69 | 12 | 72.7 | (S)-20 (1st peak) |
| [Ru(p-cymene) (S-C3-TunePhos)Cl]Cl | EtOAc | 75 | 60 | 19 | 93 | 38.9 | (S)-20 (1st peak) |
| [Ru(p-cymene) (S-C3-TunePhos)Cl]Cl | THF | 75 | 60 | 19 | 94 | 29.9 | (S)-20 (1st peak) |
| [Ru(p-cymene) (S-C3-TunePhos)Cl]Cl | CH₂Cl₂ | 75 | 60 | 19 | 99 | 34.1 | (S)-20 (1st peak) |
| [Ru(p-cymene) (S-C1-TunePhos)Cl]Cl | CH₂Cl₂ | 75 | 60 | 21 | 97 | 32.7 | (S)-20 (1st peak) |
| [Ru(p-cymene) (S-C2-TunePhos)Cl]Cl | CH₂Cl₂ | 75 | 60 | 21 | 97 | 26.0 | (S)-20 (1st peak) |
| [Ru(p-cymene) (S-C4-TunePhos)Cl]Cl | CH₂Cl₂ | 75 | 60 | 21 | 99 | 17.4 | (S)-20 (1st peak) |
| [Ru(p-cymene) (S-C5-TunePhos)Cl]Cl | CH₂Cl₂ | 75 | 60 | 21 | 98 | 7.4 | (S)-20 (1st peak) |
| [Ru(p-cymene) (S-C6-TunePhos)Cl]Cl | CH₂Cl₂ | 75 | 60 | 21 | 91 | 3.4 | (S)-20 (1st peak) |

Structures of chiral phosphine ligands used in this study are listed below.

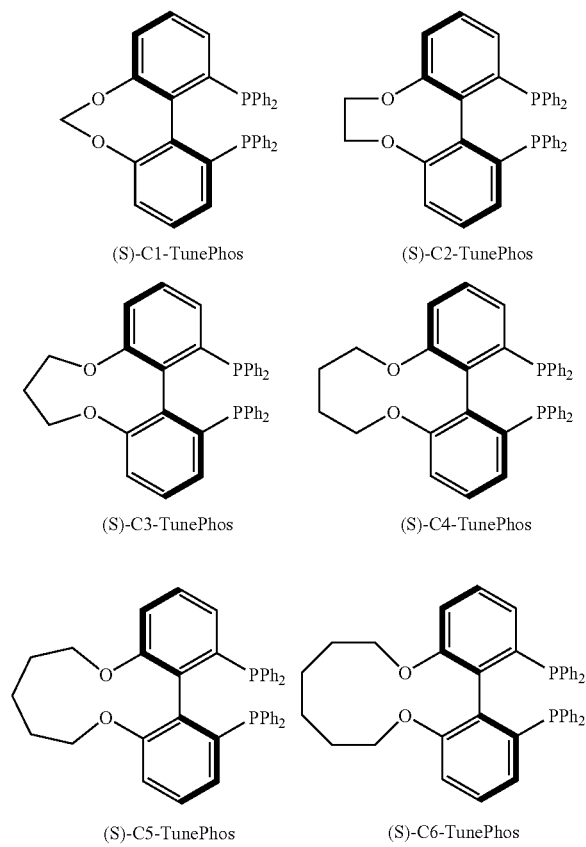

(S)-C1-TunePhos
(S)-C2-TunePhos
(S)-C3-TunePhos
(S)-C4-TunePhos
(S)-C5-TunePhos
(S)-C6-TunePhos Representative preparative asymmetric hydrogenation procedure is described below.

(S)-3-Cyclopentyl-3-(4-(7-((2-(trimethylsilyl)ethoxy)methyl)-7H-pyrrolo[2,3-d]pyrimidin-4-yl)-1H-pyrazol-1-yl) propanenitrile ((S)-20). A solution of (Z)-3-cyclopentyl-3-(4-(7-((2-(trimethylsilyl)ethoxy)methyl)-7H-pyrrolo[2,3-d] pyrimidin-4-yl)-1H-pyrazol-1-yl)acrylonitrile (19, 116 mg) in methylene chloride (CH₂Cl₂, 4.0 mL) in a pressure glass tube was treated with the catalyst [Ru(p-cymene)(S-C3-TunePhos)Cl]Cl (8.5 mg) under nitrogen before the reaction mixture was pressurized with hydrogen gas to 60 bar pressure. The reaction mixture was stirred at 75° C. under this hydrogen pressure for 19 h. When HPLC analysis showed that the substrate was completely consumed, the reaction mixture was cooled down to room temperature. The enantiomeric excess of the reaction mixture was determined to be 34.1% ee (67.05% of the first peak, (S)-20; 32.95% of the second peak, (R)-20) by chiral HPLC analysis. The reaction mixture was then filtered through a thin silica gel pad and the pad was washed with methylene chloride (CH₂Cl₂, 5 mL). The filtrate was then concentrated under reduced pressure to dryness. The resultant foamy solid (107 mg) was analyzed by chiral HPLC analysis and result showed a 34.1% of enantiomeric excess favoring the first peak (67.05% of the first peak, (S)-20; 32.95% of the second peak, (R)-20).

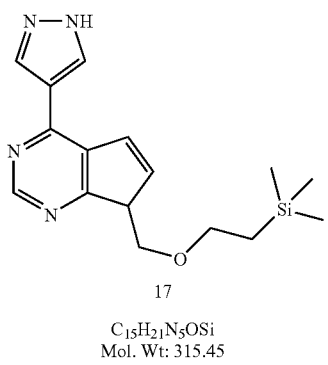
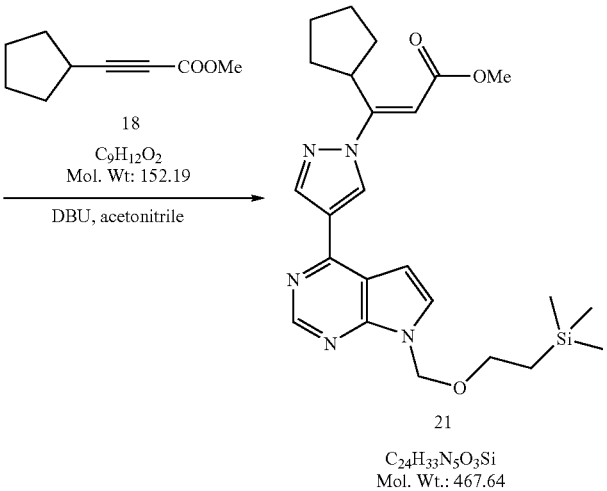
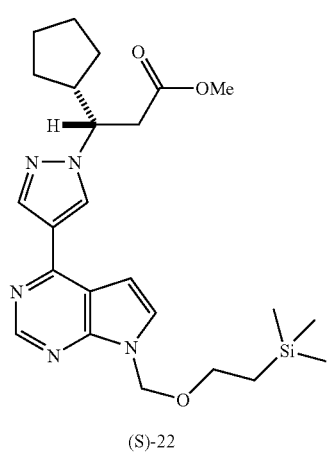
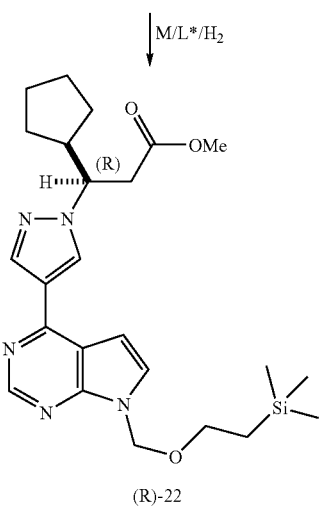

(E)-Methyl 3-cyclopentyl-3-(4-(7-((2-(trimethylsilyl)ethoxy)methyl)-7H-pyrrolo[2,3-d]pyrimidin-4-yl)-1H-pyrazol-1-yl)acrylate (21). To a stirred suspension of 4-(1H-pyrazol-4-yl)-7-{[2-(trimethylsilyl)ethoxy]methyl}-7H-pyrrolo[2,3-d]pyrimidine (17, 12.08 g, 38.31 mmol) and methyl 3-cyclopentylprop-2-ynoate (18, 8.970 g, 45.97 mmol, 1.2 equiv) in acetonitrile (76 mL, 1400 mmol) at room temperature was added 1,8-diazabicyclo[5.4.0]undec-7-ene (DBU, 2.92 mL, 19.2 mmol, 0.5 equiv). The resulting reaction mixture was stirred at room temperature for 2 h. When LCMS showed the reaction was deemed complete, the reaction mixture was quenched with water (50 mL) and 1 N aqueous HCl solution (20 mL). The quenched reaction mixture was adjusted to pH 4 after treatment with 1 N aqueous HCl solution. The mixture was then extracted with EtOAc (2×100 mL) and the combined organic layers were washed with brine, dried over magnesium sulfate (MgSO$_4$), filtered and concentrated under reduced pressure. The residue was purified by Combiflash (SiO$_2$, 0-50% EtOAc/hexane gradient elution) to afford (E)-methyl 3-cyclopentyl-3-(4-(7-((2-(trimethylsilyl)ethoxy)methyl)-7H-pyrrolo[2,3-d]pyrimidin-4-yl)-1H-pyrazol-1-yl)acrylate (21, 6.838 g, 17.92 g theoretical, 38% in yield) as a colorless, very viscous oil. For 19: $^1$H NMR (CDCl$_3$, 400 MHz) δ ppm 8.93 (s, 1H), 8.55 (bs, 1H), 8.44 (s, 1H), 7.49 (d, 1H, J=3.5 Hz), 6.86 (d, 1H, J=3.5 Hz), 6.34 (s, 1H), 5.74 (s, 2H), 4.56 (m, 1H), 3.84 (s, 3H), 3.60 (t, 2H, J=8.2 Hz), 2.01 (m, 2H), 1.96 (m, 4H), 1.77 (m, 2H), 0.98 (t, 2H, J=8.2 Hz), 0.00 (s, 9H); C$_{24}$H$_{33}$N$_5$O$_3$Si (MW, 467.64), LCMS (EI) m/e 468.2 (M$^+$+H).

(R)-Methyl 3-cyclopentyl-3-(4-(7-((2-(trimethylsilyl)ethoxy)methyl)-7H-pyrrolo[2,3-d]pyrimidin-4-yl)-1H-pyrazol-1-yl)propanoate ((R)-22) and (S)-Methyl 3-cyclopentyl-3-(4-(7-((2-(trimethylsilyl)ethoxy)methyl)-7H-pyrrolo[2,3-d]pyrimidin-4-yl)-1H-pyrazol-1-yl)propanoate ((S)-22)

General screening procedure for asymmetric hydrogenation using the substrate, (E)-methyl 3-cyclopentyl-3-(4-(7-((2-(trimethylsilyl)ethoxy)methyl)-7H-pyrrolo[2,3-d]pyrimidin-4-yl)-1H-pyrazol-1-yl)acrylate (21), to afford optically enriched product, methyl 3-cyclopentyl-3-(4-(7-((2-(trimethylsilyl)ethoxy)methyl)-7H-pyrrolo[2,3-d]pyrimidin-4-yl)-1H-pyrazol-1-yl)propanoate ((R)-22 or (S)-22): A 300 mL-volume autoclave with glass vial (20 mL) was charged with the substrate (21), the catalyst (metal, ligand, and catalyst precursor), and oxygen-free solvent (4-6 mL)

under nitrogen. This autoclave was charged with hydrogen gas to the desired pressure and stirred at room temperature or heated with oil bath. After hydrogen gas was released, the reaction mixture was concentrated under reduced pressure. The residue was purified by eluting through a silica gel pad using a mixture of ethyl acetate and methanol (v/v=9/1) to afford product, methyl 3-cyclopentyl-3-(4-(7-((2-(trimethylsilyl)ethoxy)methyl)-7H-pyrrolo[2,3-d]pyrimidin-4-yl)-1H-pyrazol-1-yl)propanoate ((R)-22 or (S)-22), for chemical conversion (HPLC and chiral HPLC), LC/MS and NMR spectroscopy and enantiomeric excess (% ee by chiral HPLC) determination.

The determination of enantiomeric excess (% ee) of the product was carried out by chiral HPLC analysis. A chiral HPLC method was developed using a Chiralcel® OD-H column (4.6×250 mm, 5 μm), purchased from Chiral Technologies, Inc., packed with a silicagel coated with cellulose tris (3,5-dimethylphenyl carbamate) (Chiralcel® OD). The two enantiomers (R)-22 or (S)-22, are separated with a resolution greater than 3.0 by using a mobile phase made of 15% ethanol and 85% hexanes at room temperature with a flow rate of 1 mL/min. The UV detection wavelength is 254 nm. The retention times for (S)-enantiomer ((S)-22) and (R)-enantiomer ((R)-22) are 5.3 minutes (the first peak) and 8.2 minutes (the second peak), respectively.

For (R)-22 or (S)-22: $C_{24}H_{35}N_5O_3Si$ (MW, 469.65), LCMS (EI) m/e 470 (M$^+$+H) and 492 (M$^+$+Na).

The following table summarizes analyses and reaction conditions for this asymmetric hydrogenation.

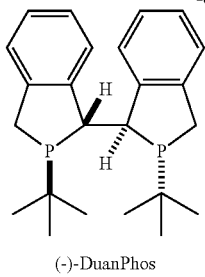

(−)-DuanPhos

Representative preparative asymmetric hydrogenation procedures are described below.

(S)-Methyl 3-cyclopentyl-3-(4-(7-((2-(trimethylsilyl)ethoxy)methyl)-7H-pyrrolo[2,3-d]pyrimidin-4-yl)-1H-pyrazol-1-yl)propanoate ((S)-22). A solution of (E)-methyl 3-cyclopentyl-3-(4-(7-((2-(trimethylsilyl)ethoxy)methyl)-7H-pyrrolo[2,3-d]pyrimidin-4-yl)-1H-pyrazol-1-yl)acrylate (21, 109 mg) in ethyl acetate (EtOAc, 5.0 mL) in a pressure glass tube was treated with the catalyst [Rh(COD)(+)-DuanPhos](BF$_4$) (5.5 mg) under nitrogen before the reaction mixture was pressurized with hydrogen gas to 20 bar pressure. The reaction mixture was stirred at room temperature under this hydrogen pressure for 19 h. When HPLC analysis showed that the substrate was completely consumed, the reaction mixture was cooled down to room temperature. The enantiomeric excess of the reaction mixture was determined to be 97.9% ee (98.95% of the first peak, (S)-22; 1.05% of the

| Metal/Ligand/Catalyst Precursor | Solvent | Temp. (° C.) | H$_2$ Pressure (Bar) | Time (h) | Conversion (HPLC area %) | % ee | Major Enantiomer (R)- or (S)-22 |
|---|---|---|---|---|---|---|---|
| Rh(COD)(SSRR-TangPhos)(BF$_4$) | CH$_2$Cl$_2$ | 50 | 60 | 17 | 99 | 93.1 | (S)-22 (1$^{st}$ peak) |
| Rh(COD)(SSRR-TangPhos)(BF$_4$) | MeOH | 15 | 60 | 67 | 99 | 92.7 | (S)-22 (1$^{st}$ peak) |
| Rh(COD)(SSRR-TangPhos)(BF$_4$) | EtOAc | 15 | 60 | 67 | 99 | 89.7 | (S)-22 (1$^{st}$ peak) |
| Rh(COD)(SSRR-TangPhos)(BF$_4$) | THF | 15 | 60 | 67 | 99 | 90.1 | (S)-22 (1$^{st}$ peak) |
| Rh(COD)(+)- DuanPhos)(BF$_4$) | CH$_2$Cl$_2$ | 15 | 60 | 67 | 99 | 95.9 | (S)-22 (1$^{st}$ peak) |
| Rh(COD)(+)- DuanPhos)(BF$_4$) | MeOH | 15 | 60 | 67 | 99 | 92.3 | (S)-22 (1$^{st}$ peak) |
| Rh(COD)(+)- DuanPhos)(BF$_4$) | EtOAc | 15 | 20 | 19 | 99 | 97.9 | (S)-22 (1$^{st}$ peak) |
| Rh(COD)(+)- DuanPhos)(BF$_4$) | THF | 15 | 20 | 19 | 99 | 97.0 | (S)-22 (1$^{st}$ peak) |
| Rh(COD)(−)- DuanPhos)(BF$_4$) | EtOAc | 35 | 20 | 21 | 25 | 95.1 | (R)-22 (2$^{nd}$ peak) |
| Rh(COD)(−)- DuanPhos)(BF$_4$) | THF | 35 | 50 | 22 | 73 | 94.7 | (R)-22 (2$^{nd}$ peak) |

Structures of chiral phosphine ligands used in this study are listed below.

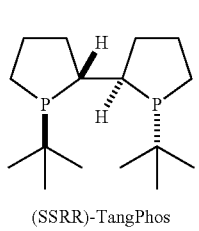

(SSRR)-TangPhos

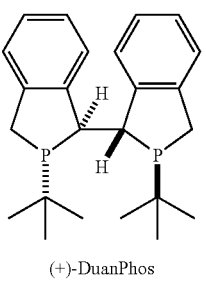

(+)-DuanPhos second peak, (R)-22) by chiral HPLC analysis. The reaction mixture was then filtered through a thin silica gel pad and the pad was washed with ethyl acetate (EtOAc, 5 mL). The filtrate was then concentrated under reduced pressure to dryness. The resultant foamy solid (98 mg) was analyzed by chiral HPLC analysis and result showed a 97.9% of enantiomeric excess favoring the first peak (98.95% of the first peak, (S)-22; 1.05% of the second peak, (R)-22).

(R)-Methyl 3-cyclopentyl-3-(4-(7-((2-(trimethylsilypethoxy)methyl)-7H-pyrrolo[2,3-d]pyrimidin-4-yl)-1H-pyrazol-1-yl)propanoate ((R)-22). A solution of (E)-methyl 3-cyclopentyl-3-(4-(7-((2-(trimethylsilyl)ethoxy)methyl)-7H-pyrrolo[2,3-d]pyrimidin-4-yl)-1H-pyrazol-1-yl)acrylate (21, 815 mg) in tetrahydrofuran (THF, 8.0 mL) in a pressure glass tube was treated with the catalyst [Rh(COD)(−)-Duan- Phos](BF$_4$) (4.6 mg) under nitrogen before the reaction mixture was pressurized with hydrogen gas to 50 bar pressure. The reaction mixture was stirred at 35° C. under this hydrogen pressure for 22 h. When HPLC analysis showed that the substrate was almost completely consumed, the reaction mixture was cooled down to room temperature. The enantiomeric excess of the reaction mixture was determined to be 94.7% ee (97.35% of the second peak, (R)-22; 2.65% of the first peak, (S)-22) by chiral HPLC analysis. The reaction mixture was then filtered through a thin silica gel pad and the pad was washed with tetrahydrofuran (THF, 5 mL). The filtrate was then concentrated under reduced pressure to dryness. The resultant foamy solid (778 mg) was analyzed by chiral HPLC analysis and result showed a 94.7% of enantiomeric excess favoring the second peak (97.35% of the second peak, (R)-22; 2.65% of the first peak, (S)-22).

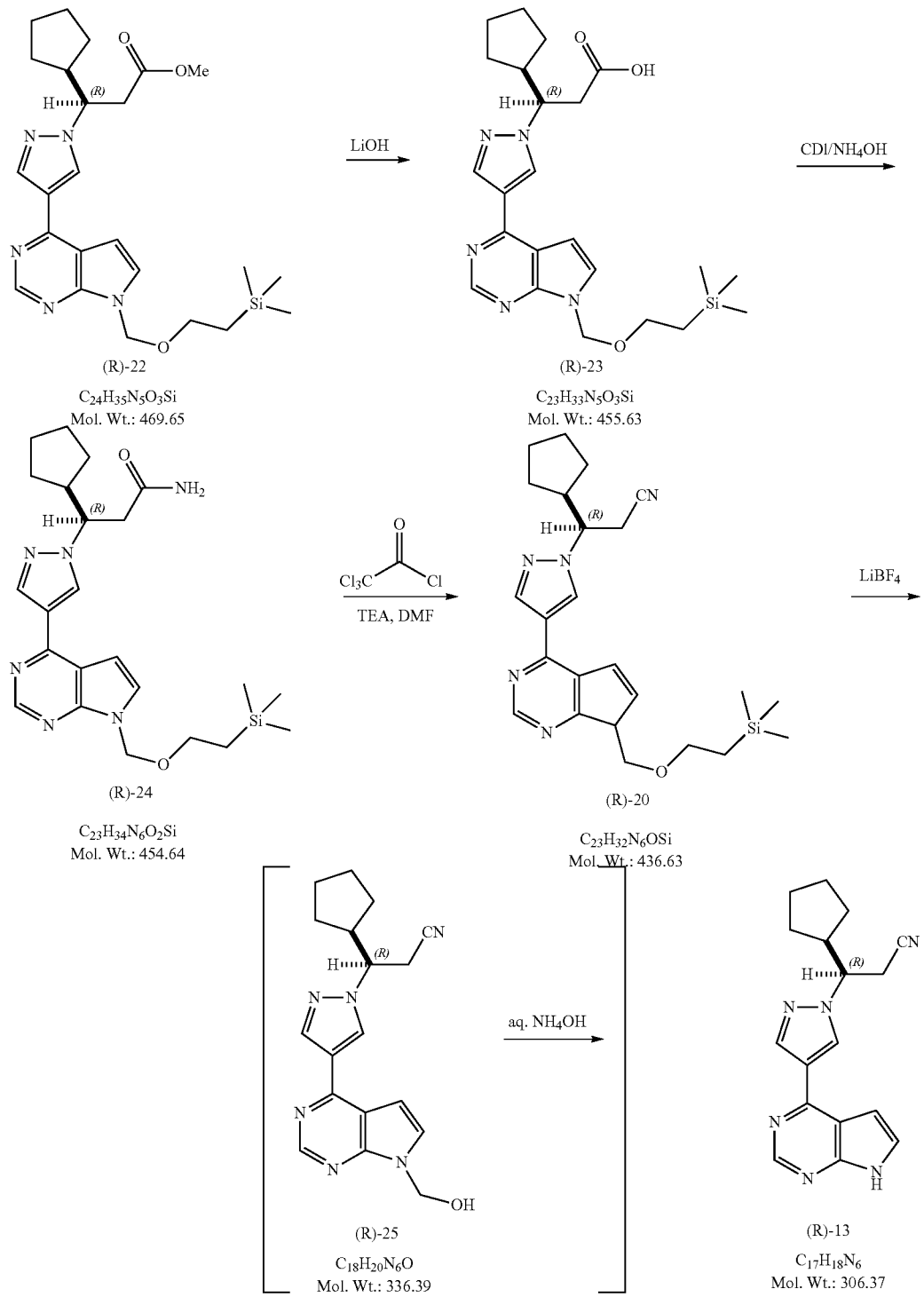

(3R)-3-Cyclopentyl-3-(4-(7-((2-(trimethylsilyl)ethoxy)methyl)-7H-pyrrolo[2,3-d]pyrimidin-4-yl)-1H-pyrazol-1-yl)propanoic acid ((R)-23). To a stirred solution of (3R)-methyl 3-cyclopentyl-3-(4-(7-((2-(trimethylsilyl)ethoxy)methyl)-7H-pyrrolo[2,3-d]pyrimidin-4-yl)-1H-pyrazol-1-yl)propanoate ((R)-22, 2.47 g, 5.26 mmol) in THF (30 mL) at room temperature was added a solution of lithium hydroxide monohydrate (LiOH—$H_2O$, 265 mg, 6.31 mmol, 1.2 equiv) in water (15 mL). The reaction mixture was stirred at room temperature for 3 h. When LCMS showed the reaction was complete, the reaction mixture was then acidified with 1 N aqueous HCl solution to pH 5 before it was extracted with EtOAc (2×25 mL). The combined organic layers were washed with brine, dried over magnesium sulfate ($MgSO_4$), filtered and concentrated under reduced pressure to afford (3R)-3-cyclopentyl-3-(4-(7-((2-(trimethylsilyl)ethoxy)methyl)-7H-pyrrolo[2,3-d]pyrimidin-4-yl)-1H-pyrazol-1-yl)propanoic acid ((R)-23, 2.40 g, 2.40 g theoretical, 100% yield) as a colorless oil, which solidified upon standing at room temperature in vacuo. For (R)-23: $^1$H NMR ($CDCl_3$, 300 MHz) δ ppm 8.95 (s, 1H), 8.95 (bs, 1H), 8.36 (s, 1H), 7.57 (d, 1H, J=3.7 Hz), 6.99 (d, 1H, J=3.7 Hz), 5.74 (s, 2H), 4.65 (dt, 1H, J=3.1, 10.3 Hz), 3.58 (t, 2H, J=8.2 Hz), 3.24 (dd, 1H, J=16.5, 10.3 Hz), 3.04 (dd, 1H, J=16.2, 3.1 Hz), 2.59 (m, 1H), 2.00 (m, 1H), 1.77-1.24 (m, 7H), 0.97 (t, 2H, J=8.2 Hz), 0.00 (s, 9H); $C_{23}H_{33}N_5O_3Si$ (MW, 455.63), LCMS (EI) m/e 456.1 ($M^+$+H).

(3R)-3-Cyclopentyl-3-(4-(7-((2-(trimethylsilyl)ethoxy)methyl)-7H-pyrrolo[2,3-d]pyrimidin-4-yl)-1H-pyrazol-1-yl)propanamide ((R)-24). To a stirred solution of (3R)-3-cyclopentyl-3-(4-(7-((2-(trimethylsilyl)ethoxy)methyl)-7H-pyrrolo[2,3-d]pyrimidin-4-yl)-1H-pyrazol-1-yl)propanoic acid ((R)-23, 20 mg, 0.044 mmol) in DMF (1 mL) at room temperature was added N,N-carbonyldiimidazole (CDI, 21 mg, 0.13 mmol, 3.0 equiv). The reaction mixture was then stirred at room temperature and TLC was used to follow the reaction for formation of acyl imidazole (consumption of acid to a higher Rf spot with 30% EtOAc/hexane). When TLC showed that the acyl imidazole transformation was complete, ammonia gas was then bubbled through the stirred solution for 30 min to afford the amide (followed by LCMS). The excess amount of ammonia gas was evaporated by bubbling nitrogen vigorously through the solution. The crude product, (3R)-3-cyclopentyl-3-(4-(7-((2-(trimethylsilyl)ethoxy)methyl)-7H-pyrrolo[2,3-d]pyrimidin-4-yl)-1H-pyrazol-1-yl)propanamide ((R)-24), in DMF was used directly to the following reaction to convert amide ((R)-24) into the corresponding nitrile ((R)-20).

(3R)-cyclopentyl-3-{4-[7-(2-trimethylsilanylethoxymethyl)-7H-pyrrolo[2,3-d]pyrimidin-4-yl]pyrazol-1-yl}propionitrile ((R)-20). Method A. To a stirred solution of (3R)-3-cyclopentyl-3-(4-(7-((2-(trimethylsilyl)ethoxy)methyl)-7H-pyrrolo[2,3-d]pyrimidin-4-yl)-1H-pyrazol-1-yl)propanamide ((R)-24, 20 mg, 0.044 mmol) in DMF (1 mL) at 0° C. was added methylene chloride (1 mL) and triethylamine (0.12 mL, 0.88 mmol, 20.0 equiv), followed by trichloroacetyl chloride (0.052 ml, 0.462 mmol, 10.5 equiv). The resulting reaction mixture was stirred at 0° C. for 1 h. When LCMS showed the reaction was complete, the reaction mixture was quenched with saturated sodium bicarbonate solution ($NaHCO_3$, 5 mL) before being extracted with EtOAc (2×10 mL). The combined organic layers were washed with brine, dried over magnesium sulfate ($MgSO_4$), filtered and concentrated under reduced pressure. The residue was purified by silica gel chromatography with 0-75% EtOAc/hexane gradient elution to give (3R)-cyclopentyl-3-{4-[7-(2-trimethylsilanylethoxymethyl)-7H-pyrrolo[2,3-d]pyrimidin-4-yl]pyrazol-1-yl}propionitrile ((R)-20, 10 mg, 19 mg theoretical, 53% yield). For (R)-20: $^1$H NMR (DMSO-$d_6$, 400 MHz) δ ppm 8.83 (s, 1H), 8.75 (s, 1H), 8.39 (s, 1H), 7.77 (d, 1H, J=3.7 Hz), 7.09 (d, 1H, J=3.7 Hz), 5.63 (s, 2H), 4.53 (td, 1H, J=19.4, 4.0 Hz), 3.51 (t, 2H, J=8.1 Hz), 3.23 (dq, 2H, J=9.3, 4.3 Hz), 2.41 (m, 1H), 1.79 (m, 1H), 1.66-1.13 (m, 7H), 0.81 (t, 2H, J=8.2 Hz), 0.124 (s, 9H); $C_{23}H_{32}N_6OSi$ (MW, 436.63), LCMS (EI) m/e 437 ($M^-$+H) and 459 ($M^+$+Na).

(3R)-Cyclopentyl-3-[4-(7H-pyrrolo[2,3-d]pyrimidin-4-yl)pyrazol-1-yl]propionitrile ((R)-13, free base). Method B. To a solution of (3R)-cyclopentyl-3-{4-[7-(2-trimethylsilanylethoxymethyl)-7H-pyrrolo[2,3-d]pyrimidin-4-yl]pyrazol-1-yl}propionitrile ((R)-20, 463 g, 1.06 mol, 98.6% ee) in acetonitrile (4.5 L) was added water (400 mL) followed immediately by lithium tetrafluoroborate ($LiBF_4$, 987.9 g, 10.5 mol, 10.0 equiv) at room temperature. The reaction temperature was observed to decrease from ambient to 12° C. upon addition of the water and then increase to 33° C. during the addition of lithium tetrafluoroborate ($LiBF_4$). The resulting reaction mixture was heated to reflux (about 80° C.) for overnight. An aliquot was quenched into ethyl acetate/water and checked by LCMS and TLC (95:5 ethyl acetate/methanol, v/v). When LCMS and TLC analyses showed both the hydroxyl methyl intermediate ((R)-25) and fully de-protected material ((R)-13, free base) produced but no starting material ((R)-20) left, the reaction mixture was cooled gradually to <5° C. before a 20% aqueous solution of ammonium hydroxide ($NH_4OH$, 450 mL) was added gradually to adjust the pH of the reaction mixture to 9 (checked with pH strips). The cold bath was removed and the reaction mixture was gradually warmed to room temperature and stirred at room temperature for overnight. An aliquot was quenched into ethyl acetate/water and checked by LCMS and TLC (95:5 ethyl acetate/methanol, v/v) to confirm complete de-protection. When LCMS and TLC showed the reaction was deemed complete, the reaction mixture was filtered and the solids were washed with acetonitrile (1 L). The combined filtrates were then concentrated under reduce pressure, and the residue was partitioned between ethyl acetate (EtOAc, 6 L) and half-saturated brine (3 L). The two layers were separated and the aqueous layer was extracted with ethyl acetate (2 L). The combined organic layers were washed with half-saturated sodium bicarbonate ($NaHCO_3$, 3 L) and brine (3 L), dried over sodium sulfate ($Na_2SO_4$), and concentrated under reduced pressure to give the crude product as an orange oil. The crude material was then purified by flash column chromatography ($SiO_2$, 40 to 100% ethyl acetate/heptane gradient elution) to afford (3R)-cyclopentyl-3-[4-(7H-pyrrolo[2,3-d]pyrimidin-4-yl)pyrazol-1-yl]propionitrile ((R)-13, free base, 273 g, 324.9 g theoretical, 84% yield) as a white foam. This material was checked by $^{19}$F NMR to ensure no lithium tetrafluoroborate ($LiBF_4$) remained and by chiral HPLC (Chiralcel® OD, 90:10 hexane/ethanol) to confirm enantiomeric purity and was used without further purification to prepare the corresponding phosphate salt. For (R)-13 (free base): $^1$H NMR (DMSO-$d_6$, 400 MHz) δ ppm 12.1 (bs, 1H), 8.80 (d, 1H, J=0.42 Hz), 8.67 (s, 1H), 8.37 (s, 1H), 7.59 (dd, 1H, J=2.34, 3.51 Hz), 6.98 (dd, 1H, J=1.40, 3.44 Hz), 4.53 (td, 1H, J=19.5, 4.63 Hz), 3.26 (dd, 1H, J=9.77, 17.2 Hz), 3.18 (dd, 1H, J=4.32, 17.3 Hz), 2.40 (m, 1H), 1.79 (m, 1H), 1.65 to 1.13 (m, 7H); $C_{17}H_{18}N_6$ (MW, 306.37) LCMS (EI) m/e 307 ($M^+$+H).

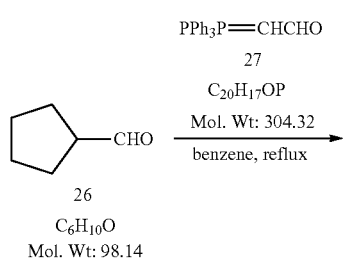
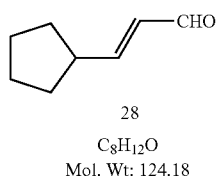

(2E)-3-Cyclopentylacrylaldehyde (28). To a stirred suspension of triphenylphosphoranylidene)acetaldehyde (27, 62.75 g, 200.0 mmol, 1.0 equiv) in anhydrous benzene (400 mL, 4476 mmol) was added cyclopentanecarbaldehyde (26, 21.36 mL, 200.0 mmol) at room temperature. The resulting reaction mixture was then heated at 80° C. for 16 h. When TLC and HPLC showed that the reaction was deemed complete, the reaction mixture was concentrated under reduced pressure. The residue was then directly purified by Combiflash ($SiO_2$) with 0-10% EtOAc/hexane gradient elution to afford (2E)-3-cyclopentylacrylaldehyde (28, 14.4 g, 24.84 g theoretical, 58% yield) as a yellow oil. For 28: $^1$H NMR (DMSO-$d_6$, 400 MHz) δ ppm $^1$H NMR ($CDCl_3$, 400 MHz) δ 9.49 (d, 1H, J=7.8 Hz), 6.82 (dd, 1H, J=15.6, 7.8 Hz), 6.08 (dd, 1H, J=15.6, 8.0 Hz), 2.72 (m, 1H), 1.89 (m, 2H), 1.67 (m, 4H), 1.44 (m, 2H); $C_8H_{12}O$ (MW, 124.18) LCMS (EI) m/e 125 ($M^+$+H).

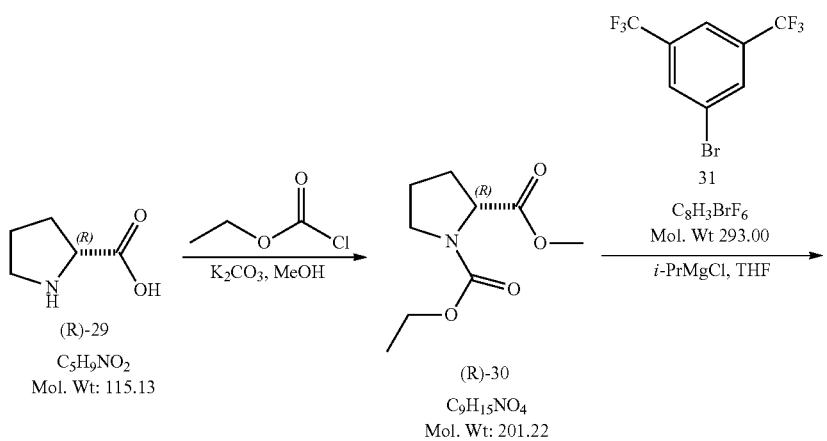

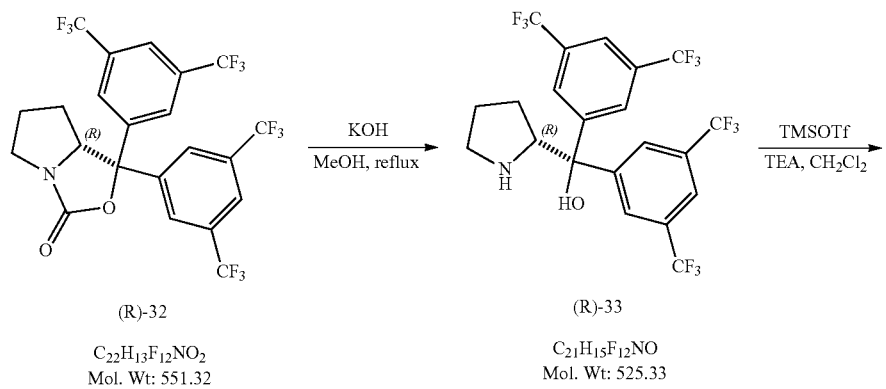

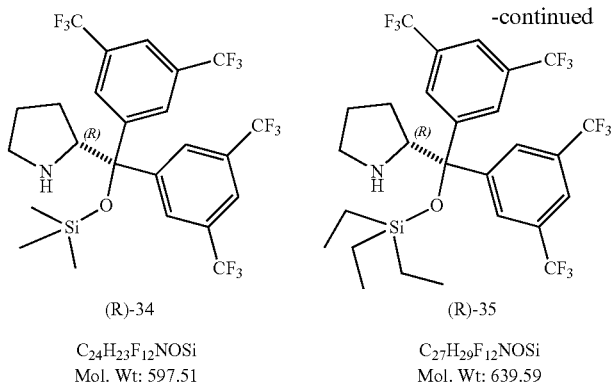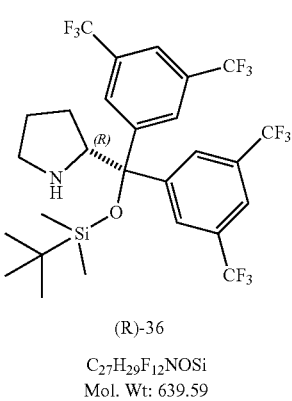

(2R)-1-Ethyl 2-methyl pyrrolidine-1,2-dicarboxylate ((R)-30). To a stirred suspension of D-proline ((R)-29, 13.955 g, 120.0 mmol) and potassium carbonate ($K_2CO_3$, 33.17 g, 240.0 mmol, 2.0 equiv) in anhydrous methanol (MeOH, 240 mL, 5925 mmol) at 0° C. was added ethyl chloroformate (28.4 mL, 288 mmol, 2.4 equiv) at room temperature. The resulting reaction mixture was then stirred at room temperature for 18 h. When LCMS showed the reaction was deemed complete, the solvent was removed under reduced pressure. The resulting residue was then treated with water (80 mL) and saturated aqueous $NaHCO_3$ (80 mL) before being extracted with EtOAc (2×100 mL). The combined organic layers were washed with brine, dried over magnesium sulfate ($MgSO_4$), filtered, and concentrated under reduced pressure to give the pure (2R)-1-ethyl 2-methyl pyrrolidine-1,2-dicarboxylate ((R)-30, 18.792 g, 24.14 g theoretical, 77.8% yield) as a colorless volatile oil. For (R)-30: $^1$H NMR ($CDCl_3$, 400 MHz) δ ppm 4.35 (dd, 0.5H, J=8.7, 3.5 Hz), 4.28 (dd, 0.5H, J=8.7, 3.7 Hz), 4.13 (m, 2H), 3.72 (s, 1.5H), 3.70 (s, 1.5H), 3.59-3.41 (m, 2H), 2.20 (m, 1H), 2.01-1.86 (m, 3H), 1.25 (t, 1.5H, J=7.1 Hz), 1.18 (t, 1.5H, J=7.1 Hz); $C_9H_{15}NO_4$ (MW, 201.22), LCMS (EI) m/e 201.9 (M$^+$+H).

(7aR)-1,1-Bis(3,5-bis(trifluoromethyl)phenyl)tetrahydropyrrolo[1,2-c]oxazol-3(1H)-one ((R)-32). To a stirred solution of 3,5-bis(trifluoromethyl)bromobenzene (31, 15.2 mL, 60.0 mmol, 3.0 equiv) in anhydrous THF (50 mL) at 0° C. was added a solution of 2.0 M of isopropylmagnesium chloride (iPrMgCl) in tetrahydrofuran (THF, 31.5 mL) dropwise. The resulting mixture was stirred at 0° C. for 1 h before being treated with a solution of (2R)-1-ethyl 2-methyl pyrrolidine-1,2-dicarboxylate ((R)-30, 4.024 g, 20.0 mmol) in anhydrous THF (14 mL) drop wise at 0° C. After the addition, the ice bath was removed and the reaction mixture was heated to 65° C. and stirred at 65° C. for 5 h. When LCMS showed that the reaction was deemed complete, the reaction mixture was quenched with saturated aqueous $NH_4Cl$ solution (120 mL) and extracted with EtOAc (2×100 mL). The combined organic layers were washed with brine, dried over magnesium sulfate ($MgSO_4$), filtered and concentrated under reduced pressure to afford the crude (7aR)-1,1-bis(3,5-bis(trifluoromethyl)phenyl)tetrahydropyrrolo[1,2-c]oxazol-3(1H)-one ((R)-32, 11.03 g, 100%) as a viscous oil, which was directly used in the subsequent reaction without further purification. For crude (R)-32: $C_{22}H_{13}F_{12}NO_2$ (MW, 551.32), LCMS (EI) m/e 552 (M$^+$+H).

(2R)-Bis(3,5-bis(trifluoromethyl)phenyl)(pyrrolidin-2-yl)methanol ((R)-33). To a stirred solution of crude (7aR)-1,1-bis(3,5-bis(trifluoromethyl)phenyl)tetrahydropyrrolo[1,2-c]oxazol-3(1H)-one ((R)-32, 11.03 g, 20.0 mmol) in methanol (MeOH, 80 mL, 1975 mmol) was added solid potassium hydroxide (KOH, 3.366 g, 60.0 mmol, 3.0 equiv) at room temperature. The resulting dark reaction mixture was heated to 65° C. and stirred at 65° C. for 22 h. When LCMS showed the reaction was deemed complete, the reaction mixture was cooled to room temperature before the solvent was evaporated under reduced pressure. The residue was then treated with water (100 mL) and extracted with EtOAc (2×100 mL). The combined organic layers were washed with brine, dried over magnesium sulfate ($MgSO_4$), filtered, and concentrated under reduced pressure. The residue was then purified by Combiflash ($SiO_2$) with 0-30% EtOAc/hexane gradient elution to afford (2R)-bis(3,5-bis(trifluoromethyl)phenyl)(pyrrolidin-2-yl)methanol ((R)-33, 8.30 g, 10.51 g theoretical, 79% yield for 2 steps) as a yellow viscous paste. For (R)-33: $^1$H NMR ($CD_3OD$, 400 MHz) δ ppm 8.24 (s, 2H), 8.16 (s, 2H), 7.85 (s, 2H), 4.49 (t, 1H, J=7.7 Hz), 2,92 (m, 2H), 1.74 (m, 2H), 1.67 (m, 1H), 1.55 (m, 1H); $C_{21}H_{15}F_{12}NO$ (MW, 525.33) LCMS (EI) m/e 526.0 (M$^+$+H).

(2R)-2-Bis[3,5-bis(trifluoromethyl)-phenyl][(trimethylsilyl)oxy]-methylpyrrolidine ((R)-34). To a stirred solution of (2R)-bis(3,5-bis(trifluoromethyl)phenyl)(pyrrolidin-2-yl)methanol ((R)-33, 8.30 g, 14.2 mmol) and triethylamine (TEA, 5.98 mL, 42.6 mmol, 3.0 equiv) in anhydrous methylene chloride ($CH_2Cl_2$, 56.0 mL, 874 mmol) at 0° C. was added trimethylsilyl trifluoromethanesulfonate (TMSOTf, 3.89 mL, 21.3 mmol, 1.5 equiv). The resulting reaction mixture was stirred at 0° C. for 1 h. When LCMS showed the reaction was deemed complete, the reaction mixture was quenched with water (80 mL) and extracted with EtOAc (2×100 mL). The combined organic layers were washed with brine, dried over magnesium sulfate ($MgSO_4$), filtered, and concentrated under reduced pressure. The residue was purified by Combiflash ($SiO_2$) with 0-10% EtOAc/hexane gradient elution to give (2R)-2-bis[3,5-bis(trifluoromethyl)phenyl][(trimethylsilyl)oxy]methylpyrrolidine ((R)-34, 6.869 g, 8.48 g theoretical, 81% yield) as a very viscous yellow syrup. For (R)-34: $^1$H NMR ($CDCl_3$, 300 MHz) δ ppm 8.08 (s, 2H), 7.92 (s, 2H), 7.84 (s, 2H), 4.32 (t, 1H, J=7.2 Hz), 2.98 (m, 1H), 2.63 (m, 1H), 1.79 (m, 1H), 1.58 (m, 2H), 1.20 (m, 1H), 0.00 (s, 9H); $C_{24}H_{23}F_{12}NOSi$ (MW, 597.51), LCMS (EI) m/e 598.0 (M$^+$+H).

(2R)-2-Bis[3,5-bis(trifluoromethyl)phenyl][(triethylsilyl)oxy]-methylpyrrolidine ((R)-35). To a stirred solution of (2R)-bis(3,5-bis(trifluoromethyl)phenyl)(pyrrolidin-2-yl)methanol ((R)-33, 3.832 g, 7.294 mmol) and 2,6-lutidine (4.27 mL, 36.5 mmol, 5.0 equiv) in anhydrous methylene chloride ($CH_2Cl_2$, 15.0 mL, 234 mmol) at 0° C. was added triethylsilyl trifluoromethanesulfonate (TESOTf, 5.0 mL, 21.9 mmol, 3.0 equiv). The resulting reaction mixture was stirred at room temperature for 21 h. When LCMS showed the reaction was deemed complete, the reaction mixture was quenched with saturated aqueous NaHCO$_3$ solution (70 mL), extracted with EtOAc (2×50 mL). The combined organic layers were washed with brine, dried over magnesium sulfate (MgSO$_4$), filtered, and concentrated under reduced pressure. The residue was purified by Combiflash (SiO$_2$) with 0-10% EtOAc/hexane gradient elution to give (2R)-2-bis[3,5-bis(trifluoromethyl)phenyl][(triethylsilyl)oxy]methylpyrrolidine ((R)-35, 4.575 g, 4.665 g theoretical, 98% yield) as a very viscous colorless syrup. For (R)-35: $^1$H NMR (CDCl$_3$, 400 MHz) δ ppm 8.06 (s, 2H), 7.86 (s, 2H), 7.76 (s, 2H), 4.29 (m, 1H), 2.94 (m, 1H), 2.53 (m, 1H), 1.83 (m, 2H), 1.53 (m, 2H), 0.85 (t, 9H, J=7.8 Hz), 0.34 (q, 6H, J=7.8 Hz); C$_{27}$H$_{29}$F$_{12}$NOSi (MW, 639.59), LCMS (EI) m/e 640.0 (M$^+$+H).

(2R)-2-(Bis[3,5-bis(trifluoromethyl)phenyl][tert-butyl(dimethyl)silyl]-oxymethyl)-pyrrolidine ((R)-36). To a stirred solution of (2R)-bis(3,5-bis(trifluoromethyl)phenyl)(pyrrolidin-2-yl)methanol ((R)-33, 1.051 g, 2.0 mmol) and triethylamine (TEA, 1.68 mL, 12.0 mmol, 6.0 equiv) in anhydrous methylene chloride (5.0 mL, 78 mmol) at 0° C. was added tert-butyldimethylsilyl trifluoromethanesulfonate (TBDMSOTf, 1.41 mL, 6.0 mmol, 3.0 equiv). The resulting reaction mixture was stirred at room temperature for 20 h before being heated at 100° C. for 10-20 h. When LCMS showed the reaction was deemed complete, the reaction mixture was quenched with water (30 mL) and extracted with EtOAc (2×50 mL). The combined organic layers were washed with brine, dried over magnesium sulfate (MgSO$_4$), filtered and concentrated under reduced pressure. The residue was purified by Combiflash (SiO$_2$) with 0-10% EtOAc/hexane gradient elution to give (2R)-2-(bis[3,5-bis(trifluoromethyl)phenyl][tert-butyl(dimethyl)silyl]oxymethyl)pyrrolidine ((R)-36, 1.167 g, 1.279 g theoretical, 91.2% yield) as a very viscous colorless syrup. For (R)-36: $^1$H NMR (CDCl$_3$, 400 MHz) δ ppm 8.09 (s, 2H), 7.87 (s, 2H), 7.75 (s, 2H), 4.33 (m, 1H), 2.98 (m, 1H), 2.54 (m, 1H), 1.86 (m, 1H), 1.70 (m, 1H), 1.56 (m, 2H), 0.95 (s, 9H), −0.21 (s, 3H), −0.45 (s, 3H); C$_{27}$H$_{29}$F$_{12}$NOSi (MW, 639.59), LCMS (EI) m/e 640.4 (M$^+$+H).

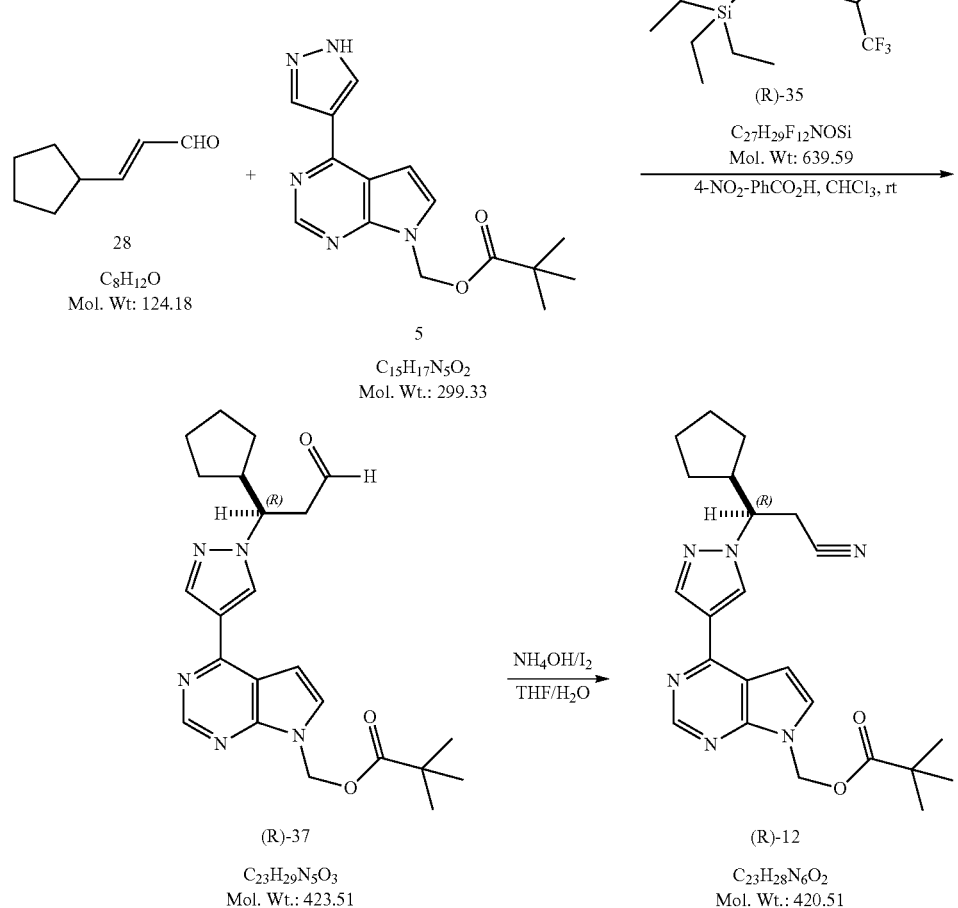

(1R)-(4-(1-(1-Cyclopentyl-3-oxopropyl)-1H-pyrazol-4-yl)-7H-pyrrolo[2,3-d]pyrimidin-7-yl)methyl pivalate ((R)-37). A solution of (2E)-3-cyclopentylacrylaldehyde (28, 345 mg, 2.50 mmol, 5.0 equiv), (2R)-2-bis[3,5-bis(trifluoromethyl)phenyl][(triethylsilyl)oxy]methylpyrrolidine ((R)-35, 16 mg, 0.025 mmol, 0.05 equiv) and 4-nitrobenzoic acid (4.3 mg, 0.025 mmol, 0.05 equiv) in anhydrous chloroform (CHCl$_3$, 2.0 mL, 25 mmol) was stirred at room temperature for 10 min before [4-(1H-pyrazol-4-yl)-7H-pyrrolo[2,3-d]pyrimidin-7-yl]methyl pivalate (5, 0.150 g, 0.50 mmol) was added. The resulting reaction mixture was stirred at room temperature for 23 h. After LCMS showed that the reaction was deemed complete, the reaction mixture was concentrated under reduced pressure. The residue was directly purified by Combiflash with 0-80% EtOAc/hexane gradient elution to afford (1R)-(4-(1-(1-cyclopentyl-3-oxopropyl)-1H-pyrazol-4-yl)-7H-pyrrolo[2,3-d]pyrimidin-7-yl)methyl pivalate ((R)-37, 169 mg, 211.8 mg theoretical, 80% yield) as a pale yellow foam. For (R)-37: $C_{23}H_{29}N_5O_3$ (MW, 423.51), LCMS (EI) m/e 424 (M$^+$+H).

(R)-(4-(1-(2-Cyano-1-cyclopentylethyl)-1H-pyrazol-4-yl)-7H-pyrrolo[2,3-d]pyrimidin-7-yl)methyl pivalate ((R)-12). Method B. A solution of (1R)-(4-(1-(1-cyclopentyl-3-oxopropyl)-1H-pyrazol-4-yl)-7H-pyrrolo[2,3-d]pyrimidin-7-yl)methyl pivalate ((R)-37, 169 mg, 0.399 mmol) in tetrahydrofuran (THF, 1.2 mL, 15 mmol) at room temperature was added a 14.3 M solution of ammonium hydroxide (NH$_4$OH) in water (1.2 mL), followed by iodine (I$_2$, 112 mg, 0.439 mmol, 1.1 equiv). The resulting reaction mixture was stirred at room temperature for 25 min. When LCMS showed that the reaction was deemed complete, the reaction mixture was quenched with 10% aqueous Na$_2$S$_2$O$_3$ (10 mL) before being extracted with EtOAc (2×15 mL). The combined organic layers were washed with brine, dried over magnesium sulfate (MgSO$_4$), filtered and concentrated under reduced pressure. The residue was purified by Combiflash (SiO$_2$) with 0-60% EtOAc/hexane gradient elution to afford (R)-(4-(1-(2-cyano-1-cyclopentylethyl)-1H-pyrazol-4-yl)-7H-pyrrolo[2,3-d]pyrimidin-7-yl)methyl pivalate ((R)-12, 145.6 mg, 167.8 mg theoretical, 86.8% yield) as a colorless foam.

A chiral HPLC method was developed for chiral purity evaluation of both enantiomers of (R)-12 and (S)-12 by using a Chiralcel® OD-H column (4.6×250 mm, 5 μm) packed with a silicagel coated with cellulose tris(3,5-dimethylphenyl carbamate) (Chiralcel® OD). (purchased from Chiral Technologies, Inc. The two enantiomers ((R)-12 and (S)-12) are separated with a resolution greater than 3.5 by using a mobile phase made from 10% ethanol and 90% hexanes at room temperature with a flow rate of 1 mL/min. The UV detection wavelength is 220 nm. The retention times are 14.1 minutes for (S)-12 (the first peak) and 18.7 minutes for (R)-12 (the second peak), respectively.

For (R)-12: achiral purity (99.3 area% by HPLC detected at 220 nm); chiral purity (94.9 area% by chiral HPLC; 89.8% ee); $^1$H NMR (DMSO-d$_6$, 400 MHz) δ ppm 8.84 (s, 1H), 8.78 (s, 1H), 8.39 (s, 1H), 7.74 (d, 1H, J=3.7 Hz,), 7.11 (d, 1H, J=3.8 Hz), 6.23 (s, 2H), 4.53 (ddd, 1H, J=9.9, 9.6, 4.2 Hz), 3.26 (dd, 1H, J=17.4, 9.9 Hz), 3.19 (dd, 1H, J=17.2, 4.3 Hz), 2.41 (m, 1H), 1.87-1.13 (m, 8H), 1.07 (s, 9H); $C_{23}H_{28}N_6O_2$ (MW, 420.51), LCMS (EI) m/e 421.4 (M$^+$+H).

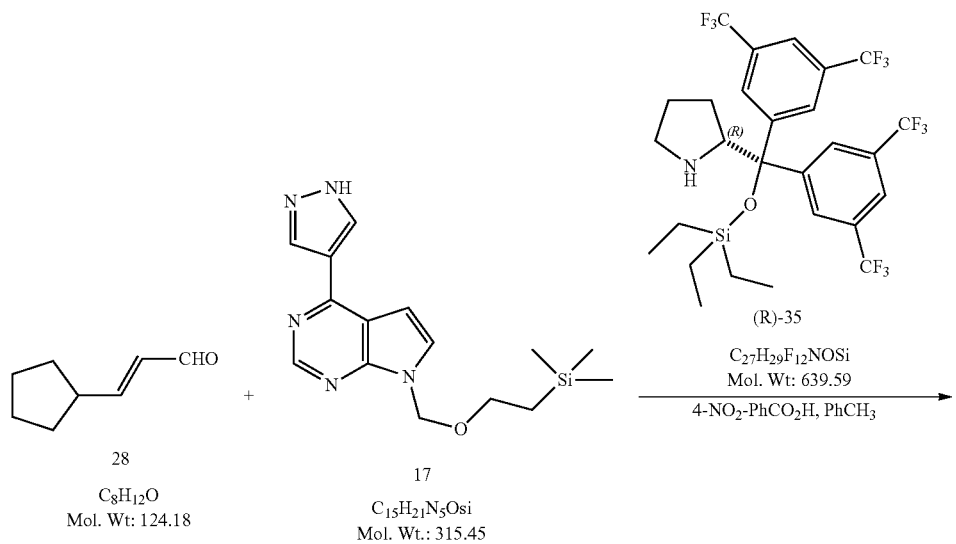

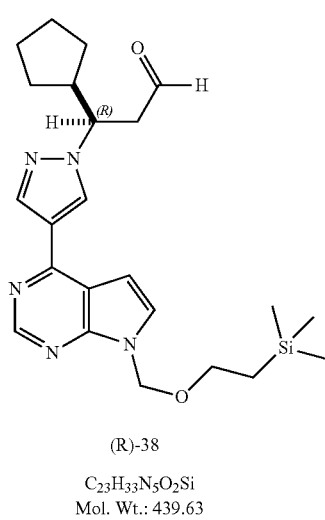

(R)-38

C₂₃H₃₃N₅O₂Si
Mol. Wt.: 439.63

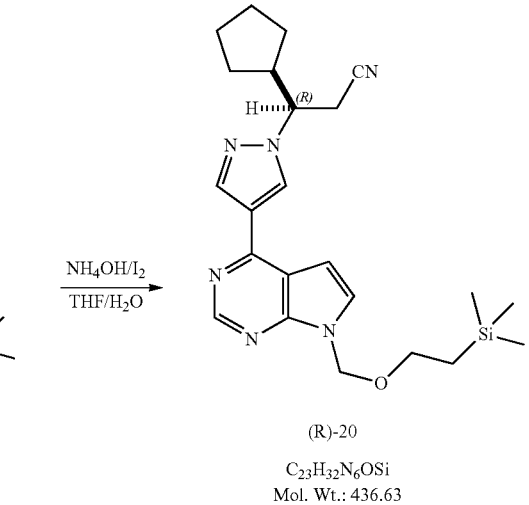

(R)-20

C₂₃H₃₂N₆OSi
Mol. Wt.: 436.63

(3R)-3-Cyclopentyl-3-[4-(7-[2-(trimethylsilyl)ethoxy]methyl-7H-pyrrolo[2,3-d]pyrimidin-4-yl)-1H-pyrazol-1-yl]propanal ((R)-38). A solution of (2E)-3-cyclopentylacrylaldehyde (28, 327 mg, 2.50 mmol, 5.0 equiv), (2R)-2-bis[3,5-bis(trifluoromethyl)phenyl][(triethylsilyl)oxy]methylpyrrolidine ((R)-35, 32 mg, 0.050 mmol, 0.10 equiv) and 4-nitrobenzoic acid (8.5 mg, 0.050 mmol, 0.10 equiv) in anhydrous toluene (5.0 mL, 47 mmol) was stirred at room temperature for 10 min before 4-(1H-pyrazol-4-yl)-7-[2-(trimethylsilyl)ethoxy]methyl-7H-pyrrolo[2,3-d]pyrimidine (17, 158 mg, 0.50 mmol) was added. The resulting reaction mixture was stirred at room temperature for 24 h. When LCMS showed that the reaction was deemed complete, the reaction mixture was concentrated under reduced pressure. The residue was directly purified by Combiflash (SiO₂) with 0-70% EtOAc/hexane gradient elution to give (3R)-3-cyclopentyl-3-[4-(7-[2-(trimethylsilyl)ethoxy]methyl-7H-pyrrolo[2,3-d]pyrimidin-4-yl)-1H-pyrazol-1-yl]propanal ((R)-38, 184.1 mg, 219.8 mg theoretical, 83.8% yield) as a pale yellow viscous oil. For (R)-38: C₂₃H₃₃N₅O₂Si (MW, 439.63), LCMS (EI) m/e 440 (M +H).

(3R)-Cyclopentyl-3-{4-[7-(2-trimethylsilanylethoxymethyl)-7H-pyrrolo[2,3-d]pyrimidin-4-yl]pyrazol-1-yl}propionitrile ((R)-20). Method B. To a stirred solution of (3R)-3-cyclopentyl-3-[4-(7-[2-(trimethylsilyl)ethoxy]methyl-7H-pyrrolo[2,3-d]pyrimidin-4-yl)-1H-pyrazol-1-yl]propanal ((R)-38, 184 mg, 0.418 mmol) in tetrahydrofuran (THF, 1.2 mL, 15 mmol) at room temperature was added a solution of 14.3 M of ammonium hydroxide (NH₄OH) in water (1.2 mL), followed by iodine (I₂, 117 mg, 0.460 mmol, 1.1 equiv). The resulting reaction mixture was stirred at room temperature for 30 min. When LCMS showed that the reaction was complete, the reaction mixture was quenched with 10% aqueous Na₂S₂O₃ (10 mL) before being extracted with EtOAc (2×15 mL). The combined organic layers were washed with brine, dried over magnesium sulfate (MgSO₄), filtered, and concentrated under reduced pressure. The residue was then purified by Combiflash (SiO₂) with 0-50% EtOAc/hexane gradient elution to give (3R)-cyclopentyl-3-{4-[7-(2-trimethylsilanylethoxymethyl)-7H-pyrrolo[2,3-d]pyrimidin-4-yl]pyrazol-1-yl}propionitrile ((R)-20, 148.9 mg, 182.5 mg theoretical, 81.6% yield) as a colorless viscous oil.

The determination of enantiomeric excess (% ee) of the product ((R)-20) was carried by chiral HPLC analysis. A chiral HPLC method was developed using a Chiralcel® OD-H column (4.6×250 mm, 5 μm), purchased from Chiral Technologies, Inc., packed a silicagel coated with cellulose tris(3,5-dimethylphenyl carbamate) (Chiralcel® OD). The two enantiomers, (R)-20 or (S)-20, are separated with a resolution greater than 3.0 by using a mobile phase made of 10% ethanol and 90% hexanes at room temperature with a flow rate of 1 mL/min. The UV detection wavelength is 220 nm. The retention times for (S)-enantiomer ((S)-20) and (R)-enantiomer ((R)-20) are 10.3 minutes (the first peak) and 13.1 minutes (the second peak), respectively.

For (R)-20: achiral purity (99.0 area% by HPLC detected at 220 nm); chiral purity (94.4 area% by chiral HPLC; 88.8% ee); ¹H NMR (DMSO-d₆, 400 MHz) δ ppm 8.83 (s, 1H), 8.75 (s, 1H), 8.39 (s, 1H), 7.77 (d, 1H, J=3.7 Hz), 7.09 (d, 1H, J=3.7 Hz), 5.63 (s, 2H), 4.53 (td, 1H, J=19.4, 4.0 Hz), 3.51 (t, 2H, J=8.1 Hz), 3.23 (dq, 2H, J=9.3, 4.3 Hz), 2.41 (m, 1H), 1.79 (m, 1H), 1.66-1.13 (m, 7H), 0.81 (t, 2H, J=8.2 Hz), 0.124 (s, 9H); C₂₃H₃₂N₆OSi (MW, 436.63), LCMS (EI) m/e 437 (M⁻+H) and 459 (M⁺+Na).

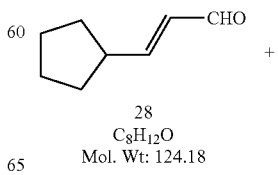

28
C₈H₁₂O
Mol. Wt: 124.18

+

-continued

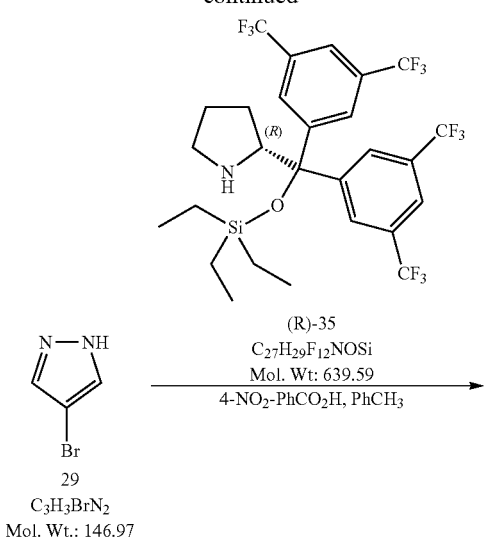

(R)-35
C₂₇H₂₉F₁₂NOSi
Mol. Wt: 639.59
4-NO₂-PhCO₂H, PhCH₃

29
C₃H₃BrN₂
Mol. Wt.: 146.97

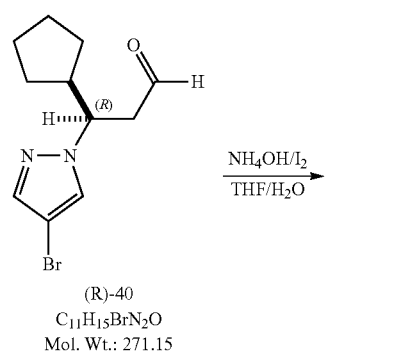

NH₄OH/I₂
─────────
THF/H₂O (R)-40
C₁₁H₁₅BrN₂O
Mol. Wt.: 271.15

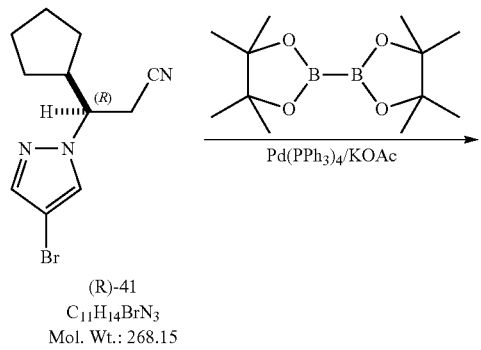

Pd(PPh₃)₄/KOAc (R)-41
C₁₁H₁₄BrN₃
Mol. Wt.: 268.15

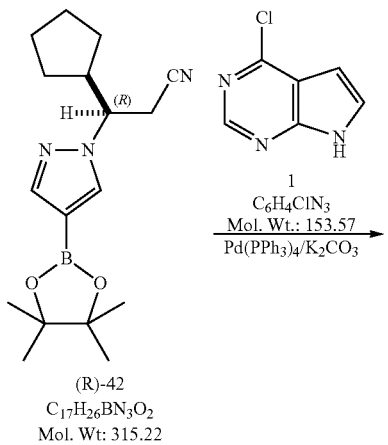

1
C₆H₄ClN₃
Mol. Wt.: 153.57
Pd(PPh₃)₄/K₂CO₃

(R)-42
C₁₇H₂₆BN₃O₂
Mol. Wt: 315.22

-continued

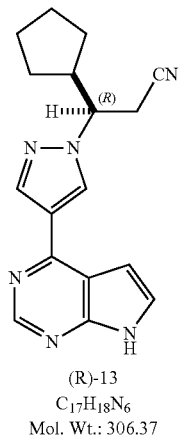

(R)-13
C₁₇H₁₈N₆
Mol. Wt.: 306.37

(3R)-3-(4-Bromo-1H-pyrazol-1-yl)-3-cyclopentylpropanal ((R)-40). A solution of (2E)-3-cyclopentylacrylaldehyde (28, 654 mg, 5.0 mmol, 5.0 equiv), (2R)-2-(bis[3,5-bis(trifluoromethyl)phenyl][tert-butyl(dimethyl)silyl]oxymethyl) pyrrolidine ((R)-35, 64 mg, 0.10 mmol, 0.10 equiv) and 4-nitrobenzoic acid (17 mg, 0.10 mmol, 0.10 equiv) in anhydrous toluene (4.0 mL, 38 mmol) was stirred at rt for 10 min, then cooled to 0° C. before 4-bromo-1H-pyrazole (39, 148 mg, 1.0 mmol) was then added. The resulting reaction mixture was stirred at 0° C. for 22 h. When LCMS showed the reaction was deemed complete, the reaction mixture was concentrated under reduced pressure. The residue was directly purified by CombiFlash (SiO₂) with 0-30% EtOAc/hexane gradient elution to give (3R)-3-(4-bromo-1H-pyrazol-1-yl)-3-cyclopentylpropanal ((R)-40, 230.5 mg, 271.2 mg theoretical, 85% yield) as a pale yellow viscous oil. For (R)-40: C₁₁H₁₅BrN₂O (MW, 271.15), LCMS (EI) m/e 271/273 (M⁺+H).

(3R)-3-(4-Bromo-1H-pyrazol-1-yl)-3-cyclopentylpropanenitrile ((R)-41). To a stirred solution of (3R)-3-(4-bromo-1H-pyrazol-1-yl)-3-cyclopentylpropanal ((R)-40, 230.5 mg, 0.85 mmol) in tetrahydrofuran (THF, 2.4 mL, 29 mmol) at room temperature was added a solution of 14.3 M of ammonium hydroxide (NH₄OH) in water (2.4 mL), followed by iodine (I₂, 237 mg, 0.935 mmol, 1.1 equiv). The resulting reaction mixture was stirred at room temperature for 30 min. When LCMS showed that the reaction was complete, the reaction mixture was quenched with 10% aqueous Na₂S₂O₃ solution (15 mL) and extracted with EtOAc (2×15 mL). The combined organic layers were washed with brine, dried over magnesium sulfate (MgSO₄), filtered, and concentrated under reduced pressure. The residue was purified by Combiflash (SiO₂) with 0-30% EtOAc/hexane gradient elution to give (3R)-3-(4-bromo-1H-pyrazol-1-yl)-3-cyclopentylpropanenitrile ((R)-41, 180.7 mg, 227.9 mg theoretical, 79.3% yield) as a colorless viscous oil.

The determination of enantiomeric excess (% ee) of the product ((R)-41) was carried by chiral HPLC analysis. A chiral HPLC method was developed using a Chiralcel® OD-H column (4.6×250 mm, 5 μm), purchased from Chiral Technologies, Inc., packed a silicagel coated with cellulose tris(3,5-dimethylphenyl carbamate) (Chiralcel® OD). The two enantiomers, (R)-41 or (S)-41, are separated with a resolution greater than 3.0 by using a mobile phase made of 15% ethanol and 85% hexanes at room temperature with a flow rate of 1 mL/min. The UV detection wavelength is 220 nm. The retention times for (S)-enantiomer ((S)-41) and (R)- enantiomer ((R)-41) are 12.8 minutes (the first peak) and 16.7 minutes (the second peak), respectively.

For (R)-41: achiral purity (99.0 area % by HPLC detected at 220 nm); chiral purity (91.7 area % by chiral HPLC; 83.4% ee); $^1$H NMR (CDCl$_3$, 400 MHz) δ ppm 7.52 (s, 2H), 4.10 (m, 1H), 3.02 (dd, 1H, J=17.0, 8.6 Hz), 2.86 (dd, 1H, J=17.0, 3.9 Hz), 2.47 (m, 1H), 1.90 (m, 1H), 1.72-1.46 (m, 5H), 1.23 (m, 1H), 1.13 (m, 1H); C$_{11}$H$_{14}$BrN$_3$ (MW, 268.15), LCMS (EI) m/e 268/270 (M$^+$+H).

(3R)-3-Cyclopentyl-3-[4-(4,4,5,5-tetramethyl-1,3,2-dioxaborolan-2-yl)-1H-pyrazol-1-yl]propanenitrile ((R)-42). A degassed mixture of (3R)-3-(4-bromo-1H-pyrazol-1-yl)-3-cyclopentylpropanenitrile ((R)-41, 363 mg, 1.35 mmol), 4,4,5,5,4',4',5',5'-octamethyl-[2,2']bis[1,3,2]dioxaborolanyl] (366 mg, 1.43 mmol, 1.06 equiv), tetrakis(triphenylphosphine)palladium(0) (Pd(PPh$_3$)$_4$, 47 mg, 0.041 mmol, 0.03 equiv) and potassium acetate (KOAc, 402 mg, 4.06 mmol, 3.0 equiv) in anhydrous 1,4-dioxane (4.0 mL, 51 mmol) was heated at 120° C. via microwave for 1 h. When LCMS showed the reaction was complete, the reaction mixture, which contains the crude desired product, (3R)-3-cyclopentyl-3-[4-(4,4,5,5-tetramethyl-1,3,2-dioxaborolan-2-yl)-1H-pyrazol-1-yl]propanenitrile ((R)-42), was used directly for the subsequent Suzuki reaction without further workup. For crude (R)-42: C$_{17}$H$_{26}$BN$_3$O$_2$ (MW, 315.22), LCMS (EI) m/e 316 (M$^+$+H).

(3R)-Cyclopentyl-3-[4-(7H-pyrrolo[2,3-d]pyrimidin-4-yl)pyrazol-1-yl]propionitrile ((R)-13, free base). Method C. To a stirred solution of the crude (3R)-3-cyclopentyl-3-[4-(4,4,5,5-tetramethyl-1,3,2-dioxaborolan-2-yl)-1H-pyrazol-1-yl]propanenitrile ((R)-42, 427 mg, 1.35 mmol) in 1,4-dioxane (4.0 mL, 51 mmol), a reaction mixture generated as described above, was added 4-chloropyrrolo[2,3-d]pyrimidine (1, 0.160 g, 1.04 mmol, 0.77 equiv), tetrakis(triphenylphosphine)palladium(0) ((Pd(PPh$_3$)$_4$, 36 mg, 0.031 mmol, 0.03 equiv) and a solution of potassium carbonate (K$_2$CO$_3$, 432 mg, 3.13 mmol, 3.0 equiv) in water (2.0 mL, 110 mmol) at room temperature. The resulting reaction mixture was degassed three times and refilled with nitrogen each time before being heated at 100° C. for 21 h. When LCMS showed the reaction was complete, the reaction mixture was quenched with saturated aqueous NaHCO$_3$ (10 mL) and extracted with EtOAc (2×25 mL). The combined organic layers were washed with brine, dried over magnesium sulfate (MgSO$_4$), filtered and concentrated under reduced pressure. The residue was purified by Combiflash (SiO$_2$) eluting with 0-100% EtOAc/hexane gradient elution followed by 0-5% MeOH/EtOAc to afford (3R)-cyclopentyl-3-[4-(7H-pyrrolo[2,3-d]pyrimidin-4-yl)pyrazol-1-yl]propionitrile ((R)-13, free base, 204.3 mg, 318.6 mg theoretical, 64% yield for 2 steps) as a colorless oil, which solidified upon standing at room temperature in vacuum. For (R)-13 (free base): $^1$H NMR (DMSO-d$_6$, 400 MHz) δ ppm 12.1 (bs, 1H), 8.80 (d, 1H, J=0.42 Hz), 8.67 (s, 1H), 8.37 (s, 1H), 7.59 (dd, 1H, J=2.34, 3.51 Hz), 6.98 (dd, 1H, J=1.40, 3.44 Hz), 4.53 (td, 1H, J=19.5, 4.63 Hz), 3.26 (dd, 1H, J=9.77, 17.2 Hz), 3.18 (dd, 1H, J=4.32, 17.3 Hz), 2.40 (m, 1H), 1.79 (m, 1H), 1.65 to 1.13 (m, 7H); C$_{17}$H$_{18}$N$_6$ (MW, 306.37) LCMS (EI) m/e 307 (M$^+$+H).

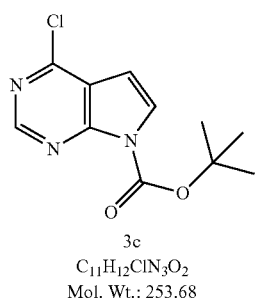

3c
C$_{11}$H$_{12}$ClN$_3$O$_2$
Mol. Wt.: 253.68

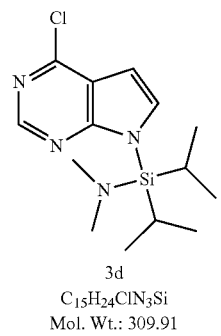

3d
C$_{15}$H$_{24}$ClN$_3$Si
Mol. Wt.: 309.91

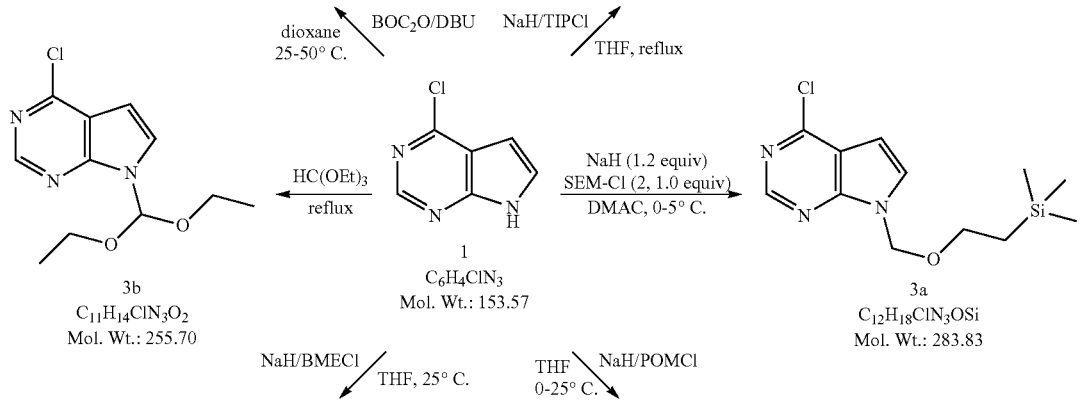

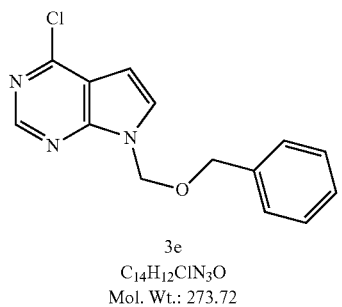

3e
C₁₄H₁₂ClN₃O
Mol. Wt.: 273.72

-continued

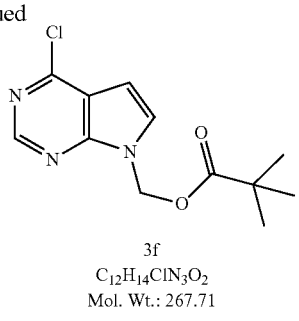

3f
C₁₂H₁₄ClN₃O₂
Mol. Wt.: 267.71

4-Chloro-7-(2-trimethylsilanylethoxymethyl)-7H-pyrrolo[2,3-d]pyrimidine (3a). To a flask equipped with a nitrogen inlet, addition funnel, thermowell, and mechanical stirrer was added 4-chloro-7H-pyrrolo[2,3-d]pyrimidine (1, 600 g, 3.91 mol) and dimethylacetimide (9.6 L). The mixture was cooled to −5° C. in an ice/brine bath and sodium hydride (NaH, 60 wt %, 174 g, 4.35 mol, 1.1 equiv) was added in portions as a solid. The mixture went to a dark solution during 15 minutes and trimethylsilylethoxymethyl chloride (2, 763 mL, 4.31 mol, 1.1 equiv) was added slowly via an addition funnel at a rate that the temperature did not exceed 5° C. The reaction was stirred for 30 minutes, determined to be complete by TLC and HPLC, and water (1 L) was slowly added to quench the reaction. The mixture was then diluted with water (12 L) and MTBE (8 L). The layers were separated and the aqueous was re-extracted with MTBE (8 L). The combined organic layers were washed with water (2×4 L) and brine (4 L), dried over sodium sulfate (NaSO₄), and solvents removed under reduced pressure.

The residue was dissolved in heptane (2 L), filtered and loaded onto a silica gel (3.5 kg) column eluting with heptane (~6 L), 95% heptane/ethyl acetate (~12 L), 90% heptane/ethyl acetate (10 L), and finally 80% heptane/ethyl acetate (10 L). The pure fractions were combined and concentrated under reduced pressure to give 4-chloro-7-(2-trimethylsilanylethoxymethyl)-7H-pyrrolo[2,3-d]pyrimidine (3a, 987 g, 1109.8 g theoretical, 88.9% yield) as a pale yellow oil that partially solidified to an oily solid on standing at room temperature. For 3a: $^1$H NMR (DMSO-d₆, 300 MHz) δ ppm 8.67 (s, 1H), 7.87 (d, 1H, J=3.8 Hz), 6.71 (d, 1H, J=3.6 Hz), 5.63 (s, 2H), 3.50 (t, 2H, J=7.9 Hz), 0.80 (t, 2H, J=8.1 Hz), 1.24 (s, 9H); $^{13}$C NMR (DMSO-d₆, 100 MHz) δ ppm 151.3, 150.8, 150.7, 131.5, 116.9, 99.3, 72.9, 65.8, 17.1, −1.48; C₁₂H₁₈ClN₃OSi (MW 283.83), LCMS (EI) m/e 284/286 (M⁺+H).

4-Chloro-7-(diethoxymethyl)-7H-pyrrolo[2,3-d]pyrimidine (3b). To a 1 liter round bottom flask equipped with a stir bar, condenser and nitrogen inlet was charged 4-chloro-7H-pyrrolo[2,3-d]pyrimidine (1, 31.0 g, 0.202 mol) and triethyl orthoformate (330 ml, 2.00 mol, 10.0 equiv). The reaction mixture was warmed to reflux to generate a clear solution. The reaction was checked after 63 hours by HPLC. When the reaction was deemed complete, the reaction mixture was concentrated under reduced pressure. The residue was purified by a silica gel flash column chromatography eluted with a 20% to 25% ethyl acetate/hexane (v/v) gradient (TLC conditions: 30% ethyl acetate/hexane) to afford 4-chloro-7-(diethoxymethyl)-7H-pyrrolo[2,3-d]pyrimidine (3b, 48.56 g, 51.65 g theoretical, 94% yield) as a light yellow oil. For 3b: $^1$H NMR (DMSO-d₆, 400 MHz) δ ppm 8.68 (s, 1H), 7.79 (d, 1H, J=3.8 Hz), 6.75 (s, 1H), 6.72 (d, 1H, J=3.8 Hz), 3.68 (dd, 2H, J=9.4, 7.2 Hz), 3.54 (dd, 2H, J=9.4, 7.2 Hz), 1.11 (t, 6H, J=7.2 Hz); C₁₁H₁₄ClN₃O₂ (MW, 255.70), LCMS (EI) m/e 182/184 (M⁺+H for corresponding 7-formylation product of 1) and 154/156 (M⁺+H for 1).

tert-Butyl 4-chloro-7H-pyrrolo[2,3-d]pyrimidine-7-carboxylate (3c). To a 250 mL round bottom flask equipped with a stir bar and nitrogen inlet was charged 4-chloro-7H-pyrrolo[2,3-d]pyrimidine (1, 5.00 g, 0.0326 mol), 1,4-dioxane (40 ml, 0.500 mol), 1,8-diazabicyclo[5.4.0]undec-7-ene (DBU, 24.3 mL, 0.163 mol, 5.0 equiv) and 4-(N,N-dimethyl)aminopyridine (DMAP, 0.80 g, 0.0065 mol, 0.2 equiv). To this solution was added di-tert-butyldicarbonate (BOC₂O, 21.2 g, 0.0976 mol, 3.0 equv) in one portion at room temperature. The resulting reaction solution becomes yellow/orange in color with the evolution of carbon dioxide. The reaction was monitored by TLC (80% hexane/ethyl acetate) and was complete after stirring at room temperature for about 24 hours. The reaction mixture was then diluted with 20% aqueous brine solution (40 mL) and ethyl acetate (40 mL). The two layers were separated, and the aqueous layer was extracted with ethyl acetate (40 mL). The combined organic extracts were washed with brine, dried over magnesium sulfate, and concentrated under reduced pressure to yield the crude, desired product (3c) as a red to orange oil. Flash column chromatography purification (SiO₂, 0 to 15% ethyl acetate/hexane gradient elution) afforded pure tent-butyl 4-chloro-7H-pyrrolo[2,3-d]pyrimidine-7-carboxylate (3c, 6.28 g, 8.27 g theoretical, 75.9% yield) as off-white solids. For 3c: $^1$H NMR (DMSO-d₆, 400 MHz) δ ppm 8.79 (s, 1H), 7.94 (d, 1H, J=4.0 Hz), 6.80 (d, 1H, J=4.2 Hz), 1.60 (s, 9H); C₁₁H₁₂ClN₃O₂ (MW, 253.68), LCMS (EI) m/e 276/278 (M⁺+Na).

4-Chloro-7-(triisopropylsilyl)-7H-pyrrolo[2,3-d]pyrimidine (3d). To a 250 mL oven dried three-neck round bottom flask equipped with a stir bar, condenser, septa, nitrogen inlet and thermocouple was charged sodium hydride (NaH, 60 wt %, 1.56 g, 0.0391 mol, 1.2 equiv) and anhydrous tetrahydrofuran (THF, 26 mL, 0.320 mol). The mixture was chilled to 0-5° C. To a oven dried 100 mL round bottom flask was charged 4-chloro-7H-pyrrolo[2,3-d]pyrimidine (1, 5.00 g, 0.0326 mol) and anhydrous tetrahydrofuran (42 mL, 0.520 mol), and the resulting slurry was then added portion wise via large bore canula over 15 minutes to the sodium hydride (NaH) suspension in THF. The reaction temperature rose to 6.8° C. after the addition of the substrate. The reaction mixture was stirred at 0-5° C. for 40 minutes before being charged neat triisopropylsilyl chloride (6.6 g, 7.24 mL, 0.0342 mol, 1.05 equiv) via syringe over 5 minutes. The cooling bath was removed and the reaction mixture was warmed to reflux for 4 hours. The reaction was monitored by TLC (80% hexane/ethyl acetate). When the reaction was deemed complete, the reaction mixture was cooled to room temperature and dilute with ethyl acetate (100 mL) and 20% aqueous brine (50 mL).

The two layers were separated and the aqueous layer was extracted with ethyl acetate (100 mL). The combined organic fractions were washed with 1M sodium bicarbonate (NaHCO$_3$) aqueous solution (100 mL) and 20% aqueous brine (100 mL), dried over magnesium sulfate (MgSO$_4$), filtered and concentrated under reduced pressure. The residue was purified by flash chromatography (SiO$_2$, 10% ethyl acetate/hexane gradient elution) to afford 4-chloro-7-(triisopropylsilyl)-7H-pyrrolo[2,3-d]pyrimidine (3d, 10.0 g, 10.10 g theoretical, 99%) as an amber oil. For 3d: $^1$H NMR (DMSO-d$_6$, 400 MHz) δ ppm 8.61 (s, 1H), 7.67 (d, 1H, J=3.7 Hz), 6.76 (d, 1H, J=3.5 Hz), 1.86 (m, 3H), 1.02 (d, 18H, J=7.5 Hz); C$_{15}$H$_{24}$ClN$_3$Si (MW, 309.91), LCMS (EI) m/e 310/312 (M$^+$+H).

7-[(Benzyloxy)methyl]-4-chloro-7H-pyrrolo[2,3-d]pyrimidine (3e). To a oven dried 250 mL three-neck round bottom flask equipped with a stir bar, thermocouple, septa and nitrogen inlet was charged sodium hydride (NaH, 60 wt %, 1.56 g, 0.0391 mol, 1.2 equiv) and anhydrous tetrahydrofuran (THF, 25.0 mL, 0.308 mol) and the resulting mixture was chilled to 0-5° C. To a 100 ml oven dried round bottom flask was charged 4-chloro-7H-pyrrolo[2,3-d]pyrimidine (1, 5.00 g, 0.0326 mol) and anhydrous tetrahydrofuran (50 mL, 0.616 mol), and the resulting slurry was added portion wise via large bore canula over 20 minutes to the sodium hydride (NaH) suspension in THF. The cooling bath was removed after the addition is complete and the reaction mixture was stirred at room temperature for 1 hour. The slurry becomes green in color after it is warmed to 16.5° C. The mixture was cooled to 0-5° C. before neat benzyl chloromethyl ether (5.28 mL, 0.0342 mol, 1.05 equiv) was charged over 13 minutes via syringe. The cold bath was removed and the reaction mixture was warmed to room temperature gradually and stirred at room temperature for 20 h. The reaction mixture was quenched with 20% aqueous brine (50 mL) and diluted with ethyl acetate (100 mL) when the reaction was deemed complete. The two layers were separated, and the aqueous layer was extracted with ethyl acetate (50 mL). The combined organic fractions were dried over magnesium sulfate, filtered, and concentrate under reduced pressure. The residue was then purified by flash chromatography (SiO$_2$, 10% to 15% ethyl acetate/hexane gradient elution) to afford 7-[(benzyloxy)methyl]-4-chloro-7H-pyrrolo[2,3-d]pyrimidine (3e, 6.31 g, 8.92 g theoretical, 70.7%) as a green oil. For 3e: $^1$H NMR (DMSO-d$_6$, 400 MHz) δ ppm 8.69 (s, 1H), 7.90 (d, 1H, J=3.7 Hz), 7.26 (m 5H), 6.71 (d, 1H, J=3.7 Hz), 5.75 (s 2H), 4.51 (s, 2H); C$_{14}$H$_{12}$ClN$_3$O (MW, 273.72), LCMS (EI) m/e 274/276 (M$^+$+H).

(4-Chloro-7H-pyrrolo[2,3-d]pyrimidin-7-yl)methyl pivalate (3f). To a oven dried 2 L 4-neck round bottom flask equipped with overhead stirring, septa, thermocouple, 500 mL addition funnel and nitrogen inlet was charged sodium hydride (NaH, 60 wt %, 29.7 g, 0.742 mol, 1.34 equiv) and anhydrous tetrahydrofuran (THF, 400 mL, 5.0 mol) and the resulting mixture was cooled to 0-3° C. To a oven dried 1 L round bottom flask was charged 4-chloro-7H-pyrrolo[2,3-d] pyrimidine (1, 85.0 g, 0.553 mol) and tetrahydrofuran (600 mL, 7.0 mol) resulting in a slurry. This resulting slurry was then portion wise added to the suspension of sodium hydride in THF via large bore canula over 27 minutes at 0-5° C. The resulting solution was heterogeneous and green in color. Following the addition, the cold bath was removed and the mixture was gradually warmed to room temperature and allowed to stir at room temperature for 1 hour before being cooled to 0-5° C. Chloromethyl pivalate (pivaloyloxymethyl chloride, POM-Cl, 103 ml, 0.692 mol, 1.25 equiv) was added portion wise into the reaction mixture over 25 minutes via syringe with stirring at 0-5° C. The addition of chloromethyl pivalate (POM-Cl) was mildly exothermic and the reaction temperature went to as high as 14° C. After addition of chloromethyl pivalate (POM-Cl), the cooling bath was removed and the reaction mixture was allowed to return to room temperature and stirred at room temperature for overnight. When the reaction was deemed complete after about 16 hours, the reaction was quenched with 20% aqueous brine (250 mL) and ethyl acetate (250 mL) producing a slurry. Additional amount of water (250 mL) was added until the mixture becomes a homogeneous solution. The two layers were separated and the aqueous layer was extracted with ethyl acetate (250 mL). The combined organic fractions were dried over magnesium sulfate (MgSO$_4$), filtered, and concentrated under reduced pressure. The residue was purified by flash column chromatography (SiO$_2$, 10% to 15% ethyl acetate/hexane gradient elution) to afford the desired product as yellow, crystalline solids (155 g). The combined solids were treated with hexanes (750 mL) and the resulting slurry was warmed to 55° C. to produce a homogeneous solution. The resulting solution was then gradually cooled to room temperature and stirred at room temperature for overnight before being cooled to 0-5° C. for 2 h. The solids were collected by filtration, washed with pre-cooled hexanes (2×30 mL), dried in vacuum to afford 4-chloro-7H-pyrrolo[2,3-d]pyrimidin-7-yl)methyl pivalate (3f, 134.9 g, 148.0 g theoretical, 91% yield) as white solids. For 3f: $^1$H NMR (DMSO-d$_6$, 400 MHz) δ ppm 8.71 (s, 1H), 7.83 (d, 1H, J=3.7 Hz), 6.73 (d, 1H, J=3.8 Hz), 6.23 (s 2H), 1.06 (s, 9H); $^{13}$C NMR (DMSO-d$_6$, 100 MHz) δ ppm 176.9, 151.2, 151.1, 151.0, 131.6, 117.1, 99.9, 66.9, 38.3, 26.5; C$_{12}$H$_{14}$ClN$_3$O$_2$ (MW, 267.71), LCMS (EI) m/e 268/270 (M$^+$+H).

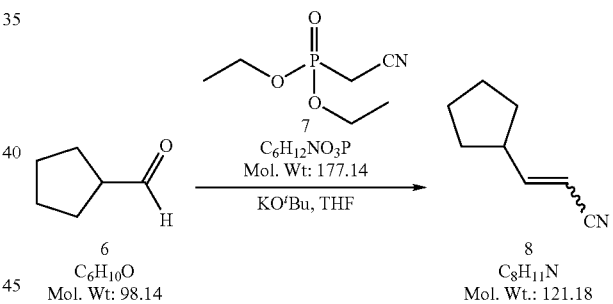

3-Cyclopentylacrylonitrile (8). A solution of diethyl cyanomethylphosphonate (7, 742.5 g, 4.2 mol, 1.1 equiv) in dry THF (5.75 L) was stirred under nitrogen on an ice-water-methanol bath and a solution of 1 M potassium tert-butoxide in THF (4 L, 4.0 mol, 1.05 equiv) was added at such a rate as to keep the temperature below 0° C. After addition of 1 M potassium tert-butoxide in THF was complete, the stirring was continued on the cold bath for 1 h and a solution of cyclopentanecarbaldehyde (6, 374 g, 3.81 mol) in dry THF (290 mL) was added at such a rate as to maintain the temperature below 0° C. The cold bath was removed, and the reaction mixture was gradually warmed to room temperature and stirred at room temperature for overnight. When the reaction was deemed complete, the reaction mixture was partitioned between methyl tert-butyl ether (MTBE, 14 L), water (10 L) and brine (6 L). The two layers were separated, and the combined organic phase was washed with brine (6 L). The aqueous phase was extracted with MTBE (10 L) and washed with brine (6 L). The combined organic extracts were concentrated under reduced pressure and the residue was distilled (65-78° C./6 torr) to afford 3-cyclopentylacrylonitrile (8, 437.8 g, 461.7 g theoretical, 94.8% yield) as a colorless oil, which was found to be a mixture of E- and Z-isomer. For 8: $^1$H NMR (DMSO-d$_6$, 400 MHz, for Z-isomer) δ ppm 6.58 (t, 1H, J=10.6 Hz), 5.55 (dd, 1H, J=10.8, 0.59 Hz), 2.85 (m, 1H), 1.9-1.46 (m, 6H), 1.34 (m, 2H) and (for E-isomer) δ ppm 6.83 (q, 1H, J=8.3 Hz), 5.66 (dd, 1H, J=16.5, 1.4 Hz), 2.60 (m, 1H), 1.9-1.46 (m, 6H), 1.34 (m, 2H); $^{13}$C NMR (DMSO-d$_6$, 100 MHz, for Z-isomer) δ ppm 159.8, 116.6, 97.7, 42.3, 32.3, 25.1 and (for E-isomer) δ ppm 160.4, 118.1, 97.9, 43.2, 31.5, 24.8; $C_8H_{11}N$ (MW, 121.18), GCMS (EI) m/e 120 (M$^+$–H).

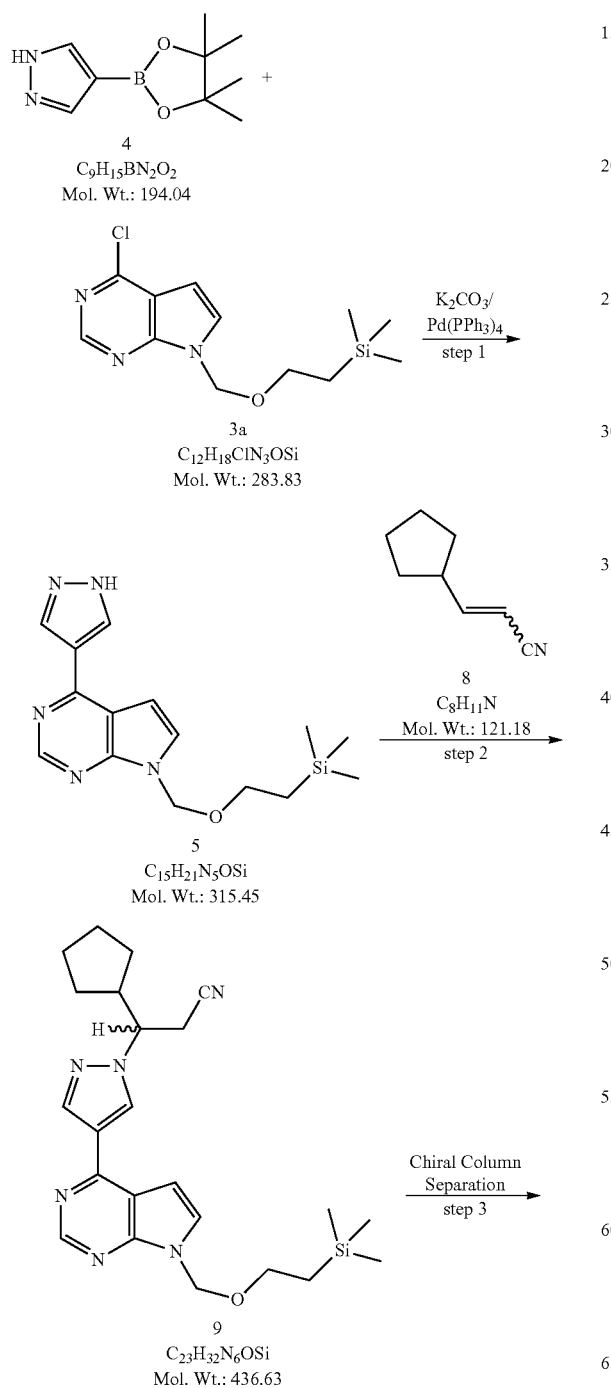

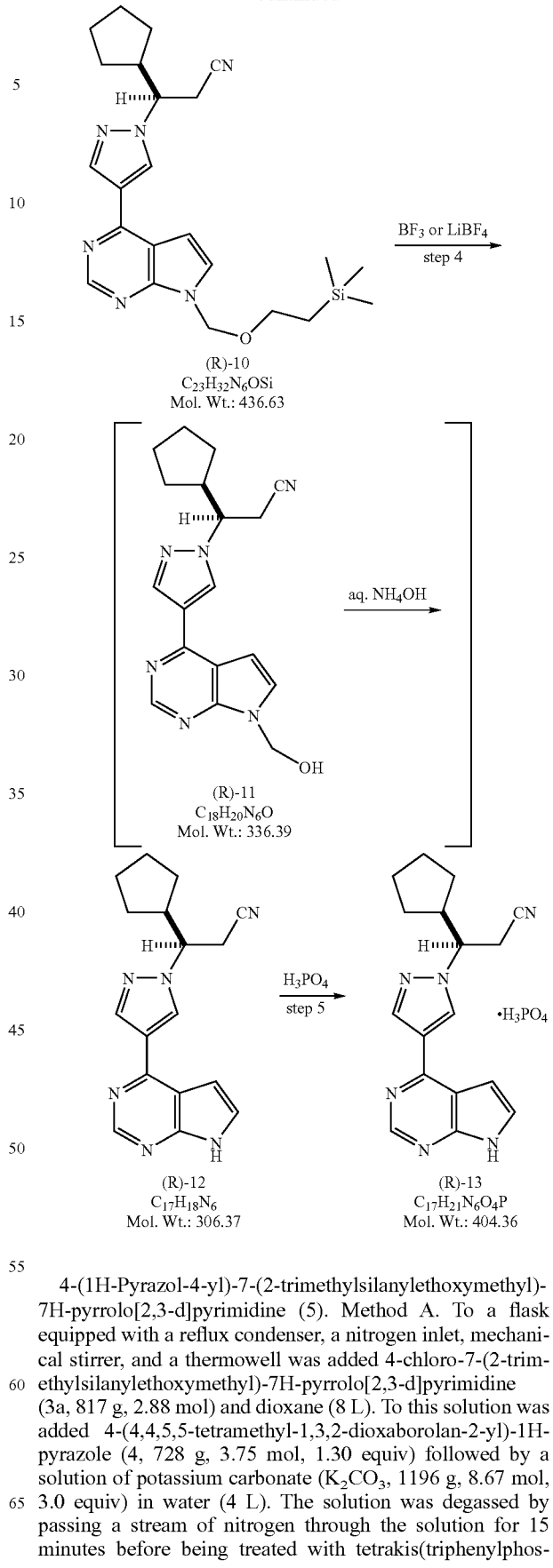

4-(1H-Pyrazol-4-yl)-7-(2-trimethylsilanylethoxymethyl)-7H-pyrrolo[2,3-d]pyrimidine (5). Method A. To a flask equipped with a reflux condenser, a nitrogen inlet, mechanical stirrer, and a thermowell was added 4-chloro-7-(2-trimethylsilanylethoxymethyl)-7H-pyrrolo[2,3-d]pyrimidine (3a, 817 g, 2.88 mol) and dioxane (8 L). To this solution was added 4-(4,4,5,5-tetramethyl-1,3,2-dioxaborolan-2-yl)-1H-pyrazole (4, 728 g, 3.75 mol, 1.30 equiv) followed by a solution of potassium carbonate (K$_2$CO$_3$, 1196 g, 8.67 mol, 3.0 equiv) in water (4 L). The solution was degassed by passing a stream of nitrogen through the solution for 15 minutes before being treated with tetrakis(triphenylphosphine)palladium(0) (167 g, 0.145 mol, 0.05 equiv) and the resulting reaction mixture was heated at reflux (about 90° C.) for 2 hours. When the reaction was deemed complete by TLC (1:1 heptane/ethyl acetate) and LCMS, the reaction mixture was cooled to room temperature, diluted with ethyl acetate (24 L) and water (4 L). The two layers were separated, and the aqueous layer was extracted with ethyl acetate (4 L). The combined organic layers were washed with water (2×2 L), brine (2 L), dried over sodium sulfate ($Na_2SO_4$), and concentrated under reduced pressure. The residue was suspended in toluene (4 L) and the solvent was removed under reduced pressure. The residue was finally triturated with methyl tert-butyl ether (MTBE, 3 L) and the solids were collected by filtration and washed with MTBE (1 L) to afford 4-(1H-pyrazol-4-yl)-7-(2-trimethylsilanyl-ethoxymethyl)-7H-pyrrolo[2,3-d]pyrimidine (5, 581.4 g, 908.5 g theoretical, 64% yield) as white crystalline solids. For 5: $^1$H NMR (DMSO-$d_6$, 400 MHz) δ ppm 13.41 (bs, 1H), 8.74 (s, 1H), 8.67 (bs, 1H), 8.35 (bs, 1H), 7.72 (d, 1H, J=3.7 Hz), 7.10 (d, 1H, J=3.7 Hz), 5.61 (s, 2H), 3.51 (t, 2H, J=8.2 Hz), 0.81 (t, 2H, J=8.2 Hz), 0.13 (s, 9H); $C_{15}H_{21}N_5OSi$ (MW, 315.45), LCMS (EI) m/e 316 ($M^+$+H).

Racemic 3-cyclopentyl-3-{4-[7-(2-trimethylsilanylethoxymethyl)-7H-pyrrolo[2,3-d]pyrimidin-4-yl]pyrazol-1-yl}propionitrile (9, racemic SEM-protected compound). Method A. 3-Cyclopentylacrylonitrile (8, 273.5 g, 2.257 mol, 1.20 equiv) and DBU (28 mL, 0.187 mol, 0.10 equiv) was added to a suspension of 4-(1H-pyrazol-4-yl)-7-(2-trimethylsilanylethoxymethyl)-7H-pyrrolo[2,3-d]pyrimidine (5, 591.8 g, 1.876 mol) in acetonitrile (4.7 L) at room temperature. The resulting reaction mixture was heated to 50-60° C. for 17 hours (a clear solution developed midway through heating) then to 70-80° C. for 8 hours. When LCMS analysis showed the reaction was deemed complete, the reaction mixture was cooled to room temperature. The cooled solution was then concentrated under reduced pressure to give the crude product (9) as a thick amber oil. The crude product was dissolved in dichloromethane (DCM) and absorbed onto silica gel then dry-loaded onto a silica column (3 Kg) packed in 33% EtOAc/heptanes. The column was eluted with 33% EtOAc/heptanes (21 L), 50% EtOAc/heptanes (28 L), 60% EtOAc/heptanes (12 L) and 75% EtOAc/heptanes (8 L). The fractions containing the desired product (9) were combined and concentrated under reduced pressure to generate a yellow oil, which was transferred to a 3 L flask with EtOAc. The solvent was removed under reduced pressure and the residual EtOAc by co-evaporating with heptanes. The residue was further dried under high vacuum for overnight to afford racemic 3-cyclopentyl-3-{4-[7-(2-trimethylsilanylethoxymethyl)-7H-pyrrolo[2,3-d]pyrimidin-4-yl]pyrazol-1-yl}propionitrile (9, racemic SEM-protected compound, 800 g, 819.1 g theoretical, 97.7% yield) as an extremely viscous yellow oil. For 9: $^1$H NMR (DMSO-$d_6$, 400 MHz) δ ppm 8.83 (s, 1H), 8.75 (s, 1H), 8.39 (s, 1H), 7.77 (d, 1H, J=3.7 Hz), 7.09 (d, 1H, J=3.7 Hz), 5.63 (s, 2H), 4.53 (td, 1H, J=19.4, 4.0 Hz), 3.51 (t, 2H, J=8.1 Hz), 3.23 (dq, 2H, J=9.3, 4.3 Hz), 2.41 (m, 1H), 1.79 (m, 1H), 1.66-1.13 (m, 7H), 0.81 (t, 2H, J=8.2 Hz), 0.124 (s, 9H); $C_{23}H_{32}N_6OSi$ (MW, 436.63), LCMS (EI) m/e 437 ($M^+$+H) and 459 ($M^+$+Na).

(3R)-Cyclopentyl-3-{4-[7-(2-trimethylsilanylethoxymethyl)-7H-pyrrolo [2,3-d]pyrimidin-4-yl]pyrazol-1-yl}propionitrile ((R)-10) and (3S)-Cyclopentyl-3-{4-[7-(2-trimethylsilanylethoxymethyl)-7H-pyrrolo[2,3-d]pyrimidin-4-yl]pyrazol-1-yl}propionitrile ((S)-10) A slurry of 1.5 Kg of 20-micron Chiralcel® OD chiral stationary phase (CSP) made by Daicel in 3.0 L of isopropanol (IPA) was packed into a PROCHROM Dynamic Axial Compression Column LC110-1 (11 cm ID×25 cm L; Column Void Vol.: approximate 1.5 L) under 150 bar of packing pressure. The packed column was then installed on a Novasep Hipersep HPLC unit. The column and the Hipersep unit were flushed with methanol (17 L) followed by the mobile phase made of a mixture of isopropanol and hexane (2:8 by volume, 17 L). The feed solution was then prepared by dissolving 3-cyclopentyl-3-{4-[7-(2-trimethylsilanylethoxymethyl)-7H-pyrrolo[2,3-d]pyrimidin-4-yl]pyrazol-1-yl}propionitrile (9, racemic SEM-protected compound, 2795 g, 6.4 mol) in the mobile phase to a concentration of 80 g/L. The feed solution was then sequentially injected into the preparative chiral column for separation. Each injection was 120 ml in volume. The chiral column was eluted with the mobile phase at a flow rate of 570 mL/min at room temperature. The column elution was monitored by UV at a wavelength of 330 nm. Under these conditions a baseline separation of the two enantiomers was achieved. The retention times were 16.4 minutes (Peak 1, the undesired (S)-enantiomer (S)-10) and 21.0 minutes (Peak 2, the desired (R)-enantiomer (R)-10), respectively. The cycle time for each injection was 11 minutes and a total of 317 injections were performed for this separation process. Fractions for Peak 1 (the undesired (S)-enantiomer, (S)-10) and Peak 2 (the desired (R)-enantiomer, (R)-10) were collected separately from each injection. The collected fractions collected were continuously concentrated in the 1-square feet and 2-square feet ROTOTHERM evaporator, respectively, at 40° C. under reduced pressure (40-120 bar). The residue from each evaporator was further dried under high vacuum to constant weight to afford (3R)-cyclopentyl-3-{4-[7-(2-trimethylsilanylethoxymethyl)-7H-pyrrolo[2,3-d]pyrimidin-4-yl]pyrazol-1-yl}propionitrile ((R)-10, 1307 g, 1397.5 g theoretical, 93.5%) from Peak 2 as a light yellow oil and (3S)-cyclopentyl-3-{4-[7-(2-trimethylsilanylethoxymethyl)-7H-pyrrolo[2,3-d]pyrimidin-4-yl]pyrazol-1-yl}propionitrile ((S)-10, 1418 g, 1397.5 g theoretical, 101.5%) from Peak 1 as an yellow oil.

A chiral HPLC method was developed for chiral purity evaluation of both enantiomers of SEM-protected compound ((R)-10 and (S)-10) using a Chiralcel® OD-H column (4.6×250 mm, 5 μm), purchased from Chiral Technologies, Inc., packed with silica gel coated with cellulose tris(3,5-dimethylphenyl carbamate) (Chiralcel® OD). The two enantiomers of SEM-protected compound are separated with a resolution greater than 3.0 by using a mobile phase made of 10% ethanol and 90% hexanes at room temperature with a flow rate of 1 mL/min. The UV detection wavelength is 220 nm. The retention times for (S)-enantiomer ((S)-10) and (R)-enantiomer ((R)-10) are 10.3 minutes and 13.1 minutes, respectively.

The quality of each enantiomer separated by preparative chiral HPLC including chemical purity (HPLC area % and wt %), chiral purity (chiral HPLC area %), and residual solvents (IPA and hexane) was analyzed and their structures are confirmed by NMRs and LC/MS. For (R)-10: achiral purity (99.0 area % by HPLC detected at 220 nm; 100.1 wt % by HPLC weight percent assay); chiral purity (99.7 area % by chiral HPLC; 99.4% ee); residual solvents (3.7 wt % for IPA; 0.01 wt % for hexane); $^1$H NMR (DMSO-$d_6$, 400 MHz) δ ppm 8.83 (s, 1H), 8.75 (s, 1H), 8.39 (s, 1H), 7.77 (d, 1H, J=3.7 Hz), 7.09 (d, 1H, J=3.7 Hz), 5.63 (s, 2H), 4.53 (td, 1H, J=19.4, 4.0 Hz), 3.51 (t, 2H, J=8.1 Hz), 3.23 (dq, 2H, J=9.3, 4.3 Hz), 2.41 (m, 1H), 1.79 (m, 1H), 1.66-1.13 (m, 7H), 0.81 (t, 2H, J=8.2 Hz), 0.124 (s, 9H); $C_{23}H_{32}N_6OSi$ (MW, 436.63), LCMS (EI) m/e 437 ($M^+$+H) and 459 ($M^+$+Na). For (S)-10: achiral purity (99.3 area % by HPLC detected at 220 nm; 99.9 wt % by HPLC weight percent assay); chiral purity (99.7 area % by chiral HPLC; 99.4% ee); residual solvents (4.0 wt % for IPA; 0.01 wt % for hexane); $^1$H NMR (DMSO-$d_6$, 400 MHz) δ ppm 8.83 (s, 1H), 8.75 (s, 1H), 8.39 (s, 1H), 7.77 (d, 1H, J=3.7 Hz), 7.09 (d, 1H, J=3.7 Hz), 5.63 (s, 2H), 4.53 (td, 1H, J=19.4, 4.0 Hz), 3.51 (t, 2H, J=8.1 Hz), 3.23 (dq, 2H, J=9.3, 4.3 Hz), 2.41 (m, 1H), 1.79 (m, 1H), 1.66-1.13 (m, 7H), 0.81 (t, 2H, J=8.2 Hz), 0.124 (s, 9H); $C_{23}H_{32}N_6OSi$ (MW, 436.63), LCMS (EI) m/e 437 ($M^++H$) and 459 ($M^++Na$).

(3R)-Cyclopentyl-3-{4-[7-(2-trimethylsilanylethoxymethyl)-7H-pyrrolo[2,3-d]pyrimidin-4-yl]pyrazol-1-yl}propionitrile ((R)-10) and (3S)-Cyclopentyl-3-{4-[7-(2-trimethylsilanylethoxymethyl)-7H-pyrrolo[2,3-d]pyrimidin-4-yl]pyrazol-1-yl}propionitrile ((S)-10)

The racemic mixture was processed on an SMB unit equipped with 8 columns. The separation was performed at various scales using various conditions presented in the examples below. The purity of each enantiomer was monitored by a chiral HPLC method using the same mobile phase and the same stationary phase used for the separation to allow rapid determination of the purity. In each case both enantiomers were recovered as concentrated solutions by evaporation under vacuum, either using a rotary evaporator or falling film evaporators. In examples 1 to 3 the desired enantiomer is recovered as the raffinate. In example 4 the desired enantiomer is recovered as the extract. The chiral purity and yield reported are data measured after the SMB unit has been operated for at least 10 to 15 cycles to ensure steady state operations. Various operating conditions were tested to ensure high purity and high product yield. In examples 1 to 3, the separation using the same stationary phase and mobile phase is tested on various SMB units with various column diameters. In example 4 the SMB is operated at two different operating pressures. In example 4, the column configuration was changed from the classical <2>/<2>/<2>/<2> to <2>/<2>/<3>/<1> to increase the purity of the raffinate and increase the throughput by increasing the length of the SMB Zone III.

Example 1

50 g Scale

| Column: | Chiralcel ® OD |
|---|---|
| Mobile Phase | isopropyl alcohol and n-heptane 20/80 (v/v) |
| Column length | 10 cm |
| Column ID | 10 mm |
| No of columns | 8 |
| Feed concentration | 80 g/l |
| Temperature: | 25° C. |

| Parameters | Example 1 |
|---|---|
| Column configuration | <2>/<2>/<2>/<2> |
| Recycling flow rate (ml/min) | 18 |
| Extract flow rate (ml/min) | 7.76 |
| Feed flow rate (ml/min) | 0.25 |
| Raffinate flow rate (ml/min) | 1.4 |
| Eluent flow rate (ml/min) | 8.91 |
| Switch time (min) | 1.52 |
| Desired enantiomer purity | 99.15% |
| Desired enantiomer yield | 94.8% |
| Productivity (kg enantiomer/d/kg CSP) | 0.41 |

Example 2

25 kg Scale

| Column: | Chiralcel ® OD |
|---|---|
| Mobile Phase | isopropyl alcohol and n-heptane 20/80 (v/v) |
| Column length | 9.5 cm |
| Column ID | 49 mm |
| No of columns | 8 |
| Feed concentration | 80 g/l |
| Temperature: | 25° C. |

| Parameters | Example 2 |
|---|---|
| Column configuration | <2>/<2>/<2>/<2> |
| Operating pressure (bar) | 25-28 |
| Recycling flow rate (ml/min) | 498.9 |
| Extract flow rate (ml/min) | 176.4 |
| Feed flow rate (ml/min) | 6.58 |
| Raffinate flow rate (ml/min) | 57.8 |
| Eluent flow rate (ml/min) | 227.6 |
| Switch time (min) | 1.11 |
| Desired enantiomer purity | 99.3% |
| Desired enantiomer yield | 85% |
| Productivity (kg enantiomer/d/kg CSP) | 0.43 |

Example 3

100 kg Scale

| Column: | Chiralcel ® OD |
|---|---|
| Mobile Phase | isopropyl alcohol and n-heptane 20/80 (v/v) |
| Column length | 9.0 cm |
| Column ID | 200 mm |
| No of columns | 8 |
| Feed concentration | 53.7 g/l |
| Temperature: | 25° C. |

| Parameters | Example 3 |
|---|---|
| Column configuration | <2>/<2>/<2>/<2> |
| Operating pressure (bar) | 35 |
| Recycling flow rate (l/h) | 355.0 |
| Extract flow rate (l/h) | 124.1 |
| Feed flow rate (l/h) | 7.0 |
| Raffinate flow rate (l/h) | 114.0 |
| Eluent flow rate (l/h) | 231.1 |
| Switch time (min) | 1.80 |
| Desired enantiomer purity | 99.8% |
| Desired enantiomer yield | 92% |
| Productivity (kg enantiomer/d/kg CSP) | 0.31 |

Example 4

100 g Scale

| Column: | (S,S) Whelk-O ® 1 |
|---|---|
| Mobile Phase | methyl-tert-butyl ether |
| Column length | 10.0 cm |
| Column ID | 10 mm |
| No of columns | 8 |
| Feed concentration | 90 g/l |

| Parameters | Example 4a | Example 4b |
|---|---|---|
| Column configuration | <2>/<2>/<2>/<2> | <2>/<2>/<3>/<1> |
| Operating pressure (bar) | 27 | 12 |
| Temperature | 23 | 22 |
| Recycling flow rate (ml/min) | 22.0 | 9.0 |
| Extract flow rate (ml/min) | 9.6 | 2.8 |
| Feed flow rate (ml/min) | 0.5 | 0.3 |
| Raffinate flow rate (ml/min) | 5.9 | 3.0 |
| Eluent flow rate (ml/min) | 15 | 5.5 |
| Switch time (min) | 0.70 | 1.48 |
| Desired enantiomer purity | 99.6% | 99.8% |
| Desired enantiomer yield | 90% | 98% |
| Productivity (kg enantiomer/d/kg CSP) | 0.92 | 0.55 |

(3R)-Cyclopentyl-3-[4-(7H-pyrrolo[2,3-d]pyrimidin-4-yl)pyrazol-1-yl]propionitrile ((R)-12, free base). Method A. To a solution of (3R)-cyclopentyl-3-{4-[7-(2-trimethylsilanylethoxymethyl)-7H-pyrrolo[2,3-d]pyrimidin-4-yl]pyrazol-1-yl}propionitrile ((R)-10, 463 g, 1.06 mol, 98.6% ee) in acetonitrile (4.5 L) was added water (400 mL) followed immediately by lithium tetrafluoroborate (LiBF$_4$, 987.9 g, 10.5 mol, 10.0 equiv) at room temperature. The reaction temperature was observed to decrease from ambient to 12° C. upon addition of the water and then increase to 33° C. during the addition of lithium tetrafluoroborate (LiBF$_4$). The resulting reaction mixture was heated to reflux (about 80° C.) for overnight. An aliquot was quenched into ethyl acetate/water and checked by LCMS and TLC (95:5 ethyl acetate/methanol, v/v). When LCMS and TLC analyses showed both the hydroxyl methyl intermediate ((R)-11) and fully de-protected material ((R)-12, free base) produced but no starting material ((R)-10) left, the reaction mixture was cooled gradually to <5° C. before a 20% aqueous solution of ammonium hydroxide (NH$_4$OH, 450 mL) was added gradually to adjust the pH of the reaction mixture to 9 (checked with pH strips). The cold bath was removed and the reaction mixture was gradually warmed to room temperature and stirred at room temperature for overnight. An aliquot was quenched into ethyl acetate/water and checked by LCMS and TLC (95:5 ethyl acetate/methanol, v/v) to confirm complete de-protection. When LCMS and TLC showed the reaction was deemed complete, the reaction mixture was filtered and the solids were washed with acetonitrile (1 L). The combined filtrates were then concentrated under reduce pressure, and the residue was partitioned between ethyl acetate (6 L) and half-saturated brine (3 L). The two layers were separated and the aqueous layer was extracted with ethyl acetate (2 L). The combined organic layers were washed with half-saturated sodium bicarbonate (NaHCO$_3$, 3 L) and brine (3 L), dried over sodium sulfate (Na$_2$SO$_4$), and concentrated under reduced pressure to give the crude product as an orange oil. The crude material was then purified by flash column chromatography (SiO$_2$, 40 to 100% ethyl acetate/heptane gradient elution) to afford (3R)-cyclopentyl-3-[4-(7H-pyrrolo[2,3-d]pyrimidin-4-yl)pyrazol-1-yl]propionitrile ((R)-12, free base, 273 g, 324.9 g theoretical, 84% yield) as a white foam. This material was checked by $^{19}$F NMR to ensure no lithium tetrafluoroborate (LiBF$_4$) remained, and by chiral HPLC (Chiralcel® OD-H, 90:10 hexane/ethanol) to confirm enantiomeric purity (98.7% ee), and was used without further purification to prepare the corresponding phosphate salt. For (R)-12 (free base): $^1$H NMR (DMSO-d$_6$, 400 MHz) δ ppm 12.1 (bs, 1H), 8.80 (d, 1H, J=0.42 Hz), 8.67 (s, 1H), 8.37 (s, 1H), 7.59 (dd, 1H, J=2.34, 3.51 Hz), 6.98 (dd, 1H, J=1.40, 3.44 Hz), 4.53 (td, 1H, J=19.5, 4.63 Hz), 3.26 (dd, 1H, J=9.77, 17.2 Hz), 3.18 (dd, 1H, J=4.32, 17.3 Hz), 2.40 (m, 1H), 1.79 (m, 1H), 1.65 to 1.13 (m, 7H); C$_{17}$H$_{18}$N$_6$(MW, 306.37) LCMS (EI) m/e 307 (M$^+$+H).

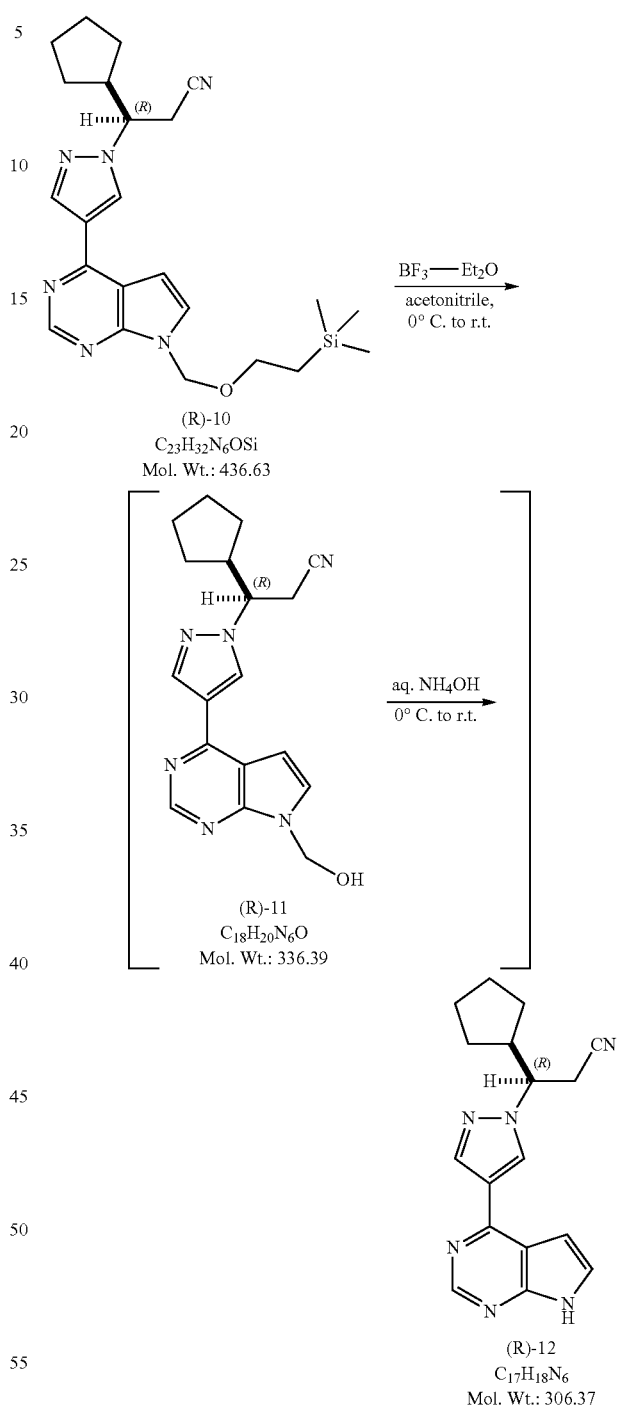

(R)-3-(4-(7H-pyrrolo[2,3-d]pyrimidin-4-yl)-1H-pyrazol-1-yl)-3-cyclopentylpropanenitrile (R)-10. A solution of (R)-3-cyclopentyl-3-(4-(7-((2-(trimethylsilyl)ethoxy)methyl)-7H-pyrrolo[2,3-d]pyrimidin-4-yl)-1H-pyrazol-1-yl) propanenitrile ((R)-10, 75.0 g, 0.172 mol, 98.8% ee) in acetonitrile (600 mL) was cooled to 0-5° C. To the cooled solution was added boron trifluoride diethyl etherate (54.4 mL, 0.429 mol) over 10 minutes while maintaining the internal reaction temperature below 5° C. Following the addition, the cold bath was removed and the reaction mixture was allowed to warm to room temperature. When HPLC analysis indicated that the level of (R)-10 was below 1%, the initial phase of the deprotection reaction was considered complete. The reaction was then cooled to 0-5° C., followed by the slow addition of water (155 mL). Following the water addition, the cold bath was removed and the resulting reaction mixture was allowed to warm to 13-17° C., and stirred for an additional 2-3 hours. The resulting reaction mixture was cooled again to 0-5° C. To the cooled reaction mixture was added slowly a solution of ammonia in water [prepared by mixing aqueous 28% ammonia solution (104.5 mL) and water (210.5 mL)] while maintaining the internal reaction temperature at below 5° C. After the aqueous ammonia solution was added, the cold bath was removed and the reaction was allowed to warm to room temperature. The hydrolysis was deemed complete when the level of the hydroxylmethyl intermediate was below 1% by HPLC analysis.

The resulting reaction mixture was diluted with ethyl acetate (315 mL) and washed with 20% brine (315 mL). The aqueous fraction was back extracted with ethyl acetate (315 mL). The organic fractions were combined and concentrated under vacuum with a bath temperature of 40° C. to a volume of 380 mL. The concentrated residue was diluted with ethyl acetate (600 mL) and washed with 1M $NaHCO_3$ (2×345 mL) and 20% brine (345 mL). The aqueous washes were combined and back extracted with ethyl acetate (345 mL). The organic fractions were combined and polish filtered into a clean 2L round bottom flask. The organic fraction was washed with warm water (50° C., 2×450 mL) and then treated with activated charcoal at 65° C. with stirring for 1.5 hours. The slurry was filtered through a celite bed. The filtrate was concentrated under vacuum with a bath temperature of 40° C. The resulting syrup was placed under high vacuum to provide (R)-3-(4-(7H-pyrrolo[2,3-d]pyrimidin-4-yl)-1H-pyrazol-1-yl)-3-cyclopentylpropanenitrile [(R)-12, 54.2g, 103% yield] as a light yellow foam. This material was checked by $^{19}F$ NMR to ensure that the product was not contaminated by any fluorinated impurities. The chemical purity of the isolated free base was 96.3%. The chiral purity of the free base was 98.8% by chiral HPLC (chiralcel OD, 90:10 hexane/ethanol). The free base was used without further purification to prepare the phosphate salt. $^1H$ NMR (DMSO-$d_6$, 400 MHz) δ 12.11 (bs, 1H), 8.79(d, 1H, J=0.43 Hz), 8.67(s, 1H), 8.37(s, 1H), 7.59(q, 1H, J=2.3 Hz), 6.98(q, 1H, J=1.6 Hz), 4.53(td, 1H, J=19.2, 4.1 Hz), 3.22(dq, 2H, J=9.8, 4.3 Hz), 2.40(m, 1H), 1.79(m, 1H), 1.65-1.13(m, 7H). $C_{17}H_{16}N_6$ (MW, 306.37), LCMS (EI) m/e 307 (M$^+$+H).

(3R)-Cyclopentyl-3-[4-(7H-pyrrolo[2,3-d]pyrimidin-4-yl)pyrazol-1-yl]propionitrile phosphate salt ((R)-13, phosphate). Method A. To a solution of (3R)-cyclopentyl-3-[4-(7H-pyrrolo[2,3-d]pyrimidin-4-yl)pyrazol-1-yl] propionitrile ((R)-12, free base, 572 g, 1.87 mol) in isopropanol (IPA, 8 L) at 60-65° C. was added a solution of phosphoric acid (186.2 g, 1.9 mol, 1.10 equiv) in isopropanol (1.6 L). No exotherm was observed while adding a solution of phosphoric acid, and a precipitate was formed almost immediately. The resulting mixture was then heated at 76° C. for 1.5 hours, then cooled gradually to ambient temperature and stirred at room temperature for overnight. The mixture was filtered and the solids were washed with a mixture of heptanes and isopropanol (1/1, v/v, 3 L) before being transferred back to the original flask and stirred in heptanes (8 L) for one hour. The solids were collected by filtration, washed with heptanes (1 L), and dried in a convection oven in vacuum at 40° C. to a constant weight to afford (3R)-cyclopentyl-3-[4-(7H-pyrrolo[2,3-d]pyrimidin-4-yl)pyrazol-1-yl]propionitrile phosphate salt ((R)-13, phosphate, 634.2 g , 755 g theoretical, 84% yield) as white to off-white crystalline solids. For (R)-13, phosphate: mp. 197.6° C.; $^1H$ NMR (DMSO-$d_6$, 500 MHz) δ ppm 12.10 (s, 1H), 8.78 (s, 1H), 8.68 (s, 1H), 8.36 (s 1H), 7.58 (dd, 1H, J=1.9, 3.5 Hz), 6.97 (d, 1H, J=3.6 Hz), 4.52 (td, 1H, J=3.9, 9.7 Hz), 3.25 (dd, 1H, J=9.8, 17.2 Hz), 3.16 (dd, 1H, J=4.0, 17.0 Hz), 2.41, (m, 1H), 1.79 (m, 1H), 1.59 (m, 1H), 1.51 (m, 2H), 1.42 (m, 1H), 1.29 (m, 2H), 1.18 (m, 1H); $^{13}C$ NMR (DMSO-$d_6$, 125 MHz) δ ppm 152.1, 150.8, 149.8, 139.2, 131.0, 126.8, 120.4, 118.1, 112.8, 99.8, 62.5, 44.3, 29.1, 29.0, 24.9, 24.3, 22.5; $C_{17}H_{18}N_6$(MW, 306.37 for free base) LCMS (EI) m/e 307 (M$^+$+H, base peak), 329.1 (M$^+$+Na).

Method B. To a solution of (R)-3-(4-(7H-pyrrolo[2,3-d]pyrimidin-4-yl)-1H-pyrazol-1-yl)-3-cyclopentylpropanenitrile ((R)-12, 54.2 g, 177 mol) in dichloromethane (782 mL) and 2-propanol (104 mL) at reflux was added a solution of phosphoric acid (19.9 g, 0.173 mol, 1.15 equiv) in 2-propanol (34.0 mL) over a period of 47 minutes. Following the acid addition, the resulting mixture was heated to reflux for an additional 1 hour. The mixture was gradually cooled to ambient temperature and stirred for 3 hours. The solids were collected by filtration and washed with dichloromethane (390 mL), followed by n-heptane (390 mL). The solids were partially dried under vacuum at room temperature and then under vacuum at 62° C. to afford (R)-3-(4-(7H-pyrrolo[2,3-d]pyrimidin-4-yl)-1H-pyrazol-1-yl)-3-cyclopentylpropanenitrile phosphate (60.1 g, 84% yield) as white to off-white crystalline solids. Analysis by chiral HPLC (chiralcel OD, 90:10 hexane/ethanol) gave the enantiopurity as 99.2% ee. $^1H$ NMR (DMSO-$d_6$, 400 MHz) δ 12.11(bs, 1H), 8.79(d, 1H, J=0.59 Hz), 8.67(s, 1H), 8.36(s, 1H), 7.59(q, 1H, J=2.3 Hz), 6.98(q, 1H, J=1.6 Hz), 4.53(td, 1H, J=19.6, 4.4 Hz), 3.22(dq, 2H, J=9.6, 4.3 Hz), 2.40(m, 1H), 1.79(m, 1H), 1.65-1.13(m, 7H). $C_{17}H_{21}N_6O_4P$ (MW, 404.36), LCMS (EI) m/e 307 (M$^+$+H) and m/e 329 (M$^+$+Na).

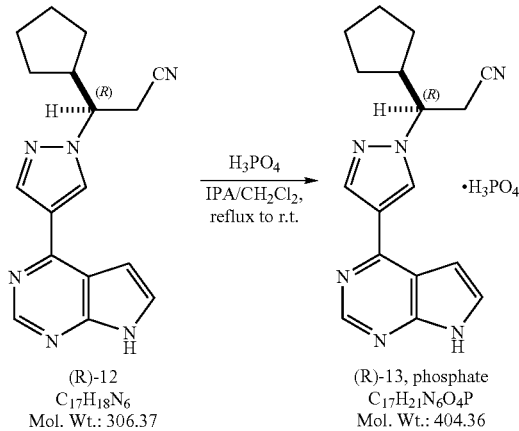

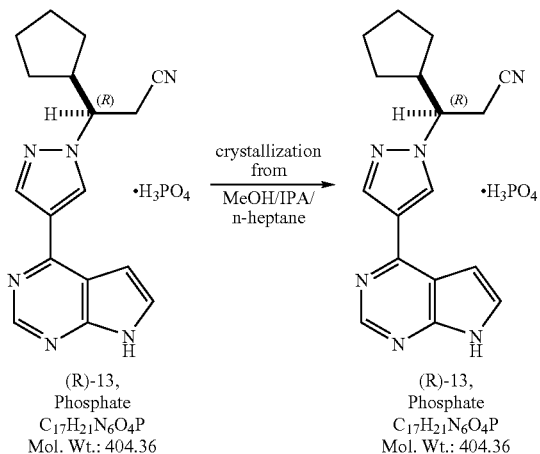

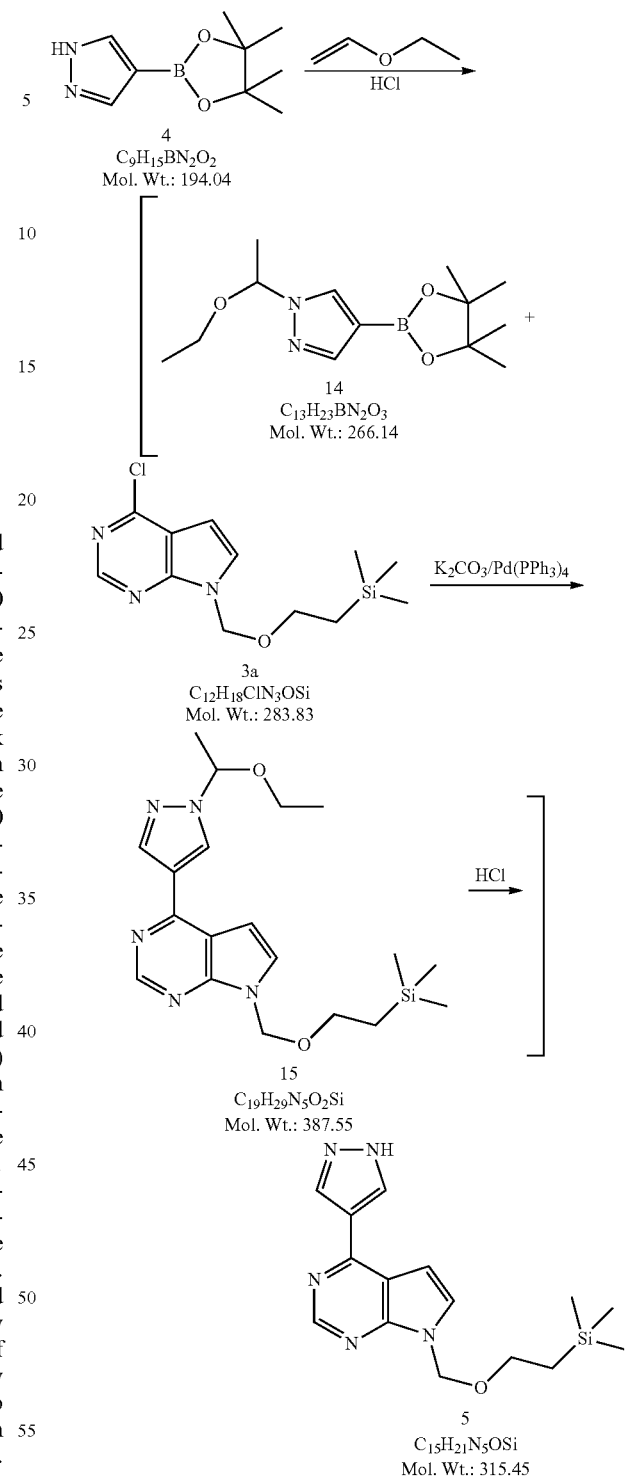

(R)-3-(4-(7H-pyrrolo[2,3-d]pyrimidin-4-yl)-1H-pyrazol-1-yl)-3-cyclopentylpropanenitrile phosphate. Into a 1 L round bottom flask, equipped with stir bar, distillation head, addition funnel and heating mantle, were charged methanol (520 mL) and (R)-3-(4-(7H-pyrrolo[2,3-d]pyrimidin-4-yl)-1H-pyrazol-1-yl)-3-cyclopentylpropanenitrile phosphate ((R)-13, phosphate, 40.0 grams, 98.92 mmol). The slurry was heated to 55° C. to generate a slightly pink solution. The solution was cooled to 50° C. and filtered into a 2 L flask equipped with an overhead stirrer, distillation head, addition funnel and heating mantle. The 1 L round bottom flask and the filter funnel were rinsed with additional methanol (104.0 mL). The filtrate solution was heated to reflux to distill methanol (281 mL) over 1 hour under atmospheric pressure. Isopropyl alcohol (IPA) (320 mL) was charged slowly via the addition funnel over 80 minutes while maintaining the internal temperature approximately at 65° C. Precipitation of the phosphate salt was observed during IPA addition. After the addition of IPA was complete, n-heptane (175 mL) was added slowly at the same temperature. Distillation was continued under atmospheric pressure. Additional n-heptane (825 mL) was added at approximately the same rate as the distillation rate while maintaining the internal temperature at approximately 65° C. The distillation was complete when the volume of the distillate reached 742 mL (excluding the volume of 281 mL of methanol from the previous distillation). The distillation took approximately 1 hour. The vapor temperature during the distillation was in the range of 54-64° C. and the internal temperature was 67° C. at the end of the distillation. The mixture was slowly cooled to room temperature and stirred for an additional 3 hours. The solids were collected by filtration. The wet cake was washed with 16.7% (v/v) of isopropyl alcohol in n-heptane (384.0 mL), followed by n-heptane (280.0 mL), and dried under vacuum at 55° C. to provide 36.1 grams of the desired product as white solids in 90% yield. The chemical purity is 99.79% by HPLC analysis. The chiral purity is 99.8% by chiral HPLC analysis. $^1$H NMR (499.7 MHz, DMSO-d6) δ (ppm): 12.21 (s, 1H), 10.71 (s, 3H), 8.80 (s, 1H), 8.72 (s, 1H), 8.40 (s, 1H), 7.60 (d, J=3.5 Hz, 1H), 7.00 (d, J=3.5 Hz, 1H), 4.51 (td, J=9.75, 4.0 Hz, 1H), 3.25 (dd, J=17.3, 9.75 Hz, 1H), 3.14 (dd, J=17.0, 4.0 Hz, 1H), 2.43-2.35 (m, 1H), 1.79-1.73 (m, 1H), 1.58-1.42 (m, 3H), 1.41-1.33 (m, 1H), 1.30-1.23 (m, 2H), 1.19-1.12 (m, 1H); $^{13}$C NMR (125.7 MHz, DMSO-d6) δ (ppm): 152.8, 151.2, 150.3, 140.0, 131.8, 127.7, 120.8, 118.8, 113.5, 100.7, 63.3, 45.0, 29.8, 25.6, 25.0, 23.2; LCMS m/z: calculated for $C_{17}H_{18}N_6$ (M+H)$^+$:=307.2. Found (M+H)$^+$: 307.0.

4-(1H-Pyrazol-4-yl)-7-(2-trimethylsilanylethoxymethyl)-7H-pyrrolo[2,3-d]pyrimidine (5). Method B. To a reactor equipped with overhead stirring, condenser, thermowell, and nitrogen inlet was charged 4-(4,4,5,5-tetramethyl-1,3,2-dioxaborolan-2-yl)-1H-pyrazole (4, 600 g, 3.09 mol), toluene (4.2 L), and ethyl vinyl ether (334.5 g, 4.64 mol, 0.44 L, 1.50 equiv) at room temperature before a solution of 2 M HCl in diethyl ether (39 mL, 0.078 mol, 0.025 equiv) was added dropwise. The resulting reaction mixture was heated to 35-40° C. for 4-8 h. When HPLC analysis showed that the reaction was deemed complete, the reaction mixture was cooled to 15-25° C. before being treated with an aqueous NaHCO₃ solution to pH >8. The two layers were separated, and the organic layer was concentrated under reduced pressure to afford the crude 1-(1-ethoxyethyl)-4-(4,4,5,5-tetramethyl-1,3,2-dioxaborolan-2-yl)-1H-pyrazole (14), which was directly used in the subsequent Suzuki coupling reaction without further purification.

To a reactor equipped with overhead stirring, condenser, thermowell, and nitrogen inlet was charged water (H₂O, 1.5 L), potassium carbonate (K₂CO₃, 1047 g, 7.58 mol, 2.45 equiv), 4-chloro-7-(2-trimethylsilanylethoxymethyl)-7H-pyrrolo[2,3-d]pyrimidine (3a, 755 g, 2.66 mol), crude 1-(1-ethoxyethyl)-4-(4,4,5,5-tetramethyl-1,3,2-dioxaborolan-2-yl)-1H-pyrazole (14, 822 g based on 100% conversion, 3.09 mol, 1.16 equiv) made as described above, and 1-propanol (6 L) at room temperature. The resulting reaction mixture was degassed three timed backfilling with nitrogen each time before being treated with tetrakis(triphenylphosphine)palladium(0) (9.2 g, 0.008 mol, 0.0026 equiv) at room temperature. The resulting reaction mixture was heated to gentle reflux (about 90° C.) for 1-4 hours. When the reaction was deemed complete by HPLC, the reaction mixture was concentrated under reduced pressure to remove solvents. The residue was then cooled to room temperature, diluted with ethyl acetate (9 L) and water (4 L). The two layers were separated, and the aqueous layer was extracted with ethyl acetate (2×2.5 L). The combined organic layers were washed with water (2×2 L) and concentrated under reduced pressure to afford the crude 4-(1-(1-ethoxyethyl)-1H-pyrazol-4-yl)-7-((2-(trimethylsilyl)ethoxy)methyl)-7H-pyrrolo[2,3-d]pyrimidine (15), which was directly used in the subsequent acid-promoted de-protection reaction without further purification.

To a reactor equipped with overhead stirring, condenser, thermowell, and nitrogen inlet was charged crude 4-(1-(1-ethoxyethyl)-1H-pyrazol-4-yl)-7-((2-(trimethylsilyl)ethoxy)methyl)-7H-pyrrolo[2,3-d]pyrimidine (15, 1030.9 g based on 100% conversion, 2.66 mol), tetrahydrofuran (THF, 0.9 L), water (H₂O, 4.4 L), and a 10% aqueous HCl solution (2.7 L, 10.64 mol, 3.44 equiv) at room temperature. The resulting reaction mixture was stirred at room temperature for 2-5 h. When the reaction was deemed complete by HPLC analysis, the reaction mixture was treated with a 30% aqueous sodium hydroxide (NaOH) solution (940 mL, 11.70 mol, 3.78 equiv) at room temperature. The resulting reaction mixture was stirred at room temperature for 1-2 h. The solids were collected by filtration, washed with water (2×0.75 L), and dried in a vacuum oven at 45-55° C. to constant weight to afford the crude 4-(1H-pyrazol-4-yl)-7-(2-trimethylsilanyl-ethoxymethyl)-7H-pyrrolo[2,3-d]pyrimidine (5, 826.8 g, 839.1 g theoretical, 98.5% yield) as off-white solids (94.2 area % pure by HPLC). This crude material was subsequently recrystallized in acetonitrile to afford pure compound 5 (738.4 g, 839.1 g theoretical, 88% yield) as white crystals (99.5 area % by HPLC), which was found to be identical in every comparable aspect to the material made from Method A.

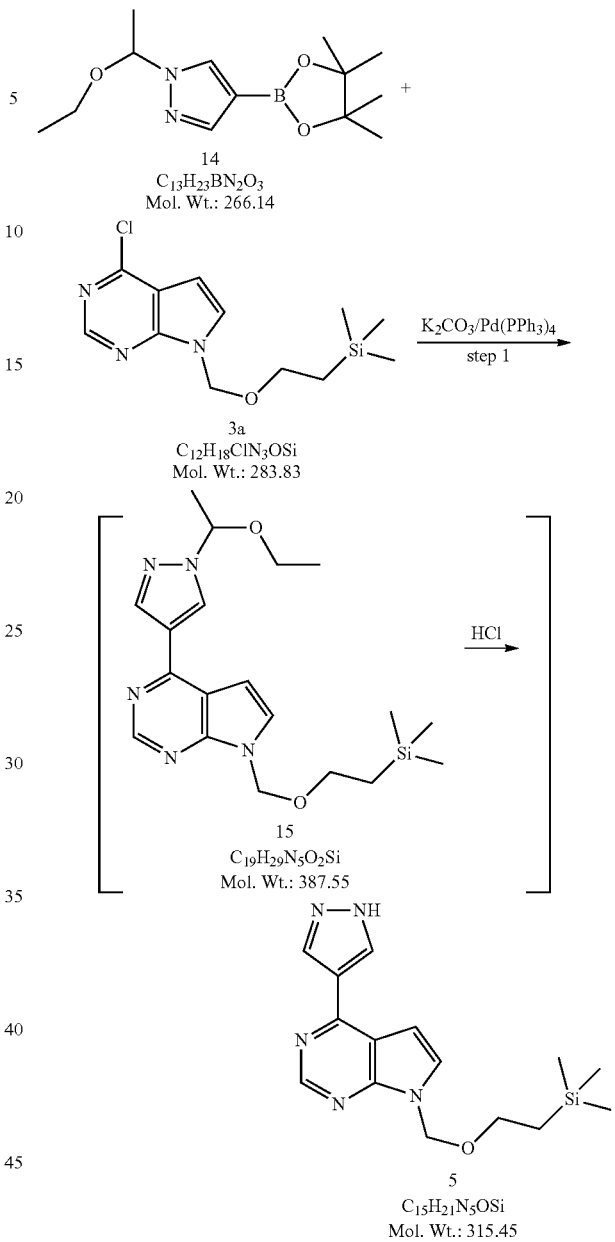

4-(1H-Pyrazol-4-yl)-7-(2-trimethylsilanylethoxymethyl)-7H-pyrrolo[2,3-d]pyrimidine (5). Method C. To a reactor equipped with overhead stirring, condenser, thermowell, and nitrogen inlet was charged water (H₂O, 9.0 L), potassium carbonate (K₂CO₃, 4461 g, 32.28 mol, 2.42 equiv), 4-chloro-7-(2-trimethylsilanylethoxymethyl)-7H-pyrrolo[2,3-d]pyrimidine (3a, 3597 g, 12.67 mol), 1-(1-ethoxyethyl)-4-(4,4,5,5-tetramethyl-1,3,2-dioxaborolan-2-yl)-1H-pyrazole (14, 3550, 13.34 mol, 1.05 equiv), and 1-butanol (27 L) at room temperature. The resulting reaction mixture was degassed three timed backfilling with nitrogen each time before being treated with tetrakis(triphenylphosphine)palladium(0) (46 g, 0.040 mol, 0.003 equiv) at room temperature. The resulting reaction mixture was heated to gentle reflux (about 90° C.) for 1-4 hours. When the reaction was deemed complete by HPLC, the reaction mixture was cooled to room temperature before being filtered through a Celite bed. The Celite bed was washed with ethyl acetate (2×2 L) before the filtrates and washing solution were combined. The two layers were separated, and the aqueous layer was extracted with ethyl acetate (12 L). The combined organic layers were concentrated under reduced pressure to remove solvents, and the crude 4-(1-(1-ethoxyethyl)-1H-pyrazol-4-yl)-7-((2-(trimethylsilyl)ethoxy)methyl)-7H-pyrrolo[2,3-d]pyrimidine (15) was directly charged back to the reactor with tetrahydrofuran (THF, 4.2 L) for the subsequent acid-promoted de-protection reaction without further purification.

To a suspension of crude 4-(1-(1-ethoxyethyl)-1H-pyrazol-4-yl)-7-((2-(trimethylsilyl)ethoxy)methyl)-7H-pyrrolo[2,3-d]pyrimidine (15) made as described above in tetrahydrofuran (THF, 4.2 L) in the reactor was charged water (H$_2$O, 20.8 L), and a 10% aqueous HCl solution (16.2, 45.89 mol, 3.44 equiv) at room temperature. The resulting reaction mixture was stirred at 16-30° C. for 2-5 h. When the reaction was deemed complete by HPLC analysis, the reaction mixture was treated with a 30% aqueous sodium hydroxide (NaOH) solution (4 L, 50.42 mol, 3.78 equiv) at room temperature. The resulting reaction mixture was stirred at room temperature for 1-2 h. The solids were collected by filtration and washed with water (2×5 L). The wet cake was charged back to the reactor with acetonitrile (21.6 L), and resulting suspension was heated to gentle reflux for 1-2 h. The clear solution was then gradually cooled to room temperature with stirring, and solids were precipitated out from the solution with cooling. The mixture was stirred at room temperature for an additional 1-2 h. The solids were collected by filtration, washed with acetonitrile (2×3.5 L), and dried in oven under reduced pressure at 45-55° C. to constant weight to afford 4-(1H-pyrazol-4-yl)-7-(2-trimethylsilanyl-ethoxymethyl)-7H-pyrrolo[2,3-d]pyrimidine (5, 3281.7 g, 3996.8 g theoretical, 82.1% yield) as white crystalline solids (99.5 area % by HPLC), which was found to be identical in every comparable aspect to the material made from Method A and B.

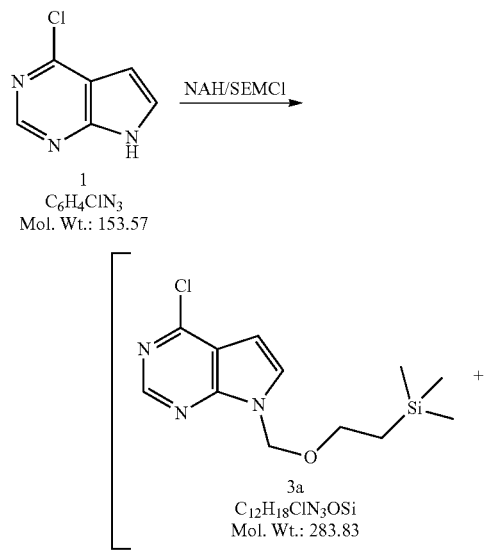

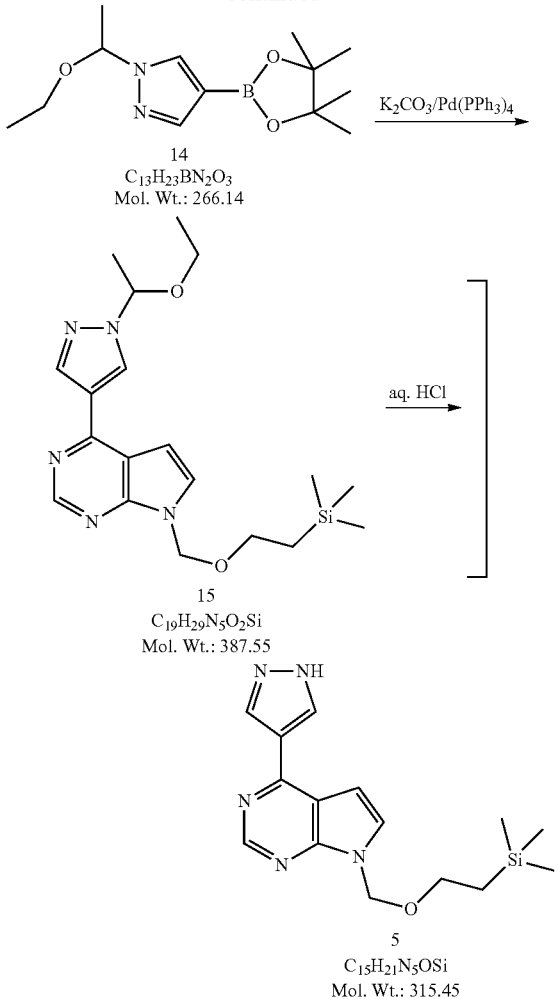

4-(1H-Pyrazol-4-yl)-7-(2-trimethylsilanylethoxymethyl)-7H-pyrrolo[2,3-d]pyrimidine (5). Method D. To a suspension of sodium hydride (NaH, 60 wt % oil disposition, 4.05 g, 101.3 mmol, 1.54 equiv) in 1,2-dimethoxyethane (DME, 20.0 mL, 192.4 mmol) at 0-5° C. (ice bath) was added 4-chloro-pyrrolo[2,3-d]pyrimidine (1, 10.08 g, 65.6 mmol) in 1,2-dimethoxyethane (DME, 80.0 mL, 769.6 mmol) slowly so that the temperature was below 5° C. (−7° C. to 5° C.). A large amount of gas was evolved immediately. The resulting reaction mixture was stirred at 0-5° C. for 30 min before trimethylsilylethoxymethyl chloride (2, 12.56 g, 75.3 mmol, 1.15 equiv) was added slowly while the reaction temperature was maintained at <5° C. After the addition, the reaction was stirred at 0° C. for 1 h before being warmed to room temperature for 23 h. When the HPLC and TLC showed that the reaction was deemed complete, the reaction mixture was quenched with water (46 mL) at room temperature, and the quenched reaction mixture, which contains the desired product (3a), was carried into the next Suzuki coupling reaction directly without further work-up and purification.

To the quenched reaction mixture, which contains crude 4-chloro-7-[2-(trimethylsilyl)ethoxy]methyl}-7H-pyrrolo[2,3-d]pyrimidine (3a, 18.63 g, 65.64 mmol) from previous reaction as described above, was added 1,2-dimethoxyethane (DME, 38 mL), powder potassium carbonate (K$_2$CO$_3$, 23.56 g, 170.5 mmol, 2.6 equiv), 1-(1-ethoxyethyl)-4-(4,4,5,5-tetramethyl-1,3,2-dioxaborolan-2-yl)-1H-pyrazole (14, 18.60 g, 69.89 mmol, 1.06 equiv) at room temperature. The resulting mixture was degassed four times backfilling with nitrogen gas each time before being treated with tetrakis(triphenylphosphine)palladium(0) (244.2 mg, 0.21 mmol, 0.003 equiv) at room temperature. The resulting reaction mixture was degassed four times backfilling with nitrogen gas each time before being warmed to 80° C. for 4-8 h. When TLC and HPLC showed that the reaction was deemed complete, the reaction mixture was gradually cooled to room temperature and filtered through a short bed of Celite (10 g). The Celite bed was washed with ethyl acetate (EtOAc, 20 mL). The two layers of the filtrate were separated, and the aqueous layer was extracted with ethyl acetate (2×30 mL). The combined organic extracts were washed with saturated aqueous NaCl solution (20 mL), dried over magnesium sulfate (MgSO$_4$), and concentrated under reduced pressure. The residue, which contains the crude desired Suzuki coupling product (15), was then transferred to a 500 mL round bottom flask with THF (22 mL) for subsequent de-protection reaction without further purification.

A solution of crude Suzuki coupling product (15) in THF (22 mL) was treated with water (108 mL) and a solution of 10% aqueous HCl prepared by mixing 19.6 mL of concentrated HCl with 64 mL of H$_2$O at room temperature. The resulting reaction mixture was stirred at room temperature for 4-6 h. When TLC and HPLC showed the de-protection reaction was deemed complete, a 30% aqueous sodium hydroxide (NaOH) solution prepared by dissolving 10.4 g of NaOH in 21.0 mL of H$_2$O was added slowly to the reaction mixture while maintaining the temperature below 25° C. The solid gradually dissolved and re-precipitated after 10 min. The mixture was stirred at room temperature for 1-2 h before the solids were collected by filtration and washed with H$_2$O (50 mL). The wet cake was transferred to a 250 mL three-necked flask and treated with acetonitrile (MeCN, 112 mL) at room temperature. The mixture was heated to reflux for 2 h before being cooled gradually to room temperature and stirred at room temperature for 1 h. The solids were collected by filtration, washed with MeCN (36 mL) and dried at 40-45° C. in a vacuum oven to afford 4-(1H-pyrazol-4-yl)-7-(2-trimethylsilanyl-ethoxymethyl)-7H-pyrrolo[2,3-d]pyrimidine (5, 15.3 g, 20.7 g theoretical, 73.9% yield) as white crystalline solids (99.4 area % by HPLC), which was found to be identical in every comparable aspect to the material made from Method A, B, and C.

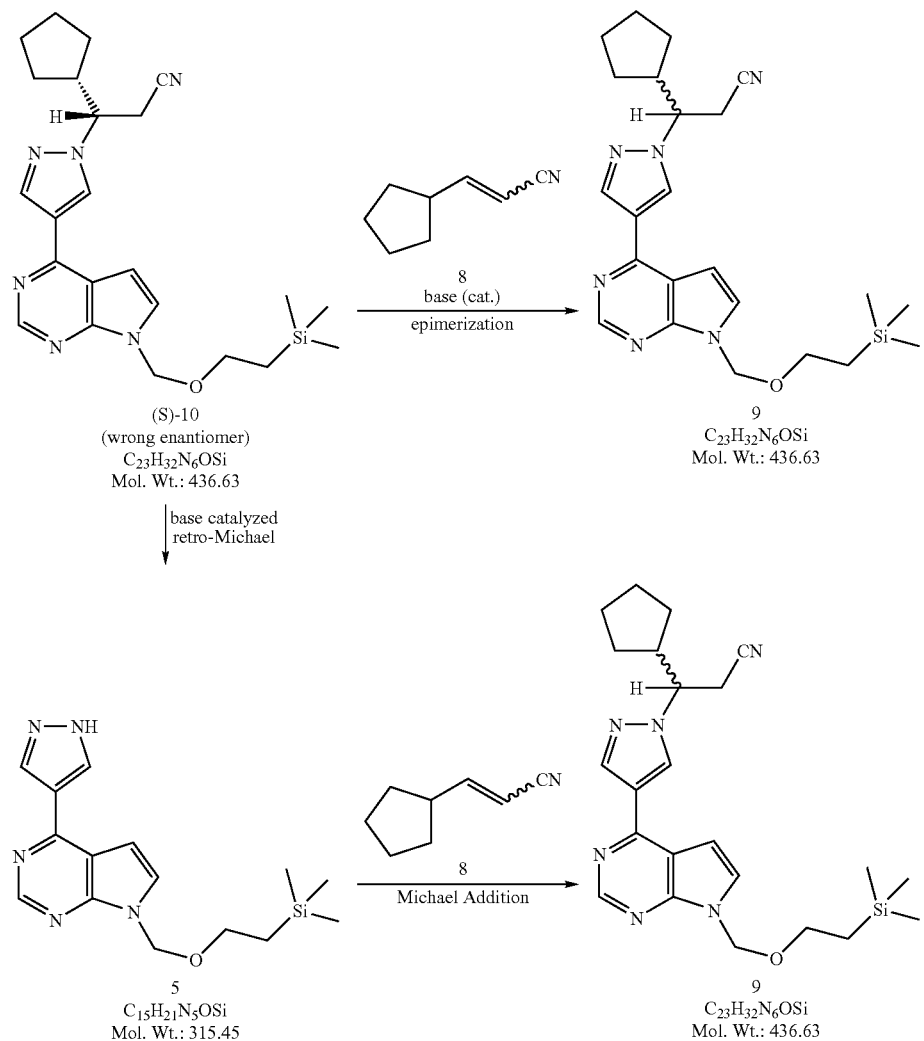

Racemic 3-cyclopentyl-3-{4-[7-(2-trimethylsilanylethoxymethyl)-7H-pyrrolo[2,3-d]pyrimidin-4-yl]pyrazol-1-yl}propionitrile (9, racemic SEM-protected compound). Method B. Into a four-neck 250 mL round bottom flask equipped with a stir bar, thermocouple, condenser and nitrogen inlet was charged (3S)-cyclopentyl-3-{4-[7-(2-trimethylsilanylethoxymethyl)-7H-pyrrolo[2,3-d]pyrimidin-4-yl]pyrazol-1-yl}propionitrile ((S)-10, 13.9 g, 31.5 mmol), acetonitrile (84 mL) and 3-cyclopentylacrylonitrile (8, a mixture of E and Z isomers, 3.82 g, 31.5 mmol, 1.0 equiv) at room temperature. The resulting mixture was then treated with cesium carbonate ($Cs_2CO_3$, 2.57 g, 7.88 mmol, 0.25 equiv) at room temperature. The reaction mixture was warmed to 65° C. and checked after 12 hours by chiral HPLC to determine the enantiomeric ratio of compound (R)-10 to compound (S)-10. When the ratio of compound (R)-10 to compound (S)-10 reached to one to one, the reaction mixture was then allowed to cool to room temperature gradually and stirred at room temperature for 24 to 48 h. The reaction mixture was monitored by HPLC to determine the level of 4-(1H-pyrazol-4-yl)-7-(2-trimethylsilanylethoxymethyl)-7H-pyrrolo[2,3-d]pyrimidine (5). The reaction was considered complete when the level of compound 5 was found to be ≦2% by HPLC area %. The reaction mixture was then filtered through a Celite pad to remove insoluble solids present in the reaction solution. The filtrates were then concentrated under reduced pressure to remove about 40 mL of solvent. The concentrated solution was diluted with ethyl acetate (40 mL) and washed with 1 N aqueous HCl solution (40 mL). The two layers were separated, and the aqueous acid wash solution was back extracted with ethyl acetate (20 mL). The combined organic fractions were washed with 1 M aqueous sodium bicarbonate ($NaHCO_3$) solution (45 mL) and 20% (w/w) brine solution (40 mL). The organic fraction was dried over magnesium sulfate ($MgSO_4$) and concentrated under reduced pressure to afford the crude racemic 3-cyclopentyl-3-{4-[7-(2-trimethylsilanylethoxymethyl)-7H-pyrrolo[2,3-d]pyrimidin-4-yl]pyrazol-1-yl}propionitrile (9, racemic SEM-protected compound, 13.6 g, 13.9 g theoretical, 97.8%) as an amber oil, which was found to be identical to the material made by Method A. This crude product was found to be pure enough (>96 area % by HPLC) and was directly used in the subsequent chiral separation without further purification.

4-(1H-Pyrazol-4-yl)-7-(2-trimethylsilanylethoxymethyl)-7H-pyrrolo[2,3-d]pyrimidine (5). Method E. Into a 22 L four-neck flask equipped with overhead stirring, thermocouple, 2 L addition funnel and nitrogen inlet was charged (3S)-3-cyclopentyl-3-{4-[7-(2-trimethylsilanylethoxymethyl)-7H-pyrrolo[2,3-d]pyrimidin-4-yl]pyrazol-1-yl}propionitrile ((S)-10, 491 g, 1.11 mol) and acetonitrile (4.5 L) at room temperature. The mixture was cooled to 0-10° C. before being treated dropwise with a 1M solution of potassium tert-butoxide in THF (KO$^t$Bu, 2.0 L, 2.0 mol, 1.8 equiv) via the addition funnel over 1.5 hours. Following the addition of base the reaction mixture was allowed to return to room temperature and was stirred at room temperature for 12-24 h. When LC/MS showed the reaction was deemed complete, the reaction mixture was diluted with ethyl acetate (EtOAc, 6 L) and 50% (w/w) aqueous ammonium chloride solution ($NH_4Cl$, 4 L). The two layers were separated, and the aqueous fraction was back extracted with ethyl acetate (2 L). The combined organic fractions were washed with water (2 L) and brine (3 L), dried over magnesium sulfate ($MgSO_4$), and concentrated under reduced pressure to afford the crude 4-(1H-pyrazol-4-yl)-7-(2-trimethylsilanyl-ethoxymethyl)-7H-pyrrolo[2,3-d]pyrimidine (5, 354 g, 350.1 g theoretical, 101.1% yield) as an amber oil, which solidified upon standing at room temperature in vacuo. This crude material was subsequently recrystallized in acetonitrile to afford pure compound 5 (308 g, 350.1 g theoretical, 88% yield) as white crystals (99.5 area % by HPLC), which was found to be identical in every comparable aspect to the material made from Method A, B, C, and D.

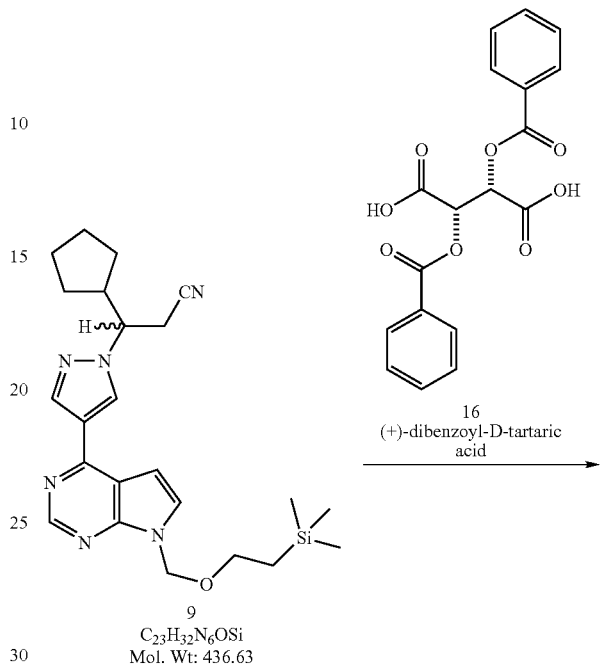

9
$C_{23}H_{32}N_6OSi$
Mol. Wt: 436.63

16
(+)-dibenzoyl-D-tartaric acid

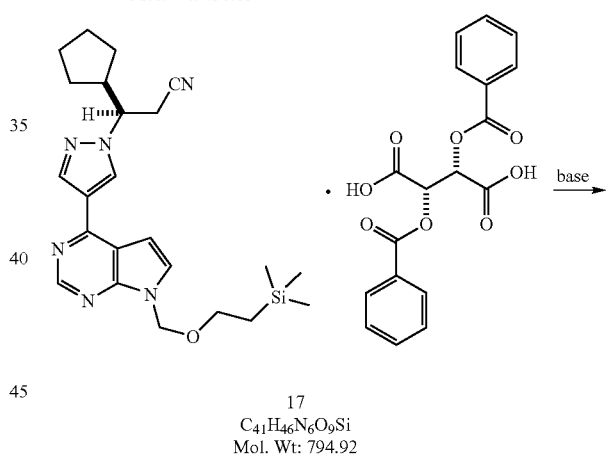

17
$C_{41}H_{46}N_6O_9Si$
Mol. Wt: 794.92

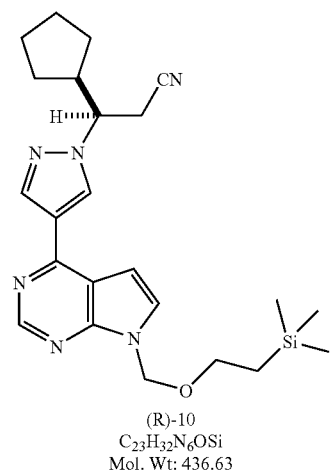

(R)-10
$C_{23}H_{32}N_6OSi$
Mol. Wt: 436.63

(2S,3S)-2,3-Bis(benzoyloxy)succinic acid-(3R)-cyclopentyl-3-[4-(7-{[2-(trimethylsilyl)ethoxy]methyl}-7H-pyrrolo[2,3-d]pyrimidin-4-yl)-1H-pyrazol-1-yl]propanenitrile (1:1; 17). To a 250 ml round bottom flask equipped with a stir bar and nitrogen inlet was charged racemic 3-cyclopentyl-3-[4-(7-{[2-(trimethylsilyl)ethoxy]methyl}-7H-pyrrolo [2,3-d]pyrimidin-4-yl)-1H-pyrazol-1-yl]propanenitrile (9, 6.92 g, 0.0158 mol), acetonitrile (89.0 mL, 1.70 mol), tetrahydrofuran (15 mL, 0.185 mol) and acetone (15.0 mL, 0.204 mol) at room temperature. The resulting solution was warmed to 50° C. before being treated with (+)-2,3-dibenzoyl-D-tartaric acid (16, 8.52 g, 0.0238 mol, 1.5 equiv) in one portion. The resulting homogeneous solution was then stirred at 50° C. for 10 minutes before being cooled gradually to room temperature and stirred at room temperature for 21 hours. The solids were then collected by filtration, rinsed with a small volume of hexane, and dried under reduced pressure to afford (2S, 3S)-2,3-bis(benzoyloxy)succinic acid-(3R)-cyclopentyl-3-[4-(7-{[2-(trimethylsilyl)ethoxy]methyl}-7H-pyrrolo[2,3-d]pyrimidin-4-yl)-1H-pyrazol-1-yl]propanenitrile (1:1; 17, 6.85 g, 12.6 g theoretical, 54% yield) as white crystals. The enantiomeric purity of the isolated salt was analyzed by chiral HPLC and found to be 74:26 favoring the desired R-enantiomer. For 17: $^1$H NMR (DMSO-$d_6$, 400 MHz) δ ppm 8.86 (s, 1H), 8.78 (s, 1H), 8.42 (s, 1H), 8.04 (dd, 4H, J=1.1, 8.4 Hz), 7.80 (d, 1H, J=3.5 Hz), 7.76 (tt, 2H, J=7.5, 1.3 Hz), 7.73 (dd, 4H, J=7.9, 7.4 Hz), 7.12 (d, 1H, J=3.7 Hz), 5.90 (s, 2H), 5.66 (s, 2H), 4.55 (td, 1H, J=4.2, 9.6 Hz), 3.54 (t, 2H, J=7.8 Hz), 3.30 (dd, 1H, J=10.1, 17.6 Hz), 3.22 (dd, 1H, J=4.2, 16.9 Hz), 2.43 (m, 1H), 1.82 (m, 1H), 1.7-1.14 (m, 7H), 0.85 (t, 2H, J=7.8 Hz), −0.083 (s, 9H).

(3R)-Cyclopentyl-3-{4-[7-(2-trimethylsilanylethoxymethyl)-7H-pyrrolo [2,3-d]pyrimidin-4-yl]pyrazol-1-yl}propionitrile ((R)-10). Method B. To a 250 mL round bottom flask was charged enantiomerically enhanced (2S, 3S)-2,3-bis(benzoyloxy)succinic acid-(3R)-cyclopentyl-3-[4-(7-{[2-(trimethylsilyl)ethoxy]methyl}-7H-pyrrolo [2,3-d]pyrimidin-4-yl)-1H-pyrazol-1-yl]propanenitrile (1:1, 17, 6.85 g, 0.00862 mol), ethyl acetate (EtOAc, 70 mL, 0.717 mol) and water (20 mL, 1.11 mol) at room temperature, and the resulting solution was cooled to 12° C. before being treated with 3 N aqueous sodium hydroxide solution (NaOH, 10.7 ml, 0.0321 mol, 3.72 equiv) to adjust pH to 8-9. The two layers were separated, and the aqueous layer was extracted with ethyl acetate (30 mL). The combined organic fractions were washed with 20% aqueous brine (20 mL), dried over magnesium sulfate, filtered and concentrate under reduced pressure to afford enantiomerically enhanced (3R)-cyclopentyl-3-{4-[7-(2-trimethylsilanylethoxymethyl)-7H-pyrrolo[2,3-d]pyrimidin-4-yl]pyrazol-1-yl}propionitrile ((R)-10, 3.31 g, 3.76 g theoretical g theoretical, 88%) as colorless oil, which was analyzed by chiral HPLC and found to be 74:26 favoring the desired R-enantiomer. For (R)-10: $^1$H NMR (CD$_3$OD, 300 MHz) δ ppm 8.77 (s, 1H), 8.68 (s, 1H), 8.43 (s, 1H), 7.66 (d, 1H, J=3.7 Hz), 7.06 (d, 1H, J=3.7 Hz), 5.7 (s, 2H), 4.53 (td, 1H, J=4.5, 10.2 Hz), 3.62 (dd, 2H, J=8.0, 16.0 Hz), 3.26 (dd, 1H, J=9.7, 17.2 Hz), 3.17 (dd, 1H, J=4.0, 17.0 Hz), 2.59 (m, 1H), 1.97 (m, 1H), 1.8-1.25 (m, 7H), 0.92 (t, 2H, J=8.4 Hz), −0.03 (s, 9H); C$_{23}$H$_{32}$N$_6$OSi (MW, 436.63), LCMS (EI) m/e 437 (M$^+$+H).

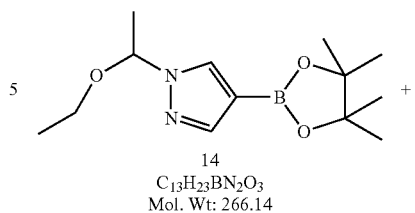

14
C$_{13}$H$_{23}$BN$_2$O$_3$
Mol. Wt: 266.14

+

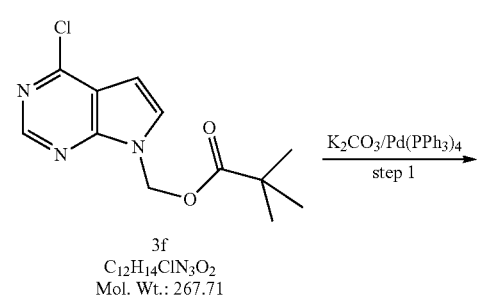

3f
C$_{12}$H$_{14}$ClN$_3$O$_2$
Mol. Wt.: 267.71

K$_2$CO$_3$/Pd(PPh$_3$)$_4$
step 1

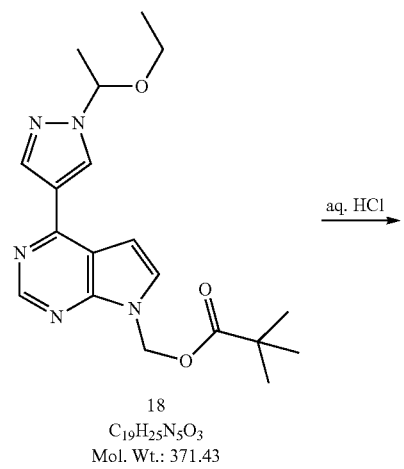

18
C$_{19}$H$_{25}$N$_5$O$_3$
Mol. Wt.: 371.43 aq. HCl

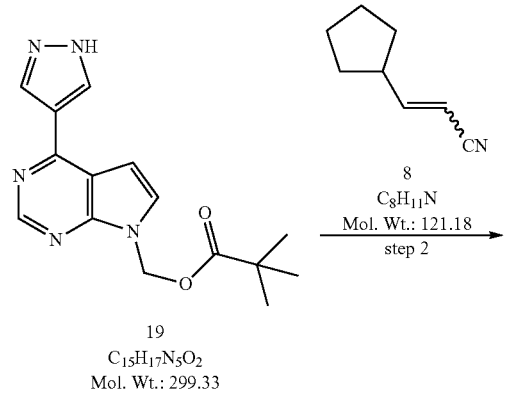

19
C$_{15}$H$_{17}$N$_5$O$_2$
Mol. Wt.: 299.33

8
C$_8$H$_{11}$N
Mol. Wt.: 121.18
step 2

-continued

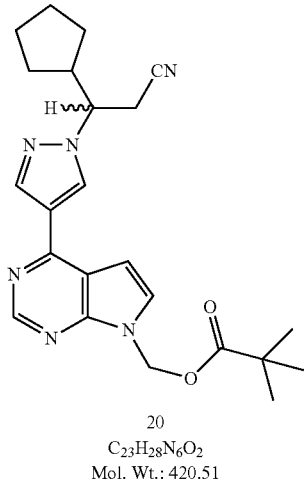

20
C₂₃H₂₈N₆O₂
Mol. Wt.: 420.51

Chiral Column Separation
step 3

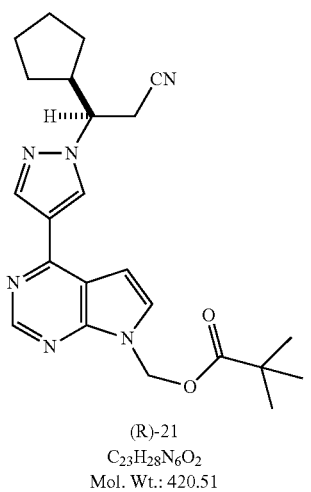

(R)-21
C₂₃H₂₈N₆O₂
Mol. Wt.: 420.51 aq. NaOH
step 4

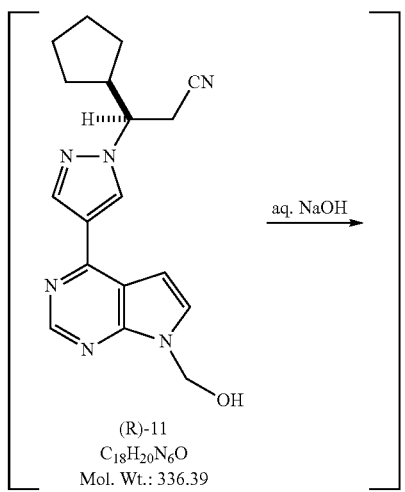

(R)-11
C₁₈H₂₀N₆O
Mol. Wt.: 336.39 aq. NaOH

-continued

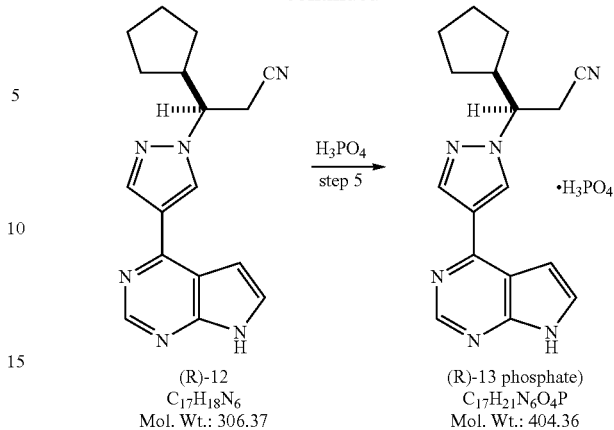

(R)-12
C₁₇H₁₈N₆
Mol. Wt.: 306.37

H₃PO₄
step 5

(R)-13 phosphate)
C₁₇H₂₁N₆O₄P
Mol. Wt.: 404.36

{4-[1-(1-Ethoxyethyl)-1H-pyrazol-4-yl]-7H-pyrrolo[2,3-d]pyrimidin-7-yl]methyl pivalate (18). To a 250 mL round bottom flask equipped with a stir bar, condenser and 3-way valve was charged 4-chloro-7H-pyrrolo[2,3-d]pyrimidin-7-yl)methyl pivalate (3f, 30 g, 0.112 mol), 1,4-dioxane (300 mL, 4.0 mol), 1-(1-ethoxyethyl)-4-(4,4,5,5-tetramethyl-1,3,2-dioxaborolan-2-yl)-1H-pyrazole (14, 35.8 g, 0.134 mol, 1.2 equiv), water (150 mL, 8.3 mol) and potassium carbonate (K₂CO₃, 61.9 g, 0.448 mol, 4.0 equiv) at room temperature. The resulting mixture was degassed four times back filling with nitrogen each time before being charged tetrakis(triphenylphosphine)palladium(0) (5.0 g, 0.00433 mol, 0.039 equiv). The reaction mixture was then degassed four times back filling with nitrogen each time before being warmed to 85° C. The reaction mixture was stirred at 85° C. for 2-5 h. When the reaction was deemed complete, the reaction mixture was allowed to cool to room temperature before being diluted with 20% aqueous brine (250 mL) and ethyl acetate (250 mL). The two layers were separated, and the aqueous layer was extracted with ethyl acetate (250 mL). The combined organic fractions was washed with water and brine, dried over magnesium sulfate (MgSO₄), and concentrated under reduced pressure. The residue was purified by flash column chromatography (SiO₂, 25% to 40% ethyl acetate/hexane gradient elution) to afford {4-[1-(1-ethoxyethyl)-1H-pyrazol-4-yl]-7H-pyrrolo[2,3-d]pyrimidin-7-yl]methyl pivalate (18) as a orange oil, which was directly used in the subsequent reaction assuming the theoretical yield. For 18: C₁₉H₂₅N₅O₃ (MW, 371.43), LCMS (EI) m/e 372 (M⁺+H).

[4-(1H-Pyrazol-4-yl)-7H-pyrrolo[2,3-d]pyrimidin-7-yl] methyl pivalate (19). Method A. To a 1 L round bottom flask equipped with a stir bar and nitrogen inlet was charged {4-[1-(1-ethoxyethyl)-1H-pyrazol-4-yl]-7H-pyrrolo[2,3-d]pyrimidin-7yl]methyl pivalate (18, theoretical amount 41.6 g, 0.112 mol) made as described above and tetrahydrofuran (THF, 610 mL, 7.5 mol) at room temperature, and the resulting mixture was treated with an 2.0 N aqueous solution of hydrochloric acid (140 mL, 0.28 mol, 2.5 equiv) at room temperature. The resulting reaction mixture was subsequently stirred at room temperature for overnight. When the reaction was deemed complete, the reaction mixture was cooled to 0-5° C. before pH was adjusted to 9-10 with a 3 M aqueous sodium hydroxide (NaOH) solution (95 mL). The mixture was then extracted with ethyl acetate (2×300 mL) and the combined organic extracts were washed with 20% aqueous brine solution (250 mL), dried over magnesium sulfate (MgSO₄), and concentrated under reduced pressure to afford the crude product as off-white to light yellow solids. The crude product was treated with methyl t-butylether (MTBE, 200 mL) and the slurry was warm to reflux for 30 minutes before being cooled to room temperature. The solids were collected by filtration and washed with MTBE (2×40 mL), dried under reduced pressure to afford [4-(1H-pyrazol-4-yl)-7H-pyrrolo[2,3-d]pyrimidin-7-yl]methyl pivalate (19, 30.5 g, 33.52 g theoretical, 91% for two steps) as white to off-white solids. For 19: $^1$H NMR (DMSO-$d_6$, 300 MHz) δ ppm 13.40 (br s, 1H), 8.75 (s, 1H), 8.66 (s, 1H), 8.32 (s, 1H), 7.68 (d, 1H, J=3.8 Hz), 7.11 (d, 1H, J=3.8 Hz), 6.21 (s, 2H), 1.06 (s, 9H); $C_{15}H_{17}N_5O_2$ (MW, 299.33), LCMS (EI) m/e 300 (M$^+$+H).

Racemic (4-(1-(2-Cyano-1-cyclopentylethyl)-1H-pyrazol-4-yl)-7H-pyrrolo[2,3-d]pyrimidin-7-yl)methyl pivalate (20). Method A. 3-Cyclopentylacrylonitrile (8, 14.6 g, 0.12 mol, 1.20 equiv) and DBU (18.2 mL, 0.12 mol, 1.2 equiv) was added to a suspension of 4-(1H-pyrazol-4-yl)-7H-pyrrolo[2,3-d]pyrimidin-7yl]methyl pivalate (19, 30.0 g, 0.1 mol) in acetonitrile (45 mL) at room temperature. The resulting reaction mixture was heated to 50-60° C. for 17 hours (a clear solution developed midway through heating) then to room temperature for 8 hours. When LCMS analysis showed the reaction was deemed complete, the reaction mixture was concentrated under reduced pressure and the residue was dissolved in 2 L of ethyl acetate. The resulting solution was washed with water (3×200 mL), dried over sodium sulfate ($Na_2SO_4$) and concentrated under reduced pressure to give the crude product (20) as a thick oil. The crude product was then purified by flash chromatography ($SiO_2$, 0-50% EtOAc/hexanes gradient elution) to afford racemic (4-(1-(2-cyano-1-cyclopentylethyl)-1H-pyrazol-4-yl)-7H-pyrrolo[2,3-d]pyrimidin-7-yl)methyl pivalate (20, 13.0 g, 42.14 g theoretical, 30.8% yield) as a white solid. For 20: $^1$H NMR (DMSO-$d_6$, 400 MHz) δ ppm 8.84 (s, 1H), 8.78 (s, 1H), 8.39 (s, 1H), 7.74 (d, 1H, J=3.7 Hz), 7.11 (d, 1H, J=3.8 Hz), 6.23 (s, 2H), 4.53 (ddd, 1H, J=9.9, 9.6, 4.2 Hz), 3.26 (dd, 1H, J=17.4, 9.9 Hz), 3.19 (dd, 1H, J=17.2, 4.3 Hz), 2.41 (m, 1H), 1.87-1.13 (m, 8H), 1.07 (s, 9H); $C_{23}H_{28}N_6O_2$ (MW, 420.51), LCMS (EI) m/e 421.4 (M$^+$+H).

Method B. To a stirred suspension of [4-(1H-pyrazol-4-yl)-7H-pyrrolo[2,3-d]pyrimidin-7-yl]methyl pivalate (19, 158 mg, 0.50 mmol) and 3-cyclopentylacrylonitrile (8, 122 mg, 1.0 mmol, 2.0 equiv) in dimethyl sulfoxide (DMSO, 1.0 mL, 14 mmol) at room temperature was added powder potassium carbonate ($K_2CO_3$, 10.4 mg, 0.075 mmol, 0.15 equiv). The reaction mixture was then stirred at room temperature for 5 h. The reaction mixture became a clear solution in 2 h. When LCMS showed the reaction was deemed complete, the reaction was quenched with water ($H_2O$, 5 mL) and extracted with ethyl acetate (EtOAc, 3×15 mL). The combined organic extracts were washed with saturated aqueous NaCl solution (10 mL), dried over magnesium sulfate ($MgSO_4$), and concentrated under reduced pressure. The residue was then purified by flash chromatography ($SiO_2$, 0-50% EtOAc/hexanes gradient elution) to afford racemic (4-(1-(2-cyano-1-cyclopentylethyl)-1H-pyrazol-4-yl)-7H-pyrrolo[2,3-d]pyrimidin-7-yl)methyl pivalate (20, 172.6 mg, 210 mg theoretical, 82% yield) as a white solid. For 20: $^1$H NMR (CDCl$_3$, 400 MHz) δ ppm 8.87 (s, 1H), 8.30 (s, 1H), 8.29 (s, 1H), 7.47 (d, 1H, J=3.9 Hz), 6.75 (d, 1H, J=3.9 Hz), 6.24 (s, 2H), 4.25 (m, 1H), 3.12 (dd, 1H, J=17.0, 8.7 Hz), 2.95 (dd, 1H, J=17.0, 3.9 Hz), 2.58 (m, 1H), 1.95 (m, 1H), 1.72-1.52 (m, 5H), 1.25 (m, 2H), 1.14 (s, 9H); $C_{23}H_{28}N_6O_2$ (MW, 420.51), LCMS (EI) m/e 421.4 (M$^+$+H).

(R)-(4-(1-(2-Cyano-1-cyclopentylethyl)-1H-pyrazol-4-yl)-7H-pyrrolo[2,3-d]pyrimidin-7-yl)methyl pivalate ((R)-21). A solution of racemic (4-(1-(2-cyano-1-cyclopentylethyl)-1H-pyrazol-4-yl)-7H-pyrrolo[2,3-d]pyrimidin-7-yl)methyl pivalate (20, 5.2 g, 12.36 mmol) in a mixture of ethanol and hexanes (1:9 by volume) was injected into preparative HPLC system equipped with the chiral column (30× 250 mm) packed with a silicagel based packing coated with cellulose tris(3,5-dimethylphenyl)carbamate (available from Daicel Chemical Industries, Ltd. (Daicel) as "Chiralcel® OD-H" (5 μm)). The chiral column was eluted with mobile phase made by a mixture of ethanol (EtOH) and hexanes in a 1 to 9 volume ratio at a flow rate of 32 mL/min at room temperature. The column elution was monitored by UV at wavelength 220 nm. Under these conditions, baseline separation of the two enantiomers was achieved and the retention times were 16.4 minutes (Peak 1, the undesired (S)-enantiomer (S)-21) and 21.0 minutes (Peak 2, the desired (R)-enantiomer (R)-21), respectively. Each injection was 1.4 mL of feed solution at a concentration of 50 mg/mL and each run cycle was 14 minutes by using stack injections. Total 75 injections were taken for this separation process. Fractions for Peak 1 (the undesired (S)-enantiomer, (S)-21) and Peak 2 (the desired (R)-enantiomer, (R)-21) were collected separately from each injection, and fractions collected for each peak were concentrated under reduced pressure. The residue from each evaporator was further dried under high vacuum to constant weight to afford (R)-(4-(1-(2-cyano-1-cyclopentylethyl)-1H-pyrazol-4-yl)-7H-pyrrolo[2,3-d]pyrimidin-7-yl) methyl pivalate ((R)-21, 2.36 g, 2.6 g theoretical, 90.8% yield) from Peak 2 as off-white solids and (S)-(4-(1-(2-cyano-1-cyclopentylethyl)-1H-pyrazol-4-yl)-7H-pyrrolo[2,3-d]pyrimidin-7-yl)methyl pivalate ((S)-21, 2.4 g, 2.6 g theoretical, 92.3% yield) from Peak 1 as off-white solids.

A chiral HPLC method was developed for chiral purity evaluation of both enantiomers of POM-(R)-21 and (S)-21 by using a Chiralcel® OD-H column (4.6×50 mm, 5 μm) purchased from Chiral Technologies, Inc. The two enantiomers ((R)-21 and (S)-21) are separated with a resolution greater than 3.5 by using a mobile phase made of 10% ethanol and 90% hexanes at room temperature with a flow rate of 1 mL/min. The UV detection wavelength is 220 nm. The retention times are 14.1 minutes for (S)-21 and 18.7 minutes for (R)-21, respectively.

The quality of each enantiomer separated by preparative chiral HPLC including chemical purity (HPLC area %) and chiral purity (chiral HPLC area %) was analyzed and their structures are confirmed by NMRs and LC/MS. For (R)-21: achiral purity (99.2 area % by HPLC detected at 220 nm); chiral purity (99.6 area % by chiral HPLC; 99.2% ee); $^1$H NMR (DMSO-$d_6$, 400 MHz) δ ppm 8.84 (s, 1H), 8.78 (s, 1H), 8.39 (s, 1H), 7.74 (d, 1H, J=3.7 Hz,), 7.11 (d, 1H, J=3.8 Hz), 6.23 (s, 2H), 4.53 (ddd, 1H, J=9.9, 9.6, 4.2 Hz), 3.26 (dd, 1H, J=17.4, 9.9 Hz), 3.19 (dd, 1H, J=17.2, 4.3 Hz), 2.41 (m, 1H), 1.87-1.13 (m, 8H), 1.07 (s, 9H); $C_{23}H_{28}N_6O_2$ (MW, 420.51), LCMS (EI) m/e 421.4 (M$^+$+H). For (S)-21: achiral purity (99.3 area % by HPLC detected at 220 nm); chiral purity (99.8 area % by chiral HPLC; 99.6% ee); $^1$H NMR (DMSO-$d_6$, 400 MHz) δ ppm 8.84 (s, 1H), 8.78 (s, 1H), 8.39 (s, 1H), 7.74 (d, 1H, J=3.7 Hz,), 7.11 (d, 1H, J=3.8 Hz), 6.23 (s, 2H), 4.53 (ddd, 1H, J=9.9, 9.6, 4.2 Hz), 3.26 (dd, 1H, J=17.4, 9.9 Hz), 3.19 (dd, 1H, J=17.2, 4.3 Hz), 2.41 (m, 1H), 1.87-1.13 (m, 8H), 1.07 (s, 9H); $C_{23}H_{28}N_6O_2$ (MW, 420.51), LCMS (EI) m/e 421.4 (M$^+$+H).

(3R)-Cyclopentyl-3-[4-(7H-pyrrolo[2,3-d]pyrimidin-4-yl)pyrazol-1-yl]propionitrile ((R)-12, free base). Method B. To a stirred solution of (4-{1-[(1R)-2-cyano-1-cyclopentylethyl]-1H-pyrazol-4-yl}-7H-pyrrolo [2,3-d]pyrimidin-7-yl) methyl pivalate ((R)-21, 376 mg, 0.894 mmol) in methanol (4.0 mL, 99 mmol) at room temperature was added 1.0 M solution of sodium hydroxide in water (NaOH, 179 μL, 0.179 mmol, 2.0 equiv). The reaction mixture was stirred at room temperature for overnight (15 h). When LCMS showed the reaction was done cleanly, the reaction mixture was quenched with water (10 mL) and saturated aqueous NaCl solution (20 mL), and extracted with EtOAc (2×10 mL). The combined organic layers were washed with brine, dried over magnesium sulfate, filtered and concentrated under reduced pressure to afford (3R)-cyclopentyl-3-[4-(7H-pyrrolo[2,3-d]pyrimidin-4-yl)pyrazol-1-yl]propionitrile ((R)-12, free base, 274 mg, 274 mg theoretical, 100% yield) as a pale yellow foam, which was found to be identical as the material made from Method A.

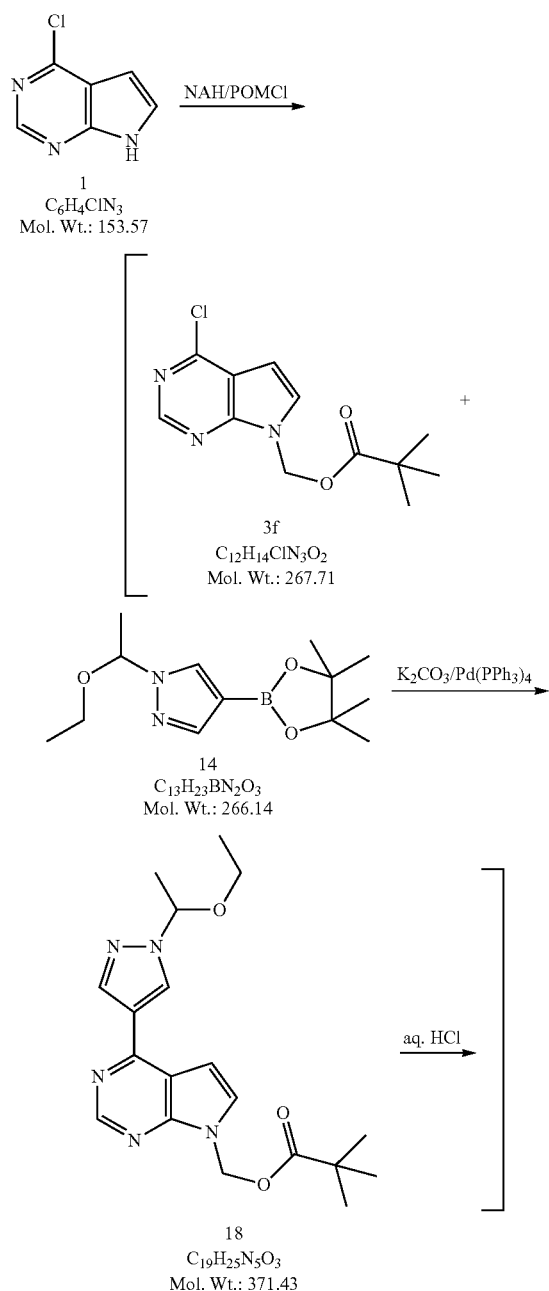

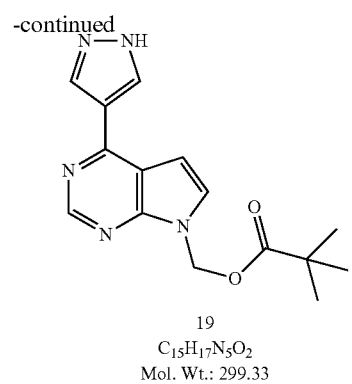

19
$C_{15}H_{17}N_5O_2$
Mol. Wt.: 299.33

[4-(1H-Pyrazol-4-yl)-7H-pyrrolo[2,3-d]pyrimidin-7-yl]methyl pivalate (19). Method B. To a oven dried 3 L 4-neck round bottom flask equipped with a stirring bar, septa, thermocouple, 500 mL addition funnel and nitrogen inlet was charged sodium hydride (NaH, 60 wt % in mineral oil, 32.82 g, 0.82 mol, 1.20 equiv) and anhydrous 1,2-dimethoxyethane (DME, 500 mL, 4.8 mol) and the resulting mixture was cooled to 0-3° C. To a oven dried 1 L round bottom flask was charged 4-chloro-7H-pyrrolo[2,3-d]pyrimidine (1, 105.0 g, 0.684 mol) and 1,2-dimethoxyethane (DME, 750 mL, 7.2 mol) and the resulting slurry was then portion wise added to the suspension of sodium hydride in DME via large bore canula over 30 minutes at 5-12° C. The resulting reaction mixture was heterogeneous. Following the addition, the cold bath was removed and the mixture was gradually warmed to room temperature and allowed to stir at room temperature for 1 hour before being cooled to 0-5° C. Chloromethyl pivalate (pivaloyloxymethyl chloride, POM-Cl, 112 ml, 0.752 mol, 1.1 equiv) was added dropwise into the reaction mixture over 30 minutes with stirring at 0-5° C. The addition of chloromethyl pivalate was mildly exothermic and the reaction temperature went up to as high as 14° C. After addition of chloromethyl pivalate, the cooling bath was removed and the reaction mixture was allowed to return to room temperature and stirred at room temperature for 90 min. When the reaction was deemed complete after confirmed by HPLC, the reaction was carefully quenched with water (100 mL). And this quenched reaction mixture, which contains crude POM-protected chlorodeazapurine (3f), was used in the subsequent Suzuki coupling reaction without further work-up and purification.

To the quenched reaction mixture, which contains crude POM-protected chlorodeazapurine (3f) made as described above was added 4-(4,4,5,5-tetramethyl-1,3,2-dioxaborolan-2-yl)-1H-pyrazole (14, 200 g, 0.75 mol, 1.10 equiv) and potassium carbonate (K₂CO₃, 189 g, 1.37 mol, 2.0 equiv) at room temperature. The resulting mixture was degassed by passing a stream of nitrogen through the solution for 15 minutes before being treated with tetrakis(triphenylphosphine)-palladium(0) (7.9 g, 0.68 mmol, 0.01 equiv) and the resulting reaction mixture was heated at reflux (about 82° C.) for 10 hours. When the reaction was deemed complete by TLC (1:1 hexanes/ethyl acetate) and LCMS, the reaction mixture was cooled to room temperature, diluted with ethyl acetate (2 L) and water (1 L). The two layers were separated, and the aqueous layer was extracted with ethyl acetate (500 mL). The combined organic layers were washed with water (2×1 L) and brine (1 L) before being concentrated under reduced pressure to afford crude {4-[1-(1-ethoxyethyl)-1H-pyrazol-4-yl]-7H-pyrrolo[2,3-d]pyrimidin-7-yl}methyl pivalate (18) as a pale-yellow oil, which was directly used in the subsequent de-protection reaction without further purification.

To a solution of crude 18 in THF (1 L, 12.3 mol) was treated with a 4 N aqueous HCl solution (500 mL) at room temperature. The resulting reaction mixture was subsequently stirred at room temperature for 5 h. When the reaction was deemed complete, the reaction mixture was cooled to 0-5° C. before pH was adjusted to 9-10 with a 1M aqueous sodium hydroxide (NaOH) solution (2 L). The mixture was concentrated under reduced pressure to remove most of THF and the resulting suspension was stirred at room temperature for 2 h. The solids were collected by filtration, washed with water (3×500 mL), and dried under reduced pressure to afford [4-(1H-pyrazol-4-yl)-7H-pyrrolo[2,3-d]pyrimidin-7-yl]methyl pivalate (19, 157.5 g, 204.43 g theoretical, 77% yield for three steps) as white to off-white solids, which was found to be sufficiently pure (>98 area % by HPLC) to do the subsequent reaction without further purification. For 19: $^1$H NMR (DMSO-$d_6$, 400 MHz) δ ppm 13.42 (br s, 1H), 8.76 (s, 1H), 8.67 (s, 1H), 8.33 (s, 1H), 7.68 (d, 1H, J=3.8 Hz), 7.11 (d, 1H, J=3.8 Hz), 6.21 (s, 2H), 1.06 (s, 9H); $^{13}$C NMR (DMSO-$d_6$, 100 MHz) δ ppm 177.74, 152.31, 152.09, 151.91, 139.52, 130.39, 120.51, 113.93, 101.91, 67.26, 38.98, 27.26; $C_{15}H_{17}N_5O_2$ (MW, 299.33), LCMS (EI) m/e 300 (M$^+$+H).

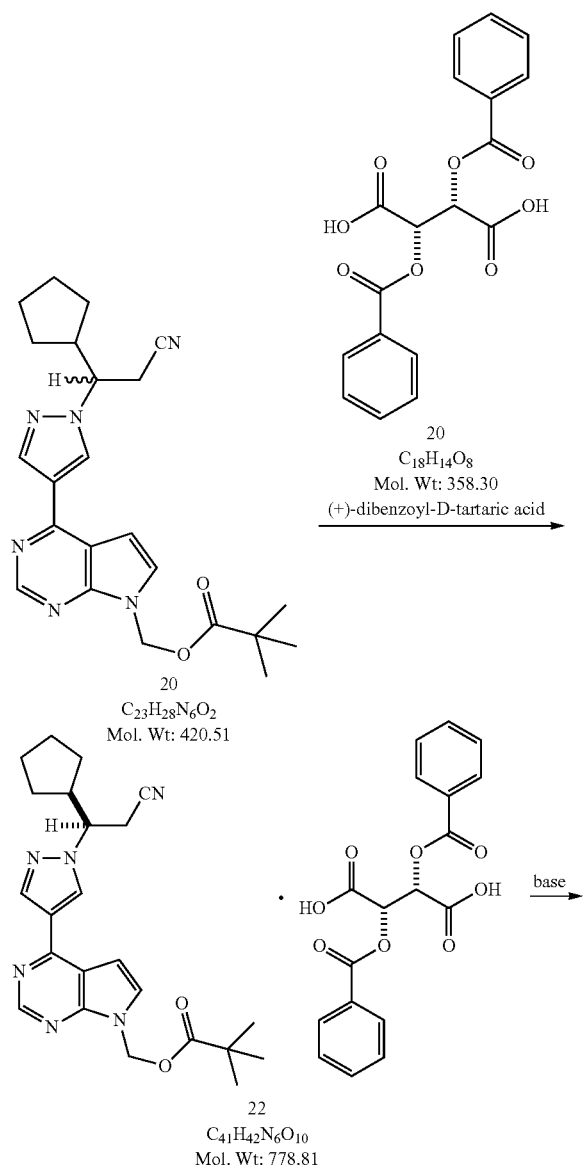
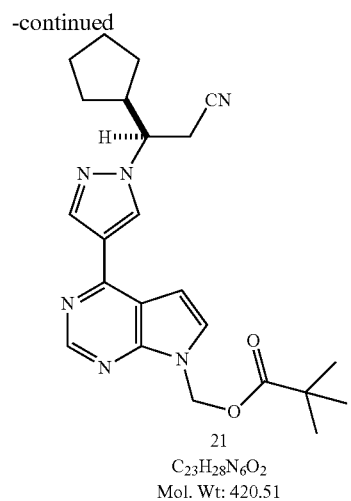

(2S,3S)-2,3-Bis(benzoyloxy)succinic acid-(R)-(4-(1-(2-cyano-1-cyclopentylethyl)-1H-pyrazol-4-yl)-7H-pyrrolo[2,3-d]pyrimidin-7-yl)methyl pivalate (1:1; 22). A solution of racemic (4-(1-(2-Cyano-1-cyclopentylethyl)-1H-pyrazol-4-yl)-7H-pyrrolo[2,3-d]pyrimidin-7-yl)methyl pivalate (20, 200 mg, 0.47 mmol) in a mixture of acetonitrile, tetrahydrofuran, and acetone (4 mL, 6:1:1) at room temperature was warmed to 50° C. before being treated with (+)-2,3-dibenzoyl-D-tartaric acid (16, 84 mg, 0.235 mmol, 0.5 equiv) in one portion. The resulting homogeneous solution was then stirred at 50° C. for 10 minutes before being cooled gradually to room temperature and stirred at room temperature for 23 hours. The solids were then collected by filtration, rinsed with a small volume of hexane, and dried under reduced pressure to afford (2S,3S)-2,3-bis(benzoyloxy)succinic acid-(R)-(4-(1-(2-cyano-1-cyclopentylethyl)-1H-pyrazol-4-yl)-7H-pyrrolo[2,3-d]pyrimidin-7-yl)methyl pivalate (1:1; 22, 145 mg, 183 mg theoretical, 79.2% yield) as white crystals. The enantiomeric purity of the isolated salt was analyzed by chiral HPLC and found to be in a ratio of 87:13 favoring the desired R-enantiomer. For 22: $C_{23}H_{28}N_6O_2$ (MW, 420.51), LCMS (EI) m/e 421.4 (M$^+$+H).

(R)-(4-(1-(2-Cyano-1-cyclopentylethyl)-1H-pyrazol-4-yl)-7H-pyrrolo[2,3-d]pyrimidin-7-yl)methyl pivalate ((R)-21). Method B. A solution of enantiomerically enhanced (2S,3S)-2,3-bis(benzoyloxy)succinic acid-(R)-(4-(1-(2-cyano-1-cyclopentylethyl)-1H-pyrazol-4-yl)-7H-pyrrolo[2,3-d]pyrimidin-7-yl)methyl pivalate (1:1; 22, 120 mg, 0.154 mmol) in ethyl acetate (10 mL) and water (5.0 mL) at room temperature was cooled to 12° C. before being treated with 2 N aqueous potassium carbonate solution ($K_2CO_3$, 0.39 mL, 0.77 mmol, 5.0 equiv) to adjust pH to 8-9. The two layers were separated, and the aqueous layer was extracted with ethyl acetate (30 mL). The combined organic fractions were washed with 20% aqueous brine (20 mL), dried over magnesium sulfate, filtered and concentrate under reduced pressure to afford enantiomerically enhanced (R)-(4-(1-(2-cyano-1-cyclopentylethyl)-1H-pyrazol-4-yl)-7H-pyrrolo[2,3-d]pyrimidin-7-yl)methyl pivalate ((R)-21, 55.7 mg, 64.8 mg theoretical, 86% yield) as white solids, which was analyzed by chiral HPLC and found to be in a ratio of 87:13 favoring the desired R-enantiomer. For ((R)-21: $^1$H NMR (DMSO-$d_6$, 400 MHz) δ ppm 8.84 (s, 1H), 8.78 (s, 1H), 8.39 (s, 1H), 7.74 (d, 1H, J=3.7 Hz,), 7.11 (d, 1H, J=3.8 Hz), 6.23 (s, 2H), 4.53 (ddd, 1H, J=9.9, 9.6, 4.2 Hz), 3.26 (dd, 1H, J=17.4, 9.9 Hz), 3.19 (dd, 1H, J=17.2, 4.3 Hz), 2.41 (m, 1H), 1.87-1.13 (m, 8H), 1.07 (s, 9H); C₂₃H₂₈N₆O₂ (MW, 420.51), LCMS (EI) m/e 421.4 (M⁺+H).

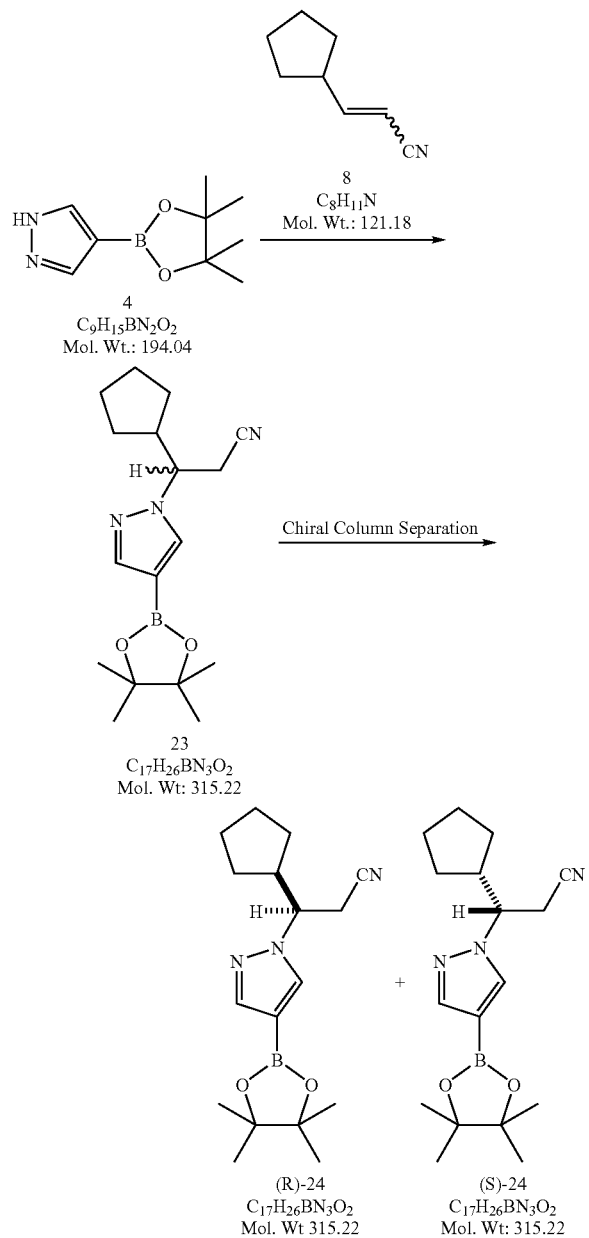

Racemic 3-Cyclopentyl-3-(4-(4,4,5,5-tetramethyl-1,3,2-dioxaborolan-2-yl)-1H-pyrazol-1-yl)propanenitrile (23). To a 500 mL round bottom flask equipped with a stir bar, condenser and nitrogen inlet was charged 3-cyclopentylacrylonitrile (8, a mixture of E and Z isomers, 8.46 g, 0.067 mol, 1.3 equiv), acetonitrile (242 mL, 4.64 mol), 4-(4,4,5,5-tetramethyl-1,3,2-dioxaborolan-2-yl)-1H-pyrazole (4, 10.0 g, 0.0515 mol), and 1,8-diazabicyclo[5.4.0]undec-7-ene (DBU, 16.2 ml, 0.108 mol, 2.1 equiv) at room temperature. The resulting solution was then warmed to reflux, and the reaction mixture was stirred at reflux for 18 hours. When the reaction was deemed complete, the reaction mixture was allowed to cool to room temperature followed by concentration under reduced pressure. The residue was purified directly by flash column chromatography (SiO₂, 0% to 30% ethyl acetate/hexane gradient elution) to afford 3-cyclopentyl-3-[4-(4,4,5,5-tetramethyl-1,3,2-dioxaborolan-2-yl)-1H-pyrazol-1-yl]propanenitrile (23, 13.1 g, 16.2 g theoretical, 81%) as off-white solids. This racemic mixture was directly used for subsequent chiral column separation with out further purification. For 23: ¹H NMR (DMSO-d₆, 400 MHz) δ ppm 8.07 (d, 1H, J=0.53 Hz), 7.65 (s, 1H), 4.42 (td, 1H, J=19.2, 4.5 Hz), 3.14 (dd, 1H, J=9.39, 17.2 Hz), 3.08 (dd, 1H, J=4.58, 17.2 Hz), 2.31 (m, 1H), 1.75 (m, 1H), 1.62-1.32 (m, 4H), 1.29-1.01 (m, 15H); C₁₇H₂₆BN₃O₂ (MW, 315.22) LCMS (EI) m/e 316 [M⁺+H].

(R)-3-cyclopentyl-3-(4-(4,4,5,5-tetramethyl-1,3,2-dioxaborolan-2-yl)-1H-pyrazol-1-yl)propanenitrile ((R)-24) and (S)-3-cyclopentyl-3-(4-(4,4,5,5-tetramethyl-1,3,2-dioxaborolan-2-yl)-1H-pyrazol-1-yl)propanenitrile ((S)-24). A solution of racemic 3-cyclopentyl-3-[4-(4,4,5,5-tetramethyl-1,3,2-dioxaborolan-2-yl)-1H-pyrazol-1-yl]propanenitrile (23, 13.1 g, 41.56 mmol) in a mixture of ethanol and hexanes (8:2 by volume) was injected into preparative HPLC system equipped with a chiral column (20×250 mm) packed with amylose tri(3,5-dimethylphenyl)carbamate immobilized on silicagel (Chiralpak® IA) from Chiral Technologies Inc. The chiral column was eluted with mobile phase made by a mixture of ethanol (EtOH) and hexanes in a 1 to 9 volume ratio at a flow rate of 18 mL/min at room temperature. The column elution was monitored by UV at wavelength 220 nm. Under these conditions, a baseline separation of the two enantiomers was achieved and the retention times were 7.0 minutes (Peak 1, the undesired (S)-enantiomer (S)-24) and 8.3 minutes (Peak 2, the desired (R)-enantiomer (R)-24), respectively. Each injection was 0.8 mL of feed solution at a concentration of 100 mg/mL and each run cycle was 14 minutes by using stack injections. Total 164 injections were taken for this separation process. Fractions for Peak 1 (the undesired (S)-enantiomer, (S)-24) and Peak 2 (the desired (R)-enantiomer, (R)-24) were collected separately from each injection, and fractions collected for each peak were concentrated under reduced pressure. The residue from each evaporator was further dried under high vacuum to constant weight to afford (R)-3-cyclopentyl-3-(4-(4,4,5,5-tetramethyl-1,3,2-dioxaborolan-2-yl)-1H-pyrazol-1-yl)propanenitrile ((R)-24, 6.19 g, 6.55 g theoretical, 94.5% yield) from Peak 2 as off-white solids and (5)-3-cyclopentyl-3-(4-(4,4,5,5-tetramethyl-1,3,2-dioxaborolan-2-yl)-1H-pyrazol-1-yl)propanenitrile ((S)-24, 6.08 g, 6.55 g theoretical, 92.8% yield) from Peak 1 as off-white solids.

A chiral HPLC method was developed for chiral purity evaluation of both enantiomers of compound 24 ((R)-24 and (S)-24) by using a Chiralpak® IA column (4.6×50 mm, 5 μm) purchased from Chiral Technologies, Inc. Two enantiomers ((R)-24 and (S)-24) are separated with a resolution greater than 3.0 by using a mobile phase made from 15% ethanol and 85% hexanes at room temperature with a flow rate of 1 mL/min. The UV detection wavelength is 220 nm. The retention times are 6.4 minutes for (S)-24 and 7.6 minutes for (R)-24, respectively.

The quality of each enantiomer separated by preparative chiral HPLC including chemical purity (HPLC area %) and chiral purity (chiral HPLC area %) was analyzed and their structures are confirmed by NMRs and LC/MS. For (R)-24: achiral purity (98.8 area % by HPLC detected at 220 nm); chiral purity (99.8 area % by chiral HPLC; 99.6% ee); ¹H NMR (DMSO-d₆, 400 MHz) δ ppm 8.07 (d, 1H, J=0.53 Hz), 7.65 (s, 1H), 4.42 (td, 1H, J=19.2, 4.5 Hz), 3.14 (dd, 1H, J=9.39, 17.2 Hz), 3.08 (dd, 1H, J=4.58, 17.2 Hz), 2.31 (m, 1H), 1.75 (m, 1H), 1.62-1.32 (m, 4H), 1.29-1.01 (m, 15H);

$C_{17}H_{26}BN_3O_2$ (MW, 315.22) LCMS (EI) m/e 316 (M$^+$+H). For (S)-24: achiral purity (98.6 area % by HPLC detected at 220 nm); chiral purity (99.6 area % by chiral HPLC; 99.2% ee); $^1$H NMR (DMSO-d$_6$, 400 MHz) δ ppm 8.07 (d, 1H, J=0.53 Hz), 7.65 (s, 1H), 4.42 (td, 1H, J=19.2, 4.5 Hz), 3.14 (dd, 1H, J=9.39, 17.2 Hz), 3.08 (dd, 1H, J=4.58, 17.2 Hz), 2.31 (m, 1H), 1.75 (m, 1H), 1.62-1.32 (m, 4H), 1.29-1.01 (m, 15H); $C_{17}H_{26}BN_2O_2$ (MW, 315.22) LCMS (EI) m/e 316 [M$^+$+H].

sodium bicarbonate (NaHCO$_3$, 0.666 g, 7.93 mmol, 4.7 equiv) at room temperature. The resulting mixture was degassed four times backfilling with nitrogen each time before tetrakis(triphenylphosphine)palladium(0) (91.6 mg, 0.079 mmol, 0.047 equiv) was added. The resulting reaction mixture was degassed four times backfilling with nitrogen each time. The reaction was then warmed to 90° C. for 2-6 h. When TLC and HPLC showed that the coupling reaction was deemed complete, the reaction mixture was allowed to cool to

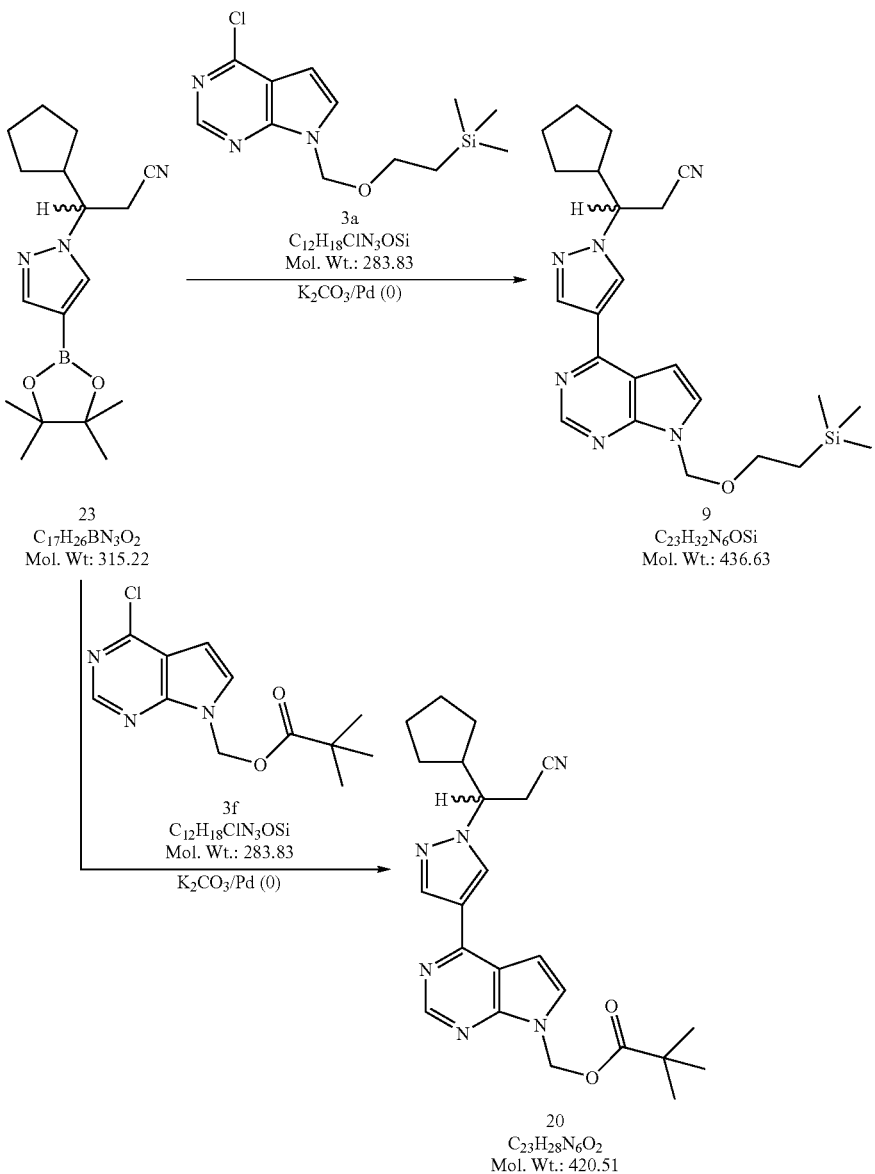

Racemic 3-cyclopentyl-3-{4-[7-(2-trimethylsilanylethoxymethyl)-7H-pyrrolo[2,3-d]pyrimidin-4-yl]pyrazol-1-yl}propionitrile (9, racemic SEM-protected compound). Method C. Into a 25 ml round bottom flask equipped with a stir bar, condenser, thermocouple and 3-way valve was charged 3-cyclopentyl-3-[4-(4,4,5,5-tetramethyl-1,3,2-dioxaborolan-2-yl)-1H-pyrazol-1-yl]propanenitrile (23, 0.697 g, 2.21 mmol, 1.3 equiv), 4-chloro-7-{[2-(trimethylsilyl)ethoxy]methyl}-7H-pyrrolo[2,3-d]pyrimidine (3a, 0.506 g, 1.69 mmol), 1,4-dioxane (4.44 mL), water (4.44 mL), and room temperature followed by dilution with water (5 mL) and ethyl acetate (10 mL). The two layers were separated, and the aqueous layer was back extracted with ethyl acetate (10 mL). The combined organic fractions were washed with water (10 mL) and saturated aqueous NaCl solution (10 mL), dried over magnesium sulfate (MgSO$_4$), and concentrated under reduced pressure to give the crude product (9) as an amber oil. The crude product was purified by flash column chromatography (SiO$_2$, 0% to 40% ethyl acetate/hexane gradient elution) to afford racemic 3-cyclopentyl-3-{4-[7-(2-trimethylsilanylethoxymethyl)-7H-pyrrolo[2,3-d]pyrimidin-4-yl]pyrazol-1-yl}propionitrile (9, racemic SEM-protected compound, 617 mg, 737.9 mg theoretical, 83.6% yield) as a yellow oil. For 9: $^1$H NMR (DMSO-$d_6$, 400 MHz) δ ppm 8.83 (s, 1H), 8.75 (s, 1H), 8.39 (s, 1H), 7.77 (d, 1H, J=3.7 Hz), 7.09 (d, 1H, J=3.7 Hz), 5.63 (s, 2H), 4.53 (td, 1H, J=19.4, 4.0 Hz), 3.51 (t, 2H, J=8.1 Hz), 3.23 (dq, 2H, J=9.3, 4.3 Hz), 2.41 (m, 1H), 1.79 (m, 1H), 1.66-1.13 (m, 7H), 0.81 (t, 2H, J=8.2 Hz), 0.124 (s, 9H); $C_{23}H_{32}N_6OSi$ (MW, 436.63), LCMS (EI) m/e 437 (M$^+$+H) and m/e 459 (M$^+$+Na).

Racemic (4-(1-(2-Cyano-1-cyclopentylethyl)-1H-pyrazol-4-yl)-7H-pyrrolo[2,3-d]pyrimidin-7-yl)methyl pivalate (20). Method B. Into a 50 ml round bottom flask equipped with a stir bar, condenser and 3-way valve connected to nitrogen and vacuum was charged (4-chloro-7H-pyrrolo[2,3-d]pyrimidin-7-yl)methyl pivalate (3f, 700 mg, 2.61 mmol), 3-cyclopentyl-3-[4-(4,4,5,5-tetramethyl-1,3,2-dioxaborolan-2-yl)-1H-pyrazol-1-yl]propanenitrile (23, 935 mg, 2.97 mmol, 1.13 equiv), 1,2-dimethoxyethane (DME, 10 mL, 96 mmol), water (5 mL, 0.28 mol) and potassium carbonate ($K_2CO_3$, 1.82 g, 7.84 mmol, 3.0 equiv) at room temperature. The resulting reaction mixture was degassed three times back filling with nitrogen each time before being charged tetrakis(triphenylphosphine)palladium(0) (30 mg, 0.026 mmol, 0.010 equiv). The resulting reaction mixture was degassed four times back filling with nitrogen each time and then warmed to 82° C. The reaction mixture was stirred at 82° C. for 6 hours. When the reaction was deemed complete, the reaction mixture was cooled to room temperature before being diluted with ethyl acetate (45 mL) and water (10 mL). The resulting mixture was stirred until the majority of solids had gone into solution. The two layers were separated, and the aqueous layer was extracted with ethyl acetate (1×25 mL). The combined organic fractions were washed with aqueous brine (2×25 mL), dried over $Na_2SO_4$, filtered and concentrated under reduced pressure. The residue was purified by flash chromatography ($SiO_2$, 0-50% ethyl acetate/hexane gradient elution) to afford racemic 4-(1-(2-cyano-1-cyclopentylethyl)-1H-pyrazol-4-yl)-7H-pyrrolo[2,3-d]pyrimidin-7-yl)methyl pivalate (20, 0.97 g, 1.1 g theoretical, 88.6% yield) as colorless oil, which solidified upon standing at room temperature in vacuo. For 20: $^1$H NMR (CDCl$_3$, 300 MHz) δ 8.85 (s, 1H), 8.29 (s, 1H), 8.27 (s, 1H), 7.45 (d, 1H, J=3.8 Hz), 6.73 (d, 1H, J=3.8 Hz), 6.22 (s, 2H), 4.23 (ddd, 1H, J=10.0, 8.6, 4.0 Hz), 3.10 (dd, 1H, J=17.0, 8.6 Hz), 2.92 (dd, 1H, J=17.0, 4.0 Hz), 2.56 (m, 1H), 2.0-1.25 (m, 8H), 1.12 (s, 9H); $C_{23}H_{28}N_6O_2$ (MW, 420.51), LCMS (EI) m/e 421 (M$^+$+H).

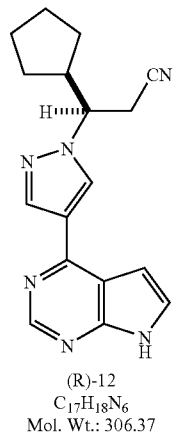

(R)-12
$C_{17}H_{18}N_6$
Mol. Wt.: 306.37

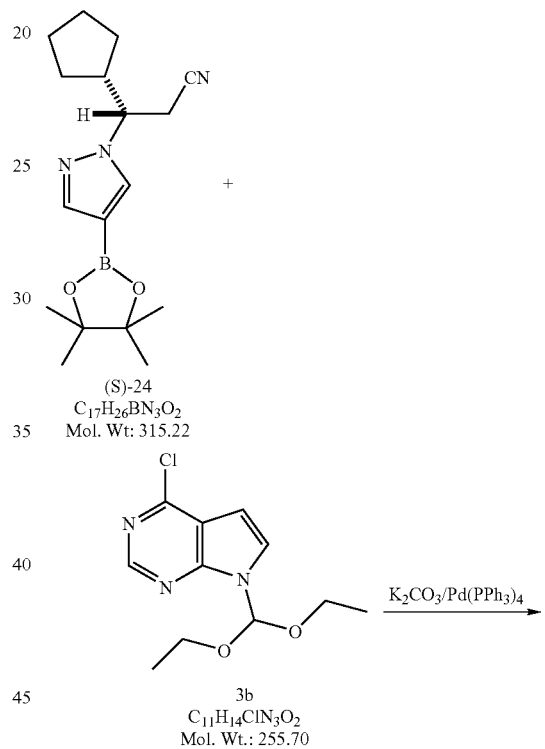

(S)-24
$C_{17}H_{26}BN_3O_2$
Mol. Wt: 315.22

3b
$C_{11}H_{14}ClN_3O_2$
Mol. Wt.: 255.70

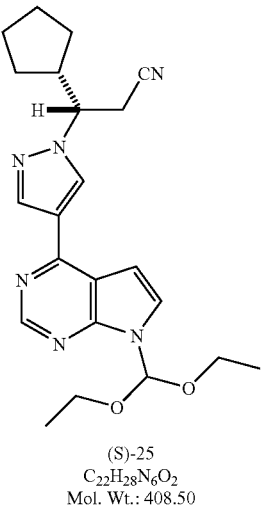

(S)-25
$C_{22}H_{28}N_6O_2$
Mol. Wt.: 408.50

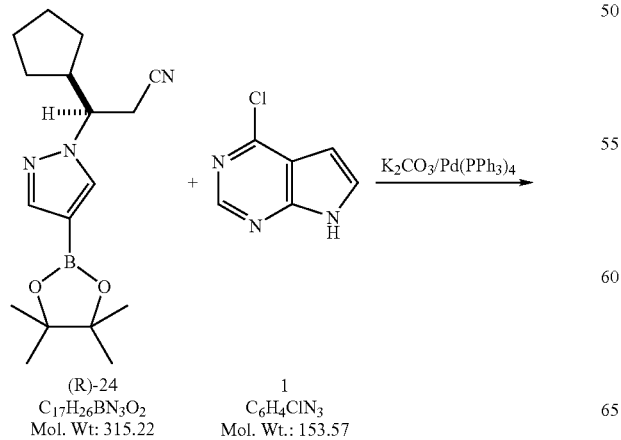

(R)-24
$C_{17}H_{26}BN_3O_2$
Mol. Wt.: 315.22

1
$C_6H_4ClN_3$
Mol. Wt.: 153.57

(3R)-Cyclopentyl-3-[4-(7H-pyrrolo[2,3-d]pyrimidin-4-yl)pyrazol-1-yl]propionitrile ((R)-12, free base). Method C. To a 25 mL round bottom flask equipped with a stir bar, condenser, and three-way valve connected to nitrogen and vacuum was charged 4-chloro-7H-pyrrolo[2,3-d]pyrimidine (1, 154 mg, 1.00 mmol), (3R)-3-cyclopentyl-3-[4-(4,4,5,5-tetramethyl-1,3,2-dioxaborolan-2-yl)-1H-pyrazol-1-yl]propanenitrile ((R)-24, 445 mg, 1.41 mmol, 1.41 equiv), 1,4-dioxane(2.78 mL, 35.6 mmol), water (1.39 mL, 77.2 mmol), and potassium carbonate ($K_2CO_3$, 693 mg, 5.02 mmol, 5.0 equiv) at room temperature. The resulting mixture was degassed three times back filling with nitrogen each time before being charged tetrakis(triphenylphosphine)palladium (0) (207 mg, 0.180 mmol, 0.18 equiv). The resulting reaction mixture was degassed four times back filling with nitrogen each time and then warmed to 95° C. The reaction mixture was stirred at 95° C. for 17 hours. When the reaction was deemed complete, the reaction mixture was cooled to room temperature before being diluted with ethyl acetate (20 mL) and 20% aqueous brine (11 mL). The mixture was stirred vigorously at room temperature until the majority of solids had gone into solution. The two layers were separated, and the aqueous layer was extracted with ethyl acetate (20 mL). The combined organic extracts were washed with saturated brine (10 mL), dried over $MgSO_4$, filtered, and concentrated under reduced pressure. The residue was then purified by flash chromatography ($SiO_2$, 0-100% ethyl acetate/hexanes gradient elution) to afford (3R)-3-cyclopentyl-3-[4-(7H-pyrrolo[2,3-d]pyrimidin-4-yl)-1H-pyrazol-1-yl]propanenitrile ((R)-12, 197 mg, 306.4 mg theoretical, 64.3% yield) as colorless oil, which was solidified upon standing at room temperature. For (R)-12: $^1$H NMR (DMSO-$d_6$, 400 MHz) δ ppm 12.1 (bs, 1H), 8.80 (d, 1H, J=0.42 Hz), 8.67 (s, 1H), 8.37 (s, 1H), 7.59 (dd, 1H, J=2.34, 3.51 Hz), 6.98 (dd, 1H, J=1.40, 3.44 Hz), 4.53 (td, 1H, J=19.5, 4.63 Hz), 3.26 (dd, 1H, J=9.77, 17.2 Hz), 3.18 (dd, 1H, J=4.32, 17.3 Hz), 2.40 (m, 1H), 1.79 (m, 1H), 1.65 to 1.13 (m, 7H); $C_{17}H_{18}N_6$(MW, 306.37) LCMS (EI) m/e 307 [M$^+$+H].

(S)-3-Cyclopentyl-3-(4-(7-(diethoxymethyl)-7H-pyrrolo[2,3-d]pyrimidin-4-yl)-1H-pyrazol-1-yl)propanenitrile ((S)-25). Into a 100 ml round bottom flask equipped with a stir bar, condenser and 3-way valve connected to nitrogen and vacuum was charged 4-chloro-7-(diethoxymethyl)-7H-pyrrolo[2,3-d]pyrimidine (3b, 3.30 g, 0.0129 mol), (3S)-3-cyclopentyl-3-[4-(4,4,5,5-tetramethyl-1,3,2-dioxaborolan-2-yl)-1H-pyrazol-1-yl]propanenitrile ((S)-24, 5.12 g, 0.0146 mol, 1.13 equiv), 1,4-dioxane (33.4 mL, 0.428 mol), water (16.7 mL, 0.929 mol) and potassium carbonate ($K_2CO_3$, 8.03 g, 0.0581 mol, 4.5 equiv) at room temperature. The resulting reaction mixture was degassed three times back filling with nitrogen each time before being charged tetrakis(triphenylphosphine)palladium(0) (1.49 g, 0.00129 mol, 0.10 equiv). The mixture was degassed four times back filling with nitrogen each time and then warmed to 95° C. The reaction mixture was stirred at 95° C. for 21 hours. When the reaction was deemed complete, the reaction mixture was cooled to room temperature before being diluted with ethyl acetate (45 mL) and water (20 mL). The resulting mixture was stirred until the majority of solids had gone into solution. The two layers were separated, and the aqueous layer was extracted with ethyl acetate (50 mL). The combined organic fractions were washed with 20% aqueous brine (50 mL), dried over $MgSO_4$, filtered and concentrated under reduced pressure. The residue was purified by flash chromatography ($SiO_2$, 0% to 50% ethyl acetate/hexane gradient elution) afford (3S)-3-cyclopentyl-3-{4-[7-diethoxymethyl)-7H-pyrrolo[2,3-d]pyrimidin-4-yl]-1H-pyrazol-1-yl}propanenitrile ((S)-25, 4.11 g, 5.27 g theoretical, 78% yield) as colorless oil, which was solidified upon standing at room temperature. For (S)-25: $^1$H NMR (DMSO-$d_6$, 400 MHz) δ ppm 8.84 (s, 1H), 8.74 (s, 1H), 8.38 (s, 1H), 7.71 (d, 1H, J=3.8 Hz,), 7.12 (d, 1H, J=3.8 Hz), 6.76 (s, 1H), 4.53 (td, 1H, J=19.4, 4.3 Hz), 3.68 (m, 2H), 3.52 (m, 2H), 3.26 (dd, 1H, J=9.6, 17.3 Hz), 3.19 (dd, 1H, J=4.3, 17.2 Hz), 2.41 (m, 1H), 1.80 (m, 1H), 1.63-1.09 (m, 13H); $C_{22}H_{28}N_6O_2$ (MW, 408.50), LCMS (EI) m/e 409 (M$^+$+H).

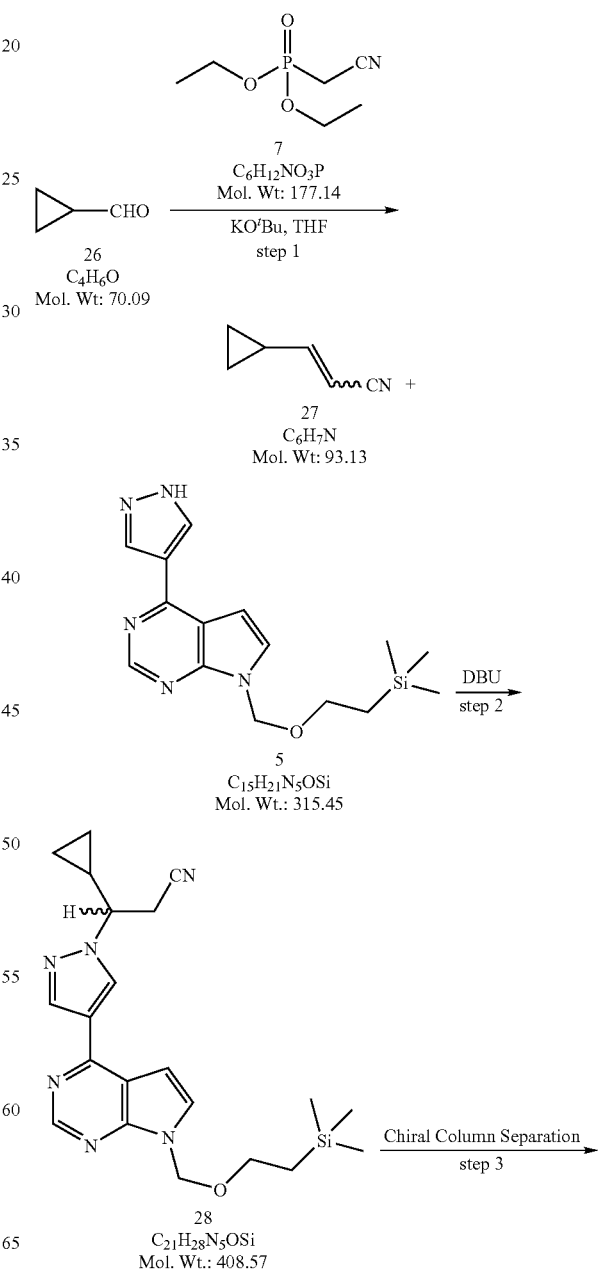

-continued

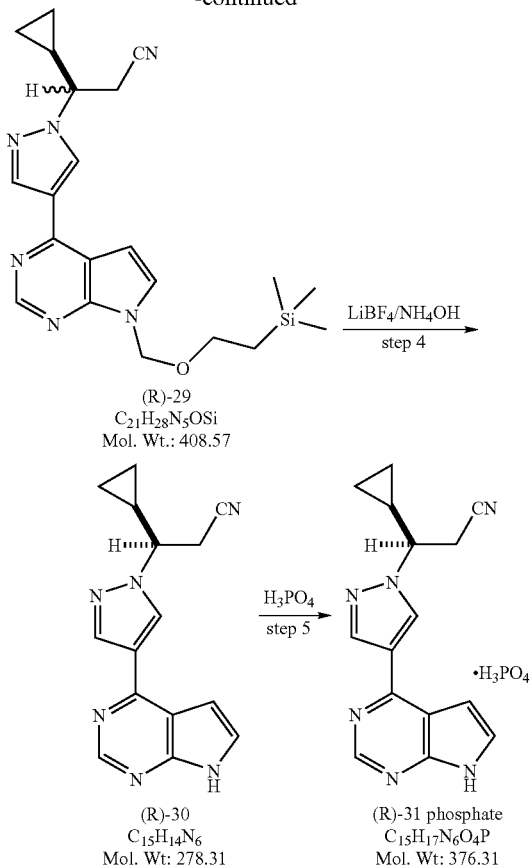

3-Cyclopropylacrylonitrile (27). A solution of diethyl cyanomethylphosphonate (7, 779.5 g, 4.4 mol, 1.1 equiv) in dry tetrahydrofuran (THF, 5.75 L) was stirred under nitrogen in an ice-water-methanol bath before a solution of 1 M potassium tert-butoxide in THF (KO$^t$Bu, 4.2 L, 4.2 mol, 1.05 equiv) was added at such a rate as to keep the temperature below 0° C. After addition of potassium tert-butoxide solution was complete, the stirring was continued at 0-5° C. for 1 h. and a solution of cyclopentanecarbaldehyde (26, 280 g, 4.0 mol) in dry THF (290 ml) was added at such a rate as to maintain the temperature below 0° C. The cold bath was removed, and the reaction mixture was gradually warmed to room temperature and stirred at room temperature for overnight. When the reaction was deemed complete, the reaction mixture was partitioned between MTBE (14 L), water (10 L) and brine (6 L). The organic phase was washed with brine (6 L). The aqueous phase was extracted with methyl tent-butyl ether (MTBE, 10 L) and washed with brine (6 L). The combined organic extracts were concentrated under reduced pressure and the residue was distilled to afford 3-cyclopropylacrylonitrile (27, 342.7 g, 372.5 g theoretical, 92% yield) as a colorless oil, which was found to be a mixture of E- and Z-isomer. For 27: $^1$H NMR (DMSO-d$_6$, 400 MHz, for E-isomer) δ ppm 6.33 (dd, 1H, J=16.3, 10.3 Hz), 5.69 (d, 1H, J=16.4 Hz), 1.66 (m, 1H), 1.02 (m, 1H,), 0.93 (m, 1H), 0.69 (m, 2H) and (for Z-isomer) δ ppm 6.05 (t, 1H, J=10.8 Hz), 5.45 (d, 1H, J=9.7 Hz), 1.82 (m, 1H), 1.02 (m, 1H), 0.93 (m, 1H), 0.69 (m, 2H); $^{13}$C NMR (DMSO-d$_6$, 100 MHz, for E-isomer) δ ppm 160.9, 118.4, 95.4, 15.4, 8.64 and (for Z-isomer) δ ppm 160.0, 117.3, 95.2, 14.8, 8.4; C$_6$H$_7$N (MW, 93.13), GCMS (EI) m/e 92 (M$^+$–H).

Racemic 3-Cyclopropyl-3-{4-[7-(2-trimethylsilanylethoxymethyl)-7H-pyrrolo[2,3-d]pyrimidin-4-yl]pyrazol-1-yl}propionitrile (28, Racemic SEM-protected compound). To a suspension of 4-(1H-pyrazol-4-yl)-7-(2-trimethylsilanyl-ethoxymethyl)-7H-pyrrolo[2,3-d] pyrimidine (5, 1.115 Kg, 3.54 mol, 1.0 equiv) in acetonitrile (11 L) was added 3-cyclopropylacrylonitrile (27, 428.7 g, 4.60 mol, 1.3 equiv) and 1,8-diazobicyclo[5.4.0]undec-7-ene (DBU, 55 mL, 0.37 mol, 0.105 equiv). The resulting reaction mixture was heated to gentle reflux for approximate 18 hours. When HPLC and TLC showed the reaction was deemed complete, the reaction micture, which was a clear solution, was cooled to room temperature before being concentrated under reduced pressure to give the crude Michael addition product (28) as a dark red oil. The crude product was then diluted with dichloromethane, divided into three portions and absorbed onto silica gel (3×2 Kg). The crude product absorbed on silica gel was purified by column chromatography on three 2 Kg silica gel columns (packed in 87.5:12.5 heptanes/EtOAc and eluted with 87.5:12.5 to 25:75 heptanes/EtOAc). The fractions containing the pure desired product (28) were combined and concentrated under reduced pressure, transferred to afford racemic 3-cyclopropyl-3-{4-[7-(2-trimethylsilanyl-ethoxymethyl)-7H-pyrrolo[2,3-d]pyrimidin-4-yl]-pyrazol-1-yl}-propionitrile (28, racemic SEM-protected compound, 1.310 Kg, 1.446 Kg theoretical, 90.6% yield) as a amber syrup, which was used for chiral column separation without further purification. For 28: C$_{21}$H$_{28}$N$_5$OSi (MW, 408.57), LCMS (EI) m/e 409 (M$^+$+H).

(3R)-3-Cyclopropyl-3-(4-(7-((2-(trimethylsilyl)ethoxy) methyl)-7H-pyrrolo[2,3-d]pyrimidin-4-yl)-1H-pyrazol-1-yl)propanenitrile ((R)-29) and (3S)-3-Cyclopropyl-3-(4-(7-((2-(trimethylsilyl)ethoxy)methyl)-7H-pyrrolo[2,3-d] pyrimidin-4-yl)-1H-pyrazol-1-yl)propanenitrile ((S)-29). A slurry of 1.5 Kg of 20-micron Chiralcel® OD chiral stationary phase (CSP) made by Daicel in 3.0 L of isopropanol (IPA) was packed into a PROCHROM Dynamic Axial Compression Column LC110-1 (11 cm ID×25 cm L; Column Void Vol.: approximate 1.5 L) under 150 bar of packing pressure. The packed column was then installed no a Novasep Hipersep HPLC unit. The column and HPLC system were flushed with methanol (17 L) and the mobile phase made by a mixture of isopropanol and hexane (2:8 by volume, 17 L). The feed solution was then prepared by dissolving 3-cyclopropyl-3-(4-(7-((2-(trimethylsilyl)ethoxy)methyl)-7H-pyrrolo[2,3-d]pyrimidin-4-yl)-1H-pyrazol-1-yl)propanenitrile (28, racemic SEM-protected compound, 2500 g, 6.119 mol) in the mobile phase to a concentration of 80 g/L. The feed solution (120 mL per injection) was then sequentially injected into the preparative HPLC chiral column for separation. The chiral column was eluted with the mobile phase at a flow rate of 570 mL/min at room temperature. The column elution was monitored by UV at wavelength 330 nm. Under these conditions, a baseline separation of the two enantiomers was achieved. The cycle time for each injection was 11 minutes and a total of 261 injections were performed for this separation process. Fractions for Peak 1 (the undesired (S)-enantiomer, (S)-29) and Peak 2 (the desired (R)-enantiomer, (R)-29) were collected separately from each injection, and fractions collected for each peak were continuously concentrated at 40° C. under reduced pressure (40-120 bar). The residue from each evaporator was further dried under high vacuum to constant weight to afford (3R)-3-cyclopropyl-3-(4-(7-((2-(trimethylsilyl) ethoxy)methyl)-7H-pyrrolo[2,3-d]pyrimidin-4-yl)-1H-pyrazol-1-yl)propanenitrile ((R)-29, 1150 g, 1250 g theoretical, 92%) from Peak 2 as a light yellow oil which solidified upon standing at room temperature in vacuo and (3S)-cyclopropyl- 3-(4-(7-((2-(trimethylsilyl)ethoxy)methyl)-7H-pyrrolo[2,3-d]pyrimidin-4-yl)-1H-pyrazol-1-yl)propanenitrile ((S)-29, 1200 g, 1250 g theoretical, 96%) from Peak 1 as an yellow oil which solidified upon standing at room temperature in vacuo.

A chiral HPLC method was developed for chiral purity evaluation of both enantiomers of SEM-protected compound ((R)-29 and (S)-29) using a Chiralcel® OD-H column (4.6× 250 mm, 5 μm), purchased from Chiral Technologies, Inc. The two enantiomers of SEM-protected compound are separated with a resolution greater than 4.0 by using a mobile phase of 15% ethanol and 85% hexanes at room temperature with a flow rate of 1 mL/min. The UV detection wavelength is 220 nm. The retention times for (S)-enantiomer ((S)-29) and (R)-enantiomer ((R)-29) are 9.4 minutes and 12.4 minutes, respectively.

The quality of each enantiomer separated by preparative chiral HPLC including chemical purity (HPLC area %) and chiral purity (chiral HPLC area %) was analyzed and their structures are confirmed by NMRs and LC/MS. For (R)-29: achiral purity (99.1 area % by HPLC detected at 220 nm); chiral purity (99.4 area % by chiral HPLC; 98.8% ee); $C_{21}H_{28}N_5OSi$ (MW, 408.57), LCMS (EI) m/e 409 (M$^+$+H). For (S)-29: achiral purity (98.5 area % by HPLC detected at 220 nm); chiral purity (99.2 area % by chiral HPLC; 98.4% ee); $C_{21}H_{28}N_5OSi$ (MW, 408.57), LCMS (EI) m/e 409 (M$^+$+H).

(3R)-3-Cyclopropyl-3-[4-(7H-pyrrolo[2,3-d]pyrimidin-4-yl)pyrazol-1-yl]propionitrile ((R)-30). A solution of (3R)-3-cyclopropyl-3-{4-[7-(2-trimethylsilanyl-ethoxymethyl)-7H-pyrrolo[2,3-d]pyrimidin-4-yl]-pyrazol-1-yl}-propionitrile ((R)-29, 102 g, 0.25 mol, 1.0 equiv) in MeCN (900 mL) and H$_2$O (75 mL) was treated with solid lithium tetrafluoroborate (LiBF$_4$, 186.0 g, 2.0 mol, 8.0 equiv) in protions (the reaction temperature increased from 15 to 38° on addition). The resulting reaction mixture was then heated at gentle reflux (light suspension formed) for 20 h. When LCMS showed the cleavage of the SEM group was complete, the reaction mixture was cooled to room temperature and subsequently to 12° before being adjusted to pH 9-10 with addition of an aqueous NH$_4$OH solution (20%, 80 mL). The resulting suspension was stirred at room temperature until LCMS showed no N-hydroxymethyl intermediate (M$^+$+H=309) remained, typically within 24-36 h. During this period the pH of the reaction mixture dropped to 7-8, additional aqueous NH$_4$OH solution (20%) was added to readjust the mixture to pH 9-10. The mixture was diluted with acetonitrile (300 mL), filtered, washing solids with acetonitrile (500 mL). The turbid filtrate was concentrated under reduced pressure to remove most of the MeCN to give a thick oil that contained some solids. The mixture was slowly diluted with H$_2$O (500 mL) and the turbid solution was seeded. The solution was then concentrated under reduced pressure at room temperature until a thick suspension had formed. The suspension was further diluted with H$_2$O (1 L) and the resulting suspension was stirred at room temperature for 2 h. The solids were collected by filtration, washed with H$_2$O (2×500 mL) and suction dried on funnel for 1.5 h. $^{19}$F NMR showed a small amount of inorganic fluoride present and TLC (5% MeOH/EtOAc) showed a small amount of baseline material existed. Therefore, the crude solids were re-slurried in H$_2$O (1 L) with mechanical stirring for 1 h before being collected by filtration and washed with H$_2$O (500 mL). The wet cake was suction dried on the funnel for 1.5 h then dried in a vacuum oven at 45-50° C. for 16 h to give (3R)-3-cyclopropyl-3-[4-(7H-pyrrolo[2,3-d]pyrimidin-4-yl)pyrazol-1-yl]propionitrile ((R)-30, 60.8 g, 69.6 g theoretical, 87.4% yield) as a off-white solid. For (R)-30: $C_{15}H_{14}N_6$ (MW, 278.31), LCMS (EI) m/e 279 (M$^+$+H).

(3R)-3-Cyclopropyl-3-[4-(7H-pyrrolo[2,3-d]pyrimidin-4-yl)pyrazol-1-yl]propionitrile phosphate salt ((R)-31, Phosphate). A suspension of (3R)-3-cyclopropyl-3-[4-(7H-pyrrolo[2,3-d]pyrimidin-4-yl)pyrazol-1-yl]propionitrile ((R)-30, 60.0 g, 0.2158 mol, 1.0 equiv) in isopropanol (IPA, 900 mL) was heated to 77° C. to give a clear pale yellow solution. A solution of crystalline H$_3$PO$_4$ (23.3 g, 0.2374 mol, 1.1 equiv) in IPA (200 mL) was added in a steady stream from an addition funnel at 77-79° C., rinsing the addition funnel with IPA (25 mL). An immediate turbidity was developed followed by formation of a white suspension. After about half amount of the H$_3$PO$_4$ solution had been added the suspension became extremely thick. An additional amount of IPA (100 mL) was added to facilitate stirring. When addition was complete the suspension was heated at 75° C. for 1 h with the suspension becoming more mobile but remaining very thick. The suspension was cooled to room temperature over 1 h and the solids were collected by filtration and washed with 50% IPA/heptane (750 mL) and dried. The solids were triturated with heptane (1.2 L) with stirring for overnight before being collected by filtration and washed with heptane (300 mL) and dried in vacuum oven at 40-50° C. to constant weight to afford (3R)-3-cyclopropyl-3-[4-(7H-pyrrolo[2,3-d]pyrimidin-4-yl)pyrazol-1-yl]propionitrile phosphate salt ((R)-31, Phosphate, 76.7 g, 81.2 g theoretical, 94.5% yield) as a fine white crystalline solid. For (R)-31: $^1$H NMR (DMSO-d$_6$, 400 MHz) δ ppm 12.2 (bs, 1H), 9.62 (bs, 3H, H$_3$PO$_4$), 8.77 (s, 1H), 8.69 (s, 1H), 8.39 (s, 1H), 7.59 (q, 1H, J=2.0 Hz), 6.98 (d, 1H, J=2.7 Hz), 4.04 (m, 1H), 3.37 (dd, 1H, J=16.8, 8.0 Hz), 3.28 (dd, 1H, J=16.8, 5.1 Hz), 1.43 (m, 1H), 0.68 (m, 1H), 0.49 (m, 3H); $^{13}$C NMR (DMSO-d$_6$, 100 MHz) δ ppm 152.2, 150.9, 149.9, 139.3, 130.4, 127.0, 120.8, 118.1, 112.9, 100.0, 62.6, 23.3, 15.7, 4.3, 3.8; $C_{15}H_{14}N_6$ (MW, 278.31), LCMS (EI) m/e 279.1 (M$^+$+H).

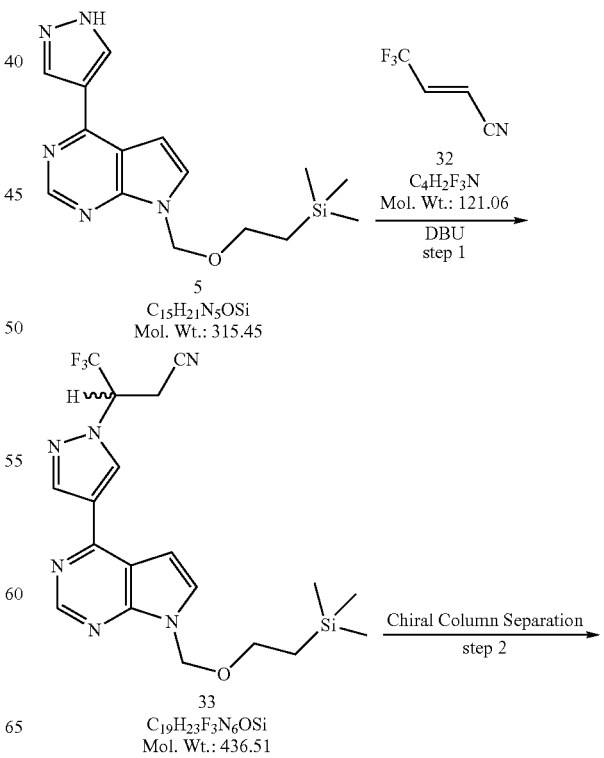

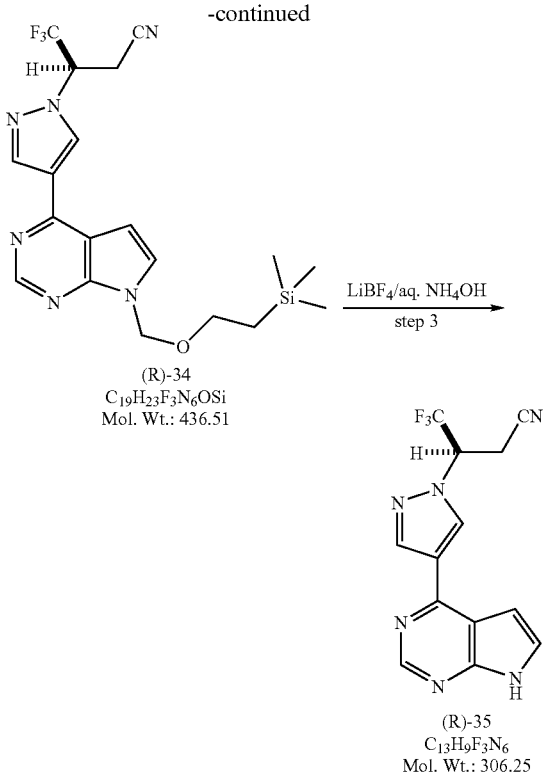

Racemic 4,4,4-Trifluoro-3-(4-(7-((2-(trimethylsilyl)ethoxy)methyl)-7H-pyrrolo[2,3-d]pyrimidin-4-yl)-1H-pyrazol-1-yl)butanenitrile (33, Racemic SEM-protected compound). To a flask equipped with a mechanical stirrer, nitrogen inlet and thermowell was added compound 4-(1H-pyrazol-4-yl)-7-((2-(trimethylsilyl)ethoxy)methyl)-7H-pyrrolo[2,3-d]pyrimidine (5, 1424 g, 4.52 mol) and acetonitrile (14 L). The resulting suspension was added 4,4,4-trifluorocrotonitrile (32, 601.6 g, 4.97 mol, 1.1 equiv) followed by 1,8-diazobicyclo[5.4.0]undec-7-ene (DBU, 67 mL, 0.452 mol, 0.1 equiv). A slight exotherm (5° C.) was noted upon the addition of the DBU. The reaction mixture was stirred at room temperature for 30 minutes when TLC and LCMS showed the reaction was deemed complete. The reaction mixture was then concentrated under reduced pressure to remove most of the solvent and the residue was purified by two silica gel columns (3 Kg each) for chromatography purification. The column was eluting with 2:1 heptane/ethyl acetate (30 L) followed by 1:1 heptane/ethyl acetate (30 L). The fractions containing pure desired product (33) were combined and concentrated under reduced pressure to afford racemic 4,4,4-trifluoro-3-(4-(7-((2-(trimethylsilyl)ethoxy)methyl)-7H-pyrrolo[2,3-d]pyrimidin-4-yl)-1H-pyrazol-1-yl)butanenitrile (33, Racemic SEM-protected compound, 1802 g, 1973 g theoretical, 91.3% yield) as a thick oil, which was directly used in subsequent chiral column separation without further purification. For 33: $^1$H NMR (DMSO-$d_6$, 400 MHz) δ ppm 8.99 (s, 1H), 8.79 (s, 1H), 8.56 (s, 1H), 7.80 (d, 1H, J=3.7 Hz), 7.09 (d, 1H, J=3.7 Hz), 6.05 (m, 1H), 5.63 (s, 2H), 3.82 (dd, 1H, J=17.5, 10.6 Hz), 3.66 (dd, 1H, J=17.0, 4.9 Hz), 3.50 (t, 2H, J=7.9 Hz), 0.80 (t, 2H, J=8.2 Hz), −0.145 (s, 9H); $^{13}$C NMR (DMSO-$d_6$, 100 MHz) δ ppm 151.7, 151.3, 149.5, 140.8, 132.9, 130.4, 123.2 ($J_{CF}$=282 Hz), 121.9, 116.2, 113.5, 100.2, 72.3, 65.7, 57.8 ($J_{CF}$=32.4 Hz), 17.1, −1.46; $C_{19}H_{23}F_3N_6OSi$ (MW, 436.51), LCMS (EI) m/e 437 (M$^+$+H).

(R)-4,4,4-Trifluoro-3-(4-(7-((2-(trimethylsilyl)ethoxy)methyl)-7H-pyrrolo[2,3-d]pyrimidin-4-yl)-1H-pyrazol-1-yl)butanenitrile ((R)-34) and (S)-4,4,4-Trifluoro-3-(4-(7-((2-(trimethylsilyl)ethoxy)methyl)-7H-pyrrolo[2,3-d]pyrimidin-4-yl)-1H-pyrazol-1-yl)butanenitrile ((S)-34). A slurry of 1.5 Kg of 20-micron Chiralcel® OD chiral stationary phase (CSP) made by Daicel in 3.0 L of isopropanol (IPA) was packed into a PROCHROM Dynamic Axial Compression Column LC110-1 (11 cm ID×25 cm L; Column Void Vol.: approximate 1.5 L) under 150 bar of packing pressure. The packed column was then installed on a Novasep Hipersep HPLC unit. The column and HPLC system were flushed with methanol (17 L) and the mobile phase made by a mixture of isopropanol and hexane (2:8 by volume, 17 L). The feed solution was then prepared by dissolving 4,4,4-trifluoro-3-(4-(7-((2-(trimethylsilyl)ethoxy)methyl)-7H-pyrrolo[2,3-d]pyrimidin-4-yl)-1H-pyrazol-1-yl)butanenitrile (33, racemic SEM-protected compound, 3100 g, 7.1 mol) in the mobile phase to a concentration of 120 g/L. The feed solution (120 mL per injection) was then sequentially injected into the preparative HPLC chiral column for separation. The chiral column was eluted with the mobile phase at a flow rate of 570 mL/min at room temperature. The column elution was monitored by UV at wavelength 330 nm. Under these conditions, a baseline separation of the two enantiomers was achieved. The cycle time for each injection was 11 minutes and a total of 210 injections were performed for this separation process. Fractions for Peak 1 (the undesired (S)-enantiomer, (S)-34) and Peak 2 (the desired (R)-enantiomer, (R)-34) were collected separately from each injection, and fractions collected for each peak were continuously concentrated at 40° C. under reduced pressure (40-120 bar). The residue from each evaporator was further dried under high vacuum to constant weight to afford (3R)-3-cyclopropyl-3-(4-(7-((2-(trimethylsilyl)ethoxy)methyl)-7H-pyrrolo[2,3-d]pyrimidin-4-yl)-1H-pyrazol-1-yl)propanenitrile ((R)-34, 1457 g, 1550 g theoretical, 94%) from Peak 2 as a light yellow oil which solidified upon standing at room temperature in vacuo and (3S)-cyclopropyl-3-(4-(7-((2-(trimethylsilyl)ethoxy)methyl)-7H-pyrrolo[2,3-d]pyrimidin-4-yl)-1H-pyrazol-1-yl)propanenitrile ((S)-34, 1488 g, 1550 g theoretical, 96%) from Peak 1 as an yellow oil which solidified upon standing at room temperature in vacuo.

A chiral HPLC method was developed for chiral purity evaluation of both enantiomers of SEM-(R)-34 and (S)-34 using a Chiralcel® OD-H column (4.6×250 mm, 5 μm), purchased from Chiral Technologies, Inc. The two enantiomers of SEM-protected compound are separated with a resolution greater than 9.0 by using a mobile phase of 15% ethanol and 85% hexanes at room temperature with a flow rate of 1 mL/min. The UV detection wavelength is 220 nm. The retention times for (S)-enantiomer ((S)-34) and (R)-enantiomer ((R)-34) are 11.2 minutes and 22.2 minutes, respectively.

The quality of each enantiomer separated by preparative chiral HPLC including chemical purity (HPLC area %) and chiral purity (chiral HPLC area %) was analyzed and their structures are confirmed by NMRs and LC/MS. For (R)-34: achiral purity (99.2 area % by HPLC detected at 220 nm); chiral purity (99.4 area % by chiral HPLC; 98.8% ee); $^1$H NMR (DMSO-$d_6$, 400 MHz) δ ppm 8.99 (s, 1H), 8.79 (s, 1H), 8.56 (s, 1H), 7.80 (d, 1H, J=3.7 Hz), 7.09 (d, 1H, J=3.7 Hz), 6.05 (m, 1H), 5.63 (s, 2H), 3.82 (dd, 1H, J=17.5, 10.6 Hz), 3.66 (dd, 1H, J=17.0, 4.9 Hz), 3.50 (t, 2H, J=7.9 Hz), 0.80 (t, 2H, J=8.2 Hz), −0.145 (s, 9H); $^{13}$C NMR (DMSO-$d_6$, 100 MHz) δ ppm 151.7, 151.3, 149.5, 140.8, 132.9, 130.4, 123.2 ($J_{CF}$=282 Hz), 121.9, 116.2, 113.5, 100.2, 72.3, 65.7, 57.8 ($J_{CF}$=32.4 Hz), 17.1, −1.46; $C_{19}H_{23}F_3N_6OSi$ (MW, 436.51), LCMS (EI) m/e 437 (M$^+$+H). For (S)-34: achiral purity (99.1 area % by HPLC detected at 220 nm); chiral purity (99.2 area % by chiral HPLC; 98.4% ee); $^1$H NMR (DMSO-$d_6$, 400 MHz) δ ppm 8.99 (s, 1H), 8.79 (s, 1H), 8.56 (s, 1H), 7.80 (d, 1H, J=3.7 Hz), 7.09 (d, 1H, J=3.7 Hz), 6.05 (m, 1H), 5.63 (s, 2H), 3.82 (dd, 1H, J=17.5, 10.6 Hz), 3.66 (dd, 1H, J=17.0, 4.9

Hz), 3.50 (t, 2H, J=7.9 Hz), 0.80 (t, 2H, J=8.2 Hz), −0.145 (s, 9H); $^{13}$C NMR (DMSO-d$_6$, 100 MHz) δ ppm 151.7, 151.3, 149.5, 140.8, 132.9, 130.4, 123.2 ($J_{CF}$=282 Hz), 121.9, 116.2, 113.5, 100.2, 72.3, 65.7, 57.8 ($J_{CF}$=32.4 Hz), 17.1, −1.46; $C_{19}H_{23}F_3N_6OSi$ (MW, 436.51), LCMS (EI) m/e 437 (M$^+$+ H).

4,4,4-Trifluoro-3(R)-[4-(7H-pyrrolo[2,3-d]pyrimidin-4-yl)-pyrazol-1-yl]-butyronitrile ((R)-35). To a flask equipped with a thermowell, reflux condenser, mechanical stirrer, and nitrogen inlet was added 4,4,4-trifluoro-3(R)-{4-[7-(2-trimethylsilanyl-ethoxymethyl)-7H-pyrrolo [2,3-d]pyrimidin-4-yl]-pyrazol-1-yl}-butyronitrile ((R)-34, 312 g, 0.716 mol), acetonitrile (4.5 L) and water (376 mL). The resulting mixture was then treated with solid lithium tetrafluoroborate (LiBF$_4$, 697 g, 7.16 mol, 10.0 equiv) in portions at room temperature. The mixture was heated at reflux for 13 hours. When TLC indicated that no starting material remained and two products (fully deprotected and the hydroxymethyl analog) were produced, the reaction mixture was cooled to room temperature and then to 0° C. in an ice/water bath before being treated dropwise with an aqueous ammonium hydroxide solution (NH$_4$OH, 20%, 245 mL) at 0-5° C. to bring the pH to between 9 and 9.5 as determined by 5-10 range pH strips. The ice bath was removed and the thick suspension was stirred at room temperature for overnight. When HPLC showed the reaction was complete, the reaction mixture was treated with water (1 L), brine (500 mL) and ethyl acetate (7 L). The two layers were separated and the aqueous layer was extracted with ethyl acetate (2×2 L). The combined organic layers were concentrated under reduced pressure and the residue was re-dissolved in ethyl acetate (4 L) and washed with brine (2×2 L). The organic layer was dried over sodium sulfate, and the solvents were removed under reduced pressure to afford a thick slurry. Heptane was added to the thick slurry and solvent removal was continued until most of the ethyl acetate was removed. The solids were collected by filtration and dried in vacuum to afford the crude product ((R)-35, 206 g, 219.3 g theoretical, 94% yield, 98% pure by HPLC) as white powders. The crude product was re-crystallized from ethanol (700 mL) to afford pure 4,4,4-trifluoro-3(R)-[4-(7H-pyrrolo[2,3-d]pyrimidin-4-yl)-pyrazol-1-yl]-butyronitrile ((R)-35, 188.6 g, 219.3 g theoretical, 86% yield, >99.5% pure by HPLC) as fine white crystalline solids. For (R)-35: $^1$H NMR (DMSO-d$_6$, 500 MHz) δ ppm 12.2 (bs, 1H), 8.95 (s, 1H), 8.74 (s, 1H), 8.53 (s, 1H), 7.63 (d, 1H, J=3.7 Hz), 6.97 (d, 1H, J=3.8 Hz), 6.04 (m, 1H), 3.81 (dd, 1H, J=17.1, 10.1 Hz), 3.65 (dd, 1H, J=17.1, 5.0 Hz).; $^{13}$C NMR (DMSO-d$_6$, 125 MHz) δ ppm 152.3, 151.0, 149.0, 140.7, 132.7, 127.2, 123.1 ($J_{CF}$=284 Hz), 122.2, 116.2, 113.1, 99.5, 57.7 ($J_{CF}$=33.0 Hz), 17.3; $C_{13}H_9F_3N_6$ (MW, 306.25), LCMS (EI) m/e 307 (M$^+$+H).

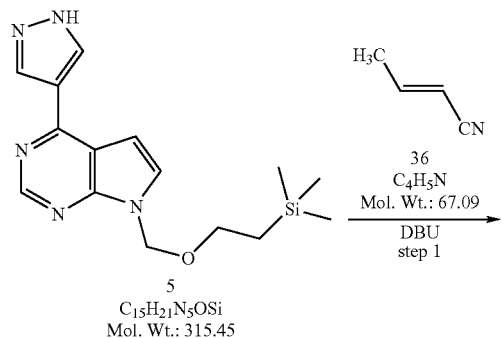

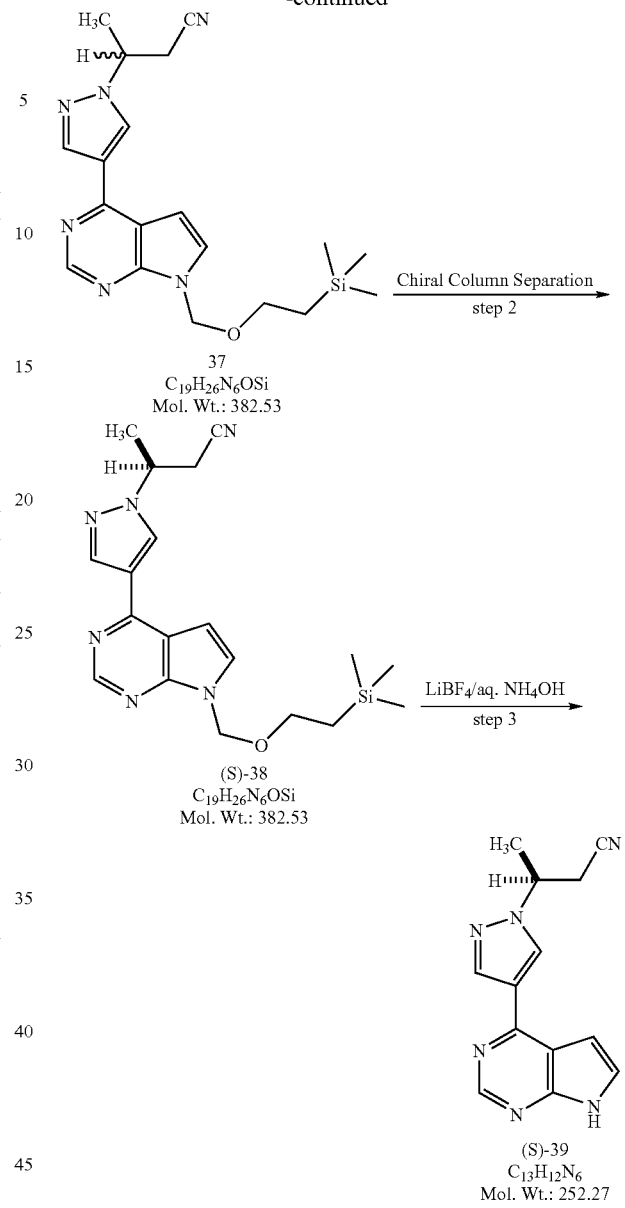

3-[4-(7-{[2-(Trimethylsilyl)ethoxy]methyl}-7H-pyrrolo [2,3-d]pyrimidin-4-yl)-1H-pyrazol-1-yl]butanenitrile (37). Into a 250 mL three-neck round bottom flask equipped with a stir bar, condenser, thermocouple and nitrogen inlet was charged 4-(1H-pyrazol-4-yl)-7-{[2-(trimethylsilyl)ethoxy] methyl}-7H-pyrrolo[2,3-d]pyrimidine (5, 10.3 g, 0.033 mol), 2-butenenitrile (36, 3.0 mL, 0.037 mmol, 1.12 equiv) and acetonitrile (100 mL, 2.0 mol) at room temperature. The resulting mixture was treated with 1,8-diazabicyclo[5.4.0] undec-7-ene (DBU, 2.0 mL, 0.013 mol, 0.4 equiv) and was subsequently warmed to 55° C. The reaction mixture was stirred at 55° C. for 15-20 h. When LC/MS showed the reaction was deemed complete, the reaction mixture was concentrated under reduced pressure to yield an orange oil. The crude product was then purified by flash column chromatography (SiO$_2$, 40-80% ethyl acetate/hexane gradient elution) to afford 3-[4-(7-{[2-(trimethylsilyl)ethoxy]methyl}-7H-pyrrolo[2,3-d]pyrimidin-4-yl)-1H-pyrazol-1-yl]butanenitrile (37, 12.3 g, 12.62 g theoretical, 97.5% yield) as a colorless oil, which solidified upon standing at room temperature in vacuo. For 37: $^1$H NMR (CDCl$_3$, 400 MHz) δ ppm 8.84 (s, 1H), 8.33 (s, 1H), 8.30 (s, 1H), 7.39 (d, 1H, J=3.8 Hz), 6.79 (d, 1H, J=3.8 Hz), 5.67 (s, 2H), 4.77 (m, 1H), 3.53 (t, 2H, J=8.2 Hz), 3.05 (dd, 1H, J=16.8, 6.2 Hz), 2.98 (dd, 1H, J=16.8, 6.3 Hz), 1.79 (d, 3H, J=6.5 Hz), 0.91 (t, 2H, J=8.3 Hz), −0.068 (s, 9H); C$_{19}$H$_{26}$N$_6$OSi (MW, 382.53), LCMS (EI) m/e 383 (M$^+$+H).

(S)-3-(4-(7-((2-(Trimethylsilyl)ethoxy)methyl)-7H-pyrrolo[2,3-d]pyrimidin-4-yl)-1H-pyrazol-1-yl)butanenitrile ((S)-38) and (R)-3-(4-(7-((2-(Trimethylsilyl)ethoxy)methyl)-7H-pyrrolo[2,3-d]pyrimidin-4-yl)-1H-pyrazol-1-yl)butanenitrile ((R)-38). A solution of racemic 3-[4-(7-{[2-(trimethylsilyl)ethoxy]methyl}-7H-pyrrolo[2,3-d]pyrimidin-4-yl)-1H-pyrazol-1-yl]butanenitrile (37, 38.3 g, 0.1 mmol) in a mixture of ethanol and hexanes (15:85 by volume) was injected into preparative HPLC system equipped with achiral column (30×250 mm) packed with silica gel coated with cellulose tri(3,5-dimethylphenyl carbamate) (Available at Chiral technologies Inc. as Chiralcel® OD-H, 5 μm). The column was eluted with mobile phase made by a mixture of ethanol (EtOH) and hexanes in a 15 to 85 volume ratio at a flow rate of 32 mL/min at room temperature. The column elution was monitored by UV detection at a wavelength of 220 nm. Under these conditions, a baseline separation of the two enantiomers was achieved and the retention times were 15.1 minutes (Peak 1, the undesired (R)-enantiomer (R)-38) and 19.6 minutes (Peak 2, the desired (S)-enantiomer (S)-38), respectively. Each injection was 0.5 mL of feed solution at a concentration of 200 mg/mL and the cycle time for each injection was 14 minutes by using stack injections. A total of 384 injections were performed for this separation process. Fractions for Peak 1 (the undesired (R)-enantiomer, (S)-38) and Peak 2 (the desired (S)-enantiomer, (S)-38) were collected separately from each injection, and fractions collected for each peak were concentrated under reduced pressure. The residue from each evaporator was further dried under high vacuum to constant weight to afford ((S)-3-(4-(7-((2-(trimethylsilyl)ethoxy)methyl)-7H-pyrrolo[2,3-d]pyrimidin-4-yl)-1H-pyrazol-1-yl)butanenitrile ((S)-38, 17.43 g, 19.15 g theoretical, 91% yield) from Peak 2 as off-white solids and (R)-3-(4-(7-((2-(trimethylsilyl)ethoxy)methyl)-7H-pyrrolo[2,3-d]pyrimidin-4-yl)-1H-pyrazol-1-yl)butanenitrile ((R)-38, 17.8 g, 19.15 g theoretical, 93% yield) from Peak 1 as off-white solids.

A chiral HPLC method was developed for chiral purity evaluation of both enantiomers of SEM-(R)-38 and (S)-38 by using a Chiralcel® OD-H column (4.6×250 mm, 5 μm), purchased from Chiral Technologies, Inc., packed with a silica-gel coated with cellulose tris(3,5-dimethylphenyl carbamate (Chiralcel® OD). The two enantiomers ((R)-38 and (S)-38) are separated with a resolution greater than 3.0 by using a mobile phase made from 15% ethanol and 85% hexanes at room temperature with a flow rate of 0.8 mL/min. The UV detection wavelength is 220 nm. The retention times are 17.8 minutes for (R)-38 and 21.5 minutes for (S)-38, respectively.

The quality of each enantiomer separated by preparative chiral HPLC including chemical purity (HPLC area %) and chiral purity (chiral HPLC area %) was analyzed and their structures are confirmed by NMRs and LC/MS. For (S)-38: achiral purity (99.3 area % by HPLC detected at 220 nm); chiral purity (99.5 area % by chiral HPLC; 99.0% ee); $^1$H NMR (CDCl$_3$, 400 MHz) δ ppm 8.84 (s, 1H), 8.33 (s, 1H), 8.30 (s, 1H), 7.39 (d, 1H, J=3.8 Hz), 6.79 (d, 1H, J=3.8 Hz), 5.67 (s, 2H), 4.77 (m, 1H), 3.53 (t, 2H, J=8.2 Hz), 3.05 (dd, 1H, J=16.8, 6.2 Hz), 2.98 (dd, 1H, J=16.8, 6.3 Hz), 1.79 (d, 3H, J=6.5 Hz), 0.91 (t, 2H, J=8.3 Hz), −0.068 (s, 9H); C$_{19}$H$_{26}$N$_6$OSi (MW, 382.53), LCM (EI) m/e 383 (M$^+$+H). For (R)-38: achiral purity (99.1 area % by HPLC detected at 220 nm); chiral purity (99.4 area % by chiral HPLC; 98.8% ee); $^1$H NMR (CDCl$_3$, 400 MHz) δ ppm 8.84 (s, 1H), 8.33 (s, 1H), 8.30 (s, 1H), 7.39 (d, 1H, J=3.8 Hz), 6.79 (d, 1H, J=3.8 Hz), 5.67 (s, 2H), 4.77 (m, 1H), 3.53 (t, 2H, J=8.2 Hz), 3.05 (dd, 1H, J=16.8, 6.2 Hz), 2.98 (dd, 1H, J=16.8, 6.3 Hz), 1.79 (d, 3H, J=6.5 Hz), 0.91 (t, 2H, J=8.3 Hz), −0.068 (s, 9H); C$_{19}$H$_{26}$N$_6$OSi (MW, 382.53), LCMS (EI) m/e 383 (M$^+$+H).

(3S)-3-[4-(7H-pyrrolo[2,3-d]pyrimidin-4-yl)-1H-pyrazol-1-yl]butanenitrile ((S)-39). Into a 5 liter four neck round bottom flask equipped with overhead stirring, condenser, thermocouple and nitrogen inlet was charged (3S)-3-[4-(7-{[2-(trimethylsilyl)ethoxy]methyl}-7H-pyrrolo[2,3-d]pyrimidin-4-yl)-1H-pyrazol-1-yl]butanenitrile ((S)-38, 82.3 g, 0.215 mol), acetonitrile (1510 mL), water (135 mL) and solid lithium tetrafluoroborate (LiBF$_4$, 206 g, 2.15 mol, 10.0 equiv). The resulting reaction mixture was warmed to reflux and stirred at reflux for 24-36 h. When HPLC and TLC showed that the reaction was deemed complete, the reaction mixture was cooled to room temperature. An aqueous ammonium hydroxide (NH$_4$OH) solution (20% v/v) was added to the reaction mixture to adjust pH to 9-10. The resulting reaction mixture was stirred at room temperature for 15-24 h. When HPLC and TLC showed the de-protection reaction was deemed complete, the reaction mixture was filtered through a Celite pad to remove the insoluble materials. The Celite pad was washed with ethyl acetate (500 mL). The filtrate was further diluted with ethyl acetate (1 L) before being washed with a 20% sodium chloride (NaCl) aqueous solution (1 L). The aqueous fraction was back extracted with ethyl acetate (2×500 mL). The combined organic fractions were then concentrated under reduced pressure to remove the solvents to generate a thick white slurry. The slurry was treated with water (2 L) and the resulting mixture was stirred at room temperature for 18 hours. The solids were collected by filtration, and the wet cake was washed with methyl tert-butyl ether (MTBE, 500 mL) and heptane (500 mL) before being dried at 50° C. in a vacuum oven to constant weight. The dried, crude product (45 g) was then re-crystallized in ethanol (500 mL) and heptane (350 mL) to afford (3S)-3-[4-(7H-pyrrolo[2,3-d]pyrimidin-4-yl)-1H-pyrazol-1-yl]butanenitrile ((S)-39, 42.8 g, 54.2 g theoretical, 79% yield) as white solids. For (S)-39: $^1$H NMR (DMSO-d$_6$, 400 MHz) δ ppm 12.1 (bs, 1H), 8.76 (s, 1H), 8.67 (s, 1H), 8.36 (s, 1H), 7.59 (d, 1H, J=3.5 Hz), 6.98 (d, 1H, J=3.5 Hz), 4.98 (m, 1H), 3.19 (d, 2H, J=6.6 Hz), 1.57 (d, 3H, J=6.6 Hz); C$_{13}$H$_{12}$N$_6$ (MW, 252.27), LCMS (EI) m/e 253 (M$^+$+H).

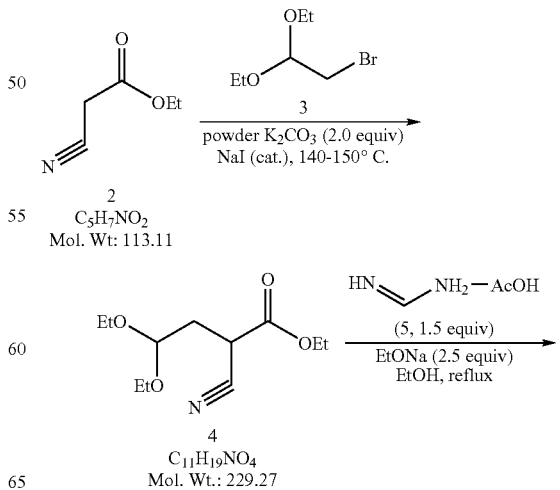

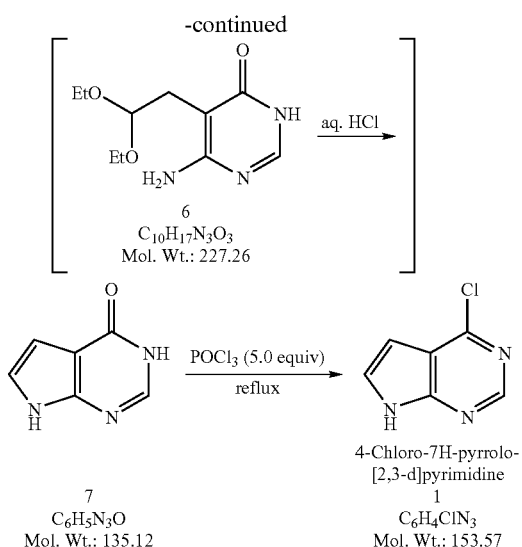

2-Cyano-4,4-diethoxy-butyric acid ethyl ester (4). Bromoacetaldehyde diethylacetal (3, 541 g, 2.75 mol) was added to a suspension of powdered potassium carbonate (379.6 g, 2.75 mol, 1.0 equiv) and sodium iodide (33 g, 0.22 mol, 0.08 equiv) in ethyl cyanoacetate(2, 1.55 Kg, 13.75 mol, 5.0 equiv). Upon addition of the aldehyde to the reaction mixture, the resulting solution turned yellow. The reaction mixture was slowly heated to 140-150° C. collecting the volatile material in a Dean Stark trap. This material was discarded. Fairly vigorous gas evolution was observed to begin at 140° C. The reaction was monitored by G.C. and was observed to be near completion at 90 minutes. Heating was continued for an additional 45 minutes when gas evolution was observed to have ceased. The reaction mixture was then cooled to room temperature and partitioned between 4 L water and 2 L methyl tent-butyl ether (MTBE). The layers were separated and the aqueous layer was extracted with an additional 2 L of MTBE. The aqueous layer was checked for product by G.C. then discarded. The organic layers were dried over sodium sulfate, filtered and concentrated in vacuum. The crude product was purified by fractional distillation (91-105° C. @ 0.53-0.65 mm/Hg) to afford 2-cyano-4,4-diethoxy-butyric acid ethyl ester (4, 359.4 g, 630.5 g theoretical, 57%) as a oil. For 4: $^1$H NMR (DMSO-d$_6$, 300 MHz) δ ppm 4.60 (t, 1H, J=5.6 Hz), 4.15 (m, 3H), 3.59 (m, 2H), 3.45 (m,1H), 2.11 (t, 2H, J=6.2 Hz), 1.22 (t, 3H, J=6.9 Hz), 1.10 (dt, 6H, J=7.1, 6.9 Hz).

7H-Pyrrolo[2,3-d]pyrimidin-4-ol (7). Formamidine acetate (5, 1.04 Kg,10 mol, 1.25 equiv) was added to 7.52 L of (21% wt) sodium ethoxide (EtONa) in ethanol (EtOH, 62.5 equiv) and the resulting solution was stirred for 60 minutes. 2-cyano-4,4-diethoxy-butyric acid ethyl ester (4, 1.8 Kg, 8.0 mol) was then added and the resulting reaction mixture was refluxed for seven hours. The stirring was turned off after the solution was cooled and the solids were allowed to settle. The supernatant ethanol solution was removed, leaving the solids in the bottom of the reaction flask. The ethanol was evaporated and the residue was added back to the solids remaining in the reaction flask with water and ice at a ratio of 600 mL/mol. A solution of 6 N aqueous HCl was added to the resulting solution at a ratio of 500 mL/mol at 15° C. The resulting solution was then heated at 45° C. for 45 minutes. The solution was again cooled to 15° C. and the pH was adjusted to 8.0 with the addition of aqueous ammonium hydroxide. The precipitated solids were collected by filtration, washed with water (2×225 mL/mol) and pulled dry. The solids were further washed with 1:1 ethyl acetate/heptane (500 mL/mol), then heptane (2×250 mL/mol) and dried in vacuum to afford 7H-pyrrolo[2,3-d]pyrimidin-4-ol (7, 738.6g, 1081 g theoretical, 68.3%) as yellow to brown to yellow crystalline material. For 7: $^1$H NMR (DMSO-d$_6$, 300 MHz) δ ppm 11.88 (bs, 1H), 11.80 (bs, 1H), 7.81 (s,1H), 7.02 (dd,1H, J=3.2, 2.3 Hz), 6.42 (dd, 1H, J=3.5, 2.3 Hz); C$_6$H$_5$N$_3$O (MW, 135.12), LCMS (EI) m/e 136 (M$^+$+H) and (M$^+$+Na) m/e 158.

4-Chloro-7H-pyrrolo[2,3-d]pyrimidine (1). 4-Hydroxy-7H-pyrrolo[2,3-d]pyrimidine (7, 306 g, 2.25 mol) was added in portions over 20 min to phosphorus oxychloride (1050 ml, 1727 g, 11.26 mol, 5.0 equiv). Stirring was continued at room temperature for 15 min then this suspension was slowly heated to reflux and the evolving hydrochloric acid was scrubbed through 20% sodium hydroxide solution. Reflux was continued for 30 min after all material went in solution. The reaction mixture was allowed to cool to 60° C. and it was poured onto ice (5 Kg) with stirring. Stirring was continued for 20 min and potassium carbonate was slowly added in portions to adjust pH to 7.5. Ice was added as needed to keep the temperature below 20° C. The precipitate was collected by filtration, washed well with water and dried in a vacuum oven (30° C.). The crude material was taken in ethyl acetate and stirred at 50° C. for 1.5 hrs. This solution was treated with charcoal, stirred at 50° C. for an additional 20 min and filtered hot through celite. The resulting solution was concentrated to 900 ml and cooled in an ice bath with stirring. The precipitate was collected by filtration, washed with small volume of cold ethyl acetate and dried in a vacuum oven (40° C.) to afford 4-chloro-7H-pyrrolo[2,3-d]pyrimidine (1, 227g, 334.8 g theoretical, 67.8%) as yellow to brown crystalline solids. Further concentration of the mother liquor produces an additional crop of the desired product (5-10%) as yellow to brown crystals of less purity. For 1: $^1$H NMR (DMSO-d$_6$, 400 MHz) δ ppm 12.58 (bs, 1H), 8.58 (s,1H), 7.69 (d,1H, J=3.5 Hz), 6.59 (d, 1H, J=3.5 Hz); C$_6$H$_4$ClN$_3$ (MW, 153.57), LCMS (EI) m/e 154/156 (M$^+$+H).

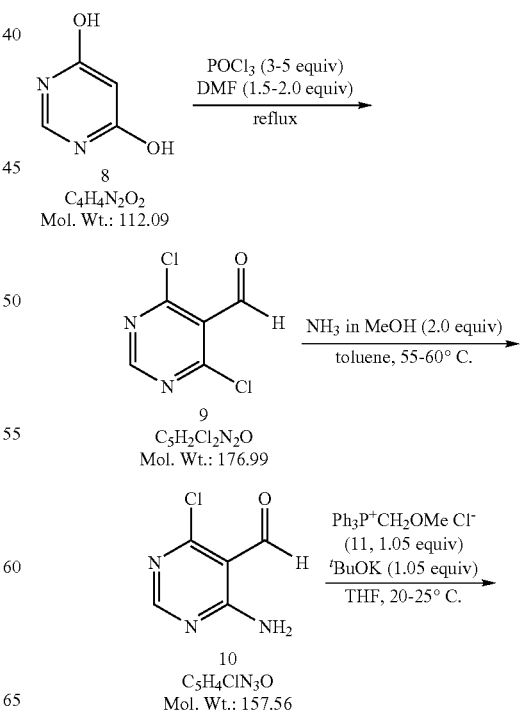

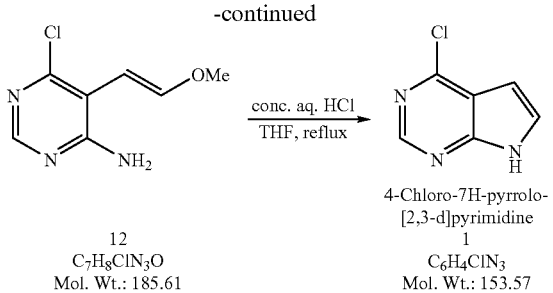

12
C₇H₈ClN₃O
Mol. Wt.: 185.61

4-Chloro-7H-pyrrolo-
[2,3-d]pyrimidine
1
C₆H₄ClN₃
Mol. Wt.: 153.57

4,6-Dichloropyrimidine-5-carbaldehyde (9). In a 5 L 4-neck flask equipped with mechanical stirrer, addition funnel, condenser, thermocouple, and a N₂ sweep into an aqueous NaOH scrubbing solution, phosphorous oxychloride (1 L, 10.572 mol, 4.82 equiv) was cooled in an ice/salt bath. N,N-Dimethylformamide (DMF, 320 mL, 4.138 mol, 1.85 equiv) was added dropwise at 0±2° C. After addition of ~100 mL of DMF (~0.5 hr) crystallization occurred and the reaction temperature was increased from 0 to 10° C. Addition was stopped and the mixture was allowed to recool to ~2° C. The remaining DMF was added over 2.5 hr at <8° C. The suspension became very thick making stirring difficult. When addition of DMF was complete, the mixture was stirred 0.5 hr at 3-5° C. 4,6-dihydroxypyrimidine (8, 250 g, 2.232 mol) was added portion wise as a solid. After about one third of 4,6-dihydroxypyrimidine was added the reaction mixture became more mobile and a slow exothermic phenomena occurred with the reaction temperature increasing to ~12° C. over 0.5 hr. The remaining 4,6-dihydroxypyrimidine was added portion wise over 0.25 hr with the reaction temperature increasing from 12 to 27° C. The reaction temperature was maintained at 25-27° C. with intermittent cooling during which time the yellow suspension became thinner, then thicker once again. After the exothermic phenomenon subsided in about 1 hr, the reaction mixture was heated slowly. At about 55° C. the reaction mixture became extremely thick and the second mild exothermic phenomenon was occurred. The heating mantle was removed while the reaction temperature continued to increase to about 63° C. and remained at this temperature for several minutes before dropping. Heating of the mixture was resumed until gentle reflux (about 100° C.) was attained. At about 95° C. a steady, fairly rapid evolution of HCl began and the reaction mixture gradually thinned and darkened. After about 0.5 hr a clear, brown solution developed with the reflux temperature slowly increasing to 115° C. over 1.25 hr. After a total of 2.5 hr at reflux, the reaction mixture was cooled to room temperature and stirred overnight. Excess POCl₃ (as much as possible) was removed under reduced pressure (bath temperature 45-50° C.). The thick residual brown oil was poured very slowly into cold H₂O (5 L) in a 20 L separation funnel, adding ice as needed to maintain the aqueous mixture near room temperature. The aqueous mixture was extracted with EtOAc (2×3 L, 1×2 L). The combined EtOAc extracts were washed with H₂O (2×2.5 L), saturated NaHCO₃ aqueous solution (1 L), brine (1 L), dried over Na₂SO₄, filtered, and concentrated under reduced pressure (bath temperature at 35° C.) to afford the crude 4,6-dichloropyrimidine-5-carbaldehyde (9, 270 g, 395 g theoretical, 68.4%) as yellow-orange solid. A 20 g portion of this crude material was purified by Kugelrohr distillation (oven temperature at 90-100° C., 225 mTorr) to give 15.3 g of pure 4,6-dichloropyrimidine-5-carbaldehyde (9) as a white solid that turned yellow on standing at room temperature. (On standing crude 9 undergoes slow hydrolysis with formation of HCl. Prior to use in the next step crude 9 was dissolved in a mixture of EtOAc and toluene and filtered to remove insoluble material. The filtrate washed with H₂O, saturated NaHCO₃ solution, brine, dried over Na₂SO₄, filtered, and concentrated under reduced pressure and the resulting yellow solid used the following day.) For 9: ¹H NMR (CDCl₃, 300 MHz) δ ppm 10.46 (s, 1H), 8.89 (s,1H).

4-Amino-6-chloropyrimidine-5-carbaldehyde (10). A solution of 7M NH₃ in MeOH (265 mL, 1.8602 mol, 2.0 equiv) was added over 1.25 hr to a solution of 4,6-dichloropyrimidine-5-carbaldehyde (9, 163.7 g, 0.9301 mol) in toluene (3 L). The reaction temperature slowly increased from 20 to 26° C. and a yellow suspension formed. Mild cooling was applied to maintain the reaction temperature at ≦26° C. The suspension was stirred 3.5 hr at room temperature before the solids were collected by filtration. The solids were washed with EtOAc (1 L). The filtrate was concentrated under reduced pressure, and the solids were triturated with toluene/heptane (2:1 v/v, 600 mL), filtered and dried to give 71.1 g of 4-amino-6-chloropyrimidine-5-carbaldehyde (10) as a yellow solid. The original solid filtered from the reaction mixture contained additional 10. The product was extracted from the filtered solid by stirring in EtOAc (1.25 L) for 1.5 hr, filtering, then stirring in THF (750 mL) for 1 hr and filtering. Both EtOAc and THF filtrates were concentrated under reduced pressure, and the resulting solids were triturated with toluene/heptane (2:1 v/v, 450 mL), filtered and dried to give an additional 44.1 g of 4-amino-6-chloropyrimidine-5-carbaldehyde (10) as yellow solids. The combined yield of 4-amino-6-chloropyrimidine-5-carbaldehyde (10, 115.2 g, 146.5 g theoretical) was 78.6%. For 10: ¹ HNMR (DMSO-d₆, 300 MHz) δ ppm 10.23 (s, 1H), 8.71 (bs,1H), 8.55 (bs, 1H), 8.39 (s, 1H); C₅H₄ClN₃O (MW, 157.56), LCMS (EI) m/e 158 (M⁻+H).

6-Chloro-5-(2-methoxyvinyl)pyrimidin-4-ylamine (12). A suspension of (methoxymethyl)triphenyl-phosphonium chloride (11, 276.0 g, 0.807 mol, 1.1 equiv) in THF (1.5 L) was cooled in an ice/salt bath to −2° C. and 1M KOᵗBu in THF (807 mL, 0.807 mol, 1.1 equiv) was added over 1.5 hr at −2 to −3° C. The deep red-orange mixture was stirred for 1 hr at −2 to −3° C. 4-Amino-6-chloropyrimidine-5-carbaldehyde (10, 115.2 g, 0.7338 mol, 1.0 equiv) was then added portion wise to the reaction mixture as a solid form using THF (200 mL) to rinse the container and funnel. During the addition the reaction temperature increased from −3 to 13° C. and a brown color developed. When the reaction temperature dropped to 10° C., the cooling bath was removed and the reaction mixture was allowed to warm to room temperature and stirred 42 hr. The reaction mixture was cooled to −2° C. before being quenched by the slow addition of saturated NH₄Cl aqueous solution (750 mL). The mixture was concentrated under reduced pressure to remove most of the THF. The residue was partitioned between EtOAc (3 L) and H₂O (1 L). The organic phase was filtered to remove insoluble material at the interface, then extracted with 2N HCl (4×250 mL) followed by 3N HCl (2×250 mL). The combined HCl extracts were back-extracted with EtOAc (500 mL) then filtered through Celite to remove insoluble material. The filtrate was cooled in an ice/brine bath, adjusted to pH 8 with a 6N aqueous NaOH solution and extracted with EtOAc (3×1 L). The combined EtOAc extracts were washed with brine (1 L), dried over Na₂SO₄, stirred with charcoal (10 g) and silica gel (10 g) for 1 hr. The mixture was filtered through Celite, washing the Celite pad with EtOAc (1 L). The filtrate was concentrated, co-evaporating residual EtOAc with heptane (500 mL). The resulting tan solid was pumped under high vacuum for 2 hr to afford crude 6-chloro-5-(2-methoxyvinyl)pyrimidin-4-ylamine (12, 72.3 g, 136.2 g theoretical, 53.1%). The crude 12 was used in the following reaction without further purification. A sample of crude 12 (2.3 g) was purified by chromatography on silica gel, eluting with 0-35% EtOAc/heptane to give 1.7 g of pure 12 as a white solid, which is a 1:2 mixture of E/Z isomers. For 12: $^1$H NMR (DMSO-d$_6$, 300 MHz) for E-isomer: δ ppm 8.02 (s, 1H), 7.08 (bs, 2H), 6.92 (d, 1H, J=13.1), 5.35 (d, 1H, J=13.0 Hz), 3.68 (s, 3H) and for Z-isomer: δ ppm 8.06 (s, 1H), 7.08 (bs, 2H), 6.37 (d, 1H, J=6.8 Hz), 5.02 (d, 1H, J=6.7 Hz), 3.69 (s, 3H); C$_7$H$_8$ClN$_3$O (MR, 185.61), LCMS (EI) m/e 186/188 (M$^+$+H).

4-Chloro-7H-[pyrrolo[2,3-d]pyrimidine (1). Concentrated HCl (5 mL) was added to a solution of crude 6-chloro-5-(2-methoxyvinyl)pyrimidin-4-ylamine (12, 70.0 g, 0.3784 mol) in THF (700 mL) and the resulting reaction mixture was heated to reflux for 7.5 hr. On warming a light suspension was formed that gradually re-dissolved. When the reaction was deemed complete, the reaction mixture was cooled to room temperature and stirred overnight. Solid NaHCO$_3$ (15 g) was added and the mixture was stirred for 1 hr at room temperature. Charcoal (7 g), silica gel (7 g) and Na$_2$SO$_4$ (20 g) were added and the mixture heated to 40° C. The mixture was cooled to room temperature and filtered through Celite, washing the Celite pad with THF (1 L). The filtrate was concentrated under reduced pressure and the resulting solid was dried under reduced pressure to afford crude 4-chloro-7H-[pyrrolo[2,3-d]pyrimidine (1, 58.1 g, 58.1 g theoretical, 100%) as a yellow-brown solid. This crude product was dissolved in EtOAc (1 L) at 50-55° C. and treated with activated charcoal (3 g). The mixture was filtered while warm through Celite, washing the Celite pad with warm EtOAc (250 mL). The filtrate was concentrated to about 500 ml, and the suspension was allowed to stand overnight. The suspension was cooled to 0-5° C. for 2 h before the solids were collected by filtration. The solids were dried to afford pure 4-chloro-7H-[pyrrolo[2,3-d]pyrimidine (1, 54.5 g, 58.1 g theoretical, 94%) as yellow-brown crystals. For 1: $^1$H NMR (DMSO-d$_6$, 400 MHz) δ ppm 12.58 (bs, 1H), 8.58 (s,1H), 7.69 (d,1H, J=3.5 Hz), 6.59 (d, 1H, J=3.5 Hz); LCMS (EI) m/e 154/156 (M$^+$+H).

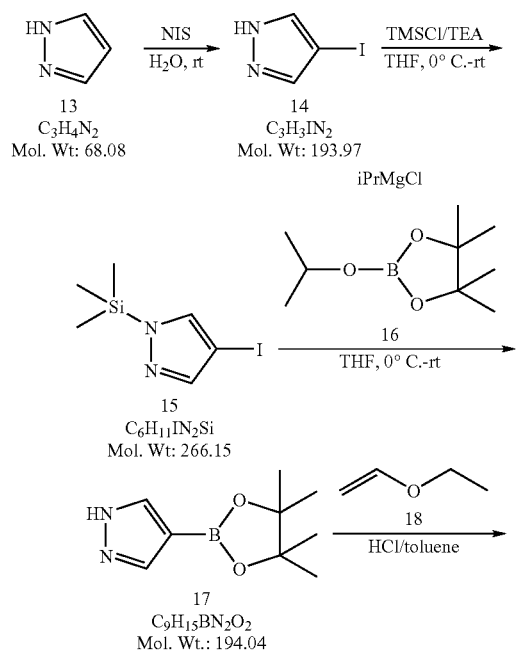

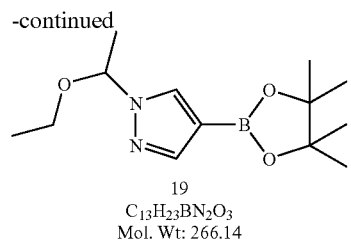

19
C$_{13}$H$_{23}$BN$_2$O$_3$
Mol. Wt: 266.14

4-Iodopyrazole (14). A flask equipped with a nitrogen inlet, addition funnel, thermowell, and mechanical stirrer was charged with pyrazole (13, 450 g, 6.62 mol) and tetrahydrofuran (5 L). The mixture was cooled to 10° C. and N-iodosuccinimide (NIS, 1490 g, 6.62 mol, 1.0 equiv) was added in portions as a solid. The reaction mixture (slight suspension) was stirred at room temperature for 1 hour (longer reaction times may be necessary depending on ambient temperature). The mixture was then filtered and the THF was removed under reduced pressure. The residue was suspended in ethyl acetate (6 L) and insoluble materials were filtered. The dark filtrate was sequentially washed with aqueous saturated sodium thiosulfate solution (2×3 L) (organic layer lightens to a pale yellow), water (2×3 L), and brine (2 L). The organic layer was dried over sodium sulfate, filtered, and concentrated under reduced pressure to afford 4-iodopyrazole (14, 1138 g, 1284.1 g theoretical, 88.6%) as white to pale yellow solids after being dried in a vacuum oven at 30° C. overnight. For 14: $^1$H NMR (DMSO-d$_6$, 400 MHz) δ ppm 13.17 (bs, 1H), 7.93 (bs,1H), 7.55 (bs,1H); C$_3$H$_3$IN$_2$ (MW, 193.97), LCMS (EI) m/e 195 (M$^+$+H).

1-Trimethylsilyl-4-iodopyrazole (15). To a flask equipped with a reflux condenser, a nitrogen inlet, mechanical stirrer, and a thermowell was charged 4-iodopyrazole (14, 200 g, 1.03 mol) and THF (2 L). To this solution was added triethylamine (TEA, 158 mL, 1.13 mol, 1.1 equiv) and the resulting solution was cooled to 0° C. in an ice-brine bath. To this solution was added chlorotrimethylsilane (TMS-Cl, 137 mL, 1.08 mol, 1.05 equiv) with rapid stirring allowing the temperature to reach 18° C. (The reaction becomes very thick and difficult to stir, but becomes manageable after over time). When the exotherm had subsided, the cold bath was removed and the reaction was warmed to room temperature. The reaction was followed by GC and was found to be deemed complete after about 1 hour (Sampling of reaction must be done out of air and diluted with dry solvent to prevent TMS hydrolysis). The reaction mixture was then diluted with heptane (2 L) before being filtered under nitrogen. The solvent was removed from the filtrate under reduced pressure venting the rotovap with nitrogen. The residual oil was diluted with heptane (1 L) and re-concentrated. If the solids formed upon adding the heptane, a second filtration is necessary. The residue was then distilled under the reduced pressure (70-90° C. at about 0.5 Torr) using a Kugelohr to afford 1-trimethylsilyl-4-iodopyrazole (15, 263 g, 274.1 g theoretical, 96%) as a colorless oil. (This material must be kept under nitrogen at all times since the TMS group rapidly hydrolyzes.) Subsequently, we have found that 1-trimethylsilyl-4-iodopyrazole can be prepared by heating the iodopyrazole (14) with 2 equivalents of hexamethyldisilazane for 1 hr.

4-(4,4,5,5-Tetramethyl-1,3,2-dioxaborolan-2-yl)-1H-pyrazole (17). A flask equipped with a mechanical stirrer, nitrogen inlet, addition funnel and thermowell was charged with 1-trimethylsilyl-4-iodopyrazole (15, 225.1 g, 0.85 mol) and THF (2200 mL). This mixture was cooled to −6° C. in an ice/salt/brine bath and isopropyl magnesium chloride (2 M in THF, 510 ml, 1.02 mol, 1.2 equiv) was added at a rate such that the temperature did not exceed 0° C. The extent of metal/halogen exchange was monitored by GC and was found complete after about 10 min. To the orange brown solution was added 2-isopropoxy-4,4,5,5-tetramethyl-1,3,2-dioxaborolane (isopropylpinacolborate, 16, 347 mL, 1.7 mol, 2.0 equiv) slowly at first keeping the temperature below 0° C. and then fairly rapidly after about ½ of the compound was added allowing the temperature to reach 5° C. (the reaction becomes quite thick and then thins out slowly). The reaction is then stirred at 0° C. for 10 min before being warmed to room temperature over 1 hr and stirred at room temperature for an additional 1 hr. The reaction was cooled to 6° C. and saturated aqueous ammonium chloride solution (2.2 L) was added with a temperature increase to 25° C. The mixture was stirred for 5 minutes before being diluted with toluene (10 L). The layers were separated (a large amount of solid is present in the aqueous layer) and the organic layer was sequentially washed with water (6×2.2 L), brine (2×2.2 L), dried over sodium sulfate, filtered, and concentrated under reduced pressure. Residual toluene was co-evaporated with heptane to afford 4-(4,4,5,5-tetramethyl-1,3,2-dioxaborolan-2-yl)-1H-pyrazole (17, 90.3 g, 164.9 g theoretical, 54.8%) as a white solid. For 17: $^1$H NMR (DMSO-d$_6$, 400 MHz) δ ppm 13.08 (bs, 1H), 7.94 (s,1H), 7.62 (s,1H), 1.23 (s, 12H); $C_9H_{15}BN_2O_2$ (MW, 194.04), LCMS (EI) m/e 195 (M$^+$+H).

1-(Ethoxyethyl)-4-(4,4,5,5-tetramethyl[1,3,2]dioxaborolan-2-yl)-1H-pyrazole (19). A 22 L 4-neck flask equipped with a mechanical stirrer, thermowell, addition funnel, condenser and N$_2$ inlet was charged with 4-(4,4,5,5-tetra-methyl[1,3,2]dioxaborolan-2-yl)-1H-pyrazole (17, 1.42 kg, 7.32 mol), toluene (9.5 L) and ethyl vinyl ether (18, 790.5 g, 1050 mL, 10.98 mol, 1.50 equiv). A 4 M HCl in dioxane (50 mL) was added via an addition funnel over 10 minutes and the resulting reaction mixture was heated at 35-40° C. for 7 hr to give a clear homogeneous solution. When the reaction was shown to be complete by GC, solid NaHCO$_3$ (130 g) was added and the mixture was stirred for 1 hr before being filtered. The filtrate was concentrated under reduced pressure. Heptane (200 mL) was added to the residue to affect crystallization. The solid was collected by filtration and dried in a vacuum oven to afford 1-(ethoxyethyl)-4-(4,4,5,5-tetramethyl[1,3,2]dioxaborolan-2-yl)-1H-pyrazole (19, 1.896 Kg, 1.948 Kg theoretical, 97.3%) as a white to off-white solid. For 19: $^1$H NMR (DMSO-d$_6$, 400 MHz) δ ppm 8.09 (s, 1H), 8.58 (s,1H), 7.62 (s,1H), 5.55 (q, 1H, J=6.1 Hz), 3.37 (dq, 1H, J=7.1, 9.6 Hz), 3.12 (dq, 1H, J=7.0, 9.7 Hz), 1.56 (d, 3H, J=6.0 Hz), 1.24 (s, 12H), 1.00 (t, 3H, J=7.0 Hz); $C_{13}H_{23}BN_2O_3$ (MW, 266.14), LCMS (EI) m/e 267 (M$^+$+H).

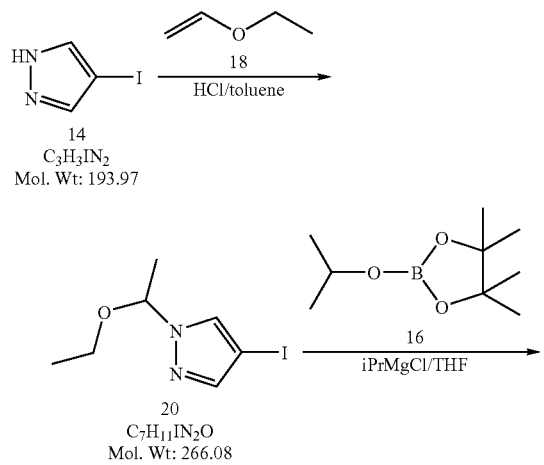

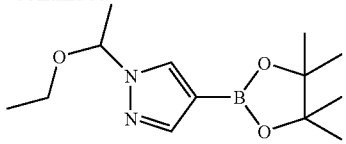

19
$C_{13}H_{23}BN_2O_3$
Mol. Wt: 266.14

1-(ethoxyethyl)-4-iodo-1H-pyrazole (20). A 22 L 4-neck flask equipped with an mechanical stirrer, thermowell, N$_2$ inlet and condenser was charged with 4-iodo-1H-pyrazole (14, 1.00 Kg, 5.16 mol) and toluene (10 L) and ethyl vinyl ether (18, 557 g, 740 mL, 7.73 mol, 1.5 equiv) was added. To the suspension 4 M HCl in dioxane (32 mL, 0.128 mol, 0.025 equiv) was added over 5 min with formation of a slightly thicker white suspension. The mixture was heated carefully to 35-40° C. at which point a mild exotherm to about 40° C. occurred with rapid dissolution of all solids to give a clear light yellow solution. The reaction mixture was heated at about 40° C. for an additional 0.5 hr until the GC analysis indicated the reaction was complete. The solution was allowed to cool to 25-30° C. and solid NaHCO$_3$ (108 g, 1.29 mol, 0.25 equiv) was added. The suspension was stirred for 1 hr at room temperature to ensure the complete neutralization of HCl. The mixture was then filtered and the filtrate was concentrated under reduced pressure. The residual liquid was fractionally distilled to afford 1-(ethoxyethyl)-4-iodo-1H-pyrazole (20, 1.346 Kg, 1.373 Kg theoretical, 98%) as a pale yellow liquid (bp 89-93° at about 1 torr). For 20: $^1$H NMR (CDCl$_3$, 250 MHz) δ ppm 7.61 (s, 1H), 7.47 (s, 1H), 5.46 (q, 1H, J=6.0 Hz), 3.48-3.23 (m, 2H), 1.60 (d, 3H, J=6.0 Hz), 1.11 (t, 3H, J=7.0 Hz); $C_7H_{11}IN_2O$ (MW, 266.08), LCMS (EI) m/e 267 (M$^+$+H).

2-Isopropoxy-4,4,5,5-tetramethyl[1,3,2]dioxaborolane (16). A 5 L 4-neck flask equipped with a reflux condenser, mechanical stirrer, N$_2$ inlet, and thermowell was flushed well with N$_2$ and charged with isopropyl borate (2.673 L, 11.5 mol, 1.15 equiv) and pinacol (1.179 kg, 10 mol). The resulting mixture was heated at reflux (80-85°) for overnight. The mixture was then cooled to room temperature, transferred to a 5 L 4-neck flask equipped with a 24 inch Vigreux column, magnetic stirrer, and thermowell. The mixture was distilled at atmospheric pressure under nitrogen. After the low boiling fraction (bp 90-180°) which contained predominately 2-propanol and isopropyl borate (GC analysis) was removed, the completed distillation afforded 2-isopropoxy-4,4,5,5-tetramethyl[1,3,2]dioxaborolane (10, 1.628 kg, 1.86 Kg theoretical, 87.5%) as a colorless liquid (bp 180-185° C. with GC purity >97.5%). This material was stored in Sure/Seal bottles to minimize hydrolysis.

1-(Ethoxyethyl)-4-(4,4,5,5-tetramethyl[1,3,2]dioxaborolan-2-yl)-1H-pyrazole (19). A 22 L 4-neck flask equipped with a mechanical stirrer, thermowell, addition funnel, and N$_2$ inlet was charged with 1-(ethoxyethyl)-4-iodo-1H-pyrazole (20, 700.0 g, 2.63 mol) and THF (5.5 L). The resulting solution was cooled to between −12° C.--15° C. A solution of 2 M i-PrMgCl in THF (1513 mL, 3.03 mol, 1.15 equiv) was added via an addition funnel over 30 min while maintaining the reaction temperature at <−5° C. and the tan suspension was stirred at <−5° C. for 0.75 hr. The resulting reaction mixture was further cooled to −15° C. and 2-isopropoxy-4,4,5,5-tetramethyl[1,3,2]dioxaborolane (16, 734 g, 805 mL, 3.95 mol, 1.5 equiv) was added rapidly via an addition funnel with the reaction temperature increasing to ~−5°. [Note: previous work with the analogous TMS-protected pyrazole has shown that slow addition of 2-isopropoxy-4,4,5,5-tetramethyl[1,3,2]dioxaborolane results in a lower yield.] A nearly clear light brown solution was developed followed by reformation of grayish light suspension. The cooling bath was then removed and the reaction mixture was allowed to warm to 16° C. over 0.75 hr. The mixture was poured into 50 L reparatory funnel containing a stirred saturated aqueous NH$_4$Cl solution (4 L). The mixture was diluted with toluene (8 L), heptane (8 L) and H$_2$O (2 L). The aqueous phase was removed and the organic phase was washed with warm (30° C.) H$_2$O (4×3 L) and saturated brine (2×3 L). The organic phase was dried over Na$_2$SO$_4$, and the solvents wereee removed under reduced pressure. The residual toluene was further removed by co-evaporation with heptane (2 L). The residual oil was transferred to a 4 L beaker using a minimum amount of heptane (100 mL) and scratched to induce crystallization. The solid was filtered, washed with heptane (200 mL) and dried overnight in a vacuum oven at 30-40° C. The filtrate was concentrated under reduced pressure and the residue was allowed to stand overnight. The resulting solid was filtered, washed with heptane (100 mL) and dried overnight in a vacuum oven at 30-40° C. The two crops were combined to afford 1-(ethoxyethyl)-4-(4, 4,5,5-tetramethyl[1,3,2]dioxaborolan-2-yl)-1H-pyrazole (19, 596 g, 700 g theoretical, 85.1%) as a white to off-white solid. For 19: $^1$H NMR (DMSO-d$_6$, 400 MHz) δ ppm 8.09 (s, 1H), 8.58 (s,1H), 7.62 (s,1H), 5.55 (q, 1H, J=6.1 Hz), 3.37 (dq, 1H, J=7.1, 9.6 Hz), 3.12 (dq, 1H, J=7.0, 9.7 Hz), 1.56 (d, 3H, J=6.0 Hz), 1.24 (s, 12H), 1.00 (t, 3H, J=7.0 Hz); C$_{13}$H$_{23}$BN$_2$O$_3$ (MW, 266.14), LCMS (EI) m/e 267 (M$^+$+H).

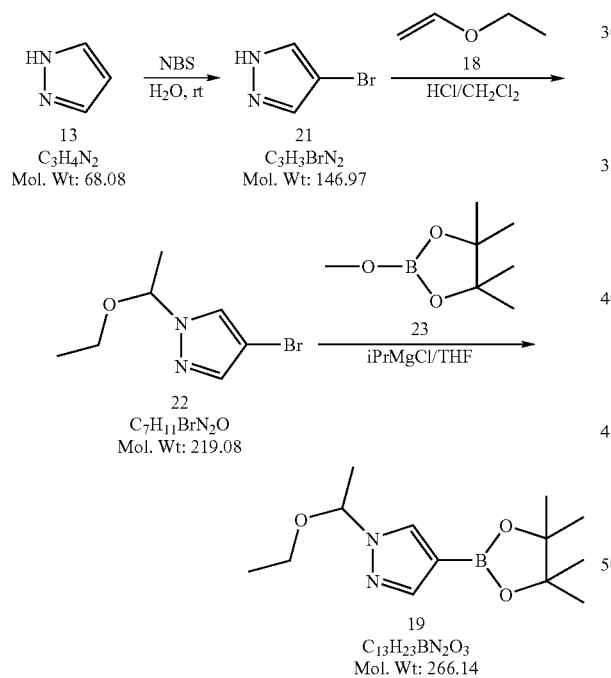

4-Bromopyrazole (21). Pyrazole (13, 34.0 g, 0.5 mol) and NBS (89.0 g, 0.5 mol, 1.0 equiv) were suspended in water (625 ml). The resulting suspension was stirred over night at room temperature. The reaction mixture was then extracted with EtOAc (2×100 mL). The combined EtOAc extracts was washed with aqueous Na$_2$S$_2$O$_3$ and brine, dried over Na$_2$SO$_4$, and concentrated under reduced pressure to afford 4-bromopyrazole (21, 72.0 g, 73.5 g theoretical, 98% yield) as a white solid (GC purity: >98%).

4-Bromo-1-(ethoxyethyl)-1H-pyrazole (22). To a solution of 4-bromopyrazole (21, 70.0 g, 0.476 mol) in CH$_2$Cl$_2$ (600 mL) was added a solution of 3.1 M HCl in dioxane (4 mL) and ethyl vinyl ether (18, 41 g, 0.569 mol, 1.2 equiv). The resulting reaction mixture was stirred at room temperature for 3 hrs. The reaction was quenched with aqueous NaHCO$_3$ and the two layers were separated. The organic layer was washed with water, dried over Na$_2$SO$_4$, and concentrated under reduced pressure to dryness to afford 4-bromo-1-(ethoxyethyl)-1H-pyrazole (22, 113 g, 104.3 g theoretical, 97% yield) as an oily (GC purity: 89%), which was directly used in the subsequent reaction without further purification.

1-(Ethoxyethyl)-4-(4,4,5,5-tetramethyl[1,3,2]dioxaborolan-2-yl)-1H-pyrazole (19). To a 100 ml solution of iPrMgCl.LiCl (50 mmol, 1.8 equiv) was added 4-bromo-1-(ethoxyethyl)-1H-pyrazole (22, 6.15 g, 28 mmol) at room temperature. The resulting reaction mixture was stirred at room temperature for 12 hrs and then cooled to −20° C. Methoxy pinacolborate (23, 10.6 g, 67 mmol, 2.4 equiv) was then added to the reaction mixture. The resulting mixture was stirred at 0-10° C. for 1 h. Aqueous NH$_4$Cl was added to quench the reaction. The mixture was then extracted with petroleum ether (PE). The combined PE extracts were washed with saturated NaHCO$_3$, dried over Na$_2$SO$_4$ and concentrated under reduced pressure. The crude product was crystallized in PE to afford 1-(ethoxyethyl)-4-(4,4,5,5-tetramethyl[1,3,2]dioxaborolan-2-yl)-1H-pyrazole (19, 4.2 g, 7.45 g theoretical, 56.4% yield) as a white to off-white solid (GC purity: ~99%). For 19: $^1$H NMR (DMSO-d$_6$, 400 MHz) δ ppm 8.09 (s, 1H), 8.58 (s,1H), 7.62 (s,1H), 5.55 (q, 1H, J=6.1 Hz), 3.37 (dq, 1H, J=7.1, 9.6 Hz), 3.12 (dq, 1H, J=7.0, 9.7 Hz), 1.56 (d, 3H, J=6.0 Hz), 1.24 (s, 12H), 1.00 (t, 3H, J=7.0 Hz); C$_{13}$H$_{23}$BN$_2$O$_3$ (MW, 266.14), LCMS (EI) m/e 267 (M$^+$+H).

A number of embodiments of the invention have been described. Nevertheless, it will be understood that various modifications may be made without departing from the spirit and scope of the invention. Accordingly, other embodiments are within the scope of the following claims.

What is claimed is:

1. A process of preparing a compound of Formula XII:

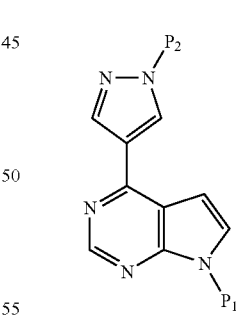

XII comprising reacting a compound of Formula X:

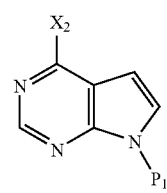

X with a compound of Formula XIII:

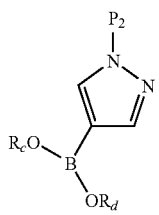

XIII in the presence of a palladium catalyst, base, and a solvent, to form a compound of Formula XII;

wherein:

$X_2$ is a tosylate group, a triflate group, iodo, chloro, or bromo; and $R_c$ and $R_d$ are each independently H or $C_{1-6}$ alkyl; or $R_c$ and $R_d$, together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups;

$P_1$ is independently a protecting group; and $P_2$ is a protecting group selected from the group consisting of 1-(ethoxy)ethyl, p-methoxybenzyl, triphenylmethyl, diphenylmethyl, hydroxymethyl, methoxymethyl, and t-butyldimethylsilylmethyl.

2. A process according to claim 1, wherein said compound of Formula XIII has formula:

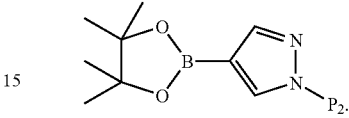

3. A process according to claim 1 to 2, wherein $P_1$ is —$CH_2OC(=O)C(CH_3)_3$ or —$CH_2OCH_2CH_2Si(CH_3)_3$.

4. A process according to any one of claims 1 to 3, wherein $P_2$ is 1-(ethoxy)ethyl.

* * * * *

UNITED STATES PATENT AND TRADEMARK OFFICE
CERTIFICATE OF CORRECTION

PATENT NO. : 8,410,265 B2  
APPLICATION NO. : 12/687623  
DATED : April 2, 2013  
INVENTOR(S) : Zhou et al.

Page 1 of 1

It is certified that error appears in the above-identified patent and that said Letters Patent is hereby corrected as shown below:

Title Page, Other Publications, column 2, line 17, delete "Struction-" and insert -- Structure- --.

In the Claims

Claim 1, column 202, line 3, delete " $C_{14}$ ", and insert -- $C_{1-4}$ --.

Signed and Sealed this  
First Day of October, 2013

Teresa Stanek Rea  
*Deputy Director of the United States Patent and Trademark Office*